US008399640B2

(12) United States Patent
Ryan

(10) Patent No.: US 8,399,640 B2
(45) Date of Patent: Mar. 19, 2013

(54) ISOLATED GENOMIC POLYNUCLEOTIDE FRAGMENTS FROM THE P15 REGION OF CHROMOSOME 11 ENCODING HUMAN SMS3

(75) Inventor: James Ryan, Augusta, GA (US)

(73) Assignee: Ryogen LLC, Suffern, NY (US)

( * ) Notice: Subject to any disclaimer, the term of this patent is extended or adjusted under 35 U.S.C. 154(b) by 0 days.

(21) Appl. No.: 13/239,327

(22) Filed: Sep. 21, 2011

(65) Prior Publication Data

US 2012/0010269 A1  Jan. 12, 2012

Related U.S. Application Data

(62) Division of application No. 09/999,121, filed on Oct. 31, 2001, now Pat. No. 8,039,602.

(60) Provisional application No. 60/244,705, filed on Oct. 31, 2000.

(51) Int. Cl.
| C07H 21/02 | (2006.01) |
| C07H 21/04 | (2006.01) |
| C12Q 1/68 | (2006.01) |
| C12P 19/34 | (2006.01) |
| C12N 5/00 | (2006.01) |
| C12N 5/02 | (2006.01) |

(52) U.S. Cl. ............ 536/23.1; 536/24.3; 536/24.33; 536/24.5; 435/6; 435/91.1; 435/325; 435/375

(58) Field of Classification Search ............... 536/23.1, 536/24.3, 24.33, 24.1, 24.5; 514/44
See application file for complete search history.

(56) References Cited

U.S. PATENT DOCUMENTS

| 5,582,979 A | 12/1996 | Weber |
| 5,591,623 A | 1/1997 | Bennett |
| 6,150,092 A | 11/2000 | Uchida |
| 6,184,212 B1 | 2/2001 | Miraglia |
| 6,537,751 B1 * | 3/2003 | Cohen et al. ............ 435/6.11 |
| 6,566,135 B1 | 5/2003 | Watt |
| 6,812,339 B1 | 11/2004 | Venter |
| 7,125,858 B2 | 10/2006 | Fillion |
| 8,039,602 B2 | 10/2011 | Ryan |

FOREIGN PATENT DOCUMENTS

| WO | WO95/20678 | 8/1995 |
| WO | WO9844152 | 10/1998 |
| WO | WO99/18198 | 4/1999 |
| WO | WO00/15795 | 3/2000 |
| WO | WO01/62778 | 8/2001 |

OTHER PUBLICATIONS

GenBank Accession No. AC002536, authored by Evans et al., submitted on Dec. 10, 1997.*
Wade-Martins et al. Nucleic Acids Research, 1999 vol. 27:1674-1682.*

Alders et al. "The human Achaete-Scute homologue 2 (ASCL2, HASH2) maps to chromosome 11p15.5, close to IGF2 and is expressed in extravillus trophoblasts." Human Molecular Genetics, 6: 859-867. 1997.
Altschul et al. Gapped BLAST and PSI-BLAST: a new generation of protein database search programs. Nucleic Acids Res. 25: 3389-3402. 1997.
Andria et al. "Genomic organization and chromosomal localization of the TAPA-1 gene." J. Immunol. 147: 1030-1036. 1991.
Bowie et al. "Deciphering the message in protein sequences: Tolerance to amino acid substitutions." Science 247: 1306-1310. 1990.
Burge et al. "Prediction of complete gene structures in human genomic DNA." J. Mol. Biol. 268: 78-94. 1997.
Examiner's Interview Summary dated Jul. 14, 2009 for U.S. Appl. No. 09/999,121.
Itoh et al. "Proportions of cells with paternal 11p15 uniparental disomy correlates with organ enlargement in Wiedemann-Beckwith syndrome." J. Med. Gen. 92: 111-116. 2000.
Kenmochi et al. "A Map of 75 human ribosomal protein genes." Genome Research 8: 509-523. 1998.
Koi et al. "Tumor cell growth arrest caused by subchromosomal transferable DNA fragments from chromosome 11." Science, 260: 361-364. 1993.
Lee et al. "Two novel genes in the center of the 11p15 imprinted domain escape genomic imprinting". Hum. Mol. Gen. 8: 683-690. 1999.
Ngo et al. "Computational complexity, protein structure prediction, and the Levinthal Paradox." in The Protein Folding Problem and Tertiary Structure Prediction Merz, Jr., K. and LeGrand, S. eds. Birkhäuser. Boston. 1994.
Notice of Allowance/Allowability dated Jun. 3, 2011 for U.S. Appl. No. 09/999,121.
Office Action dated Aug. 24, 2004 for U.S. Appl. No. 09/999,121.
Office Action dated Sep. 8, 2005 for U.S. Appl. No. 09/999,121.
Office Action dated Jul. 27, 2006 for U.S. Appl. No. 09/999,121.
Office Action dated Oct. 6, 2008 for U.S. Appl. No. 09/999,121.
Office Action dated Jul. 7, 2009 for U.S. Appl. No. 09/999,121.
Office Action dated Jan. 5, 2010 for U.S. Appl. No. 09/999,121.
Office Action dated Nov. 8, 2010 for U.S. Appl. No. 09/999,121.
Oren et al. "TAPA-1, the target of an antiproliferative antibody, defines a new family of transmembrane proteins." Mol. Cell. Biol. 10: 4007-4015. 1990.
Pileri et al. "Binding of Hepatitis C Virus to CD81" Science 282: 938-941. 1998.
Reik et al. "Imprinting in clusters: lessons from Beckwith-Wiedemann syndrome." Trends in Genetics 13: 330-334. 1997.
Segade et al. "Differential Regulation of the Murine Ribosomal Protein L26 Gene in Macrophage Activation." Life Sciences 58: 277-285. 1996.
Sequence: EMBL Database 'Online' 1997 "Human chromosome II pac pdJI075f20" see nucleotides 17080-34380.
Sequence: GenBank Accession No. 003693 (version 003693.1) Human Chromosome 11 p15.5 PAC clone pDJ915f1 containing KvLQT1 gene, complete sequence, PRI Sep. 30, 1995.

(Continued)

*Primary Examiner* — Terra Cotta Gibbs
(74) *Attorney, Agent, or Firm* — Cheryl H Agris

(57) ABSTRACT

Provided herein are isolated genomic polynucleotide fragments from the from the p15 region of chromosome 11 encoding human SMS3 (SMS3) and methods of use.

22 Claims, No Drawings

OTHER PUBLICATIONS

Sequence: GenBank Accession No. AC026645 submitted by Waterston, R. H. et al. Mar. 22, 2000 bases 2312-4001.
Sequence: GenBank Accession No. BE295955 (version BE295955.1) 60117424SF1 NIH_MGC_17 *Homo sapiens* cDNA clone IMAGE: 3529954 5-, mRNA sequence, Entry Created: Jul. 5, 2000 (Entry Updated: Jul. 20, 2000).
Sequence: GenBank Accession No. BE560890 (version BE560890.1) 601346329F1 NIH_MGC_5 *Homo sapiens* cDNA clone IMAGE: 3679567 5-, mRNA sequence, Entry Created: Aug. 10 2000 (Entry Updated: Aug. 15, 2000).
Sequence Alignments from Office Action dated Sep. 8, 2005 for U.S. Appl. No. 09/999,121.
Sequence Alignments from Office Action dated Jul. 27, 2007 for U.S. Appl. No. 09/999,121.
Sequence Alignments from Office Action dated Jul. 7, 2009 for U.S. Appl. No. 09/999,121.
Sequence Alignments from Office Action dated Jan. 5, 2010 for U.S. Appl. No. 09/999,121.
Siebert et al. "An improved PCR method for walking in uncloned genomic DNA. Nucleic Acids Res." 23: 1087-1088. 1995.
Virtaneva et al. "Chromosomal localization of three human genes coding for A15, L6, and S5.7 (TAPA1): all members of the transmembrane 4 superfamily of proteins." Immuogenetics 39: 329-334. 1994.
Westerman et al. "The human Achaete-Scute Homolog 2 gene contains two promoters, generating overlapping transcripts and encoding two proteins with different nuclear localization." Placenta 22: 511-518. 2001.
Witherden et al. "CD81 and CD28 costimulate T cells through distinct pathways." J Immunol. 165: 1902-1909. 2000.
Examiner's Interview Summary dated Oct. 6, 2005 for U.S. Appl. No. 09/999,121.
Examiner'S Interview Summary dated Mar. 4, 2009 for U.S. Appl. No. 09/999,121.
Examiner'S Interview Summary dated May 21, 2010 for U.S. Appl. No. 09/999,121.
Examiner'S Interview Summary dated Mar. 31, 2011 for U.S. Appl. No. 09/999,121.
International Search Report from counterpart international application PCT/US01/45381.
International Preliminary Examination Report from counterpart international application PCT/US01/45381.
Office Action dated May 14, 2012 for U.S. Appl. No. 13/235,404.
Office Action dated May 10, 2012 for U.S. Appl. No. 13/239,243.
Office Action dated May 11, 2012 for U.S. Appl. No. 13/244,463.
Office Action dated May 11, 2012 for U.S. Appl. No. 13/244,465.
Sequence Alignments from Office Action dated May 11, 2012 for U.S. Appl. No. 13/244,463.
Sequence Alignments from Office Action dated May 11, 2012 for U.S. Appl. No. 13/244,465.

* cited by examiner

SEQUENCE LISTING

<160> NUMBER OF SEQ ID NOS: 14

<210> SEQ ID NO 1
<211> LENGTH: 193
<212> TYPE: PRT
<213> ORGANISM: Homo sapiens

<400> SEQUENCE: 1

Met Asp Gly Gly Thr Leu Pro Arg Ser Ala Pro Pro Ala Pro Pro Val
1               5                   10                  15

Pro Val Gly Cys Ala Ala Arg Arg Arg Pro Ala Ser Pro Glu Leu Leu
            20                  25                  30

Arg Cys Ser Arg Arg Arg Arg Pro Ala Thr Ala Glu Thr Gly Gly Gly
        35                  40                  45

Ala Ala Ala Val Ala Arg Arg Asn Glu Arg Glu Arg Asn Arg Val Lys
    50                  55                  60

Leu Val Asn Leu Gly Phe Gln Ala Leu Arg Gln His Val Pro His Gly
65                  70                  75                  80

Gly Ala Ser Lys Lys Leu Ser Lys Val Glu Thr Leu Arg Ser Ala Val
                85                  90                  95

Glu Tyr Ile Arg Ala Leu Gln Arg Leu Leu Ala Glu His Asp Ala Val
            100                 105                 110

Arg Asn Ala Leu Ala Gly Gly Leu Arg Pro Gln Ala Val Arg Pro Ser
        115                 120                 125

Ala Pro Arg Gly Pro Pro Gly Thr Thr Pro Val Ala Ala Ser Pro Ser
    130                 135                 140

Arg Ala Ser Ser Ser Pro Gly Arg Gly Gly Ser Ser Glu Pro Gly Ser
145                 150                 155                 160

Pro Arg Ser Ala Tyr Ser Ser Asp Asp Ser Gly Cys Glu Gly Ala Leu
                165                 170                 175

Ser Pro Ala Glu Arg Glu Leu Leu Asp Phe Ser Ser Trp Leu Gly Gly
            180                 185                 190

Tyr

<210> SEQ ID NO 2
<211> LENGTH: 132
<212> TYPE: PRT
<213> ORGANISM: Homo sapiens

<400> SEQUENCE: 2

Met Gly Arg Thr Trp Cys Gly Met Trp Arg Arg Arg Pro Gly Arg
1               5                   10                  15

Arg Ser Ala Val Pro Arg Trp Pro His Leu Ser Ser Gln Ser Gly Val
            20                  25                  30

```
Glu Pro Pro Asp Arg Trp Thr Gly Thr Pro Gly Trp Pro Ser Arg Asp
            35                  40                  45

Gln Glu Ala Pro Gly Ser Met Met Pro Pro Ala Ala Ala Gln Pro Ser
 50                      55                  60

Ala His Gly Ala Leu Val Pro Pro Ala Thr Ala His Glu Pro Val Asp
 65                  70                  75                  80

His Pro Ala Leu His Trp Leu Ala Cys Cys Cys Leu Ser Leu Pro
                 85                  90                  95

Gly Gln Leu Pro Leu Ala Ile Arg Leu Gly Trp Asp Leu Asp Leu Glu
                100                 105                 110

Ala Gly Pro Ser Ser Gly Lys Leu Cys Pro Arg Ala Arg Trp Gln
                115                 120                 125

Pro Leu Pro Ser
        130

<210> SEQ ID NO 3
<211> LENGTH: 290
<212> TYPE: PRT
<213> ORGANISM: Homo sapiens

<400> SEQUENCE: 3

Met Val Thr Leu Thr Tyr Phe Gly Ala His Phe Ala Val Ile Arg Arg
 1               5                  10                  15

Ala Ser Leu Glu Lys Asn Pro Tyr Gln Ala Val His Gln Trp Ala Phe
                 20                  25                  30

Ser Ala Gly Leu Ser Leu Val Gly Leu Leu Thr Leu Gly Ala Val Leu
                 35                  40                  45

Ser Ala Ala Ala Thr Val Arg Glu Ala Gln Gly Leu Met Ala Gly Gly
 50                      55                  60

Phe Leu Cys Phe Ser Leu Ala Phe Cys Ala Gln Val Gln Val Phe
 65                  70                  75                  80

Trp Arg Leu His Ser Pro Thr Gln Val Glu Asp Ala Met Leu Asp Thr
                 85                  90                  95

Tyr Asp Leu Val Tyr Glu Gln Ala Met Lys Gly Thr Ser His Val Arg
                100                 105                 110

Arg Gln Glu Leu Ala Ala Ile Gln Asp Val Phe Leu Cys Cys Gly Lys
                115                 120                 125

Lys Ser Pro Phe Ser Arg Leu Gly Ser Thr Glu Ala Asp Leu Cys Gln
                130                 135                 140

Gly Glu Glu Ala Ala Arg Glu Asp Cys Leu Gln Gly Ile Arg Ser Phe
145                 150                 155                 160

Leu Arg Thr His Gln Gln Val Ala Ser Ser Leu Thr Ser Ile Gly Leu
                165                 170                 175

Ala Leu Thr Val Ser Ala Leu Leu Phe Ser Ser Phe Leu Trp Phe Ala
                180                 185                 190

Ile Arg Cys Gly Cys Ser Leu Asp Arg Lys Gly Lys Tyr Thr Leu Thr
                195                 200                 205

Pro Arg Ala Cys Gly Arg Gln Pro Gln Glu Pro Ser Leu Leu Arg Cys
                210                 215                 220

Ser Gln Gly Gly Pro Thr His Cys Leu His Ser Glu Ala Val Ala Ile
225                 230                 235                 240

Gly Pro Arg Gly Cys Ser Gly Ser Leu Arg Trp Leu Gln Glu Ser Asp
                245                 250                 255

Ala Ala Pro Leu Pro Leu Ser Cys His Leu Ala Ala His Arg Ala Leu
                260                 265                 270
```

```
Gln Gly Arg Ser Arg Gly Gly Leu Ser Gly Cys Pro Glu Arg Gly Leu
        275                 280                 285

Ser Asp
    290

<210> SEQ ID NO 4
<211> LENGTH: 145
<212> TYPE: PRT
<213> ORGANISM: Homo sapiens

<400> SEQUENCE: 4

Met Lys Phe Asn Pro Phe Val Thr Ser Asp Arg Ser Lys Asn Arg Lys
1               5                   10                  15

Arg His Phe Asn Ala Pro Ser His Val Arg Arg Lys Ile Met Ser Ser
            20                  25                  30

Pro Leu Ser Lys Glu Leu Arg Gln Lys Tyr Asn Val Arg Ser Met Pro
        35                  40                  45

Ile Arg Lys Asp Asp Glu Val Gln Val Val Arg Gly His Tyr Lys Gly
    50                  55                  60

Gln Gln Ile Gly Lys Val Val Gln Val Tyr Arg Lys Lys Tyr Val Ile
65                  70                  75                  80

Tyr Ile Glu Arg Val Gln Arg Glu Lys Ala Asn Gly Thr Thr Val His
                85                  90                  95

Val Gly Ile His Pro Ser Lys Val Val Ile Thr Arg Leu Lys Leu Asp
            100                 105                 110

Lys Asp Arg Lys Lys Ile Leu Glu Arg Lys Ala Lys Ser Arg Gln Val
        115                 120                 125

Gly Lys Glu Lys Gly Lys Tyr Lys Glu Glu Leu Ile Glu Lys Met Gln
    130                 135                 140

Glu
145

<210> SEQ ID NO 5
<211> LENGTH: 236
<212> TYPE: PRT
<213> ORGANISM: Homo sapiens

<400> SEQUENCE: 5

Met Gly Val Glu Gly Cys Thr Lys Cys Ile Lys Tyr Leu Leu Phe Val
1               5                   10                  15

Phe Asn Phe Val Phe Trp Leu Ala Gly Gly Val Ile Leu Gly Val Ala
            20                  25                  30

Leu Trp Leu Arg His Asp Pro Gln Thr Thr Asn Leu Leu Tyr Leu Glu
        35                  40                  45

Leu Gly Asp Lys Pro Ala Pro Asn Thr Phe Tyr Val Gly Ile Tyr Ile
    50                  55                  60

Leu Ile Ala Val Gly Ala Val Met Met Phe Val Gly Phe Leu Gly Cys
65                  70                  75                  80

Tyr Gly Ala Ile Gln Glu Ser Gln Cys Leu Leu Gly Thr Phe Phe Thr
                85                  90                  95

Cys Leu Val Ile Leu Phe Ala Cys Glu Val Ala Ala Gly Ile Trp Gly
            100                 105                 110

Phe Val Asn Lys Asp Gln Ile Ala Lys Asp Val Lys Gln Phe Tyr Asp
        115                 120                 125

Gln Ala Leu Gln Gln Ala Val Val Asp Asp Asp Ala Asn Asn Ala Lys
    130                 135                 140
```

-continued

Ala Val Val Lys Thr Phe His Glu Thr Leu Asp Cys Cys Gly Ser Ser
145                 150                 155                 160

Thr Leu Thr Ala Leu Thr Thr Ser Val Leu Lys Asn Asn Leu Cys Pro
            165                 170                 175

Ser Gly Ser Asn Ile Ile Ser Asn Leu Phe Lys Glu Asp Cys His Gln
            180                 185                 190

Lys Ile Asp Asp Leu Phe Ser Gly Lys Leu Tyr Leu Ile Gly Ile Ala
        195                 200                 205

Ala Ile Val Val Ala Val Ile Met Ile Phe Glu Met Ile Leu Ser Met
    210                 215                 220

Val Leu Cys Cys Gly Ile Arg Asn Ser Ser Val Tyr
225                 230                 235

<210> SEQ ID NO 6
<211> LENGTH: 329
<212> TYPE: PRT
<213> ORGANISM: Homo sapiens

<400> SEQUENCE: 6

Met Ala Glu Ala Gly Thr Gly Glu Pro Ser Pro Ser Val Glu Gly Glu
1               5                   10                  15

His Gly Thr Glu Tyr Asp Thr Leu Pro Ser Asp Thr Val Ser Leu Ser
            20                  25                  30

Asp Ser Asp Ser Asp Leu Ser Leu Pro Gly Gly Ala Glu Val Glu Ala
        35                  40                  45

Leu Ser Pro Met Gly Leu Pro Gly Glu Glu Asp Ser Gly Pro Asp Glu
    50                  55                  60

Pro Pro Ser Pro Pro Ser Gly Phe Leu Pro Ala Thr Val Gln Pro Phe
65                  70                  75                  80

His Leu Arg Gly Met Ser Ser Thr Phe Ser Gln Arg Ser Arg Asp Ile
            85                  90                  95

Phe Asp Cys Leu Glu Gly Ala Ala Arg Arg Gly Pro Ser Ser Val Ala
        100                 105                 110

His Thr Ser Met Ser Asp Asn Gly Gly Phe Lys Arg Pro Leu Ala Pro
    115                 120                 125

Ser Gly Arg Ser Pro Val Glu Gly Leu Gly Arg Ala His Arg Ser Pro
130                 135                 140

Ala Ser Pro Arg Val Pro Pro Val Pro Asp Tyr Val Ala His Pro Glu
145                 150                 155                 160

Arg Trp Thr Lys Tyr Ser Leu Glu Asp Val Thr Glu Val Ser Glu Gln
            165                 170                 175

Ser Asn Gln Ala Thr Ala Leu Ala Phe Leu Gly Ser Gln Ser Leu Ala
        180                 185                 190

Ala Pro Thr Asp Cys Val Ser Ser Phe Asn Gln Asp Pro Ser Ser Cys
    195                 200                 205

Gly Glu Gly Arg Val Ile Phe Thr Lys Pro Val Arg Gly Val Glu Ala
210                 215                 220

Arg His Glu Arg Lys Arg Val Leu Gly Lys Val Gly Glu Pro Gly Arg
225                 230                 235                 240

Gly Gly Leu Gly Asn Pro Ala Thr Asp Arg Gly Glu Gly Pro Val Glu
            245                 250                 255

Leu Ala His Leu Ala Gly Pro Gly Ser Pro Glu Ala Glu Glu Trp Gly
        260                 265                 270

Ser Pro His Gly Gly Leu Gln Glu Val Glu Ala Leu Ser Gly Ser Val
    275                 280                 285

```
His Ser Gly Ser Val Pro Gly Leu Pro Pro Val Glu Thr Val Gly Phe
        290                 295                 300

His Gly Ser Arg Lys Arg Ser Arg Asp His Phe Arg Asn Lys Ser Ser
305                 310                 315                 320

Ser Pro Glu Asp Pro Gly Ala Glu Val
                325

<210> SEQ ID NO 7
<211> LENGTH: 17290
<212> TYPE: DNA
<213> ORGANISM: Homo sapiens

<400> SEQUENCE: 7
gcccctgcct ggatcacaac aggcaggacg gctgagcagg cacacatctg tctctccctc      60
tgctgatctg tggccttgga caggggctac tctgggggag ctgacaggtg accccccag     120
gaggcccctc cctgcctctg gctgggaat ccacctctgt ggagccctg gaatggcct       180
gtttcaaata cgtaagtggg agcaaggtct catcctcagc gggggacatc gctgggggca    240
aggccagtgg gtgggtggga aggtttctgt ggcactgggg cctcctgttg attgattcac    300
ccaattaatc acagccagca gctggggagg gggtaggaag gcggtgaagg gaaaaggagc    360
ccacagccgg gaggccctgg gaggttggca gaggcctgca cctgcctgca gccagccctc    420
cggcccagcc ctcttccctc ctttcggagg ggccagagca tggggtgcta agggctcagt    480
cttttaacccc tccccagctc tcaggggagcc cctcccatgc tccccaggcc tctgccccac   540
ttgcacctcc ccgggcccca gggcacagga cgctttcccc acccttttggg aggctgaggg   600
tgtcaggagg cctgggctga gtgctggctt ccgtctcact ggcttgcaga caagaccctc    660
catttcggtg gaaaaacagc aagaacagca ccccccctcca ggcagaccca agggaggcat   720
cggtgtgagg gcttcaagct ctgtactgtg ggtttaagcc ttgcacctct ggatacctgt    780
gggcctcggg cagatcactg agcctccctg catctggaag tcggggtgag acccctcaga    840
gggggctggg aggaggaagg gcccctcttg atgggcagcc cccaccctcc acctactgcc    900
ctgccctccc agccttcagg gtcctcccca gcttctgtgg gctcccaggt ggacctgggc    960
caccccctgag accccgaaga gctcaaggcc agctaatagc ccacaggctc aggacagcac    1020
tggacaggcc tctgggccca cctggcccca ctcccgattt ttatgggaac aaagactgaa    1080
ggtgtggccc caaaggaacc accccctcccc cagtgccccg ctgctgggaa aagggtcagc    1140
agagtttggg tctccccccca caagcccttct gggctgtgcg tgctacagct gaggacatgg    1200
cgttgagggg caggccgcct ccaacccgt ccaccttgcc ctgtctagct ctgtccaagg      1260
ctctctccgg ctggctaatc acctctgggc acagctgtgc tgctgaggtc tctgggatga    1320
ctgaaggtct ttgaaggcca ctttgggaga agcgaaggtg catggacacc agggaccctg    1380
ctcacagcga gtgtccctgc cccatcccctt tctgcattga gtgggacaag cttgcttcca    1440
tttgggggat cgccatctga ctattccact tgtcttaggg tggggcagag attaggtgat    1500
gtggaggggc ttctctacat ggcccccctg ccccagctct gagggtagc accagagtgg     1560
gtttcaccag cgtagggcac gtaggccccg ccatgaacag ggcccaacc ttggtttaat     1620
gctttgctac tgccatctta aagttctttt tttattttttt attttgcttt atttttttatt 1680
agagatgggg tctcccagtg ttgcccaggc tggtcttgaa ctcctggctc aagcaatcct    1740
ccggcctcag cctcccaaag cactgggatg acacgtgtga gccaccttgc ctggcctttg    1800
gaatctgact actttatct tctaacttgt tttgcaggtg caggccaacg gcatacagca     1860
gcactcacat aagcaaagga gagcgtgcac aaggcgccaa atgtatatcc accctcactc    1920
```

```
gtcccccac ttgagtagcg catccacgat gcccacagac accaggccac acagaaaagg    1980
tgccagggac ccacagcagt gcaaggcagc gtgtcacacc tacgcatgag caagccgggc    2040
gctgatggcc accgagcagc cacgttttcc attcaaatcc gcacttgcta aggatgcagc    2100
aggaagccag tggtgttcta caaacgtgc aggacccggg aacctgtcat gtcctttctt    2160
acttgtgcga cttctctgtg ttagccgagg tctcttgctg atggatctac ccacagtgcc    2220
ttttgtcttt gaacttgtcc cttccctcct tcctcgccca tcagcgagca ggaggtggag    2280
ggtgctggtg aacaagcct gcgtcaagga gtgaaatcag ctgatttcat ttttgtgcag    2340
tttccactgt tctagtagca aatgaaatag agacgcctgt gccaggacaa aacacacact    2400
gtgtcattcc agtgattccg catagaagtt aaatgctctt atgcttgcat tttaaactgg    2460
catcacataa tataaagatg gataactaca ttcacgctag tcacttaaat tcctaatctt    2520
tcttactcag aatggcatta aatagtgagt ataaaataag aagtataaaa tagtaagtca    2580
agaggttgac tatagaagaa agaaaaatgc tttatatttt agcaccttga acatgacatc    2640
acgatcacct tctccctgga atcagtttct aacttccagg tggggactag gcctggacca    2700
tgagctccta gcagagccct gctgccccca cagcagagcc caggacaggc tggcacctgg    2760
gccaggtgag gctctgtcca ggctcactga tctcaaatgc tgaactgcta aggatgtcat    2820
gtccccaaag gagccgccag gctcagcctc acttcctgga aggcgtgaac attgcaagaa    2880
tgtggaagtg aaagagtcca gggcttaaat ctcaattctc atcattttca agctgagtcc    2940 aaggagaga agacagtcat ggattcttag tttctgtttc tggttgagcc agcagggtcc    3000
cttcctcatc cctcttttct gcttatcact agagacagaa actaaaacca tgactttagg    3060
ctgctgagag cctaaaacaa aacgacagca agagaaggtg ggttggacca gcttgcctgt    3120
gacttcaggc acttcatctt tactgggcac tgggtgaatg acagtgtggg gaggggtctt    3180
cataacacgg caatcagcag cccactgtgc ccaggagact cgcctgtggt cctggttatc    3240
aaccacagcc cttccagtc tcaaaaatgt ccccgctggg acagcaagtt acatcgtcgc    3300
tacaagtcct gtctcctggg agatgcagtc cagcagcact acatcctctg agcagcaggt    3360
gccaagtggg atgaactgga taaggactgc attcggggaa acgcccgtgt gaaaggaaat    3420
acacaggaag gaggtggcaa cgggtgggaa gccactagac cacgacgcga ttctgcccca    3480
gtgaaggcga ggggatagcc tgggcctaga tcgctgtgag gtctatggaa gtttccacaa    3540
gcttgctggg tagttctcga ggcaaactcg gaaagggagt cccttgtctc cctggaacgg    3600
atctttcttg gcatctctgt cacactcatt aggtgggcct ggtgtcaacc ccatttgcag    3660 gccacccccaa acttgatcaa aggtccgctt ctggcacccc ataccctgtc ctacaggaaa    3720
tacagggaca ggctcccaat aacaacaccc agcacggtgc catcaacacc accacgcaca    3780
cgggggctca acggaacaga catctccgct tcttcaatga agacactgga gggaaattgc    3840
ttacaaggcg cttaagagac ctattaagca aacttgatgt gtggacctgc ggcggatccc    3900
gattctataa ggccaactgc acaaaaccac gagaccccct gaggactgcg ccattggctg    3960
ggtccccgat gatatgaaag aacggtggtt catttgagcg ggtgatgttt ttgcggtttc    4020
ctttagaggc acacgtgaaa catgacgggt gaaaggattc aaagtctggg atttgcttca    4080
aagcaacgca gggatggcgt gggggatgga tgggcagga agggccttga aactggtgct    4140
ggaggcttcc cagggctgcc ctggagccca gtgcgtcctc caccggccag actgtacaac    4200
ggttggatcc tgtgtccact gctaggaccc aggctcacg agcacgggct tgtgtggcac    4260
acggatgcac cctaagtcct ggcacagaga ctgctcaaca aaggcctcgg tgcttttgtg    4320
```

```
tatgtttgaa attttccata ataaaatgaa aaatgggaaa atgggaaaac aaaaatggca      4380
gcactactta ccctctgcag agttttgtcc gcttcacgcc agtgggtggc agtcgtttcc      4440
tctgccctgg ccttccatcg tttccccct accctcttca cccacccaac agccccctgt       4500
ggtcctggca gctgtgggcc tttccttgag gtcaaggtgt ggagtcctgg ggagggctca      4560
gggaggccac cgacccgggt gtggattctg ggagaagcct gtgggatgtc cctccctggg      4620
tgaccacggc aatgtgcccc ctcctgtccc ttggccaagg ccagttccct gagccctgca      4680
gccccaagcc acagctggtc cactgacccc agttgagcct ggtcctcatc agaccagctg      4740
accccttga cccccgctac agactcggct ttgaccttgg ctgctgagga gcccccacct       4800
ggactgaggc tgcagctggc gagagaggag ccctgagctc ctctgataag aagggacctg      4860
gccagcctga cgtttgagac ccaggcatcc cggtagcctg ggtgtcctgt tgccgtggtt      4920
attcaggagc cacccactct gggacaacac cagctgctcc cacctcgcag ggctcccacg      4980
gctctgtccc aaccactcct ttctgaagga aggggtgcct ctgcgcccta aagaaaccgg      5040
gggagcccca caaccctcc cccaccagga cactaaaagg cagctttcgg tacagtgaga       5100
catcaaagcc tcctaggccc tgagtcaaag gtatagccgt gtaatatccc agtgccagct      5160
ctccggctgc ggggagcctg gcgcaaagct tccaagcctt ccttgttcct ttcaagagcc      5220
gctcttagaa ttcaggtgag cggagacctg cagggcctcc ccagtgcggg caaaacccaa      5280
agctagcgag agggcagcct ccaggcacct ctcactaact cctcccagag gccgttgagg      5340
tgggtctggt caaacccatt tgcaagttaa cccacttgcc ctgggctgcc agctgccac       5400
gttagtggag atctgagcgt ggtggcctgc gcaggagccc atgccctcag ccccacagcc      5460
ggtgctctct ggtcagacca cctcagccta gccccacacc cagcacttac cccagccctc      5520
gggatgggtc agcagcctcc agcctgcagc ttccaagcca gcgagtagcc ctgtctggac      5580
aaccaccag cccaccacct cctggaggat gcccccagcc tcacaaggtg tcccaatggc       5640
tccgctatca acggcctggc tgcactccag atctcaccca gacccaccct acggaggagg      5700
cagcagggtt tgaggagtag tgaccacgga agtctggccg tcacctggga agtgtaggtg      5760
ataggagcca ctggtaaaca gaactgattt atttataaag ttcacgctcc cttgaagagg      5820
tgtgccccac acaggcttct ccctagcaga gcagcagtgc ccacaaaccc accccagggt      5880
gggctgtcac gggggcctca cgccagggac cccgcccctc agggactgct cgtgtccaga      5940
tcttggccag catggaaaac tccagatagt gggggcaggg gtccaggtca tctttattac      6000
gccccaggtc aagggttctt tgtacaaaaa taggtctccg tttgccagca gtgtccctcc      6060
agcagctcaa gttaatgtgt agaaaatgga ttctctgtgc ccttagaaaa tcctctcccc      6120
tccggaaaaa tctccaagtg ttggtgcccc ccgcccact gcagtcgaga agctgtgggg       6180
aggggcggcg tcgaggaag ccgccagccc ttatggggcc agctccaagc ccgtttccac       6240
cgcggcattg gtcaggctgg gccggacgaa cgaggcggcg tcggcggtgc ggggggtggt      6300
gggtgggtcc ccggctcgct gggggcggag cgcgggccgg tccacctggc gggctccccg      6360
gcgatgagcg cgccggccgc tcgctcggct tccgggctg aggctgcggg gggaaggtgg       6420
ggaaccaaac gcgcgtcaac gcgggcgcgg gcccggggca gacccgcccc gggccggccc      6480
tgcccgcacc tccccaagc gaactcggca gtttcgtttg ctcggttggt tttggagtct       6540
tgagtccgtg ggtgccgcga ctcggtctga gacacggcgg gggcggggcg ggcgctcgga      6600
gccgcggtga gtcagggctc cgcgcccgcc gactcatttc tgccgccccg gcccgggagc      6660
gcgatttgca atgcaaagtc accccgcctc cagcaccca atctgcccca ggatccgcca       6720
```

```
gcactagaga cctcaacggc ccgacggccg ctcccctccc ctcgtctacc cctccctcgt    6780
cggcggctga gccgcgaggg gaagttttgc aatcccggac aaacaaacgc cggtcttgca    6840
cgggcttgaa aaactttggg ggaaatgaag agtgagcgaa atcgaagcca tcgctcgggc    6900
ctggcgctcg gctccgcggg ctcctggggg cgcgacccgc cgggcctgcc caccccgtcc    6960
ctccaccccg gcccccggcc ctccctcctc cctgcctccc ggctgttacc tcataggtcg    7020
agggcgctca gtagccccct aaccagctgg agaagtcgag tagctcgcgc tccgcaggac    7080
tcagcgcgcc ttcgcagccg ctgtcgtccg acgagtaggc ggaacgcggg gagccgggct    7140
ccgagctgcc cccgcggccc ggggacgaag aagcgcggga gggcgaggcg gcgaccgggg    7200
tggtccctgg cggcccgcgg ggcgcagacg ccgcacggc ctgcggcctc agccctcccg    7260
ccagcgcgtt gcgcacggcg tcgtgctcgg ccagcaggcg ctgcagcgcg cggatgtact    7320
ccacggctga gcgcagcgtc tccaccttgc tcagcttctt gctggcgccg ccgtgcggca    7380
cgtgctgccg cagcgcctgg aagcccaagt tcaccagctt cacgcggttg cgctcgcgct    7440
cattgcgccg cgctacggcc gctgcgccgc ctccggtctc tgcggtggcc ggtcgccgcc    7500
gccggctgca gcgcaacagt tccggggacg cgggtctccg ccgggcagcg cagccgacag    7560
ggacgggggg cgcaggggc gcggacctgg gcagtgtgcc gccgtccatc gcgcctgcat    7620
ccacccgccc gctccaggtc ccggcgcgcc gcaggaaggt gcaggcagag gaaccggagg    7680
cgacggggaa aactgtggcg ccccaagggg gcttctggca cggcgccgcc aggcaactcc    7740
ccagggcacg cgtcctaggt cgtctggagc ccggggatag gaggcctagt ggtggcaggc    7800
cgtacgcgcc agggagcgtg ggacgctcgt gtcccgcgcg tgcggccgga ctctcccagg    7860
tctccgcagg cgcggcgcag gcggctggtt tttaaatgta tagataaccc tcctccgcgc    7920
cgccgccgtc gcctttctca cgccctcctt ccttcgcctc gccctcccgc cacgcttcgc    7980 cctcccctc gcgcgatcac attctgtaag gcccaaagcg tgcgcatgtc ccctagccc    8040 atcccccgga cgcagtccac agatccccag tgcgcccaac tggcgaaatc tgcgagttcc    8100
cggtgcgccc cctgctcccg gcaggtgctt agtgcgcccc caaagcaagg tacgcaggtc    8160
ctgggttgag ccttcccgta ccccaccct aacccgcgc gcagcccgc cagtcccaag    8220 agccgccaga ccttcgcacg cgcagcgcgc gctgtgggag ggaaggcgcg gccctggcga    8280
caacacggct gttcgggagg cgcgcaagat ccccgggggc agcacgcgcc gcgcagccca    8340
cacccacgcc ccaccctcct ggggccgagg aggcggggc cagggtctca gccaatcgtg    8400
ggccacccgt ttggccaatc gcgcagggcg cggctccacg cccggcccca ttgaggaagc    8460
gcgtacgcgt ggcgcgtggc tcacggggag catcgctaac aaagctgggt tcctgctggg    8520
ccccgccctg ctcctcgccc ccgcgactgg gctgggcgcg ctgtcccta gcgcagctat    8580 gtcccgagcg cgccccacc tgtgcgttaa tctactggga atggggtgg actgcgcctt    8640 acctggggcg gggtggggct taaggagtgg tcgagactga ggcggggtgg gaggttcagg    8700
ttcccggggc gccttcccca acccgccccg ctttccccgt ccctccacgc gcaccctgcc    8760
tgtggtttcc gtgcgcccc ggcctgaggg ctctgggcgg caccttaacc cggagggcct    8820
ggaggtctgc acccgaccgc cttgtgccag gacggtcagg tccacgccct cccccaccgt    8880
ggctccctcc atctgcagta tccccacct ccagcccgtc ctgccctcct gttctccgtc    8940
tcgcttcccg tcggtgcctc cgggatctca cagccctcgc acctcttttg tgacccaggc    9000 tgttttttctg cacccccctc tccctgagg gcactgagat tgggccattg gcctgaaggt    9060
ctctgggagc agcacccttc caggggaggt gggacgtcga gaacttctcc ctaagagatg    9120
```

```
cggggaaatg gtggggcctg agagtgcaaa cactgcagaa atgcgaaaaa tgtagtgtta   9180
acggaagagt ttaggtcctg cctcactgtc cgggaaacgc gtgccctcgg gggagccttt   9240
gccaagccgg ttttcccga aggtgaccag atgctcctgg ccactgcct ctgagacctc    9300
agggaacgga gattttgtg gacccagctg cctggagctg ctttcctgtt ccggccggag   9360
gaggtgaggc ccaagacccc tcctgggagc ctggggcag atagccagtg tttactgcca    9420
gcctcgggt gcccacctgc tcccattacc ctgcaggatg ctgctggctg cccacctgg    9480
gcccccagca cacctgtgtc tcgagtacgc ctggccctcc tgccttggga ggggccggaa   9540
gagtagcacc tgcctgggag ctggtggtct gcggtctcta tttggcagat gaggaagccg   9600
acttggagag aaccctggat gtgtccacag tcactcctcc gcccagtgga gcgatccagg   9660
cagaaatcgg ggccctgagt ctgaatccgg gttctgcaac cagggcagat gcgggcttgc   9720
ctctgctccc tgtccctggt ctgagagccc attcttccca gatggtcact tggcaaatca   9780
cagcctggca tggattgttc tgccctcctt ctgctgcctc cctccttccc cttgtcaagg   9840
ctgcaagacc aggatctagg aacgatcctg gagccctgca aactaggcct tggaaatccc   9900
tgctggattt ccacctcccg ggctgggagc ccctcggtca tctgttgctg tgtaaggagc   9960
caccaggatt ttagcggtct gaacaacgat gtattatttc tcaggattct gtgacttgat  10020
gggtgggccc tctgctgctc tgggtgtggc tgcatacacc ccggggggtca cagggacga  10080
gcggtacagc ggctgggttg ctctctaccc ggtcttcgtc caagcccctc cacagctggt  10140
aagatctccg gagcaggacc tgcaagccct cttcagatca ccccagaact tcctgtctaa  10200
aaactgaagc ctctcactgc ccaggcatgg cttcttgcta ccctgccctc aggcacagtc  10260
ctgcacccac ctgcgtctgc tgtgccatgt ccaggccagt ccccccccac caccaacacc  10320
tctctctatc ttcatcctct tcccaatctg gtcctccac cgctgtggaa accccgtctg    10380
cccccaaagc ctagcttaaa aataattccc tagggacctg tgtctctccc tgcctcggcc  10440
cctccttcat tcctgggtgc ctccggctgt gcagcatttg acactgcagc accccctta    10500
attcggaagc atgctgtctc ctggactggt gagtctccac actatctgag ccgtcttctc  10560
tggaactctt ggcctctcag tccgttctga aatacagcc ttggtaagca cggtgcccac   10620
atgaatgttt ccagcagcag gattcaaaat agccacatgt ccatcaacag atgagtggat  10680
aaacaaaaca tggtccagaa taatggaaga ttactcagcc ctaaaaagag acgaagctgg  10740
tgaacctcga gaacacgagg ccgcgtgaac gaagccagac accgaggacc acgtagcgtg  10800
agactctcag tctatgaaat gtgcggagtc gataaattca cagagacaga aaggagattc  10860
acggttgcca ggggctgggg agtgacaaca gagggatggg ggtgactgtg aaagggtacg  10920
tggtttcttt cccagaggat aagaacgttc taacatggcc tgtcctgttg gcttcacagc  10980
tctgtacaac acacaaaaaa accattgaaa tgtacacttt gtggaatgtg aactgtatct   11040
tgataaagca gttagaagac cttcgaacat aagcatgcgg cctcatgggg cctttgcctg   11100
ggcaccctgg cacctctccc aggctctacc tatctccgac ttcattcctg agctcttgaa   11160
caggggtaag gcaaactttt tctgcaaagg aacacgtggg aagtattttc ggccttgacg   11220
gtcacatgtc tctgccacga gtcgtctgcc ttggggcgca aatgcaggct gggcaggga    11280
agaaataaca aaacttgctt cctggtcact gaaacatgaa gtccaggtca cactcactgt   11340
tacaaaatac tccgaatttt cagactgtgg ttcaatacac atgacataaa atggaccttc   11400
ttaaccattt gtaagtgcac ggttccgtgg aattcagtat attcatgtgg ctgtgcaatc   11460
atcaccacca tccatctcca aaagtttctc attttcccaa accgaaagtc tgtccccatt   11520
```

```
aaacagcagc ttcccatgac ccttccccca gccctggca cccaccatcc actctgtgtc   11580
tgtagatttg actgctctgg agacctcctg taagtggaat cctacagcat ctgtcttttt   11640
gtggaccggc ttcttacact gatgctgatg ccctcgagct tcatccatgt cgtagcctgc   11700
ataaggattt cctctctttt tatgggtgaa taatattcca ctgtatgggt agaccacggt   11760
gttgatccgt tcctccgtca gtggatgctg gggtggtttc cacccttggg ctaccgtcag   11820
tgacgctact gtggacatgg gggtacaaat atctctttga gatcctgctt tcagttcttt   11880
tggggataga cggagaagcg gagttgccag gtcatacggc aaacctctgt ttaaccttt   11940 gagggaccac catgttgttt tccgcagtgg ctgcccacag tacattcctg ctgcgcacga   12000
ggttctgatg tctccacatc cccgcccaca cttggtgctt tctgggtttg tttcgtttcg   12060
ttttgttttt gtttgttttt gagacggagt ctcgctctgt ctcccaggct ggagtgcagt   12120
ggcgcaatct tggctcactg cgacttctgc ctcccgagtt ccagccattc tctagtttca   12180
gcctcccgag tagctgagac tacagatacg tgccaccatg cccggccaaa tttttatttt   12240
ttgtagagat agagtctgac tatgttgccc agcctggctg aggtgataat agttttttga   12300
tgatagctaa tgggtatgga ttttaatttt ttaaccactt aagaatttaa agaaaattcc   12360
tagcttttgg gcaatacaaa agcaggccag gggctggatc tggcccatgg gcctcggtct   12420
gctgacagct gctccagagg actggtatgt ccacgtgaca cctggcccga cccccatcct   12480
cctgcagctc ctcaaaactca acttgttgca ggttgaactc ggcctccttt cctctaagga   12540
aagatcccct ccgcagcaga gaacaccagg tcggcagtgt gggcactgcc ttcctctcc   12600 cctgccctct gctgtacgtc agcccagccg cttctccagc caggtcccca tcttgccttg   12660
gacactgccc ctgcctctgc cctggtctcc tgggttctca gtttgctgct tctgtctgtg   12720
caccgcctgg aagtggggg gccttaccca gcatccagcc cagctagatc atgtccgggc   12780
cctcggggtt caggcccagc accctcacgt gccatcactc actgcctcct ctccagctcg   12840
gacgttgtat ctcctggaag ccttccctga tcccagtggc ctcctgaagc ctcctcgccc   12900
ctgtgctcca cagggagctg tgctgccgg gcctgctctg tccaataggc taacctgacc   12960
tgctccttcg acatctaagg tgctgctcat gtgtattcat gacctgggtg gatgttgggg   13020
agcccaggcc cagcaaagag gggcaggagc aggcagttcc ggggttggcg atggcccagg   13080
ggaagctttc ggcctggttg gtcagagctc ctggtgacca agggtgactt caaagtcaac   13140
gtgagcctca ctcacatgag atgagcctag agcgtccaag aacagctctg tagctggcca   13200
gccgggagct gcagccctcg gtcctgctgt ccccccgggg agccggctcc tgctccaggg   13260
atgagcaagg ctcaaattga ctttgaagtc tcccacaggc cgtttggaac tggggtgcag   13320
gagctggaag tgtgggcac cctggggagt cacgaagcct gactgattgt caggcagatg   13380
tgtggcggga gttggggaga tgcggtagga cacaggggg atctgggggg tgccagtgtg   13440
ggccgcgggc tgggaggtat catcagtaac ttcagatcgt ttcgtagcga cacttaaaaa   13500
atacctgaag agggacgggt ggaatgaact tcaacatcat acccaaaata ttagcatttc   13560
aacatgtaat cagtataaaa attacttgag agctgtttca catttctttt tcataccaag   13620
gtttttgaaa tccggcgtgc gtctttttac actcacagta cctctcactg tggaccggcc   13680
acgtctcaat gctcagtggc acccagggct ggtggctccc gtcttagaca acacacatct   13740
ggaccgggag agcctcaggt cccctgtgat accagttttc tagtctctgt atctgacagt   13800
gtgacatctt ggggacttgc tgactatgaa gggccacccc tcccaggata aactaattcc   13860
tagagacagt gaaggagacc cttttcatgg gcaaacccac caacgcagag cccaacccct   13920
```

```
tcctctatca gggtcttacc tttgagggca ctacacctgc ccttgttacc ccaagggaag   13980
gtcccagaca accagcagcc cctaggccct agagttctga acttatgtca gcctggccaa   14040
tcctaaaccc atataccctg ccttgcccat tccttctaca gaaaccacaa gaaaggttct   14100
tgcccaggtc tccctgtggc tcccccacct tctgaccgac cctgtgcctg tgcccgcccc   14160
gctgcctgtg gcatgccacc cgctttgaga actgtgagct aacaattatc tcttctatgg   14220
caattgactc tcgatctgtt ggcctcacca tacctgaata ataacggaac tacattttag   14280
aaagccagta gaaagccatt gcctcgcatg acagaccagg aagctggggc ccagagaaaa   14340
gccacgtgct caaggctggc cagtgagtga gaggcagaga ctcaggagtg gatcatgggc   14400
ttcccttggt tcagcctcct ttacatccgt ccccttaccc caccgtggag gcttggggct   14460
gagagggaga ttctgtggct gcactccaag gactggccag ttccaggcag gaggcggcac   14520
tcccagctgg ctggaaaaga agaggctgct tctctgtcaa gctcatgtca ttcccccatg   14580
aaactgaaag ctgcccgggt atgagaccat ggagaagaca ggtctcattc tctgggccac   14640
gtttcctaac cacagtacaa taaggctaga agaaaaccc  caaagtccca gctctaacat   14700
ggcaaatgca tgaagaaaag aacagtcttc taaacaactc ttaggtttaa gaagaatgaa   14760
aacagtgatc atgggccttt cgaaaatcaa cagccaaaaa actttataac ctcaaacaaa   14820
ttcctccgaa acaagaaact ctgaacaaaa gtgaacaaag cattcaactc taggagatca   14880
ggaaaacaaa acccgaaata tgtgtgaaag aagtaataag ggctaattaa tgatgaggag   14940
gagagaaatt aacaaggcag aaaagtgaac tgttaactaa gttgatataa tgaaaaactg   15000 ctgttttta aaagaccaac aaaataggcg catttaaata agaaagaaga cacattttta   15060
aaataccaga aagggtgaaa ggtgacttaa gtacaaatat gtaaaagatt aaaaacagga   15120
tgttcattta tgaccacgat ggagtaacag ggactgaatt tactgctctc ctcccgcccc   15180
ctccaaaaca acaataacaa caaaaaggat caaattcagg aaacaacagt tttcaataca   15240
ctgcacatac gacaacaaag gacagtagtc ctcaagagat ggcaaacagg tgaacggggc   15300
cctacagctt cccagctgct cccctgagtt tcccaaccat ggcccagaag gaggtacctg   15360
ggcagagccc agtggagtac ttggaggagg agacagagct cagagccaag gaggcccagg   15420
cagctgggtt ctcaggacag aggagtggat tggagagagc tgcatagagg gagagcccta   15480
gagagctgca gaaagttcct ccaaggactc agcagagaac tgatcaggga tgtgtgtgaa   15540
gagccagagg ctagggaaga aattgtccgg aaggatcaga gagaagtgcc cagttctcac   15600
tcaggactgg aggagggctg tcctaaccag cccacatggg aaactcatag ttcatgaggc   15660
cgtggacaga gtatacagca ggctcttgcc tcactggcgg ggatcatttg ccctagactg   15720
gacaccgttc caatcccacc tcaccccaaa aaatcaagtg tttctaagta actcaactat   15780
gccccaggca aaactaaaaa ataggaatac aaaaatatct ggcatctaaa aagataaaga   15840
ttacaatgta tgatatttaa taaaaaatgc caagcatgca taaagcagaa aaatatgcca   15900
tctaataagg atatagataa aaagtaaata aatatccaga gctgacaaag gcattaacaa   15960
ggaaagaaca tcaaaacagg tgttatgact gtatttccta tgttgaaagc caagtggaga   16020
catggaagag atgtatatat attacatatg tctcttctat gtctctagtt aggggattc   16080 tatggctgca ctccaaagac tggccaatca ctggccagag gcagcacccc cagcctgctg   16140
gaagaggaga ggctgcccct ctgtcaacct catgtcattc tcccatgcaa ccagaagctg   16200
tccggatatg agatcatgca gaaagtgacc atatactcag gacaggacag gttcatttgg   16260
gactatttat ttatttattt agagatgata gctacaatgt ctgagacaaa gaatacactg   16320
```

```
agctggaaaa acagtaagga tattatgaaa gaaaaggtta atgaacttga agacattgca    16380
atagataata ttcaaaatta agcatagaga gaaaacagaa ttgtttaaaa gtgaagagag    16440
cagcagtgag ctatggaaaa attcaagtgg tctaatatac atgtaatcaa agtccctgaa    16500
tgaaaggaca gaagagacag aaaaagtatt tggagaaaat aaatgacaga aaattttcca    16560
aagttgatga aaattataac acacagatct gcaaagctca acaaattctg ataaggagga    16620
acttgaagaa aatgacagca tcaagacaca tcttctttgt atatcttcat cttttctgag    16680
atagggtttc actcttgtcg cccaggctgg agtgcaatgg tgcgatctcg gctcaccgca    16740
acctctgcct cctaggttcc agcgattctc ctgccttagc ctcccgagta actgggatta    16800
caggcatgca tcaccatgcc cagctaattt tgtatttta gtagagatgg ggtttctcca    16860
tgttggtcag gctggtctca aattcccgac cttgggtgat cctcccacct tggcctccca    16920
aagtgctggg attacaggaa gacatatctt aatcaaattg cttgaaacca gtagtaaagc    16980
aaaataaaat aaaatgaaat aaaaccttaa aagcaaccag aggaaaaaag atacatttac    17040
atatgtacaa aagaatgact tatatacaga ggaatagaaa taaggatgaa acaatatttg    17100
tacacctgtg ctcatagcag cactatttac aatagccaaa aagtgaaagc aaccgactat    17160
ccattgatga tgaatgaata aacaaaatgt ggtccatcca tgcagtggaa tattatccag    17220
ccttaaaaag caagggaatt ctgatacatg tcacaacata gatgaacctg gaggacatta    17280
tgctgagtag                                                          17290

<210> SEQ ID NO 8
<211> LENGTH: 25970
<212> TYPE: DNA
<213> ORGANISM: Homo sapiens

<400> SEQUENCE: 8
aataagccag acacaaatat tgtatggttc cgcttacatg aggtagcatc attaaatcca      60
taaaggcaga cagtaaaatg gtggttgcca aggcctagga gttagtgatt aatgggatcg     120
agatacagtt tggaaagatg aaaaagttct ggagatggat ggtgataatg gctgcacaac     180
aatatgaatg tacttaatac cattgagtta tatacctaaa aatgattaag gtagtaaatt     240
tgtatgtcat gtatatttta ccacaattaa aaaattagac aaaatacaaa ataaaaaag     300 gatgatacaa atttctcact ggaaacaatg caaggagaag acaatggagc aacatcttta     360
aagaactaaa aaaatactgt caacctagaa ttctataccc agtgaaaata tctttcaaaa     420
gtacagatga aatcgtttgt tcagacattc aaaagctgaa agaattcatc accagcagac     480
ctgcactaca aaaatattaa aggaagtctt tcaggaagaa ggaaaattat atgagataga     540
attatagaat tagcaaacgg atgaagagca ccagaaatgg taactatatg gataaaataca    600 tataaatttt tgttgctatt taaatatttt taaaaaatag gtgactactt aaacaaaaac     660
agtaactgat agggagttga taccatatgt aaaaatagat catatggcaa taccacaaag    720
gcaaggaggg gagaaatgga ggtatactat cataaaattc tcatactgta tgtgaagttg     780
tatcatttca ctttaaggtt gactgtgata agttgaagat gtaagctata taccctacag     840
gaagcactaa atttaaaaaa aagaattaca gtaaataaat taattaaaaa ttaatggaat    900
cattaacaaa ttattcaatt aattcttacc accaaaaaaa aaaaaaaaag aaacagaaaa    960
agagacgaaa tgggacaaag acagatagaa cgaatagaaa tgacaggttt atatactcag   1020
gcctaaccat aacaataaac acattaaatg tcaatggtct aaataccag ttaaaacctc    1080 atagtcaggt tggataacaa agtaatacct aactgtctgc tgccttcaag aaacatgctt   1140
```

```
caaatataaa tatataaata tgtttaatgt aagatggtgc tatggtaagt ggcttttaag    1200
gaggcccgaa gcatcttagt attcacatcc atggctggga ctaggggag gcaagtaagc     1260 cacttgcctc ggtcatgaaa ttcaaagaag gaccacaaaa ttcagtaatc aagacaaata    1320
atatttcaat gcaatatttt taaaaataca aattaatgca aaaatatatg aagaccaaat    1380
tttcagaatt ttaaataaag acaggatgag taacagtacc atactatgct gagcctctgt    1440
tggagcctga agcaaaaggg aaaattcagc cttctgagaa gccctgattc ggaggcacca    1500
agataaactg tgcttagttt cctggcccac aggaatctgt gagataagta tctgttgttt    1560
taagctacta agttttgggg tatttgttag acagcagtag atagtatgaa gttcaggatt    1620
ctatgtcaaa accaatcaaa agaaagcaga agtggccatt ttaatagatt tcaggataaa    1680
gaatattacc aggcattaag aaggtcactt cagaacaatt aaggggccat tcatgagggc    1740
atgacaatcc caaatgttaa cgaataaagc aaaagcatca tgatagacct acaaggagaa    1800
atagattaac ccacaattac agtcagagtc ttcaacactc ctttctagat acttgataga    1860
ataaatagac agaacatcat aaaaaatata gaaaaggtaa acaacactat caacttgctt    1920
gacctaattg acattaatgg aaaatcccac ctgttaacag caaaatacac attcttttaa    1980
agtgcacgtg aagtatttac caaggtaaat tgtcttatgg gcaatagaac aagtcttgga    2040
aaatgtaaaa gaggattcaa gtcatacaaa gtatattctc tgaccataat gaagttaaat    2100
tctgctaata acagagatat atgaaaaatg cccaaatatt tggaaataaa taaaatagat    2160
ctaaataacc catggtttaa caaataaatc aaaagagaaa ttagaaacta ttttaaacca    2220
agtaaaaatg aaaacacagc atttcaaaat ttatgcaatg cagtacttgg agggggattt    2280
agacagctaa acacatatat tagaataaaa taaaagcctg aaatcaatga caccagctcc    2340
ttagaaacta ggaacacaaa cccaatgtaa gtgcaaggag tacaaaataa gaatcagagt    2400
agaatcagtg aaacagaaaa aaatagagct atcagtgaaa cacaaagctg gttcattgag    2460
aaggtcagta atatcaataa aagccagaat ggtcaggagg aaaaggaaaa agatgctatt    2520
tgccaatatc atgaatgagt gagaggtcat cattacagat cctacaggta ttaaaagtat    2580
aataaaagaa tattaggaac aactttatac caataaattc accgacttag atgaaataga    2640
caaaatcttt gtgagacaca aactaatagc acttacttaa gaagaattga ataaccagaa    2700
tagcaccata tttattcagt aaattaaatg tgtaggtaaa atccttcctt caaagaaaac    2760
cccaggccta tgtgatatca ctagtgaatt ctatcaaata tttaaggaag agataaaacc    2820
aattctacat aaataaatcc agaagaattg aaaaagatgg aatactttta aattcattct    2880
ataagaacag cattaccctg ataccaaagc cagacaatca caacacaagg gaagaactac    2940
aggctgatat tcctcatgaa cgtagatgca agaattctaa aaaaaagttt agcaaattga    3000
acccaaccat atacaagtgg ggcctattca aggaatcaag gtgcgtttaa cattcaaaag    3060
atcaactcaa cgaattgacc atattaaatt taaaagaag gaccatataa taatgtcaat    3120
agcacagaaa aagcatttga caaaatccag tggccattca tgattttaa aatctcagcg    3180 aactaggaat agaaagaagg acaatttctc agcctgtaaa gggtatcaaa cttaatggta    3240
caagactggt tactttcctg ctaaaacaca tagacaagac aaaggtgtcc tcataatttc    3300
tatttagcaa tgtcctagag gttttagtca gtggaacaaa gcaagaaaaa ggaacaaaag    3360
ccttccagtt tggaaggagt aaaactatcc tcattcacag aaaatgatca gctgtgaaga    3420
aaatctgacc aaatctgcaa aaacactaca ttaattaaag tgagtttagc aaggttgcag    3480
gatacaagat caatctagat aatcaattgt atttccatat agtagcaaag aacaattgga    3540
```

```
aattgaagta aaaaatgcca tttgcaaaaa catcaaatat taaatactca gctataaata  3600
tggcaaaaga tttgcaaacc tgtacactga aaactgaaaa acattgatga gggacattaa  3660
agaagactta tctaagtgga gagatatgct gtgttaatgg attggaaaat tcagtattaa  3720
gatgtcaatt ttcctcacgt taatctatga attcaacaca attcaaataa aaaaaatatc  3780
agaaggcttc tttgtagaaa ctggcaaaat ggttttaaaa tctgtaaatt cttaatttcc  3840
catacgaatg tattttcgtt cttcaactga cattttatct gtaaaaatct gagaagtgtc  3900
aggttggcat ggagcatatc ataattttc acattaaaaa tattggaaat attttgttt  3960 aattgctttt tctttcacag aagggcagtt atgaatgaat gtatatctct ataatacaa  4020 tatacatata tataatacat atatagtata cataatatat atataatatg tattgcatgc  4080
atatattcag agacagaatc tcactgtgtt gcccaggctg gagtgcagtg gtgcgatcat  4140
agctcactgc ggcctcaaac tcctgacttc aagatatttt cttgcctcgg cctcccaaag  4200
cactgtgatc acaggcatgt gagccactgc acccagccta aatggatgtt tgtaagtgtg  4260
gaatatgtgc atacaggagt ctgcctccaa actctctacc cctctgtctt tggtctaact  4320
ttcctcttat gccaatccca tgggattttc ctattaggct tcactgtatg tcttcatatc  4380
agacagagca aattcctctc tttttgttct tttcaatcaa agttgacatg taacaggcat  4440
atgccagaca tcactgtgga aacgctatac tcaactgagg actttggtag atttacggag  4500
agtacgcaga cagacatttc gtgtgggaat gccttaatat tacaaagctg tcaaaccccc  4560
ctacatgaac gtaaggatcc agtgcaatcc cagtccacat ctcagctggg gtgtggcaaa  4620
cgctccacga ccttactcca acactaagat cgaagtgtag aagtccgtga gtagctcagt  4680
cagctttgag tgtttgcaaa gtgagtgttt cagtggcaaa tattcctaat attctctgag  4740
gcttggtgtg cctaagggta ttttcatctc gctgctgcat ttaaacaata atcatacccg  4800
taaaatcctg tgttcaaagt taccttccac gcctttgaaa tattattctt ttgtcttctc  4860
acatccggta tcgctcttga gaagaatgat gcgattcttt cttgctcttt ttaggcaatt  4920
ctgccgattc tctatgggcc aattcaggac tttgatattt taaaacttca ccgtaacgca  4980
tctatgttct ttcttatctg tcctcgccgg cctgtcaaga gcccttgcgt gtgtttctgt  5040
aattctgggg tatttatttt cattatttct ttaaatacct cctctcttcc tctgctttct  5100
gagactcttc ctagccaatc cactactttc tccttttctc ctcaaacgtc tctgcttccc  5160
ttttaagttt ttttctcatt attgctcctg aaccttctag aacaattcca ccacacttga  5220
tattttatct cacttgtttc ctagcagcac ccatgctgtg atgtacccca ttcactgttg  5280
aactggcatc ttcctcacac tcagtatttt cccccagctc cttgtatatg cctcttcatc  5340
ccatttcaca ctgtgccagc accatcccctt atgttttga gggttttttt ctttcaagtc  5400
tggagtgcag tggcacaatc ttggatcact cagcctcaat ctcctgggct caagcaatcc  5460
tcctgcctca gcctcccaag tagctgggac aacaggcacg aaccgccatg gttggttaat  5520
gtttgtatgt tttgtagaga tgggatcttg ctacgttacc caggctggtc ttgaactcct  5580
cagcccaagc gatgcgctca cctctgcttc ccaaaatgct gggattatgg catgaatcac  5640
tgcacccagc catgttttg agtttctacc aggattgctt tagcctcaca gttcatgttt  5700
ttcagcagtt cttgtctgta tgcaatgtga tgatcagatt gctgcctttc cattctcgca  5760
ggtatgccca tgagttcagg ctccacctga agtgacggtg actgcgtcgg gcagtgtgtt  5820
gggggaggaa ccagggcctg gcctggctg ggccatccca ggccgtggaa tgtagggacc  5880
agccccacag ggtcggtggg tctctccccg tgtgcggcga cgagagagtg taaaaataaa  5940
```

```
gacacaggac aaagagataa aagaaaagac agctgggccc gggggaccac taccaccaat    6000
gcgcggagac cagtagtggc cccgaatgtc tggctgtgct gatatttatt ggatacaaag    6060
caaaaggggc agggtaaaga gtgtgagtca tctccgatga tagataaggt cacgtgggtc    6120
acatgtccac tggacagggg gcccttccct gcctggcagc cgaggcagag agagagggga    6180
gacagagaga gaaacaactt acaccattat ttctgcatat cagagacttt tagtactttc    6240
actaatttgc tactgctatc tagaaggcag agccaggtgt acaggatgga acatgaagga    6300
ggactaggag cgtgaccgct gaagcacagc atcacaggga gacggttagg cctccggata    6360
actgcgggtg agcctgactc atgtcaggcc ctccacaaga ggtggaggag cagagtcttc    6420
tccaaactcc accagggcaa gggagactcc ctttcccggt ctgctaagta gcggatgttg    6480
ttccttgact cttttgcta ccgctagacc acggtccgcc tggcaacggg cgtcttccca     6540
gacgctggcg tcaccgctag accaaggagc ccttctggtg gccctgtctg gcataacag     6600 aaggcttgca tgcttgtctt ctggtcactc ctcactatgt cccctcagct cctatctctg    6660
tatggcctgg tttttcctag gttatgatta tacagtgagg attattataa tattggaata    6720
aagagtaatt gctacaaact aatgattaat gatattcata tataatcatg tctatgctcg    6780
agatctagta taactcttgt tgttttatat attttattat actggaacag ctcgtgccct    6840
cggtctcttg cctcggcacc tggatggctt gccgcccacc gtggaagaag aggaaagcgt    6900
tcctcttccc ttcccttccc ctttccttta acacttaaaa catatttatc cctcccctcc    6960
catctcccct cccaactcat aaatatagta ggattccaac taataaacat agaaggcatt    7020
tggcaaccag cacagcaatt atttaggcac aaatcctcaa ctgatgctaa aacgagtgag    7080
taaaagtcta agaagcaaca ggaagttaca cggcatcacg tttctcccca caaactggaa    7140
attacaaagc acagaacatc aacgtgacat tggagaaacc tgccagctac aattttaacc    7200
gtgttccaag ttaacactgc cgggtccttc ttcctctttg ggccgtgata gagcagttag    7260
gaccacacgt ggccttcact gcacacaacc agcaaccagg atgcagtcac acagtttgtg    7320
aggcaagttc tcaaacgctg acagcgcgc cgtgggtggt ctgtgaagga cgtgaaacca     7380
gccgggggag cctggtgatc ttccagccga ccgagagtct ctgggctggg ccctgggtct    7440
cactgaggtg aggagacaga ggtcagagct cagcgaggat gaggcaacta gaattttcag    7500
ggtagatctt tgaagaggag gtgggggaaa gagagaaaga cagaggagag agacagaggc    7560
agagatacgc agagagggag agagagagag cgggagaggg agagaggggg aagagaggga    7620
ggaagagatg aagaaagggg gagaaacagg gatacagaca gggagagaga taactaggca    7680
gagagagtta gaaaggggag aagagagaga tagagaaaga cagagagaga gagagaaaga    7740
gatacagaga gagagagaga gaaaaaaaaa aactccaggg atctgcagag accctcaggt    7800
ccttggctga atatggatcc acacatgcat gaagataaac cacctgaggc cagagaaaaa    7860 accccgtag ctcaggtcac acggtctgga gacagtttgt gttcccacaa aactatataa     7920
tacacaggat gtcgggaagg gtcctcataa gagcctctct tgagtgctga ttctaaacca    7980
accctagact aaaggcagcc ctggattcac cctacaaagc atagaagcaa agctccaaag    8040
atccgatggg tatcaggaac tcatggatgc cagaacaaaa tccgacagca attaaaggaa    8100
tacaacaaaa tctagcaacg gactgtgcaa tatttgcaaa aaaaaaaaaa aaggccaggc    8160
atgcagagga acagggaaac gtgacccaga accaggagaa aagccagtca gtggaggcag    8220
gtgcagaaag gccagaggtg ctactgtgac cagacaagga ttgaaacagc tgttttagag    8280
gggccctacg tgtaagaagg tccagtaata gaaagagggt gataaagcaa tggtggtagg    8340
```

```
gtgctcacag ttggagaata ggcggaggta caggaatcct ttgtactatt aatgaagctt    8400
ttctgcacat tggaaatgat acaaaacaaa aagttaaaaa atgaaagaga ggtggggtga    8460
gcctagagca tggagcccca ggacccatag aattttgttg attcctctta gtgttcctgc    8520
tagccaggca ccttgtgtga aatttgccat taactctctg gaaaaaatcc gctttgggag    8580
gaggccactg cccgtgtggc cacctccagc cttgagacca gagcagaagg atacaggagc    8640
aactgcttgg agacggctgg cagatctgca cgtgtttcta tccatcccac ttcccctctg    8700
taaggttcta actctgccct gctgttctcc ctgctgtcca ggccattgct gctgatttct    8760
gcagtgacgg ggccagcaac aactgtctca aggcagcttg ggaaaagaca agcctgcctc    8820
caactgttgc tcttgtcact gcttctagct gtctcctccc caggttgcag ttcccaacac    8880
cacacacacg tgtgcacaca catgcatgca tgcacacaca tgcacatata gcacagcatt    8940
catgcataca catgtaccca cacacgcaca cacttgcaca cacatgcaca atgcatacac    9000
atgcacatac atgtgcacat gcacaccagc tcaccacagc ctgtagtctt ttttttttga    9060
gacggagtct cactctctcg cccaggctgg agtgcagtgg tgcaatcttg gctcactgca    9120
agctccgcct cccaggtttc caccattctc ctgcctcagc ctcccgagta gctgggacta    9180
caggcacgcg ccaccacgcc cggctaattt tttgtatttt tagtagagac ggggtttcac    9240
cgtgttaacc aggatggtct cgatctcctg acctaatgat ctgcccacct tggcctccca    9300
aagtgctggg actacaggcg tgagccaccg cgccctgccg cctctagtat cttagagat    9360 gtgccacatt gttgatttt cctcaaggct gtttctccct ctagatgctg gagcttctcc    9420
agcattgatt ttggggacgg aagcctgggc gaggtacaca ttccggcagc cagtgccagc    9480
tcttagaagg tcacactgcc tattgtgtgg acagattaga tggggtgggg gtgggacttg    9540
tgagtccagc aaggggggcta ttgtaggcag agctgcaaga ggcaccagca ggctgcatgg    9600
gctccaggag agaggtgcga cctgagagcc attctggaca ctgggctcag tgaaagaagc    9660
cggtcagaaa aggacaaatc ctgtgtgatt ccctgggtag aaggtcccta gggtggtcaa    9720
atccatagag acagaaagtg gatggtgggt gccaggggcct aggagagggg atggggaacg    9780
agtgtttaat ggggatagag tttcagtttg gaagatgag aaagttctgg agatgaaggg    9840
tggtgacagc tgcacaacag cacgaatgtg tctaatgacg ctgaagtgta gtttaaaatg    9900
gttaagatgg tcagttttgt attatgtcga ttttaccaca ctgtttttaa aaagaagcat    9960
cctggagaaa gcgtcagtac tgctcatggg ggtggggtga ggagtcagct ccagtggctg   10020
ctgggctctc gtccgagagg agaagggagg ctggccctcg ggggaagggc tgcagggatc   10080
cagggttcct gggtggatgt gcggagtctg gggtacctgg gaactatccc cacagaaatg   10140
ggaggccacc actgaaattc caatgagggg ctcgaagtta aaacttaaca catgaaagat   10200
aagtggggtg acagcgtgga gccccaggac ctgttgattc ctcttaccgt tgctgagggg   10260
ctaatggaag gggctgggct ggagggtccc ctgcagtcag tggcaactca gcccctgggc   10320
actgagggac catgcaagaa gcgggagaga aacagaaaa ggcaggaaga gccctttttcc   10380 tccactgagg gagtaggcag agtcagggag tggctgagaa agggcaacac agtcagcaac   10440
gggaaatgca aggaagacat gaggacccgg tccccccatg cctggagggc tggagtgagg   10500
acagaggggg cctgctggac ccaggagcgt ggagctcact ggtgactcct gagagtcagg   10560
ggactcccag gaatggcgtg gaatccagga tgccacttcc tcctgcctgg cagcagggca   10620
ggcagctggc tggggcccag actcccagga ggatgccact gctgcccaga cctactgcag   10680
tgcacagcag agcggcaagg gcccctggtg cgttgagcaa acttccaggc ttaaaaagag   10740
```

```
cgtggctgcc tcatccctcc accacccaga gctggctcag gccacgtgtg acccacccta   10800
cccttaacaa ggcagctccg ggagtcctgg aagatgaaca tcccgctcag ctagggcgac   10860
actgtgccaa tccctcccat gggcttccac ctgtacctct tgttttctac acagctttat   10920
tgaaatataa ttcacatact ataaaattca ctgttttaac tgtaccattc aggggctttt   10980
agtatattca cagaagcatg cctccctcag cacccccaaa aacaactccc cgctttagta   11040
tattcgcaga ggcgtgccac ccgcagcacc cccaaaaaca actccccact ttattcgcag   11100
aggcgtgcct cccgcagcac ccccaaaaac aactccccgc tttagtatat tcgcagaggt   11160
gtgcctcccg cagcaccccc aaaaacaact ccccgcttta gtatattcgc agaggtgtgc   11220
ctcccgcagc accccaaaa acaattcccc gctttattca gagaggcatg ccacccgcag   11280
cacccccaaa aacaactccc cgctttagta tattcagagg cgtgccaccc gcagcacccc   11340
caaaaacaac tccctgcttc agtatattca cagaggcgtg cctcccgcag cacccccaaa   11400
aacaactccc tgctttagta tattcagagg cgtgcctccc tcagcacccc caaaaacaac   11460
tccccgcttt agtatattca cagaggcgtg ccacccgcag cacccccaaa aacaactccc   11520
cgcttcagta tattcacaga ggcgtgccac ccgcagcacc cccaaaaaca actccccgct   11580
ttattcacag aggcgtgcca cccgcagcac cccaaaaac aactcccac tttattcgca   11640 gaggtgtgcc tcccgcagca ccccaaaaa caactcccg ctttagtata ttcacagagg   11700
cgtgccaccc gcagcacccc aaaaacaac tccccgcttt agtatattca gaggcgtgcc   11760
acccgcagca cccccaaaaa caactccccg ctttagtata ttcagaggcg tgccacccgc   11820
agcaccccca aaacaactc ccgctttag tatattcaca gaggcgtgcc acccgcagca   11880
cccccaaaaa caactcccg ctttagtata ttcagaggcg tgcctccctc agcaccccca   11940
aaaacaactc ccgcttcag tatattcaca gaggcgtgcc acccgcagca cccccaaaaa   12000
caactcccta cttcagtata ttcacagagg cgtgccaccc gcagcacccc caaaaacaac   12060
tccccgcttt agtatattca cagaggcgtg cctccctcag cacccccaaa aacaactccc   12120
cgctttagta ttttcacaga ggcgtgccac ccgcagcacc cccaaaaaca actccccact   12180
cactagcagc cgctccccctt gccccagcct ctgccaaaca ctgacccact tcccacctcc   12240
atggagttgc acgttctgga catttcatac aaatggggtc ctctgattcc ccacccacaa   12300
tttttaatca tacttaactt ccaaataaag acaaagtcaa atccctcttc cacccaacaa   12360
gatgtggcca agcgtataca agagaacagc atgtccccct ctcccccaga gaagaggaga   12420 gccctgatc ctgattcatc tctgggtgtt cttccctta aaaaaaaaa aaaaaatca   12480 aagggggaat aggattcagc tggaatggga ttcagctgat tctcattctc cctttgatat   12540
cctaattttt tttttttttt tttttttttt ttttgagac agactctgtc agccaggctg   12600
gagtgcagta gtgcaatctc ggctcactgc aacctccacc tcctgggttc aagcaattct   12660
cctgcctcag cctctcacat agctgggata caggcacgg ccatcacgc ccggctaatt   12720 tttgtatttt tagtagagac ggggtttcac cacattggcc aggctggtct caaactcctg   12780
acctcaggtg attcgcctgc ctcagcctcc caaagtgcta gattacatg cctgagccac   12840 cgtgcccagc ctgatagcct aaaatttaaa cactgagatg tttgaaataa ttaaatatca   12900
actactatca aacgtacact tcatacacta gtaccgtatg aagtggtagg gaatggaaga   12960
ggagaagaaa cagtggctaa tgtggtccta cccaatacac tcggatcaaa ataagaaaca   13020
cgcacacctg tgataggctt cgtttctgca gcagccgagc agcgggaact agcgtttcag   13080
cctccgtctc ccgcatagcc ttcgcctccg caagcactca gctgatgtgg ctctttgcct   13140
```

```
ggtgggatgc cctaagcctt cattcctgga gagcctgggt cctgaatgac cctgcttgga   13200
tcaggggtga tggttttcca tgattttaat cacaggacat gggaacctta agaggcgctg   13260
caggggaccc tccgcattcc agacgtgctc ctcctcatcc tccttgtgca acccggccga   13320
ttccgcccga taaaatcagt cccgtggccc gggcagtaac tgccttttt acctattgat   13380 tctctgcagt gaggatccca aaatggcctg gtgcaatctc accttccagt ctggtggagc   13440
cgttggtgtc tctgcgggaa actctcctcc ctcgagaact cagacttcta caccaagagg   13500
acctagagtt gtggggacag ggagcaaaca catcaccagc agaatgtcat gagggtgaag   13560
agaagccatt gccacttccc cttctggact cccagaaccg tgaggtctgg gcggcaggag   13620
aaaccgctcc atagactgac tctaattcag agcctggacc gcctcctgga ggacacggcc   13680
ctctctgcaa agcgtcccca ctcagcaggc gccgtgtgag tctcccgaag gccattccac   13740
ggtcctgttc gtgagctgct cggggagag gaggaccacg gaagacctcc aaggtcacaa   13800
gcattgggcc tttgccctac tccattaact gtggtgaatt ccttgagcag cagtgtgaga   13860
atgccgaatg aggcgctcca gagtccacag gtggtttcgg caaaagcacc gtgggcaagg   13920
agggccagtc cacctgcaga gcaagcctct atcctggtga aagcgcagcg gtgccagttc   13980
catgccggca gctgtctcat atcatccact ccacctggag gctggcagat cccctgcaac   14040 actgggcag gcgggcactt agtggatggg ccttggtgag tggagcccct gtgccgatcc   14100
catgtgtgac ctccatccct gctaccacag tctctatctt caccagcctg ctgacaatga   14160
cagggtggct ggggaaggag cctgactgat gcccaaagaa agggccatct tgtctacctg   14220
gtcactgagc ttctcctcgg ctgaggcggt tgccctttgg caaatgtcac atgggctgcg   14280
aggatcttca cgctctgccc tttcagagac ctctaaccac acaacacttc cccacacctc   14340
ctgctaccgt tttcccaaat gtgttccttt caagtccctg accatccatc tggccaagcc   14400
aggagcaact gaccatgagt gggtggcacc tgtagctccg aactctcctt ccaggaaaaa   14460
tgaaaacacc taggggccct gcccagagta tggaccacgg gtgttggaac cacttttca   14520 tgtaacttgc ttgtgacttc agggcctgcc tgagccccgg gttgtatatt gctgcttcca   14580
cttgaagaca gaacacagct gtgcatgccc aactctgtgg ctcgctgggt ccagcaacat   14640
cccactcatg acgtacagtt cagatcacgt ggcgacttag tggcctgtcc agtctctatg   14700
gaggcctgga cgcaatccac agagttatcc agagaggatg gcagagcttg actccaaaat   14760
cctaagggcc ctgggctgtg attcacctgc aggagcctat catggccccc acgcagcatc   14820
cttacctgcc acagacacct caaatgccat gggatctgtt ggtcccgtgg ctcaagtggc   14880
tcagcagctt tcatgaccac atgcacttgc tgcagagcct tctcttgttc tgggactccc   14940
agaaagcaga cagcatttta ggtcattcct acatgggttt tcctacccat gtcttcctac   15000
ctacccgtgg gtcatatggc ccatgttgca aacatttg gaaaaggcaa aactatgcag   15060
acaatgaaat gatcagtggt ttccaggagt cagtggggag ggagggaaga ataaatggag   15120
cacagacgga ttttagggca gtaaaataat tctgtgtgac actgtaatag tggagatatg   15180
ccattacaca tttgcccgaa ctcacagcat gtacaacaag aagagtgaac cctcatgtaa   15240
cctgatcaat gactaggtca atattggttc atcaattgca aagatgtatc acagtaattc   15300
aagatatgaa taataaggga aactgtgtgt agggagagat gctatgagga ctctcaaaa   15360 tatgctcaat ttctctgtaa acatgaaact gctctgaaaa ataaaatcta tattaaaaat   15420
taaagctttc accagatcaa tggctgtaga ccaggtgtcc ggggatgctt tgatttgccc   15480
cagtgatcag tagtcatatc tggaacagca gttgcaattg gagtcctggt taagtttacc   15540
```

```
aggattcact gtccttcttt ctccgggacc ccctgtctt ccacacaagc caattagacg   15600
agtggaacga ggctgcagtg ggggtcacca ccctgcatct tccaagtcct cgatggcggc   15660
actgaccttt gcagtccctc cagggctgca ggttgctttt gactgacaat tttcctaggc   15720
agagttcacc ccaatggctt ccacctggcc tttcccagca tagtagcccc caccctcagg   15780
tcagggaaca aatgtggggg ctctgctggc tgccacatac gtctgtttac tcacccatct   15840
gaggctaggg aagtgaccctc tgcacccacc gagggttgga cctgagctag aactccgtga   15900
gcccactgac ctccatacgc ccctcctctg actattagat ccgatgggtg tttgtgtccc   15960
caggagtggg tgtcaggtta gagttagagt ccagtaatcc ccctgagtct gatgatcccc   16020
ctttccacta gccaccccag caaatggctg caggtccctg aggggagact ggggaaagaa   16080
gaataatgta aatttgtagg agtatggcaa ggtccttcct caggggcacc cagtcctcct   16140
tcactcaggc accaggcaag ggaggccacc cattgctcca gctcccgtgg caccgtgagc   16200
caccggccaa ggccacaggg ctccatgggc tggactgttc caatcactgc cggtgccagt   16260
tgccatctca gccacaggcc cggggcctcg tggccacccc cactgggctg tgccctgcct   16320
ccttaaagac tgtgagcgag ctcccaactg ggacacccct gaccagctca ctcttatttt   16380
gtctgccctg gccctgatgc tggtgtttga gatatcagaa ctcacctcaa accaccctaa   16440
gcagagatca ctccggctga cgcagggtg cggcccacat gtgagggacc ctcaggctgg   16500
gcagcattgg ctgagccccc accgcaccctt ccctcccacc ctggggtcct cagcctccgc   16560
ccaaggcagg ggggacactg ctggcaactg gtcacccaga gagcatgggc tgcagggatg   16620
gccctgagta ggacacacag ctcccgagac ccctcactgg ggacacaggg gggccctgca   16680
gccagggtgt cagtgtgggg acagcccagc agacccccaag ccacccactg aggttgcttc   16740
tcaggggagc accactggtg ggctgtcagc tcctgcctgg gccccggcct cttgcccctg   16800
tcccacctcc cacctgcacg gcctccagca ttgcccaaat tcactgcctt cactcccaag   16860
tccacagagg tgtctcatcc aggcgggtga acactcgtgt gttgggaggc tggtgaagcc   16920
tggcattggg gggcaccacc catctcccctt ctttgtctca ctgccttgaa acaccccaca   16980
tctatcacct ctgccccccga ggctccccag gttcaccccca tgccagcctc agcccaacaa   17040
ggcctgtgct tctgaccagc accgctgggg ttctcagggc atctacccctt tccgctgtag   17100 cccactgtct ctaaacatat ttcacacgtt gctgggggca gtgtgtgtga ctcactgctt   17160
cccagagcca gcccagagct gtttagtaga catgaggtga gtgaatgaat gaatgaatga   17220
atgagtgctg ggagctgtct cagttagctc caatctgcca taaggaagca ctgcaggctg   17280
ggcatgtaaa cagcaggtgc ttatttcttg cagttctgga ggctggaagt ccaatatcaa   17340
ggtgctgctg attccagtct tggtgagggc tctcttcctg gcttacagat ggctgccttc   17400
tctctgtgtc ttcatacagc tgtccttcag tgcatgtaag gagagagaga gagaagaggg   17460
agctcctaaa tgtctcttgg tataagggca ctaatcctat gggaccaggg accttcatgt   17520
cctcatctgt ccctaattac ctcccagaga tccacttcct aacactatct cattgcgggg   17580
cagggcttca acctatgaat tttgcaggaa cacgattctg tccatagcga acactgacac   17640
tgaacccgcc tcctaaagcc ttctctcacc atattcctca tgctgctcaa agatcctctg   17700
caaccttgtg ccctcccaa gggtccctgc acctgtccca gagagagggc agcctggcaa   17760
tgggcctggg ccctgacgct tgagcatcgg ggtctggcct gaaaggggat gggcgttcac   17820
ttctaggttc ctgagagagg caacactgca cctttaaagg tgtcaggagc tcactgcccc   17880
agctggtcat gaaacagtct cttcatcaag ggctaaataa agcacgctga ccaccaggaa   17940
```

```
tggggcagga agcttctgcc ctgcagcctg ccttgtctgc acagggagtg tggggaccat    18000
tagggggagg gtccgatgtg cattttttctg ccagcgggac cttcccctgc ccccagtcct   18060
gcccaggccc gggggggtcac tctgaaggca tctggctctt accccaggca tctcctgcct   18120
ctgccccact cctccacccc cacggggtgc cgagtctcag cccaggctgg ggtggcccag    18180
gcaggacagc aggcttggtg gtgcccggcc ccacatacta gtgggtggca cagcgtggat    18240
gtggatagag acgcctcccc tacagtctgt ccctggtatc tgtgacgcag gtgtggggtc    18300
cctttagact cccctgggag acagctgtgt ctatgaaggg gcagccatcc ctgggtcccc    18360
tctgccctca ctgagggcag agcctaggct ccttgggggg ggaagcaggg tgcccctcag    18420
tgcccactgg agttggccag cggaggcagc agcccacggc actgagaggg aaggcccggg    18480
cagccatgcc ccagaaactc ccttggttgg gagcagagca gtgcccagag cccagaaccc    18540
agtttgagta tggtcttggc tctcaaggga caggccaggg tgcctccagg ggaagggggc    18600
tgcccaggca gtagggggttc aaaggtcccc tggggcccac ccagctgacc caggcctagg   18660
gtaatccaga aggggagctg ccctcctcct ccctgggctc aggagaggct gcaaaggcag    18720
ctcctgggac gtggatttca gaatcagggc aaaggacaga catgagccag attcaggtgc    18780
ccgcgtggcc cccacaggtc tcttcaagct ccaggcccca ctcgctgtga cgcaggtggg    18840
aagctcttga gtgcctcccc ggtgggaggg gccgcgctca cagacagcac aggggccccc    18900
aggctccagc ctcagagccc ggctgctcac ctctgatgga cagaaaaggg tccctgtctc    18960
aggaaggtag aggctgccac ctcctggccc gaggacacag ctttccagag gaggggcctg    19020
cttctaagtc caagtcccat cccagccgga tagccagggg caactgccca ggtaaactga    19080
gacagcagca gcaggcaagc cagtgcagag ctgggtgatc cacaggttca tgagcggtgg    19140
caggtggaac aagggcacca tgggcggagg gttgggcagc tgcaggtggc atcattgagc    19200
caggggcctc ctggtgggta aggacattgt agagtgagcg ggcgcacctg ggacccagga    19260
attcacagga aggagagagg aaaaaggaag tccctggcgg gtaaacacat atgcatgcac    19320
acacatccac gtctgcacac gcatccacgc ctgcacacgc atccatgcct gcacatgcat    19380
ccacgcccaa tctcttccct ggaaataaag ccaggggccc ttaggccagc ttgcagtggg    19440
gcccagccct taggacaggc tccttggtgg ggtagggggtg ggggcagctg tcctcctggg   19500
ccagctcctt ggggctgaac ccgctgctcg aggggtcttc caggctccca gcggccggca    19560
ccacctctag agcaggtggg caggggtgtg tggggtgggc aggggtttgt gagggtgggc    19620
aggggtgtgt ggggtgggca ggggtgtgtg gggtgggcag gggcatgtgg ggtggcagg    19680
ggtgtgtgag gttgggcagg ggcgtgtggg gtgggcaggg gtgtgtgagg gtgggcaggg    19740
gtgtgtgggg tgggcagggg tgtgtaaggt tgggtagggg tgtgtggggt gggcagggat    19800
gtgtggggtg ggcagcggtg tgcggggtgg gcagggtgt gcggggtggg caggagggtg     19860
tggggtgggc agcagcctgc acagtggctt cccctcaaca agccacttcc tcttgcagag    19920
ggaatgttgg ggtgggaggg tgtggctcag caaaggggcgt ggggggttcca ccggctccct   19980
gccccccgctg gtgggggcaca gtgagggggg ctgtggtcag acctggtctc tggagggcca    20040
gccgggggtt cccgtccacc tgtcagggggg ttcgacgcca ctttgagatg acaagtgagg    20100
ccacctgggc acagcgctgg tgtgagaagg aggccatcag gacaggtcaa gaacccaggc    20160
ccgcccctgct ccgaaattct tcagacctga tgaagaggtg tcccagaagc gggtggtgct    20220
ccaggcccgc ctcaccagct ccaggaggt caaggttgga gagagacaat tctagggggcg    20280
aaccagacat agccaagagc agctcatctt ccctggagag gacgggctgc ccacttgcac    20340
```

```
agcccggggg cctcctgccc ctagacctgg taccttcact cttgttgcca cccctacatt    20400
catacctgcg ccccagtctg agccacacct aggcccccag ctgaagtgac actgtgggtg    20460
ccaggcatct gaggtctcca caagccccca cagactcagg gtgggaattc ctgggggcca    20520
gagctgcaga gggtgctgcc tgggggtgct gggctggacg ggggtcctgg ttgtccctcc    20580
tggttctcct ggttctccct ccgcagaggg agggaggcgg tggcctcagc agttcctcca    20640
gcagcgttcc tgagcgggcg gcagctgggc cctcttccca cagccacgct ggggttgcca    20700
tgcctgcagg tcttgggcc cctccccct tgatgaggtc ctgaccaaat gcaggaggag    20760
caattccagc accgaggggc gagcagagcc gcctgttagc actcctggga gggcccggag    20820
tggtccctga atgatggatt cacctggaac attttcaccc tcttcaggcc caccctgccc    20880
cagaggccca cggaaaccct gcctgtactg gggccgcagc gctgccccca cccatacgta    20940
attacacggc tcggtgtaat tgcaaattcg aggtttacaa agcctccccc tggaggcccc    21000
acgtgagtgt gagcgaggcc ccagcccacc cctgtggccc caagaaggct ctgcgacaaa    21060
atatccatga gtgccgccca cgaaggcatt aaaaccaacg accttctcaa aacttaagct    21120
gtcacaggac atttcaaagg gtgtttccta agaacacctc aataatgatg ttccaaggag    21180
accccatcca aattcctcca aggattacgc ccccaaggcc cagtccacac ttgctcactc    21240
ccaggacggg gagctcacct cctcctcccc gggcgccgtc tcctccacat cccacaccag    21300
gtcctgccca tgactttccc cctctcagcg ccgtcctcag tggccacacc aagaacgagg    21360
ccatgtcttc ctgggaaggg cctcagatgt cagcaaatgc cctggtgtct tgggctgggc    21420
tgggggcacc agggtgaggt ggtgggggga gccaacctca ctgcccctcc ccttcctgcc    21480
tgcccttctt ccggggcacc cagcagctcg gtcctagggc gatgttgaca gacagacaga    21540
ggggcggatg cagcctacct cctgggcagt gagctgcggt ctgaggcccc tgcccagctg    21600
gaaaccacag ggaggggaag ggaggggagg agaggagagg agaggaaccg tcatggggcc    21660
ttggagtcga gtcagggttg ccaaatgcca gatgctggtc acctgcttct ttatcttggt    21720
aacaggcagg tcgggcagga gtgggtggtg gtgggggtg agcaggggtg aggggtggca    21780
gggcctcagc acagggatta tccctcccct gacacacaca ccagccctac tgtccctgtc    21840
ctgcccttgc agacatgtgt cctgcccttg cagacagccg caggcaggca gggaccacca    21900
tgagcaaccc cgtctctcct cctgaggggc agcacagagc ctggaggagg cctgagtggg    21960
gctgaggcct ggggcgagct gggtgagg ggcactggct gccgggctcc agggatcttc    22020
tccccttcct gccccggagg gtgctggcac aggggtgggg ctcactccca ctccgtagac    22080
acaatgatca gaggtcctgg gtgtctgggg aagctgggct gtgcgtgtat gcgtctacca    22140
tgtgggggtg cctgtgagtg tgctggggcg tctgcagtga aggcctcctg agaccactcc    22200
acggaaacac cgggaatccc tgcagctgag cctgtctctc acgggaccgg gaagctggag    22260 agagcccaa ccctgcccgc tggggccgag ctccctgctc ctgcagcagt cccatgcccc    22320
acactctgag tctgccctat ccacagctgc tgggcctctc tgtggccacc atggtgactc    22380
ttacctactt cggggcccac tttgctgtca tccgccgagc gtccctggag aagaacccgt    22440
accaggctgt gcaccaatgg ggtaagtgag gtccaggcct ggctgcatcg ggagggcct    22500 cgggtgcaag ggtggctggc acgagcccag ctggacgcct cacagccaga atggtgccag    22560
gccctaggca ggagccagag gtggtcaggg gcagggaggg gctgccctgg agtcctagct    22620
cccctgggca gggcctcggg tctgggtgac agccagtgtt cctgcctggt tctcgtgccc    22680
cacaggagcg tgggcacagt gtgggtatat gtcgggcagg gtcaggaagt ggctctgtgc    22740
```

```
ggtcaggacc tggctctgtg cagtcagggc tcagtcccag gcaggcctgg gactggcctg   22800
gggctgggca cagcaggtcc atgagggctc cacatggctg atgttccact caggacctgg   22860
gatgtgggtg ggggaggggt gggggctgct ctagccagac gcctccctgc agggactcag   22920
cagcgactta tccaacatcc agagagcggg agcgagggcc agagcctgct ggggccactc   22980
aggggtaagg ctgaggaagg ccccctttaat gaggggatgt cagagccaga tctgcagggg   23040
actctcaggc aggagctcag ggggcccagg aaggctgcag cccggtgggc agatgtaggg   23100
aaactgaggc ccaggaggtc agggatactg ccttagaacc caatgctttt ccccaagtcc   23160
taggaccagg gcctccctgg aggaggacgc ctggggccca ggtccaggtc cggactgata   23220
agattacagc tccagtccgg ccacttgtca ctaggacatg gcaggaggat gcctggggcc   23280
caggtccagg tccagactga taagattaca gctccagtcc ggccacttgt cactagggca   23340
tggcagggag catgtggctt ccaagatagc cccacaggca tggagggcag ggaggaaaag   23400
agggaaggag gggcagtccc ccaggctgaa cgagtcccac ctccctcctc cttccctcag   23460
ggccgtctga tggagagaca ggcccattca gagcccccca ggagtccctc acggcccctg   23520
actcccaagt tagatttcac acccaggctg tgtgcactca ggacctgtcc tgggcacccc   23580
taaccctcct cctctctcct cccaaccagc cttctctgcg gggttgagcc tggtgggcct   23640
cctgactctg ggagccgtgc tgagcgctgc agccaccgtg agggaggccc agggcctcat   23700
ggcaggggtg agttcattgt gttcccagat gcccaggccc ccagaaaaga attagaaagg   23760
agtgaagagc tggcagggct gtgtgccacc cccacacctg agtgaccagg cagaaccaga   23820
ggccccaggg atgctggcca gccgagaccc ccacgtcaac cccacacctg agtatctagg   23880
cagaaacaga ggccccaggg atgctagcca gccgagaccc cctacctggg tagccaaggc   23940
ccctccacca ggccctacct caccctgtca tctacacgcc caacaagggt tcctatagga   24000
gctctgaaag agagagacgg ccctcctgac cctgggagct gtttccaaag tccctgggag   24060
ggtctggttc tattgcccag caagctctgg gagggcactg ggagcatccc atttcctgtt   24120
cggaggaggc cgggccaggc tcaggaaacg ccccttgagc tctccagcct gggctctccg   24180
gagctgcaca ctctccttcc cagctgccgg aggtgtctcc ccagccccga ggtcccatag   24240
gcccctccac cccacccccat agcagtggcc tcttgtcacc ctcattccta ctcctcccca   24300
tgggcttctg tcttggtccc tgccactcga tggtcatcgc agaccccacc tggcggcagc   24360
ctccccacgc ctgtcctgcc cctgctaggc ccacagccct cttctctcac cccagctggg   24420
gcagctcctc cctggcgccc cgggctccca cctgtccctc tagcctcccg tctccccttt   24480
ccagccatga ggagcttgtg ctgggggctt tgcttccctg tttagcctgt gaagctggac   24540
cactctgggg gtccctgagg gcagagcctc ctggtcccc agggctggca gggttttcag   24600
ctcagccttc aagttcagca aatgcttgtt taatgaccct ggtttataaa tgtctccaag   24660
aataggaata gagtcacctc ctggagctgc tgccgggcca accagccctg ggtgggccca   24720
tggtgggcag aggaggaccc agcagctcca gcactagcca ggattcctgc tccggggcac   24780
acgagcatgg gcaggacaa ccccggcctg tgctatctgg cttcagggcc aggtgggagg   24840
ccccagtggg gagatgacaa ggcaggtagt ctgccccccc ccccagaggg tgtgtggcct   24900 gcaagggac acctggatgg aagaaaaggt tggcaacagg gccaggccaa ggggtccagg   24960
tcagagctgg aggcccagaa agaaccagcg ctggggctgc agtaccgtcc accaggggt   25020 gccatggtgc tgggcttgag gccacatatg cagaagccag ccgctgggcc acggggctcc   25080
tgtcccagtc accagccttt cccaccccac cttgccccg tgcacaaacc agtctagcac   25140
```

| | |
|---|---|
| cctcatctgt ggccaaggcg gtcagggagc acctgggctc aggttctgtg tccccagcca | 25200 |
| gccccaaggc cagggtgact tgacatgtgg gtcaggcctg tagagcagcc ttggaggccc | 25260 |
| ccaactggat gcctgcactg ggctggggtc ctgaggacac tccagtccca gctgggtggg | 25320 |
| ctccagcaca gctcccaagc cccaatgcac ttagacccag cctggatggt gagctcagca | 25380 |
| tggccacagc agggagctgg gagacccag tcaagagacc tgctccattg agctgcatgc | 25440 |
| atgtgtgtgc atgagggtga gcctatgtgt atgcgtgtgc aaatatacat gtgtgtgtgc | 25500 |
| atgtgcatga gtgtgtgtgt gcatgtgtgt gtgcgtgtgc aggtgcctct gtgtgtgtgt | 25560 |
| gtgtgtgtgt gtgtaagtat ctgtcaccgg tcttcacctg cccctgttgc catacgggtg | 25620 |
| tggtgtctgc gtgttgcatc tggcacatct gtatgtgtgt ctgcacgcat gagcacaagt | 25680 |
| gaagggcta gggaagggga gcagggagtg gaaagatttt ttccaatggg ctgggcgcct | 25740 |
| ggatgctccc cacaaagccc cttcctgcct gccccaccc ctccggcctc tccctagct | 25800 |
| ggcctctcgc acaggaaatg aaagagcttg ctgggctgag agagcagagc tggcagcgcc | 25860 |
| gcccaaggaa gcacattcaa ttcgcttatg tatctattta tttatttcca tttagaatga | 25920 |
| ggagaaagaa aatggccagg gcagacctga ccacccagca gcctctgatg | 25970 |

<210> SEQ ID NO 9
<211> LENGTH: 30196
<212> TYPE: DNA
<213> ORGANISM: Homo sapiens

<400> SEQUENCE: 9

| | |
|---|---|
| tggtgagggc tctcttcctg gcttacagat ggctgccttc tctctgtgtc ttcatacagc | 60 |
| tgtccttcag tgcatgtaag gagagagaga gagaagaggg agctcctaaa tgtctcttgg | 120 |
| tataagggca ctaatcctat gggaccaggg accttcatgt cctcatctgt ccctaattac | 180 |
| ctcccagaga tccacttcct aacactatct cattgcgggg cagggcttca acctatgaat | 240 |
| tttgcaggaa cacgattctg tccatagcga acactgacac tgaacccgcc tcctaaagcc | 300 |
| ttctctcacc atattcctca tgctgctcaa agatcctctg caaccttgtg cccctcccaa | 360 |
| gggtccctgc acctgtccca gagagagggc agcctggcaa tgggcctggg ccctgacgct | 420 |
| tgagcatcgg ggtctggcct gaaagggat gggcgttcac ttctaggttc ctgagagagg | 480 |
| caacactgca cctttaaagg tgtcaggagc tcactgcccc agctggtcat gaaacagtct | 540 |
| cttcatcaag ggctaaataa agcacgctga ccaccaggaa tggggcagga agcttctgcc | 600 |
| ctgcagcctg ccttgtctgc acagggagtg tggggaccat taggggagg gtccgatgtg | 660 |
| cattttctg ccagcgggac cttccctgc cccagtcct gcccaggccc ggggggtcac | 720 |
| tctgaaggca tctggctctt accccaggca tctcctgcct ctgccccact cctccacccc | 780 |
| cacggggtgc cgagtctcag cccaggctgg ggtggcccag gcaggacagc aggcttggtg | 840 |
| gtgcccggcc ccacatacta gtgggtggca cagcgtggat gtggatagag acgcctcccc | 900 |
| tacagtctgt ccctggtatc tgtgacgcag gtgtggggtc cctttagact cccctgggag | 960 |
| acagctgtgt ctatgaaggg gcagccatcc ctggtccccc tctgccctca ctgagggcag | 1020 |
| agcctaggct ccttgggggg ggaagcaggg tgccctcag tgccactgg agttggccag | 1080 |
| cggaggcagc agcccacggc actgagaggg aaggcccggg cagccatgcc ccagaaactc | 1140 |
| ccttggttgg gagcagagca gtgcccagag cccagaaccc agtttgagta tggtcttggc | 1200 |
| tctcaaggga caggccaggg tgcctccagg ggaaggggg tgcccaggca gtaggggttc | 1260 |
| aaaggtcccc tggggcccac ccagctgacc caggcctagg gtaatccaga agggagctg | 1320 |

```
cctcctcct ccctgggctc aggagaggct gcaaaggcag ctcctgggac gtggatttca   1380
gaatcagggc aaaggacaga catgagccag attcaggtgc ccgcgtggcc cccacaggtc   1440
tcttcaagct ccaggcccca ctcgctgtga cgcaggtggg aagctcttga gtgcctcccc   1500
ggtgggaggg gccgcgctca cagacagcac aggggccccc aggctccagc ctcagagccc   1560
ggctgctcac ctctgatgga cagaaaaggg tccctgtctc aggaaggtag aggctgccac   1620
ctcctggccc gaggacacag ctttccagag gaggggcctg cttctaagtc caagtcccat   1680
cccagccgga tagccagggg caactgccca ggtaaactga gacagcagca gcaggcaagc   1740
cagtgcagag ctgggtgatc cacaggttca tgagcggtgg caggtggaac aagggcacca   1800
tgggcggagg gttgggcagc tgcaggtggc atcattgagc caggggcctc ctggtgggta   1860
aggacattgt agagtgagcg ggcgcacctg gacccagga attcacagga aggagagagg   1920
aaaaaggaag tccctggcgg gtaaacacat atgcatgcac acacatccac gtctgcacac   1980
gcatccacgc ctgcacacgc atccatgcct gcacatgcat ccacgcccaa tctcttccct   2040
ggaaataaag ccaggggccc ttaggccagc ttgcagtggg gcccagccct taggacaggc   2100
tccttggtgg ggtaggggtg ggggcagctg tcctcctggg ccagctcctt ggggctgaac   2160
ccgctgctcg agggtcttc caggctccca gcggccggca ccacctctag agcaggtggg   2220
caggggtgtg tggggtgggc aggggtttgt gagggtgggc aggggtgtgt ggggtgggca   2280
ggggtgtgtg gggtgggcag gggcatgtgg ggtgggcagg ggtgtgtgag gttgggcagg   2340
ggcgtgtggg gtgggcaggg gtgtgtgagg gtgggcaggg gtgtgtgggg tgggcagggg   2400
tgtgtaaggt tgggtagggg tgtgtggggt gggcagggat gtgtggggtg gcagcggtg   2460 tgcggggtgg gcagggtgt gcgggtggg caggagggtg tggggtgggc agcagcctgc   2520
acagtggctt ccctcaaca agccacttcc tcttgcagag gaatgttgg ggtgggaggg   2580 tgtggctcag caaagggcgt gggggttcca ccggctccct gccccgctg gtggggcaca   2640 gtgaggggg ctgtggtcag acctggtctc tggagggcca gccgggggtt cccgtccacc   2700 tgtcagggg ttcgacgcca ctttgagatg acaagtgagg ccactgggc acagcgctgg   2760 tgtgagaagg aggccatcag acaggtcaa gaacccaggc ccgccctgct ccgaaattct   2820
tcagacctga tgaagaggtg tcccagaagc gggtggtgct ccaggcccgc ctcaccagct   2880
ccagggaggt caaggttgga gagagacaat tctaggggcg aaccagacat agccaagagc   2940
agctcatctt ccctggagag gacgggctgc ccacttgcac agcccggggg cctcctgccc   3000
ctagacctgg taccttcact cttgttgcca cccctacatt catacctgcg ccccagtctg   3060
agccacacct aggcccccag ctgaagtgac actgtgggtg ccaggcatct gaggtctcca   3120
caagccccca cagactcagg gtgggaattc ctggggccca gagctgcaga gggtgctgcc   3180
tgggggtgct gggctggacg ggggtcctgg ttgtccctcc tggttctcct ggttctccct   3240
ccgcagaggg agggaggcgg tggcctcagc agttcctcca gcgcgttcc tgagcgggcg   3300 gcagctgggc cctcttccca cagccacgct ggggttgcca tgcctgcagg tcttggggcc   3360
ccctccccct tgatgaggtc ctgaccaaat gcaggaggag caattccagc accgagggc   3420 gagcagagcc gcctgttagc actcctggga gggcccggag tggtccctga atgatggatt   3480
cacctggaac attttcaccc tcttcaggcc caccctgccc cagaggccca cggaaaccct   3540
gcctgtactg gggccgcagc gctgccccca cccatacgta attacacggc tcggtgtaat   3600
tgcaaattcg aggtttacaa agcctccccc tggaggcccc acgtgagtgt gagcgaggcc   3660
ccagcccacc cctgtggccc caagaaggct ctgcgacaaa atatccatga gtgccgccca   3720
```

```
cgaaggcatt aaaaccaacg accttctcaa aacttaagct gtcacaggac atttcaaagg    3780
gtgtttccta agaacacctc aataatgatg ttccaaggag accccatcca aattcctcca    3840
aggattacgc ccccaaggcc cagtccacac ttgctcactc ccaggacggg gagctcacct    3900
cctcctcccc gggcgccgtc tcctccacat cccacaccag gtcctgccca tgactttccc    3960
cctctcagcg ccgtcctcag tggccacacc aagaacgagg ccatgtcttc ctgggaaggg    4020
cctcagatgt cagcaaatgc cctggtgtct tgggctgggc tggggcacc agggtgaggt     4080
ggtgggggga gccaacctca ctgcccctcc ccttcctgcc tgcccttctt ccggggcacc    4140
cagcagctcg gtcctagggc gatgttgaca gacagacaga gggcggatg cagcctacct     4200
cctgggcagt gagctgcggt ctgaggcccc tgcccagctg gaaaccacag ggaggggaag    4260
ggaggggagg agaggagagg agaggaaccg tcatggggcc ttggagtcga gtcagggttg    4320
ccaaatgcca gatgctggtc acctgcttct ttatcttggt aacaggcagg tcgggcagga    4380
gtgggtggtg ggtggggtg agcaggggtg agggtggca gggcctcagc acagggatta     4440
tccctcccct gacacacaca ccagccctac tgtccctgtc ctgcccttgc agacatgtgt    4500
cctgcccttg cagacagccg caggcaggca gggaccacca tgagcaaccc cgtctctcct    4560
cctgaggggc agcacagagc ctggaggagg cctgagtggg gctgaggcct ggggcgagct    4620
ggggtggagg ggcactggct gccgggctcc agggatcttc tccccttcct gccccggagg    4680
gtgctggcac aggggtgggg ctcactccca ctccgtagac acaatgatca gaggtcctgg    4740
gtgtctgggg aagctgggct gtgcgtgtat gcgtctacca tgtgggggtg cctgtgagtg    4800
tgctggggcg tctgcagtga aggcctcctg agaccactcc acggaaacac cgggaatccc    4860
tgcagctgag cctgtctctc acgggaccgg gaagctggag agagcccaa ccctgcccgc     4920
tggggccgag ctccctgctc ctgcagcagt cccatgcccc acactctgag tctgccctat    4980
ccacagctgc tgggcctctc tgtgccacc atggtgactc ttacctactt cggggcccac     5040
tttgctgtca tccgccgagc gtccctggag aagaacccgt accaggctgt gcaccaatgg    5100
ggtaagtgag gtccaggcct ggctgcatcg ggaggggcc cggtgcaag ggtggctggc      5160
acgagcccag ctggacgcct cacagccaga atggtgccag gccctaggca ggagccagag    5220
gtggtcaggg gcagggaggg gctgccctgg agtcctagct cccctgggca gggcctcggg    5280
tctgggtgac agccagtgtt cctgcctggt tctcgtgccc cacaggagcg tgggcacagt    5340
gtgggtatat gtcgggcagg gtcaggaagt ggctctgtgc ggtcaggacc tggctctgtg    5400
cagtcagggc tcagtcccag gcaggcctgg gactggcctg gggctgggca cagcaggtcc    5460
atgagggctc cacatggctg atgttccact caggacctgg gatgtgggtg gggaggggt     5520
gggggctgct ctagccagac gcctccctgc agggactcag cagcgactta tccaacatcc    5580
agagagcggg agcgagggcc agagcctgct ggggccactc agggtaagg ctgaggaagg     5640
cccctttaat gagggatgt cagagccaga tctgcagggg actctcaggc aggagctcag     5700
ggggcccagg aaggctgcag cccggtgggc agatgtaggg aaactgaggc ccaggaggtc    5760
agggatactg ccttagaacc caatgctttt ccccaagtcc taggaccagg gcctccctgg    5820
aggaggacgc ctgggcccca ggtccaggtc cggactgata agattacagc tccagtccgg    5880
ccacttgtca ctaggacatg gcaggaggat gcctgggcc caggtccagg tccagactga     5940
taagattaca gctccagtcc ggccacttgt cactagggca tggcagggag catgtggctt    6000
ccaagatagc cccacaggca tggagggcag ggaggaaaag agggaaggag gggcagtccc    6060
ccaggctgaa cgagtcccac ctccctcctc cttccctcag ggccgtctga tggagagaca    6120
```

```
ggcccattca gagcccccca ggagtccctc acggcccctg actcccaagt tagatttcac   6180
acccaggctg tgtgcactca ggacctgtcc tgggcacccc taaccctcct cctctctcct   6240
cccaaccagc cttctctgcg gggttgagcc tggtgggcct cctgactctg ggagccgtgc   6300
tgagcgctgc agccaccgtg agggaggccc agggcctcat ggcaggggtg agttcattgt   6360
gttcccagat gcccaggccc ccagaaaaga attagaaagg agtgaagagc tggcagggct   6420
gtgtgccacc cccacacctg agtgaccagg cagaaccaga ggcccaggg atgctggcca     6480 gccgagaccc ccacgtcaac ccacacctg agtatctagg cagaaacaga ggccccaggg    6540
atgctagcca gccgagaccc cctacctggg tagccaaggc ccctccacca ggccctacct   6600
caccctgtca tctacacgcc caacaagggt tcctatagga gctctgaaag agagagacgg   6660
ccctcctgac cctgggagct gtttccaaag tccctgggag ggtctggttc tattgcccag   6720
caagctctgg gagggcactg ggagcatccc atttcctgtt cggaggaggc cgggccaggc   6780
tcaggaaacg ccccttgagc tctccagcct gggctctccg gagctgcaca ctctccttcc   6840
cagctgccgg aggtgtctcc ccagccccga ggtcccatag gcccctccac cccaccccat   6900
agcagtggcc tcttgtcacc ctcattccta ctcctcccca tgggcttctg tcttggtccc   6960
tgccactcga tggtcatcgc agaccccacc tggcggcagc ctccccacgc ctgtcctgcc   7020
cctgctaggc ccacagccct cttctctcac cccagctggg gcagctcctc cctggcgccc   7080
cgggctccca cctgtccctc tagcctcccg tctccccttt ccagccatga ggagcttgtg   7140
ctgggggctt tgcttccctg tttagcctgt gaagctggac cactctgggg gtccctgagg   7200
gcagagcctc ctgggtcccc agggctggca gggttttcag ctcagccttc aagttcagca   7260
aatgcttgtt taatgaccct ggtttataaa tgtctccaag aataggaata gagtcacctc   7320
ctggagctgc tgccgggcca accagccctg ggtgggccca tggtgggcag aggaggaccc   7380
agcagctcca gcactagcca ggattcctgc tccggggcac acgagcatgg gcagggacaa   7440
ccccggcctg tgctatctgg cttcagggcc aggtgggagg cccagtgggg gagatgacaa   7500
ggcaggtagt ctgccccccc cccagaggg tgtgtggcct gcaaagggac acctggatgg    7560
aagaaaaggt tggcaacagg gccaggccaa ggggtccagg tcagagctgg aggcccagaa   7620
agaaccagcg ctgggctgc agtaccgtcc accaggggt gccatggtgc tgggcttgag     7680
gccacatatg cagaagccag ccgctgggcc acggggctcc tgtcccagtc accagccttt   7740 cccacccccac cttgccccg tgcacaaacc agtctagcac cctcatctgt ggccaaggcg    7800
gtcagggagc acctgggctc aggttctgtg tccccagcca gccccaaggc cagggtgact   7860
tgacatgtgg gtcaggcctg tagagcagcc ttggaggccc ccaactggat gcctgcactg   7920
ggctggggtc ctgaggacac tccagtccca gctgggtggg ctccagcaca gctcccaagc   7980
cccaatgcac ttagacccag cctggatggt gagctcagca tggccacagc agggagctgg   8040 gagacccag tcaagagacc tgctccattg agctgcatga atgtgtgtgc atgagggtga    8100
gcctatgtgt atgcgtgtgc aaatatacat gtgtgtgtgc atgtgcatga gtgtgtgtgt   8160
gcatgtgtgt gtgcgtgtgc aggtgcctct gtgtgtgtgt gtgtgtgtgt gtgtaagtat   8220
ctgtcaccgg tcttcacctg cccctgttgc catacgggtg tggtgtctgc gtgttgcatc   8280
tggcacatct gtatgtgtgt ctgcacgcat gagcacaagt gaaggggcta gggaagggaa   8340
gcagggagtg gaaagatttt ttccaatggg ctgggcgcct ggatgctccc cacaaagccc   8400
cttcctgcct gccccaccc ctccggcctc tcccctagct ggcctctcgc acaggaaatg    8460
aaagagcttg ctgggctgag agagcagagc tggcagcgcc gcccaaggaa gcacattcaa   8520
```

```
ttcgcttatg tatctattta tttatttcca tttagaatga ggagaaagaa aatggccagg    8580
gcagacctga ccacccagca gcctctgatg gtgaaggccc tggggaggtc tgggtgggcc    8640
catccaccac ccaagatcct ctctgcgcgg gaggttggtg gtgggggag agagagaaag     8700 agagaaagag agaaagagag agagaggccg tggatgctct ttctcctgag gaatgaaatg    8760
gtttctggaa aatgctggtc tcctgagctg gctcagggcc tcaagcctgg gaggcagcat   8820
tgagtgatag cttccagatg gggatggtgg ccctcagcca gcaaggagga ggaggaggag    8880
gacgaagaag gaggagggca gaggagaagg agggagaaag agggagaggg aagaggagga    8940
aaaggaggga aaaggggga gaagggagag ggagagggg agggagaggg aggggaggg       9000 gggagaagaa ggagggaggg ggagaaggga agaggaggga gaaggaggga ggacaaggga    9060
ggaggagatg gaggagggg aaggaggaga aggaggaggg agaaggagga ggaaagagaa    9120
aagaggaaag aaggtgagga gaagaaagaa ggggagggtg gaaggaggag gaggaagagg    9180
aggaaggagg aggagagaga agagaggagg aggaggcagc tcccaggcca tccccatca    9240 ggccttgcag cctccagggc aggcaggagg gccatgagga gccgccagcg ccctgtccct    9300
gcagggctgg aggccccatg ctcacgcctg tgcttggggg ccagcagggc tccccagctc    9360
tttccacgcc cctctggccc agcttcccct ggcatgccag cgttgtcgct gcccacctgc    9420
cagcatgtgt gggtctccgt ctatcccacg ggcacccatg ctcctggcat caccctgaat    9480
ggggccccag ggtttgaagg gcccagaccc aacctgctcc agcctgtgga ccacccaggc    9540
gggcacagtg ctgcctgagg gggctggcgt ttcaccgggg cctcaggact cctggggag     9600 ctgcccggtc ggtggctaga ctcaccgtca ggtactccag gtcctcaggg caccagcatg    9660
aaggcaaagg cggctgccca gaccctgagt gggaggacat ccccagggtt cttagcctgg    9720
gtgacctctg ccaccatcca taaaactgta tcgggggcat ctgtatgctc tcagaggagg    9780
ggtctctcgt gttccttagc ttccgcaagg gggctctcaa aagcctggaa gccttgaccg    9840
agagaacaac gggcaagtgc cgggggcggg tgcgcagacg tttccaccag agaacgcccc    9900
actccacgac tagggcacg ggcatcagtg agagagaggg gacagtggtt ggccgggcca    9960
tggagaccca ggcagagtat ggagagaaag tgaggtgagg gaggtgggct caactgcaaa   10020
gagagaggcc acagcatcct gagcaggcac cacacctgtc ccaagcctca ccagcactgg   10080
gctagctggt gccttgttc agaaaagaag gcaaaacaga agatcctaca gccccggccc    10140
tggagaggct caggctcagg ggagactctg cccggccctg tccaggtcca tgcccctcag   10200
gaagcagccc cagtgggcag aggtctccat cttctcaggg gtgccctgcc cctgctgggc   10260
aggggtgcag tgttgccatc aacaggcccc tggggccaa aatgggagaa caagggatga    10320
attcccaaaa agcgcagggg aaggggatgg gaaggtgcta tggaacccac gcacccagcg   10380
cccacgctct ccccaggcca agtctccctc tcaggcagtg gggagcggga ctcagaccca   10440
cacctcgacc aagcatcctg ctgggggcgc agcctgaggg cactgccctg cccaggcctg   10500
ccaggcccca ccaggccccg cagtgactgc cccccacccc gcagtgacca ccccccaca    10560 gtgaccggcc ccccgcagtg accagccccc cgcaatgacc agccccccaac agtgaccagc   10620 cccccatagt gaccggcccc ccacagtgac cagcccccg caatgaccag ccccaacag     10680 tgaccagccc cccatagtga ccggcccccc gcagtgacca gccccccgca atgaccagcc    10740
cccaacagtg accagccccc catagtgacc ggcccccac agtgactggc ccgcccacag     10800
tgaccggccc ccccagcag cgaccagccc ccgcagtga ccagccctca acagtgacca     10860
gccccgctct gccccaggg cttcctgtgc ttctccctgg cgttctgcgc acaggtgcag    10920
```

```
gtggtgttct ggagactcca cagccccacc caggtgagca ccagctgccc ctaccctgca   10980
gtggagggtc ccccagtaag ccagtgggca cctggggact ggggagcagt cctgggagga   11040
gcagccccag cttccaggct tgtgctgacc gggtggggtg ggggagaccg cagcctgggt   11100
tccctctgcc tgaggcttca gggaggccaa gcgctggagg tgggtgaggg ccagcagctc   11160
cctggtgggg agggacctat gctgtacccc tgccttcgcc ccagtctcat tttcttaaag   11220
cccctcagcc cacccctcc tgagctgatg ccctcgggt ttgagggagg gaatgaggag      11280
gaagaagaag gaaagccact ggcttggcct taggggttga ctagaaggag cagagtgttc   11340
cagaaaatga gacctgaggg ccagcgctcc tgatggcctg gtggggcaga cggtaccagt   11400
ggggaaggga cctggagacc cgcggactgg ggtgtcgcag cctccacccc ctccacggaa   11460
cagcacccat ccttccgtcc tggatgctga cctgcctgga ggagggtccg gcctagctga   11520
ccgtgggcag gggccaaggg cgtccccgtg gaaaggccag cagcttggag aggaaggagg   11580
cctccctggc ccagcagaga atgagagctc ggtagcagag ccagcccac cttccccttg      11640 agagccagac ctggtgagag ccccagggc agccgggcgg caccagggac agccacgggc     11700
agggtcatgg agtggggcag gagagcctgg caggtcacaa gaggtgattt cttggagccc   11760
tagctggagt cctagtggcc tcgtgtattc aagtgcctgg ttgcccaggg ccctcaaaca   11820
caggcttggc catgagagat accgaggctg gtagcaggca ggtcctctgg ctgagctctg   11880 caggggggcct gctgtgcagt ttcttgagct gtgctggcag cctgagtgtg gtggtcccca   11940
ccgtggtttg caaatggggg gactcaggcc ctctgggggt gggggagct caaggttacc      12000 ctggcagtgc cggggctgga tgggggctcc aggcttacga caaaggctct tggccccaaa   12060
gtgcccaccc acccctggca tcatttggga ggaaccgcct gaaccaggtg ggagaaacac   12120
cattttatca ggcccagaag gatcccagag gggctgagcc cccagaagag ggctgtggct   12180
ttgaggactg gcacaggagt cttaccaggg tggtgagctg ggccaggtcc gtgtttcggc    12240
ctcacgtttc ctgtccactg aggggtggtc tggctcattt gaggtctggg tcacagtgtg   12300
ggtggccgag gtcaagacag ctgccagggt tccccgggct cgtctggggc agctgcggcc   12360
catgccccat gcttctgtgt gtttatggct ctgatcgtgg agccacaatt ctggagggga   12420 ggggggccata caggggccac aggacagaac gcagctgggg cctgctctcc aggaagggaa    12480 ggggggtgcaa gaagatagat gccccagccg ggctcaccta tggcctgtcc cagccccagg    12540
cagcatcccc cacacacatg gtccttgtct ggcccgtgcg cccagctgcc cttcaggggt    12600
cagttctcag ggccttgcct gaccccaggc aggggactgg ggcttcctcc tgggcctctg   12660
gtccccatct gccctccca gtgggtcttg acttctggca tcatctgtgt caggcctggt      12720
ggccatggag gtggcctggg tgaaggagct ctgaatatga agtcagtgtc cttgggccgc   12780
ccttgggcaa gccactttaa cttcctgggc ctcagtttcc ttttctgtga agggagcacc   12840
aagatccagg ggctgcatgg gtgggaatgg ccaggtgtgt gcaaagactc ttcctcctca   12900
cctgcgtgcc tcctgccgtg ccccgttgcc caggctggtc ctccaggacg tgggacttgc    12960
tcgaagctgt cctgggtgtg gatggagtgg ctttggtgcc agggcccggg ccctgagcag   13020
gaggggcggc tgcacatccc gtctcctgcc ctccaccctc agggcccacc agagccgaat   13080
gggcttcaac cttgggctcc ctgtccaaca aagtcctgct ggcagcctag acagtggcaa   13140
aggccaaagg ccccaagctg ttggcaccgg aaacgtcgag gtgagagccg ggggcccaga   13200
gcccagcccg gcccattcac ccattccccc tgtcctccc cacagggcca ctgaggtgtc      13260
ctgaacacag ggtcagggtg actcatgtgg tgcccctgcg gatgggaagg cagaggacag   13320
```

```
aggagggaag ggaccagcca catgcccttg gtggtgccct gtggccacag acccgggccc   13380
agagctgaaa gtggggtgcc cctccacctc cccaactctt gccccaggga gtcctggctg   13440
ccacttccct gggatgctca tgcgggcagg aggcgtggac cgggcttcag ggatgaatgt   13500
ggagcttgag ggctattaat tacgttctcc tcgagggctg agagccactt tgccttaacc   13560 ctcccctgt gccctgacga gtctgcttcg ggaataattc atgctcaaat taagtacagc   13620 agtgtgggt gcagcctcgt cctcacagtc tgccccaccc tggagccact accctccctg   13680
gatcctccag ccgccgagtg ggctcaggcc agagccagct ctgtacctgt ggggctggtc   13740
cacaggcctc ctgcagctcc tggtccccac ctgccgttca ggacctgtct gtaccttcct   13800
gagcactttc agcagacaca ggatggggtc gccaagccca ggcagacacc agggaagatc   13860
tggtcatggg gaaaagcccc cgggcaccgg aagacggagc ttagtgcgtt gatacctgtc   13920
aggcagcacc ttcccccagg tgtcctgaga acacaggcc ccaggctcct tcagagcccc   13980
cagagcctgg aatggagaca gacggtgaag catcacctag gagcccaggc cccgtggaga   14040
gcagccggcc cggcctccag ggccctccag ggccagacaa ccggctttgg ggtaggaggc   14100
ctacctcgct gagctctgct tccccagtcg tggggagagc tgcttggcag agccaggcag   14160
ggcaggaaga gccaggcagg gcaggcaggg caggcagggc aggcagagcc aggcagggca   14220
ggcagagcag gcccctcagc cactagcagg agttgtcact ctcgcccatg ctgtggtaat   14280
aatgacacct tgctcacagc ctcagaggca cctttgtcct ccttgggcca tggcaggcgc   14340
ctgacaatgg gaacagtcat tggagttggg agggaagcag gagggaggt ccgagccaac   14400 ccccgggccc actccgctgg gcctccagtc ctcaccagga cctccaccca cgaggacaca   14460
atggccaggc cagactccac ccccatttca cactcacaga cgctgaggct gaacaaggcc   14520
cccgccctgg ccgacagtgg tgtggccagc ttggtgcctg cccgcccctg ggcactgcgg   14580
ggaggacaag gctggctgag tcggggatga ctcacggaga gtggtctgac ttttattagc   14640
atcaatggga gggatgcatt agggtcagga gccaagtttg gcctggaaag tccatctgac   14700
tcctgttggg gcctccaggc ttgggcaggg ctgaccgaga gcctccactg cccactgccc   14760
gcccagttgg ccgctgtcag ggcctgccac gggggctggg ccccagtgca atgaggaccg   14820
ccgtaagcca cccttccttt ctggagggca ggtgtgagtg gctagagcgg gcctggggct   14880
tccatcctcc cccagcccctt tggggcagct gctgagcacc cccttcatgt gtcttgactg   14940
tcagcatggc atttgggga gaactgaggg cctctgaggc aggaaggaga catcagaggg   15000
cagggacctc aaagagggcc tcgccctgtg ccaggagacc agcgactcct ggagcagtca   15060
cagaagcctt cctgtaggag gcgagattcc agtttgtctt tgaaggagta acttggcagg   15120
ggagagcatc ttgcttagga gggtggagac atgaggtcca ggtgttggtg aggtgtggag   15180
cgcaggcagc acatccagcc aggccccgtc accttccacc ttcttcaccc cctgccccac   15240
agtggcctcg tccacccaga tctggcctca ggtgcccaag gcttctctgg tcaaaagcct   15300
tacccggagc ccagctgccc gggcttccag aaggcagccg ggtgattctt gggaaagatc   15360
tagaatcccc aagctttctg ggagctgagg tcctggcaca gggtctctca gccttttcc   15420 accaggccca gccccatccc ccatttccgg gtcaacagta gcgtgctgga aacttctgtg   15480
ggccaacctt gtaagaccac agcggaggcg gacgcagagc ttggcctctg ctttatcctg   15540
cgggaccctc tgggggcagg agggccactc tgacggccat tgtgtgaagg ccccatcgtt   15600
gatgttggga agcactgtga ctggctgccc agggacccag gttccgcttt ggggagatcc   15660
acctgctaca aggagggcag tgctgggacg tcactcagca ctaagggccc actagcgttt   15720
```

```
gggatgtcgt ggggaggggg ctgtgtcccc ggatctccca ccaggccag gacctccctg   15780 tggtctctcg gtgcaggtgg aggacgccat gctggacacc tacgacctgg tatatgagca   15840
ggcgatgaaa ggtacgtccc acgtccggcg gcaggagctg gcggccatcc aggacgtggt   15900
gagcgtgggg acggctgggt ggcagggcgg tcagcttctg cttggactgc agttcagaga   15960
acaggcgcag ggtggccagt gagaggtctg gccaggcacc gaggggttc caggacacag    16020 gccagagttg cccctcaggg ctgggggcaa aaagctccca ccctctgtct gcccaggaca   16080
aggccgccta ccagattctc gaggcccagt gcaaaacgag agggcagggc cctgtattca   16140
gaaacactga aggatttcaa gagcattaaa gcaaatacgg ggccgaacat agtggctcac   16200
acctgtaatc ccagcacttt gggaggaggt tgaggcaggt gaattgcttg agcccaggag   16260
ttcgagacca gcctgagcaa catagggaga ccttgtctct actttaaaaa aaaaaaaaa    16320 agaaaagaaa aaataaaagc acatacagcg cacaggccct gtgaacaggg cggggaagct   16380
gcctggctcc agcaggtgtt ctgtcaccag caggcaggca gcgcagcttg agagagctcc   16440
ccttaccagg gcccggctgt gcaatggctg gagcccagc agaagcagct gcaataccag    16500
tagccccagc cctggcctgc agggaacccc acctggatac ttgtggtgcc tcagtttccc   16560
catatgtgct gcccgcctcc tggggtctcg ggagcacatc accactccct cccttctgtt   16620
cctgtagttt ctgtgctgtg gaagaagtc tcctttcagc cgtctgggga gcacagaggc    16680
tgacctgtgt cagggagagg aggcggcgag agaggtgagg gggggacctg gatgctggcc   16740
aggcaagacc ctcgggggct ggacaccctg ggcccaacc caagaccca gggccatcct     16800 cccacccac ccctttggcct ccccagaccc ttgggaactg ccgctgaagg gctcagggaa   16860
ggttctgatg tgatcggagg ctagttaggg ttcatggtac gccaagccca ttgggtggcc   16920
aggctgggct caagacataa acacaggccc cttttgcccag ctggacgcag gccccatgcg   16980
ccattcactc cttcaagcca gttccagcct ggggacttcc caaggccagc taagtccaca   17040
gaagcctctt ggagtgcacc catgagggct ctgtgccaag ggctgcaggg ctggtgtggt   17100
gggctctgtc tagggggaag ggtgcaggcg tcctgggggg catcagaagg agttgaaggg   17160
cactcagagg agaagaagta ggccagggtg tggccagggc ttcagcaaca acagagcggg   17220
gcccgaggcc aggaagcctt tcctcccag ggcctggga gagactgggc cctcctctct     17280
ttctcctggt gcccggcagc cctcccccag cccaccctgc cccctccctg ctcccctccc   17340
cgctcccctc ccctactgtc ctggaaacaa acccaccccta tctcacagtg ggaggcacct   17400 ggcgacccctc caagaaacag aggggaggag agcaaatggc tggaggcctg gtgagggtg    17460 gagccacagc caaggctctg agggcagaag ggctggcgct gaggatggtg ctggggaggg   17520
accagcggca ttgggggcag ggctaacagt caggacccct gtgccaccca aggagagact   17580
gaaaaggccc ccgactgaaa agcaggagcg agggcctgcc tcgagcaccc ttgggatggc   17640
agggccatgg gcccgactgc aaagcctcct ggggagccgg aagagccagc acaggcggca   17700 ggcacgagc cacccagatg ggctggcatg ggcgggaggg aggcagacct gcctgcgggg    17760
gacaggaggg tgagccctga gaccctgcgg aggcctccac aggccgcccc agttgccatc   17820
atctccaggg ttcagagaca ggcctgccac ctccctttc tgaaaagatg cctctggtg     17880 ccatgccctg gggtggcact ggaagcctgg gatggaacca ggaagctggg actgtgcggg   17940 gaccccctc acaccctcc accagctggc ttcctgccct ccctgttagc catcaccctc     18000
tggtcaccaa ggtgctgtgc ccggccctgg gctggatgct gggaacccag agtgaattcg   18060
aagtggcccg gcccagggga gccaacgtgt ggcccaacat ggacgctcag gacagctggg   18120
```

```
agacggcacc ggccgggccc agggcagtgc cagagtgccc acagaggcca gccctgtccc   18180
actgggcttc acctgctcgt gctgccttc cctagagccc tggggcttc ctaggaatgt    18240 gccgcacccg ccgccctgct gccctggcat tggcctaggt gggcgctgca gctccatggc   18300
cccacagagg ccgcttgtcc aggcagggag ggccgctcag ggcgggtacc atgcctgctg   18360
ccctctcaca ggactgcctt cagggcatcc ggagcttcct gaggacacac cagcaggtcg   18420
cctccagcct gaccagcatc ggcctggccc tcacggtacc ctctcgcctc cctcactgcc   18480
ccttcccacc tcctgcccct cagcctgcca gccccgac tcagatggaa gggtgacccg     18540
ggacaggatc tctggtcttg agcctcactg gctgccaacc tcagggagct gctctggtgt   18600
gacagggcct gcctcctaca gctgggccgc ccccttacac tgcagagtcc tgatgcttcc   18660
tggggagggg cgcccgcacc ctgggcagt ggggcagccg cgggtgtctc cctcccaggt    18720
gtccgccttg ctcttcagct ccttcctgtg gtttgccatc cgctgtggct gcagcttgga   18780
ccgcaagggc aaatacaccc tgaccccacg gtagggcccc ctgcctgccc ccacaccctc   18840
tggaagggtc ctccagctct gctcgagagg catctgctct gccagctgct aggagggagc   18900
cccgggacca agccccaggc tgacactgta gaggaaacgc tttgggggtg gctgagcacc   18960
agggtggggt gggagacctg gagagtttcc agacccaatg caccgcaccc catggcccac   19020
atggggaccc ccctttgctt accccaggc cttaccaaga cctggagatg gatgcttctg    19080
ggcctccagg ttatagcccc aggccaggat ctctgtgctt gaataccca gagctcctca    19140 tgcttagggg gcagggaggg tccaacccac agccaggcag ctcttcctgc ccccacggag   19200
cctggcccgt ctctgcctgc catgcccatt aacccaccca cttgctcttc ctggccatcc   19260
aagccctcat ccctgggtcc tctgcattct acaatagcct cacagtcccg tctagaacat   19320
tctgcaacag cctcacagtc ccctagaac attccacagc agctccataa tcccctccag    19380
aacattctgc aacagcccca tgatcccctc tagaacattc cacaatagcc tcacaggtcc   19440
cctgtagaac attccaccac agccccatga tcccttgct cctcagagca tgtggccgcc    19500
agccccagga gccagcctc ttgagatgct cccagggtgg acccacacat tgtctccact    19560
ccgaagcagt tgctattggt ccaagaggat gctcgggtag tcttcggtgg ctgcaggaga   19620
gcgatgctgc gcctctgccc ctctcctgcc acctggctgc ccacagaggt gaagacgccc   19680
ctgctgtcag ccctcatggg atccctgagg ggagggtccg agctgtgagg agggaaggga   19740
gtgaaggccc agccagagag ccaggctcca ttgggaacag atgcaagggt aaggggtagc   19800
tcaccaaatc cctccatggg aacgggctgg gagcaagcac aaaggaaacc acactggagg   19860
cagcagccca gggcagactg caagacactg gtgggccacg gcctggaggg ctccacccag   19920
acacaagctg cactggtttt ctatgctgcg taagaagcag catggatgta aggactgcaa   19980
gcagtgccca tttatgatct cgcagctctc cagggcagaa gtcgcggtgg gctcagtggg   20040
tgccctgagc ggggtctctc agactgacgt caggccttgg tgggctgcac tctcacctgg   20100
aggctccggg gaagcatctg cctccaggac cattcaggct gttgacaagt caactcctca   20160
tggctgtagg actgaggatc ccaagtcctt gtccctggtc ctgtggtccc tccaccttca   20220
aaccagcaat ggtgcattga gcaaattgtg tcaaatata catcacatca aatttaccat    20280
cttaaccatt gttaagtgta tggtttgtgg cattaaatac attcacattg ttgtgcaacc   20340
atcaccacca tctatctcca gaactttcca tcttctcaag ctgaacctct gtccccagta   20400
aacaccaact cccattctct gccccggtcc ctggcaccca ccatccactt ttcgtctcta   20460
tggattcagc tgctccagga acctcatatg tgtggggtca cacaggattc atccttttgt   20520
```

```
gtctggttta tgtcacttac tgttatgtcc ataaggtcca tccgtgttgt agcctgtgtc    20580
agaattcttg aaagagaaat cttatcagct ttcccatcat ctcacagcca catggtccgt    20640
gattaaggca ggacatttag tgggaagcgt ggagcatttt agatattctg cctgccacac    20700
ccactcttac tggacgttca gaccacgttg atgacgaatt agctctaatg gtccctaaat    20760
gtttgcacaa tttgctcaaa attctaagtc ctgggtggaa cgccaagttg cccagccta    20820 ggccaaggtc ctaatgaagc cgacaaaaga gaaggaatgt caaggccctt ctaacttcca    20880
tagagggtgt gtggcccat ctcccaccaa caatcctgta atcccaacac tttgggaggc    20940
cgaggcagga gactgcttga agccaggagt ttgagaccag cctgggcaac atggcaagat    21000
cttgtttcta caacaacaac aaaagaaaa cattagccag gcatggtggc acacacctgt    21060
ggtcccagcc actcagggggg ctgaggtggg aggatctctt gagcccagga tgtcgaggct    21120
gcagtgagcc atgatcacgg taccgcactc cagcctgggt gacagagtga gaccctgtct    21180
caaaatataa acaaataggc gggggggcagt ggctcacgcc tgtaatccta gcactctggg    21240
aggccgaggc aggcagatct cttgaggtca ggagttcaaa gccagcctgg ccaacatagt    21300 gaaacccat ctctactaaa aatacaaaaa aaattagcca ggtgtggtgg cgggcgtctg    21360
taatcccagc tactgagcag gctgaggcgg gagaatcgct tgaacttagg aggcagaggt    21420
tgcagtgagc cgagatcgca ccattgcacc ccagcctggg tgacaagagc aaaactccat    21480
ctcaaataaa taaataaata ataaaataa ataaagtaca aaaaaattag ctgggcatgg    21540
tggtgggtgc ctgtaattcc agctactcag gaggctgagg cagaagaatc acttgaagtc    21600
aggaggtgga gggtgcagtg agccaagatt gcgccactgc actccggcct gggtgacaga    21660
gcaagacacc atctcaaaaa aaaaaaaaa tttaatatat atatatatat gtgtgtgtgt    21720
gtgtgtgtgt gtgtgtgtgt gtgtacat atatacacat atatgactaa ctaaataaat    21780
aaatgctaat aaataaaata aataaattaa aataaatctc caaactagaa gagtaaggac    21840
taacagggcc aagaggtaaa cttttgtgaa tgttccaacc ataagtgctg ccctcactct    21900
cacccgtagg cccccggcct gtggattctg gtttaggga acggcaccat tcaccagggt    21960
ccagggtcat atgctgtagg actctctgca gtcttgtggt ggcatcttcc agctgagctc    22020
ctaaataatc ctgagtggtc ctgagaagcc agatcaccat cccacagggg tgggtcctgt    22080
ggagggacag ggtacatgga accctagtga atcccatggg gtctccccac tgccctgtcc    22140
tttggctgta aaggcgatgc cttggctgga aacagcagta cgtgcaggag caggcagtag    22200
gctgggaagg aaagtgccgg tgccggagga agcagtgcta gtggagggga gtgggtccag    22260
atcaagaagg gttaagtgca gtcatctttc ccatcatctc atagttgcac ggtccaggga    22320
tgaagacagg acagttagca aggagagggg aaccggatca tttaagacca cagctggaag    22380
atgtccctga atgttgcac aatttgttga aggttctaag tcccgggtcg aacaccaagt    22440
tggcccagcc taggctgagg ccctaatgta gcttggctaa caagagagaa ggaatgttgg    22500
ggcccttcta acctccatag ggggtgtgg ccccccatga agtggaaata gtgccagtgg    22560
gggagcatca aggagcaggg ccatatccta taggacttca ctgcagtctt gcggtggcat    22620
ctcccagctg tgctcctaaa tgattctgtc ccctccgcac taaatgtcct cccttcgtcc    22680
ctgggaaaag ctagaccctc tccatgaagg aaggcgtcca aagccagtca gcccttggcc    22740
aggtgaccaa tcggtctccc atgagatgtg gtgcgcttct gcggggcggg acggcacact    22800
gctgaccttg atcgggcatc ggctgcagtg caggggtgtc tggaagagct tggtaagctg    22860
agtccctgtg gctgggccac ggcggctccc ctcccctcca tgtctgcctc agggcagcaa    22920
```

```
cagctccctt ggggcagagg ctgcctgtct gccacgggtt ccaagaacct tattagagta   22980
cagtacccca tgcgcttgac agtatgccca gcctgtccag ctacaggact cagcagacaa   23040
acaacaccca ggtcagacta cacctgatgc ccatagacag ggctcagtct ccacccaggc   23100
ccaggggaaa ccgagcgctg tatatccaag cgagaagagg tcctggacac agagggcaaa   23160
ctctgctctc ctcgacgggc actgtggcct ccaccatggc ttggctcagg ctccgagggc   23220
gccttggtca gccaagaccc caagaggacc cttaggtccc tgggtcacaa ctgagtggct   23280
cagtccacac aggaacaaga ccacatgggc atcgtcactg gctgtgcctc ctgcagaaag   23340
caggccaccc ctggcgtgcc tggacacagg ggaagcacac acccaaatgc aggctgtgtt   23400
tcctccaaag agtgctgcgc acggatgact caggqtgcag gactggtcct tcaccaccac   23460
ggagtaggca tgcccggctt cgttggaccc agagagagc ttcaggagaa agcaggagtc   23520
tctgttttta cagggtttcc ttctcaccct gccactcatg gttttgtta aagcaaccta   23580 caacttcctc acctccaggt catatcagcc caatgtcctg tgggctgggg agacggtcaa   23640
ggtccacatg ggctaaattg tggctgagag ctaggttatt catgtaatcc caaggcaggt   23700
ccacgctgct gtccctccca ggtgagagca aaccacctttt atggttttct atatgttggg   23760
atagactgaa aaacaacaac aaaacaggtg tttgctggcg aaatagctgc ttgccagtac   23820
aaatgcctgt gctgatttgt tccaattaag aagaaaactg gtgcttgctt cagccacaca   23880
tacactaaaa ttggaaccat acagagaaga ttagcatggt cctccctgcg caaggatggc   23940
acgcaaattc ttgatgcatt ccatattttt ggaacatacc tcaaaataat aagagccata   24000
tatgacaaac ccacaaccaa tatcgtactg aatgggcaaa agctggaagc gttcccccttg   24060 aaaaccagcg caagacaagg atgtcctctc tcaccactcc tatttaacat agtagtgggga   24120 agttctggcc agggcaatca gacaagggaa agaaataaaa agtattcaaa taggaagaga   24180
ggaagtcaaa ctatctttat ttgcagataa catgatccta tatctagaaa accccatcat   24240
ctcagcccaa aagcttctta agctgataag caacatcagc aaagtctcag gatacaaaat   24300
caatgtgcaa aaatcgctag cattcctgta caccaacaac aggcaagcca atgaactct    24360 cattcacaat tgccagaaaa agaataaaat acttaggaat acagctaaga agggatgtga   24420
aggacctcct caaggagaac tacaaatcac tgctcaaaga aatcagagat aacacaaaca   24480
aatggagaaa cattccatgc tcatggatag gaagaatcaa tatcatgaaa atggcctcac   24540
cgcccaaagc aatttatgga ttcaatgcta ttcccattaa actaccattg acattcttca   24600
cagaattaaa aaaactattt taaaattcat atggaatcaa aaaagagcct gaatagccaa   24660
ggcaatccta agcaaaaaga acaatgctaa aggcatcatg ctacccaact tcaaactata   24720
ctacaggaat acaataacca aaacagcatg gcactggtac aagaacagat acgtagactg   24780
atggaacaga ataagaaca cagaaataaa actgcacacc tgcaaccatc tgatctttga   24840
caaacctgac aaaaataagc aatggggaaa ggattcccta tttaataaat ggagctgtga   24900
gaactggcta gccatatgca gaaaattgaa actggacccc ttccttacac catatataaa   24960
aatcaactca aggtggatta aaaacgtaaa tgtaaaaccc aaaactttaa aaaccctaga   25020
caaaaaccta gcaataccca ttcaagacac aggcatgggc aaagatttca taacaaagac   25080
accaaaagca attgcaacat aagcaaaaat tgacaaatgg gatctaatta aactaaagag   25140
cttctgcaca gcaaaagaaa ctataaacag agtaaacaca cagcctaagg aatgggagaa   25200 aattttttgca acctatgcat ctgacaaagg tctaatatcc agtgtctata aggaacataa   25260
acaaatgtac aagaaaacaa acaaacaaac aaacaaaccc attaaaaaag tgggcaagg    25320
```

```
acttgagcaa atacttctca caagatgaca tacacgcggc caacatttga aaaaaagctc   25380
aacatcactg accattagca aaatgcaaat gaaaaccaca atgaaatact atcccacacc   25440
agtcagaatg gccattatta aaagtcaaa aaataacaga tgctggtgag gttgtggaga    25500
aaaaggaatg cttttacact actggcagga gtgtaaatta gttcaaccat tgtggaagac   25560
agtgtgataa ttcctcaaaa acctagaggc agaaatatca ttctacccag caatcccatt   25620
gctaggtata tacccaaagg aatataaatt gttctgccat aaagacacat gcacgtgtat   25680
gttcacttca gcacaattca caatagccaa gacatggaat caagccaact gctcatcaat   25740
gatagactgg ataagaaaaa tgtggtacat atacaccatg tagtactatg cagccataaa   25800
aagaaacgag ttcatgtcct ttgcaggac atggatggag ctggaggcca ttatcttcag    25860
caaactgaca caggaacaga aaccaaata ccgcacgttc tcacttataa gtgggagcta    25920
gatgatgaga acacaaggac acatggggggg aaacaacaca cagtgggacc tgttgttggg   25980 ttggggtgg gaggagggag agcatcagga agaaatagcta atggatgctg ggctgaatac    26040
ctgggcgatg gaatgatctg tgcagcaaac cgccatggca catgtttacc tatgtaacaa   26100
acctgcacat cctgcacatg taccoctgaa cttgaaagct ggaattttt tttttttttt    26160 ttttacttt taagctcttt tgttaaaaac taagacacaa acacacatag cctcggcctg     26220
cacagggtca gaatcatcag tttcactgtc tttcactgtc acatcttgac cagttttgtg    26280
accggaaggt cttatgggca gtgacatgca tgcaactgtc atcttacgtt atagcaatgc    26340
cttcttctgg atacctcctg aagaaactgc ctgaggttgt tttacattta acttgtttta    26400
tatataagta gaaggagtac actctaaata aaaagtatag taaatacata aacgagtaac    26460
gtagttgttt gttatcattg tcaagtactg tgtgctgtgc ataaatatat gtgccagatt    26520
tttatatgac tggtagcacg gcaggtttac ttacaccagc attgcacaaa acacaggagt    26580
aattgatacg gtttggctgt ttccccaccg acatctcatc ttgaatcgta attcccataa    26640
tccccatgtg ttctgaaagg gacccggtgg gaggtaattg aatcatggag gtggttaccc    26700
ccatgctgtt ctcgtgatag tgagtgagtt ctcacaagat ctgatggttt tataaggagt    26760 ttttcccct ttcatttggc acttctcctt gctgctgcca tgcgaagaaa gacctgtttg    26820
ctcccccttc caccatgatt gtaagttttcc tgaggcctcc ccagccatgc ttaactgtga   26880
gtcaattaaa cctctttcct ttataaatta cccaagttcg ggtatgtctt tattagcaat    26940
gtgaggatgg actaatacaa aatgcattgt gctacaacat cattaggtga taggaatttt    27000
tcagctccac tataatctta tgggaccact atcacacatg tacccgttct tgaccaaagc    27060
atcctcatgc tgtgcacaac tgtactcagc caccggctga gtccccacat tggtttcctg   27120
acgtgtgggg tgagggccac tattgtgggc caactggaag ccattagagg tgcctctacc    27180
tagaaaaata gtcaaaagcg atacaataat agtcagtcaa aagctgcatt tccagaggaa    27240
tttcagaggt tagtgccacc atcaaatacc tgaaagatgc agggcagtg atccccacca     27300 cagccccatt ccactcacct atttggccag tatggaagac aggcgggtcc tggagaatga    27360
caagggattg tcctaagctt gactccaact gcagctgctg ggccagattt ggttccattg    27420
cttgagcaaa ttagctcatc tcttgctacc tggtgtgcag ttattgatct ggcgaatgtg    27480
tccttctcca cccctgtcca caaggcccag cagaagccag gccagcaatg caccctcact    27540
gtcccacctc aggggcctct cgcctctcca gcctgtgtca gaggtaatcc tcagggtct    27600 ggatcaccct tcccttcccc ggcatgtcac actggcccat tacactgatg acattatgct    27660
aactggacat aaggcacaag aagcagcaat tattctatac ttgttggtgt cagagggtgg    27720
```

```
gaaataaatc caactaaaat tcagaacctt ctacctcggt gaaattttta ggagtctagt   27780
gctgtgggc ctgctctaag gtgatacata gattgttgca actgaaccct cccacgatca   27840
aaagagaacg acaccaggtg agcccgtttg atgtgaggaa gacaggttct tcctcattta   27900
ggtgtctgac tctggcccat ttactgagtg atttgaaaag ctgctagttt tgaatgtggc   27960
ccagcagcag gtccaggctc tgtgcaagct gttctgccac ctgggccaat gacccagcag   28020
atccagtctg aggtgtcagt ggcagacagg gacactgtgt agagcctttg ccaagcccca   28080
gtaggtgact catagctcag gcccttacag ttttggagca aggccctgtc atcatccaca   28140
gataaccact ccgttttgag aaacaggttt tggactgtgt attagtctgt ttcacactgc   28200
tataaagata ttacctgaga ctgggtaatt tataaagaaa aggggttag ttgactcact    28260
gttctgcatg gctggggagg cctcaggaaa cttacaatca tggcggaagg gaaagcagac   28320
acattttaca tggcggccag tgggagaaga atgagcaaga caggaactac caaaacttat   28380
aaaaccatca gatctcgtga gaactcactc attgtcatga ggacagcatg gaggaaacag   28440
cccccacgat ccagtcacct ccggccaggt ctctcccctta acacctgggg attacaattc   28500
aagatgagat ttgggtgggg acacaaagcc taatcatatc agcctgtgtc taggtcttca   28560
tagaaactaa acacttgacc aagggccacc aagttaccac atggcctgag ctgcccatca   28620
tgatctgggg attatctgac ccatgttgct ataaagttgg gcgtgcacag cagcgctcca   28680
tttgaatgaa agtgatgtat tgtgatcagg ctcaagcagg tcctgaaggc aaaagtaggt   28740
tacgtgaaga agtggcccaa atgcctgtgg ccccccactcc tgctccaggt gccttctctc  28800
tccccacctg catctgttgc tgcacaggga ggtccctctc atcaattgac atgggaagag   28860
aagactcagg ccatacttac aagtggtctg ctcgatatgc aggtgctatc agaaaatgga   28920
cagctgcagc cctacagccc ctgcggcaga ggcaaaggat ggaaaattcc attccaaaca   28980
cgagaaatgg gaaggaaagg actaactgag catgaccaaa tccaaaaccc aacaggacaa   29040
aattaaatct taaagctgaa gaataatttt cttttgactct ttgtcctacc ttctggacac   29100
actgggacaa ggctcctggt ggccccactc ctacggcttt gtgtgcctgt ggctttccca   29160
ggctggtggt gcatgctggt ggctctacag gtcccgagtg tcctctgctc ccttgggcac   29220
cactacacat tgtcctgtgg ggactctcca tggcccaaac ctgtagcagt tctcggcctg   29280
ggccccaggg tctccatgac acccagtgga atccaggagc aggaacttt cctccacagc    29340
acgtgcactc cgtgcatctg cagagctggc accgtgctga caccatcgag gtttaccgcc   29400
tgcgccttct gggctggcag cccaaggaac acctgtaccc acgtgagcct ccatgggggt   29460
gggccaggag tgatgcacca gcttgcaggg aggaacagag attgaggcaa gtctgggcag   29520
cacgccccga ggtctcatgg aggccctggg cccttctttt gaagccattc tgccctcaag   29580
accccggcac cctgagcctg tgatgggcat gacagtctgg aaggtctcgg aaatgccttg   29640
ggggtcattc tcccattgtc ttgatgagca gcttctgacc tccttctacc cgtactaatc   29700
tccttatcca aatttgcttg actacaccct tgctattctc tcctgaacat gctttcttat   29760
tcttttttt ttttttatta tactttaagt tttagggtac atgtgcacaa tgcgcaggtt    29820
tgttacatat gtatacatgt gccatgctgg tgtgctgcac ccattaactc gtcatttagc   29880
attaggtata tctcctaatg ctatccctcc ccgctccccc cacccaaaa cgggcccag    29940
agggtgatgt tccccttgac gtgggcaggc taagagtttt ccaagtcttt aagttttgtt   30000
tcctttctat tatcaattct ttaactcatt tctcttttct cgccttttgc tataagcggt   30060
caacagaagt catgcagtac ccggagtgct ttgcttagag atttcttcca acaaatattc   30120
```

| | |
|---|---|
| tagttcatcg cttttaaatt ctgcctccca caaagcccca gggcatggac acaattcagc | 30180 |
| caagttcttt gccact | 30196 |

<210> SEQ ID NO 10
<211> LENGTH: 21630
<212> TYPE: DNA
<213> ORGANISM: Homo sapiens

<400> SEQUENCE: 10

| | |
|---|---|
| tgttgttggg ttggggggtgg gaggagggag agcatcagga agaatagcta atggatgctg | 60 |
| ggctgaatac ctgggcgatg gaatgatctg tgcagcaaac cgccatggca catgtttacc | 120 |
| tatgtaacaa acctgcacat cctgcacatg taccccctgaa cttgaaagct ggaattttt | 180 |
| tttttttttt ttttactttt taagctcttt tgttaaaaac taagacacaa acacacatag | 240 |
| cctcggcctg cacagggtca gaatcatcag tttcactgtc tttcactgtc acatcttgac | 300 |
| cagttttgtg accggaaggt cttatgggca gtgacatgca tgcaactgtc atcttacgtt | 360 |
| atagcaatgc cttcttctgg atacctcctg aagaaactgc ctgaggttgt tttacattta | 420 |
| acttgtttta tatataagta gaaggagtac actctaaata aaaagtatag taaatacata | 480 |
| aacgagtaac gtagttgttt gttatcattg tcaagtactg tgtgctgtgc ataaatatat | 540 |
| gtgccagatt tttatatgac tggtagcacg gcaggtttac ttacaccagc attgcacaaa | 600 |
| acacaggagt aattgatacg gtttggctgt ttccccaccg acatctcatc ttgaatcgta | 660 |
| attcccataa tccccatgtg ttctgaaagg gacccggtgg gaggtaattg aatcatggag | 720 |
| gtggttaccc ccatgctgtt ctcgtgatag tgagtgagtt ctcacaagat ctgatggttt | 780 |
| tataaggagt ttttcccccct ttcatttggc acttctcctt gctgctgcca tgcgaagaaa | 840 |
| gacctgtttg ctcccccttc caccatgatt gtaagtttcc tgaggcctcc ccagccatgc | 900 |
| ttaactgtga gtcaattaaa cctctttcct ttataaatta cccaagttcg ggtatgtctt | 960 |
| tattagcaat gtgaggatgg actaatacaa aatgcattgt gctacaacat cattaggtga | 1020 |
| taggaatttt tcagctccac tataatctta tgggaccact atcacacatg tacccgttct | 1080 |
| tgaccaaagc atcctcatgc tgtgcacaac tgtactcagc caccggctga gtccccacat | 1140 |
| tggtttcctg acgtgtgggg tgagggccac tattgtgggc caactggaag ccattagagg | 1200 |
| tgcctctacc tagaaaaata gtcaaaagcg atacaataat agtcagtcaa aagctgcatt | 1260 |
| tccagaggaa tttcagaggt tagtgccacc atcaaatacc tgaaagatgc aggggcagtg | 1320 |
| atccccacca cagcccccatt ccactcacct atttggccag tatggaagac aggcgggtcc | 1380 |
| tggagaatga caagggattg tcctaagctt gactccaact gcagctgctg ggccagattt | 1440 |
| ggttccattg cttgagcaaa ttagctcatc tcttgctacc tggtgtgcag ttattgatct | 1500 |
| ggcgaatgtg tccttctcca cccctgtcca caaggcccag cagaagccag gccagcaatg | 1560 |
| caccctcact gtcccacctc aggggcctct cgcctctcca gcctgtgtca gaggtaatcc | 1620 |
| tcagggggtct ggatcaccct tcccttcccc ggcatgtcac actggcccat tacactgatg | 1680 |
| acattatgct aactggacat aaggcacaag aagcagcaat tattctatac ttgttggtgt | 1740 |
| cagagggtgg gaaataaatc caactaaaat tcagaaccctt ctacctcggt gaaattttta | 1800 |
| ggagtctagt gctgtggggc ctgctctaag gtgatacata gattgttgca actgaaccct | 1860 |
| cccacgatca aaagagaacg acaccaggtg agcccgtttg atgtgaggaa gacaggttct | 1920 |
| tcctcattta ggtgtctgac tctggcccat ttactgagtg atttgaaaag ctgctagttt | 1980 |
| tgaatgtggc ccagcagcag gtccaggctc tgtgcaagct gttctgccac ctgggccaat | 2040 |

```
gacccagcag atccagtctg aggtgtcagt ggcagacagg gacactgtgt agagcctttg    2100
ccaagcccca gtaggtgact catagctcag gcccttacag ttttggagca aggccctgtc    2160
atcatccaca gataaccact ccgttttgag aaacaggttt tggactgtgt attagtctgt    2220
ttcacactgc tataaagata ttacctgaga ctgggtaatt tataaagaaa aggggggttag    2280 ttgactcact gttctgcatg gctggggagg cctcaggaaa cttacaatca tggcggaagg    2340
gaaagcagac acattttaca tggcggccag tgggagaaga atgagcaaga caggaactac    2400
caaaacttat aaaaccatca gatctcgtga gaactcactc attgtcatga ggacagcatg    2460
gaggaaacag ccccacgat ccagtcacct ccggccaggt ctctccctta cacctgggg    2520 attacaattc aagatgagat ttgggtgggg acacaaagcc taatcatatc agcctgtgtc    2580
taggtcttca tagaaactaa acacttgacc aagggccacc aagttaccac atggcctgag    2640
ctgcccatca tgatctgggg attatctgac ccatgttgct ataaagttgg gcgtgcacag    2700
cagcgctcca tttgaatgaa agtgatgtat tgtgatcagg ctcaagcagg tcctgaaggc    2760
aaaagtaggt tacgtgaaga agtggcccaa atgcctgtgg cccccactcc tgctccaggt    2820
gccttctctc tccccacctg catctgttgc tgcacaggga ggtccctctc atcaattgac    2880
atgggaagag aagactcagg ccatacttac aggtggtctg ctcgatatgc aggtgctatc    2940
agaaaatgga cagctgcagc cctacagccc ctgcggcaga ggcaaaggat ggaaaattcc    3000
attccaaaca cgagaaatgg gaaggaaagg actaactgag catgaccaaa tccaaaaccc    3060
aacaggacaa aattaaatct taaagctgaa gaataatttt ctttgactct ttgtcctacc    3120
ttctggacac actgggacaa ggctcctggt ggccccactc ctacggcttt gtgtgcctgt    3180
ggctttccca ggctggtggt gcatgctggt ggctctacag gtcccgagtg tcctctgctc    3240
ccttgggcac cactacacat tgtcctgtgg ggactctcca tggcccaaac ctgtagcagt    3300
tctcggcctg ggcccaggg tctccatgac acccagtgga atccaggagc aggaactttt    3360
cctccacagc acgtgcactc cgtgcatctg cagagctggc accgtgctga caccatcgag    3420
gtttaccgcc tgcgccttct gggctggcag cccaaggaac acctgtaccc acgtgagcct    3480
ccatgggggt gggccaggag tgatgcacca gcttgcaggg aggaacagag attgaggcaa    3540
gtctgggcag cacgccccga ggtctcatgg aggcctgggg cccttctttt gaagccattc    3600
tgccctcaag accccggcac cctgagcctg tgatgggcat gacagtctgg aaggtctcgg    3660
aaatgccttg ggggtcattc tcccattgtc ttgatgagca gcttctgacc tccttctacc    3720
cgtactaatc tccttatcca aatttgcttg actacaccct tgctattctc tcctgaacat    3780
gctttcttat tcttttttt tttttattta tactttaagt tttagggtac atgtgcacaa    3840
tgcgcaggtt tgttacatat gtatacatgt gccatgctgg tgtgctgcac ccattaactc    3900
gtcatttagc attaggtata tctcctaatg ctatccctcc ccgctccccc cacccccaaaa    3960 cgggcccag agggtgatgt tcccttgac gtgggcaggc taagagtttt ccaagtcttt    4020
aagttttgtt tcctttctat tatcaattct ttaactcatt tctctttct cgccttttgc    4080 tataagcggt caacagaagt catgcagtac ccggagtgct ttgcttagag atttcttcca    4140
acaaatattc tagttcatcg cttttaaatt ctgcctccca caaagcccca gggcatggac    4200
acaattcagc caagttcttt gccactttgt aagagggaca gccctccccc agttctaat    4260 aagatagttc tcatgtctgt ctaagacctc acgagaatgg ctttgactgt gtggatctcc    4320
accagcattg tgatcacgac cactgagatc attgctacca gccagaggc tctctctaca    4380 gccctgccct cctcggcctg cactggagtc accttagcac caactccgtt cgcaggagtg    4440
```

```
tgtgctttc  cagcgtgcac  ttcaaaacgt  ttccagcctc  tcccgtgacc  cggttccggc   4500
tctgctgcca  cattttcagg  tgtttgttac  agcaacagcc  ccgcttcctg  gtagcaatgt   4560
ctgtcttagc  ctgtttgtgc  tgctgtaaca  aagcaccata  gaataggtca  tttatacgtc   4620
atagaaattg  attgctcaca  gttccagagg  ctgggaatcc  tgcactgcag  gtgatgtctc   4680
gagaggacct  tcttgccgcg  tcctcacatg  gcagaaaggg  aaagggcaca  caggcaccga   4740
gctcattcct  cgccctttc  taaagcactg  atcccaccca  ggagggcgga  gccccacgg    4800 cctcatcgcc  ttccaaaggc  cccacctctc  actaccgttg  cgttgggac   ttttcaacat   4860 gaattttgga  gggacacaaa  tattcagacc  acagtaagcc  atgactaatg  cacacagaaa   4920
actgaagttt  caggatgtat  ttgctctcat  tcctctccat  caactcaatg  gcagctgtca   4980
gaaggctctc  agacttgaat  gggccttaat  cccatctttg  tcttctgttg  atcggtccaa   5040
gtcaggcatt  ttattgggcc  tttgtctccc  aaagcttgtt  aaaatcctaa  ctcttggagc   5100
agttggtttt  tctgcccttg  cggtgctctg  aatttctgga  tccatctctc  tgttcactt   5160 catctctgct  tgtaagctgg  gccttctttc  tcaagctggt  ctccgtctcg  tgttgcggga   5220
cctaacacaa  aactcgcaat  gtggtgtttt  cccacttcgc  cccttatgct  cctggctgag   5280
ccttcttgta  ttcagcctgc  caggtcacca  ggagtgattt  tagcaagttt  gctgctccag   5340
ctccaccaag  tccccatcac  tcgggccccc  ggtgcctgct  ctcttggcag  cagctgggtt   5400
tgggggttcc  gactgctacc  acaatacagc  ctggcctgtc  ctgactaata  cagaagcagg   5460
ctctgtgaag  gagggtgctg  ccataagaag  aaacgcaaat  taacacgtat  ctacacagtc   5520
tccgtggtgc  acaacagtca  gcttttcctg  cttatgtgtc  tgggctctgc  ttgactgatc   5580
ttggctgggt  gcattcccaa  gacagcaagt  cgtggctggc  ctcgggcaca  ggaaagggcg   5640
agagactggg  gtcacagata  caatctagca  taggggaca   gataactcaa  tgtttaaatt   5700
catagggtgc  tggaccaaga  gagggcatat  ccaaacctga  tgtgctcatc  catcggagat   5760
gctgggtctg  gagaaggtgt  agtgactggg  tggactttgg  caggtcaaca  gagggtgga    5820 tggcggaaca  gacgatacca  tgtgttcacc  acactgtttc  ttcctcctag  gcaaatggaa   5880
agactgcatt  tcccagtcac  ctctatggtt  agtgtggttg  catgagggtc  atgtgaccga   5940
gttctgacct  gtgggatatg  ggaggaagca  acgtaagcta  cttcccaatc  gcccttccct   6000
ttccaaggtg  accttacagg  acacacgttc  ccaaagtcag  ctcaaagatg  aagagtcact   6060
tgaccaccat  atgcaagtga  aaaataaccc  cgagacctca  gggggtattt  gttaactgca   6120
acgtagccta  ctttcaaagc  atggttcctg  gaccagctgc  atcacccggg  aatgcggtag   6180
aaatgcagat  tctcaggccc  tgcccaggcc  tccaaatta   aggatgctgg  ggtggagcct   6240
agcaatctgc  gtctaaaaag  ctctccaggg  caatctgaag  gctgttcctg  gccaggaaca   6300
gtggctcatg  tctgtaatcc  cagcactttg  ggattacttg  agaggacctt  cttgccgtgt   6360
cctcacatgg  cagaaaatga  aagggcacac  aggggatcg   aggcgggtgg  atcacttgaa   6420
gtcaggagtt  ggagacaagc  ctggccaaca  tgatgaaacc  ccatctctat  taaaaataca   6480
aaaattagcc  aggtgtggtg  gtgcatgcct  atagtcctag  ctactcagga  ggccgaggca   6540
ggagaattgc  ttgaacccag  gaggtggagg  ttgcagtgag  ccgagatcgt  accactacgc   6600
tcccgcctgg  gcgacagagc  cagattccat  ctcaaaataa  ataataaat   aaaggctgtt   6660 ccaactatat  aggagttcag  gatactggca  agggtgtgat  taaagtgaag  gaccaggtgt   6720
tcccagctgt  gcaggcaaag  aagtgcagtg  aggaaagcat  gcagtacggc  tgcgtagagc   6780
actcccagca  aagcaggtgg  gcaaagcaaa  cacacagggc  ctggaggtgt  ggaaggggtg   6840
```

```
caaggtttgg actttaaatc tcagagagga agcaacccaa aattaaagag accccaggga    6900
tggtgatggg cacagtgggg cagatgaagt tcactggaca ggggaggtca ggggcctagg    6960
ggccgtggtg tggggttgct tgtcccagct gggatggaca caggaattgg gctggagaag    7020
atgtacatga ggtggtcttg tctaaaccct gcacatccag ctccaagcat gcaggtaaat    7080
tcccccggaa ccaactccca tgccaacgtc agactcgaac aagtccaagg atgctgagta    7140
acagtcaggg ttctccagag aaaccgagtc agtaagatgt gtacatacac acagagagag    7200
attattgtaa ggacttggct cacacaatta cagaggctga gcagtcccaa gatccgtagt    7260
tgggaacctt ggagacccag gaggactgat ggtgtaagct cccgtctgaa aggcagcagg    7320
ctcaagaccc aaggagagcc aatgtttcag tttgagtttg aagacaggaa aaaaccaatg    7380
tcccagctca cccaggtaag aggacttccc tcttatttgt cacgcgcctc tgtgtgaaga    7440
gaccaccaaa taggttttgt gtgagcaatg aagcttttta atcacctggg tgcaggcaga    7500
ctgggtccaa aaaaggagtc agcaaaggga gataggggtg gggcagtttt ataggatttg    7560
ggtaggtagt ggaaaattac agttaaaggg ggttttttctt ttgtgggcag gggcgggggg    7620
gttacaaagt gctcggtggg gaccttctga tactcattga ccaggagaag gaatttcaca    7680
aggtcaattg attagttagg gtggggcagg aacaaatcac catggtggaa tgtcatcagt    7740
taaggcagca actgtctact ttcacttctt ttgtggttct tcagttgctt caggccatct    7800
ggatgtatac atgcaggctt gggctcagaa ccctgacacc actcagccat tttgttctat    7860
gcaggccttc agtgggtggg atgaggccct ctagaaaata aaaggtttcg ctctccctct    7920
ccctctcctt ctccctctcc gtctccctct ccctctcccc acggtctccc tctcatgcgg    7980
agccgaagct ggactgtact gctgccatct cggctcactg caacctccct gcctgattct    8040
cctgcctcag cctgccgagt gcctgcgatt gcaggcacgc gccaccacgc ctgactggtt    8100
ttggtggaga cgggattttg ctgtgatggc cgggccggtc tccagcccct aaccgcgagt    8160
gatccgccag ccttggcctc ccgaggtgcc gggattgcag acggactctc gttcactcag    8220
tgctcaatgg tgcccaggct ggagtgcagt ggtgtgatct cggctcacta caacctacac    8280
ctcccagccg cctgccttgg cctcccaaag tgctgagatt gcagcctctg cccggccgcc    8340
accccgtctg ggaagtgagg agtgtctctg cctggccgcc catcgtctgg gatgtgagga    8400
gcccctctgc ctggctgccc agtctggaaa gtgaggagcg tctccgcccg gccgccatcc    8460
catctaggaa gtgaggagcg cctcttccca gccgccatca catctaggaa gtgaggagtg    8520
tctctgcccg gccgcccatc gtctgagatg tggggagcgc ctctgacccg ccgccccatc    8580
tgggatgtga ggagcgcctc tgcccggccg agacccgtc tggaggtga ggagcgtctc    8640 tgcccggccg ccctgtctga aagtgagga gaccctctgc ctggcaacca ccccgtctga    8700
gaagtgagga gcctctccgc ccggcagcca ccccatctgg gaagtgagga gcgtctccac    8760
ccggcagcca ccccgtccgg gagggaggtg gggggggtca gcccccgcc cggccagtcg    8820 ccccatccgg gagggaggtg gggggggtca gcccctgcc cggccagtcg ccccatccgg    8880
gagggaggtg gggggtcag cccccagccc ggccagccgc cccgtctggg aggtgagggg    8940
cgcctctgcc cggccgtccc tactgggaag tgaggagccc ctctgcctgg ccagccgccc    9000
cgtccgggag ggaggtcagg gggtcagccc ccgcccggc cagccgcccc gtccgggagg    9060
tgaggggcgc ctctgcccgg ccgccctac tgggaagtga ggagcccctc tgccctctgg    9120
gcccgtctgg gaggtgtgcc caacagctca ttgagaacgg gccaggatga caatggcggc    9180
tttgtggaat agaaaggtgg gaaaggtggg gaaaagattg agaaatcgga tggttgccgt    9240
```

```
gtctgtgtag aaagaagtag acatgggaga cttttcattt tgttctgcac taagaaaaat   9300
tcttctgcct tgggatcctg ttgatctgtg ccttacccccc aaacctgtgc tctctgaaac   9360
atgtgctgtg tccactcagg gttaaatgga ttaagggtgg tgcaagatgt gctttgttaa   9420
acagatgctt gaaggcagca tgctcgttaa gagtcatcac caatccctaa tctcaagtaa   9480
tcagggacac aaaacactgcg gaaggccgga aggccgcagg gtcctctgcc taggaaaacc   9540
agagaccttt gttcacttgt ttatctgctg accttccctc cactattgtc ccatgaccct   9600
gccaaatccc cctctgtgag aaacacccaa gaattatcaa taaaaaaata aattaaaaaa   9660
aaaaaaaaag ttactcagga gacccttttta gaaatactta gggaaagata agctgtctcc   9720
ttgggatgac tgggctggtg tctgtgcata tgccttctct ggatccaagt gactttacca   9780
caccaagcct taagactgcc agactgttct ctccattgaa agccattctg caccactggc   9840
catacagaag gaatctcata ttccaggaga ctggcccaaa caggactgtt gagtggcctc   9900
taaggctttt agacgtcaaa agggtttata agaataatca tcataatata gttatgaatc   9960
agaaacatgc atacattttc ttaaatgacc ctgtggggac tggagttaaa aagggaggag  10020
tacccagatg caggcgtcta gcagaatgga cttgcttgag aatatcaagc aagacagcca  10080
aagaggactc ctaggattgt ctcaccagga cttctgaggc gactctaatg aaatgactta  10140
aaagtgtggt ggagtggctt ctgtggctcc cacaccggcc taatcctggt tgatattgca  10200
caaccagggt gcactgacaa tctctgggaa aaaagcaagg tctaatattc aaagcttggc  10260
aaacatgacc aagactttt ctctttcctt tgaattattt tagttcccta attttttgtc  10320
ccatatgcca cttaattctt tttattttgt attaaaagtt gtgctcttgt ctcaaccttc  10380
tttctagatt ggatcctgca tgttttttt atcattatac ttttggcagc cctaccacta  10440
ggcttcctga aatatagcac ctttgttttt gtttgtttgt ttgtttgttt tgagaccgag  10500
tttcgctctg tcacccaggc tggagtgcaa tggcacaatc tcagctcact gcaacctctg  10560
cctcctgggt tcaagcgatt ctcctacctc agcttcctga gtagctggga ttacaggtgc  10620
gtgccaccac ccccggctaa ttttttgtgtt tttattgaga tggggtttca ccatgttggc  10680
cagactggtc tcaaactcct gatcccatga tctgcctgcc taggccttcc aaagtgctgg  10740
gattataggt gtgagccacc gcgccctgcc tgcacctttg ttatatagaa aattcttatc  10800
aacattattg tctactttta gactttattt tgttctattg aactattctg gttctagtac  10860
catacattaa aattatagct ttataatact ttttaacatc tgacaggatg tgctcccctt  10920
atcatccttc tttttcaata ttttatcatt ctcacagttt ttctcagatc aacttcacat  10980
gtaatttaca aaagaaatta aaattacatt ggtatttagg tggaaattat gttaaattta  11040
tgtactaatc tggagaagtc ttgttttgta ataataattc ttaccatgaa ggaaaatagc  11100
ttctctctcc gctgattcat gtttttttctc atgtctctca gtagagttta tagcttttt   11160
tgtataagtt ctcataattg cttgaatata ttcctaatta tttaaaaaaa aaaaaagaa   11220
aataaaaggt ttccacttc aaagttcccc ttccttgttaa agaatgaatc ataagtgtta   11280
gaaataacag tttcttttt ttttttttg gaagcatttc ccatttttat tcataaaatt   11340
attacttaaa attgcaaaag tagatttaca gagccacagg taacaaaaca ggaaatgaaa  11400
tgttccagac attccgaaaa gttcgaaaga aacacaccct agcctcaaaa tctccggtta  11460
aaccgtggtt gcacaacagg ttctatttat tcctgcattt tctcaataag ttcttcttta  11520
tatttgcctt tctcttttcc aacttgttga gacttggctt tgcgttcaag aatttttttc  11580
cgatccttgt ccagttttag cctggtgata accaccttgc ttgggtgaat gcccacgtgg  11640
```

```
acagtcgtgc cgttggcctt ctcacgctgc acccgctcga tgtagatgac atatttcttt   11700
ctgtacacct ggattacctt gccaatttgc tgacctttgt agtgtcctcg aactacctgg   11760
acctcgtcgt ccttgcggat gggcatggag cggacattgt acttctgccg cagctccttg   11820
gagagcgggg atgacatgat cttcctgcgc acgtgtgagg gggcattgaa gtaacgtttg   11880
cggttttttac tgcggtccga ggtaacgaag ggattgaact tcatggtgac cctccggcta  11940
ctagctgcct cagaccctca acagtttctt ttaaagacta actttcttca agcctccttg   12000
ctttgtgcta ataactcttt gttaagctct atcctatgta actgttggac atcctcacca   12060
acatattcca gctcacagcc tatgccccttt ccttatttgg tgatgttatt gcctcctgag  12120
acttttcata agcaacttat tgttcttcc ctgcacttac ctatttagga aagtttcagg    12180
ttattagcaa atcgggtatc actttaagat tgtgaggtcc cactccagcc aatggatgca   12240
ggacatagca gtaaggacaa cccaaatgcg taagggataa atacatctgc ttttcctttg   12300
ttcaggtgtg ctctcaccat tgttccatct gcgactgagc accatttctg caaaaagtaa   12360
agatggcctt gctgagagat cttttgtctc tgtgctgact tttcttcacg gcactgatta   12420
tcttttctta acaattttgg tggcaattgt atggggatat acttcctcc aggggcgtct    12480
ctagtcctct ctcacgaggg ggcactctgc tgcctcttgc agtggcctca ggggtaaggg   12540
accgagaccc atccggtgtg accaataaac ccggactctc agcaatgtgg aaagaaactg   12600
gccaacaacc tggggtaaag gatcctcaca taccgaggtg acgactctgt gcacagacca   12660
acgaaggaga agccacggga gccggtaaag tacttcttgg tggtcagatt ctgggggggct  12720
gaatgtgtgt gtgcacgtga atgatcacag acaaccctgc ttgcggtgtt gtgtggatgg   12780
tgacaaatcc tactgctgga cggagtgttt gggtcctctc tgtgcttcca gagcaacctc   12840
agatggctta gggcagatcc tgccatggga tttatactgg cacgccaact ctaagagggg   12900
cctagctctc ccttggggga gtggccagag aggacaacac aagtgggaag tgtgcaaggg   12960
accttcagag gaggaaaggg aggaaacagg tcaacctctc acggcaggca aggcaagaca   13020
cccccctggtt tgagggggtc ttctgcaaat ttcaggagt tgaacctcat acaaacctcc    13080
ggtagtaaga aaatattca gagttctcct ttcccttctt ctcggggggaa gaaagaggct     13140
aagctccact ccgcttgtcc cttccctagg ggaaggggaa ggagaaggga gaatagcagc    13200
ataagcgact ggcagaggca gggaaagacc ggcagaaagg aaagagaaac tgggagagga   13260
agtcagagag agagagagac aaagagggag tcaaagagag agaaagagag agacagagag   13320
tcagagagag agaaagagag agacagagac aaagagggag ttagagagag aaaagagag    13380
acagagagta agagagagag agtcagagag agagaaagag aagtagtaaa gagaaaacag   13440
tgtaccctat tcctttaaaa gccagggtaa atttaaaacc tataattgat cattgaagat   13500
cttctctgtg accctagaac actccaatac tgcctgtaaa gaagcaagac gagtcacacc   13560
agtgactgca agaccctaga gctattaacc agttagtcca aactacccac cctgttgtta   13620
cagtaataga tgtaaaagat gccttctggg cttgtccatt tgcagaggac agccaggacc   13680
tatatgcctt tgagtgagaa gaccctcact ccggtggaaa atggtaatac caatagacgg   13740
tcttacccca agggtttacg gagtctccaa atttatttgg tcaaatattc aaataagtca   13800
tttaattagc aaaggtaaac agaaaattga gcttgaatgg attgaaggca tcacattctt   13860
gcctctgctg gagactaaat aagagcttag aaaattttgg gattagttgt atggataccg   13920
tcgtctatgg gtagactcat gccctaaaaa caaaactctt acacaaaaag ctcacacgag   13980
acagaccaaa ccccctcatg tggcaattac cagaaatcca acaggtggga aggttaaaac   14040
```

```
atctattagt aactgcccct gtcctagctt tactctcctt aagcagccat tccaccttgt   14100
tggtggtgta aacaacggcg tagcccaaaa acactgaggc cactgacaac ccatagcctt   14160
cctaatcaaa aatccttaac ccagtaaccc gcggatggtc caaatgcatt caatctgtag   14220
cagcaacttc tttgctgaca aagaaagta gaaaataac tttgagaaga aacctcattg   14280
tgagcacacc tcaccaggtc agaactatcc taagtcaaaa aaaaaaaaaa aaaaagaaaa   14340 gcaaaaggt agcttactaa ctcaaaaaat ttaaaatatg aagcgattct gtcagaaaaa    14400
gatgatttaa cattaaccac tgatcattcc cttaacccag caggtttgct aacaggggat   14460
ctaactctta atgaattacc atacaaaggt ccaaccagac ctagaaggaa ctcccttcaa   14520
gacaggacaa tagatggttc ctcccaggtg aatgagggaa aaagccacaa tgggtattca   14580
ttaagtaatg gggaaatagg agtagagtta ggaaaattgc ctaggagttg gggagttgtt   14640
tgcactgagc caagccttaa gatactgaca gaatcaggaa ggagtcattg tgaaaagtga   14700
agtagagttt acctcctcaa aagactttcc tcccccatct aatcaggaat aaatagtaac   14760
ttctcttagt agcaaaatgt attcaaagac cagcgctaac attcttaaat atctgctaga   14820
cgtaataaag aaatcaatgt actttatgtc cttagctccc acaatttagt ctaaatgttt   14880
gctctggcat gcttatactg gtccaggcaa gcattaggtc ctatcctgtt cctcttcctt   14940
gtttgtgtct cacatgtccg tgtgaaaaga ccaccaaaca ggctttgtgt gagcaacaag   15000
gctgtgtatt tcacctgggt gcaggcgggc tgagtccgaa aagagagtca gcaaagggtg   15060
gtggattatc attagttcct acaggttttg gggtaggcgg ttgggttagg agcaatgttt   15120
tgccagcagg gggtggatct cgcagagtac attctcaagg gtggggagaa ttacaacgaa   15180
ccttcttaag ggttggggag attacagagt acattgatca gttagggtgg ggcagaaaca   15240
gatcacaatg gtggaatgtc atcagttaag gctattttca cttcttttgt ggatctttgg   15300
ttgcttcggg ccatctggat gtatacgtgc aggtcacagg ggatatgatg gtttagcttg   15360
ggcccagagg cctgacagtt tgaaggtgtt tttacctttc tcagcattcc acgagttact   15420
tcttcctttg ttctcctctg cctttgcctc ttttaaaaag ttctaagttg ctagccagtc   15480
gggacaaatg cagaatgtca ggcctctgag cccaagctaa gccatcgcat ccctgtgac    15540 ttgcacgtat atacgcccag atggcctgaa gtaactgaag aatcacaaaa gaagtgaata   15600
tgccctgccc caccttacct gatgacattc caccacaaaa gaagtgtaaa tggccggtcc   15660
ttgccttaag tgatgacatt accttgtgaa atcccttctc ctggctcatc ctggctcaaa   15720
aatctccccc actgagcacc ttgcgacccc ccactctgct cgccagagaa caactccact   15780
ttgactgtaa ttttccttta tctacccaaa tcctataaaa cggccccacc cttatctccc   15840
ttcgctgact gtcttttcgg actcagcccg cctgcaccca ggtgaaataa acagccgcgt   15900
tgctcacaca aagcctgttt ggtggtctct tcacacggac gcgcgtgaaa cagaatgtga   15960
ggtcccgttc cagccaatgg aaaccagaca cagcagtagg gtggacgcgt caggttataa   16020
atgaccctgt ctcctttgct cagtgtactc tcgtggcaaa actgctgccg agtgtaccct   16080
ttctacagaa agtataaaaa tgaccttgcg taggaaatta aatttatgtt caagtgccat   16140
ttctttatgg caccggggag caagcatttc aaacatcatt tgtaccaatt ctaagttaaa   16200
tttggactaa acaaggtctt attaatagca aaggataatt gaaatcccaa acttacaagg   16260
ttttcaacaa aagtaaagtt tgctaaaagt aacagtata acatgtatta tcctaacttc    16320
taatgttgtg accttaggct gtctagtcca cagacataaa ggaagttcgc tttggaaaag   16380
aatggttatc atctttgaga gaaaaaaaat tgtttcgaag gtttaagcaa gttttgaaat   16440
```

```
attcattgta aaggaaacat attggctaaa gttaaagggg tatcttccag ttttctgtg    16500 aactggacat taaaataaaa gcccagtggg tttttcttaa agcgctaacc tgctctttaa    16560
caaaaattac gaaaggttaa aaattataaa agtttaaaaa aagagtctgg aaatctcacc    16620
ttgtggtcag accttaaaat tggatacata tgtctacaag gttttattaa aatgaagttt    16680
aacacgaata acacactaat gtaaaggtga aatttagctg atctggtata aaatcacaca    16740
ggaagcactg tcaaatataa aatggtgttt ggctttcttt ggtctaaaaa ctaataaaaa    16800
taggtactaa aggaaatttc tcagcaagaa ggcactaagg actataaaat ccactgctga    16860
tgtccccacc tttaaaacaa aagatcaatt tttagaaatg atatacttgg tttatcctcc    16920
acccttaaaa caaaaggtct tctagcacag gccctgccct gagagtttcc agtacatcag    16980
caccagcctg gggatcccgt tctcatcaaa gggtggaaaa aagggaaact ggagccagcc    17040
tgggaaggac cctgccttgt gctgctgact accgagattg ctattcgtac aacggaaagg    17100
gggtggacac gtcccaccag agtcaagcaa gcaccattat caacagaatc atgggccatt    17160
gtttctggat caagccctac caaattaaag ctaaggaaag ctgagtctat ctctttcctt    17220
tcctttccta acccagtgcc tatatccatg actattccta ccactagcaa ctctaacccc    17280
actttagaga gtttctgtgg tttgggagca gaggtcactg gaagggatcc tataggcttc    17340
aaggtgcgct ttgttctccc tcctccacct cctacgactg cccctttccc aaacctacaa    17400
catcaaacta tgcctcgcct catgccaaat gacacaagca agttcttaga agtagaaata    17460
ggagacccaa ggcaaaccct agccattgaa agagggtata agacataaa tgccggttaa    17520 aacggattaa atatcccgtt cgcactttaa gcaaagtga ccattaagct tgtgggcgcg    17580
gtaggccaga ggctcaggat gcctcctttc cactgggacg gtcctcaaat caagcggaca    17640
tggagtgcgt ggtagctctt ttcgaagatt ccaccacctg gaataacgaa ttgtgccaag    17700
ctctttctct gctatttcct gaagttcagt gccctgtggg tcagccccg agggccatcc    17760 agccttcatc ttccaaaacc aattttacct cgtgtctcca acaacgaggg gaaaaaactt    17820
ggcattcctt ggagacttaa aaggttgcag taaagtcagg cacctccaaa agctgaccca    17880
tcggtctgcc cttattcatc cctgagcgga tgtatggtgg tattatggag gacctttact    17940
ggacactctg ccaaataatg agagcagtac tgatgctgta gttcagttgg ctatcccttt    18000
tactctggca tttcatcaac cagaaaaaga aaaaaaaatg tagcctcaat tcttacctct    18060
ttaacaacgc taataagtat actctttctt cgtaggtgtt atgtcgtacc atacatccag    18120
gagttcatca aaacaactaa gccaagacat gctaagaaag tttgaagagg aaaactatac    18180
agtaaaagag gagggaattg taggaagtaa aaagtttctg cttcaaagtt cccttcttg    18240 ttaaagaata aatcataagt cttagaaata atagattctt ttaaagacta attttcttca    18300
agcctccttg ctttgtgcta atagctcttt gttaagccct atcctatgta actgttggac    18360
atgctcacag acacattcca gctcacagcc tatgcccctt ccttaattgg aaatgttatt    18420
gcttcctgaa acctttgta agcaacttct ttgttcttcc ttgcacttac ctatttagga    18480
aagtttcaaa tcgggtatca gtttaagata gtgaggtccc actccagcca atggatgcag    18540
gacacagcag taaggacaac ccaaatgcgt aagggataaa tacatctgct tttcctttgt    18600
tcaggtgtgc tctcaccatt gttccatctg cagttgagca ccctttctgc agaaagtaaa    18660
gatggccttg ctgagagatc ttttgtctct gtgctgactc ttcttcgcag caccgattat    18720
ctatttctaa caattttggt atttctaaca ggcccacaca cactgtgtgg gccaagctgc    18780
ttcactcagt ccactgatca aatgctcatc tcatcctcac agacacaccc aggatactgc    18840
```

```
ttgaccaaat atctggacaa cccatggccc agtcaagtcg acagaccaaa tgaactgtca   18900
cagacagctt ctgtccttgg aacggggtgg gattccacgg actctctccc ttcacagtgg   18960
agatgctcag tcagcaagct gccagaagtt cagagctggg gaagatataa agaggactgg   19020
gcatggaagc tgcaggaact agtcaggaac tgggagtacc taggagtcag ctcctgagtg   19080
tgcaggatca tggtgaaata gaaagttaga gaaggaagag tgtgtcaata tcagagcatt   19140
gtcttatagc acaggactta accctctcct aaggttccag ggagacagtg ccaaatcatc   19200
acttgagtgg tgcttagaag cttcagggca aaagagccaa ccctaagtac atttgtctac   19260
tggggctgcc atcacaaagc accgcagaca gggtggctta tacaacagac tcattgtctc   19320
acaatcctgg cggctggagt ccaagatcaa ggttttgcaa ggctagctcc tcctgaggcc   19380
tctcttggct tgtagatgac cggggccttc tctctgtgtc ctcacagggt cttccctcag   19440
tgcgtgtccg tgtcctcacc tcctcttgta agactccagt cctatgagat taggacccac   19500
tgtcatgaac tcatttactg ttgattacct ttgttttatg ttttttgttt ttttgagaca   19560
gggtcagtct ctgtcaccca ggctggagtg cagtggtgca atcatggctc actgcagcct   19620
caaactcctg ggctcaagga atcctcccac ctcaatctcc caagtagctg ggactacaga   19680
tgcataccac tgtgcctggg tgtattagtc tgttattgca cagctataaa gaaatacctg   19740
agagtgggta acttataaag aaaggaggtt taattggctc acggttcata gctgcttctg   19800
gggaggcctc aggaaagttt cagtcatggt ggaaggtgaa ggggaagcag acacgtctta   19860
cacggccaga cagttcctcc tacactggct gacactctct cctgccacct tgtgaagaag   19920
gtgcctgctt ccttttctgc catgactgta agtttcctga ggcctcccca gccatgtggg   19980
actgtgagtc aattaaacct cctttgttta taaattgccc agtctccggt agtatcttta   20040
taacagtgtg aggatgagct aatacacaca ggaagcagca atgccatcaa agagccaggg   20100
gccttgactg gcagaactag tgagaccatc accaaaacat ggcattcctt gggcaaggca   20160
ggtgcgcagc cagcaaggta ttgcttaatc tacatgatca aaagacatca ggatggttgt   20220
tcaggaggct gagaacagcc atcctattat ggctgagttg tgtccctca aaatttatat   20280 actgaagtct taacccccca ggacctcagt gtgtaagtat ttggagaaag ggcctttaaa   20340
gatgtagtta aattaaaatg aagacattag ggtgggccct aatccaatct gactggtgtc   20400
cttgtaagaa gaggagatga ggacacatgc agaggcatga ccacatgagg acacagggag   20460
aaggtggcca tctgcaaatc aaggagtgag gcctcgggag gaaccagcac taccaacacc   20520
ttgatctcgg acttccagtc tccagaacca tgagatgatg aaagtctgtg tttaagctgc   20580
ccagtctgtg atattgtttt gcaaccctaa tagatgaata catacccaa tgaaaaagca   20640 tgatctcttg cccagtttct gcacctgaga cagttttcaa acccaaaccc cactgattga   20700
aggagggatt aggtcccagg aggacggacc ctgcagtacc atagcaggct cccccagtcc   20760
ttccccaccc caccactaaa ggtgtatttc agtaactgtg cactaggaaa agggcaatgc   20820
ccagggctgg gggactccgg gaccaagttg acactgagag ctggagtcaa ggtaccatca   20880
tgggcccact agagtagggc gtatggaggc cagcaaagtg caatcctggt ccacctctag   20940
ctcacactga gtcatccctt tgcattccca gaatgctgca tattccccca gaccctaaaa   21000
gtacactcag acaatcttgg tagttggcag aatcctcacg taggctcatt gtcctgtagg   21060
gtaaaaacta tcatagtgtt accaagtaga aacttctgaa actgccccacc accttagcca   21120 aggcaataca ccaaaaagaa aatctcattg gtggggaatg gcagagatgt gggcccttt   21180 ggaagacttg aaggttgcag gtgaggcgat tcccatcatc tcccccattt tccagagaat   21240
```

```
gctaacagac tactgtcaac ttgtgatggg aaattttatg cgtccacttc actgggccat    21300
ggtgcccaga tgtttggtta acattattc tgggtgtgtc tgcaaggtgt ttctggatat     21360
gcttagcatt tgaatctgtg gactgagaaa agcaggtcac tctctctggt aaaggtgggc    21420
ctcatccaat cagttgaagg tctgactaaa acaaaaagat taagcaagag aaaattcgct    21480
ctccctgcct gtcttagtct gtttatgttg ctataaagga atattggagc ctgggtaatt    21540
gataaagaaa agaggtttat ttggctcatg gttctgcagg ctgtacaaga aacatgacat    21600
ctgcatctgc tgctggtgag ggcctcaggc                                     21630

<210> SEQ ID NO 11
<211> LENGTH: 37113
<212> TYPE: DNA
<213> ORGANISM: Homo sapiens

<400> SEQUENCE: 11
tgtgggctcc cctctgctga tgggttcccc tctccagctg tggcttccct ctgctgatgg      60
ggtcccctct ccagctgggg ctccctccac tgatgggtt ccctctacag ctgtggctct     120
ctccactgat ggggtcccct ctccagctgg ggctccctcc actgatgtgg tcccctcttc    180
agcttgggct ccctccactg atggggtccc ctcttcagct ggggctcctc tccactgaca    240
gggtctcctt tccatctggg gctccttgg ctgatgaagt cccttctcca ggtgaggctg    300
ctctctgctg acagggtccc ctctccagct aggtctcctc tctgttgata gggtcccctc    360
tccgggtggg ctcccctctg ctgacggggt cctctgatgg ggtccctact ccaggggggc    420
tcccctccat agatgagctc cccttcctgg gttgggtgac cctccgccc tatctgtgtc     480 tgcaggttgg ggctaggcag tgctggccag catctgacaa cctccccttt ctgttcttgg    540
gcactgctca cttattcagg tctcagccag gcagccctc caatggtaat cttcagagtc     600
cccttcagca acacagcttc ccctctgtgg cccagctcat gctgaagtaa acaaggcaat    660
gtcattaacg gctggtatca gcttgtacgg ggaaccagtg gccccagaag cctctgggga    720
ggcccaggct gtgaggatca gggtccgga agagcctcta gagcgggaga aagaggcctc    780
aggggtccct cctcacaggg gatggtgaca acacggtagg gaatggaggg gtcagggctg    840
ggtccaggac acggtgaccc tggccagaaa aggccgggcc tggctggcac ccgcacgaag    900
ggaacggagc cagtgtggaa aagcaggccc gcgtcctctt ctgcactccc agcccctta    960 aactacacac agcttgtagg aaggggatca gaggccctg ggcgtcccat ggctatgctg    1020
cacctgggga catgaagcct agggtagctc agccagctct ggtcacggct gacagacagc    1080
ctcaccccaa cagcctcacc catccctcct cagggaacag gtcctaaca agctgctttc    1140 cccatcccag tgttgaacaa aaactcatgg gtttagacaa gagtgaaggt gactcctcca    1200
ccacccatcc cacctccagc aggcagccac cccaaaatt attgatttat taataaatca    1260
atgacaggtg ccagccagcc ccacctgtcc ccaacctgca aatgcagaca ggggtcactt    1320
ggtccaggga gaggagaccc tcagtggagg ggagacaccc tggagagggg accccatcag    1380 caaagggag cccagctgg agacagtaaa taggcagact attcactgtc ttcccctca    1440 agccaggccc acagagtcac agagtatagc caccagcctc ctgggccac ccggaggcc    1500 ccaaccacac tcccctgct cagctcagcc cggatttctg gattctgctg cctgccaggg    1560
atcctgagga ggagatggta tcagagcctc accagccctt ctcataccca ggagtcctca    1620
tgatgataac agtgtgtgcg ccaggctgtg caggtgctgg ccgggatcct ctgagggac    1680 gagatctcca tgggagggca ccactctgat gtccatcctg ggcttccgtg gccctgcctg    1740
```

```
gccactgccc gctgctcttg gtcaagatca tggaccctca gaggccaacc aggcctcagc   1800
ctgtgcctac agcatcctct ctactgccgg gcttctgaat tgctccttcc tcctgtctcc   1860
cacccagagc aagaacgaag gggaggcccc cagagccctg cagcgccggg agagactccc   1920
atccccaccc cgcatgccat caacacaaac tgccggagag tttaggggat cccacgactt   1980
ggggtctcca aagagacccc cgggacatct catcgagacc ccctgggca ctgcatgctc    2040 aggcttccca ccccctggccc accccatggg gtgtgcccag tcccgcatct caccccatat  2100
ccatgcatgc atgcatgaac ctgaaagcac cccacaccct ctggtgctca gtcctcccct   2160
cctccctggg gtcccctccc ctccctgccc cccaagcctt gcatccccct gcaaacctca   2220
caagggggaa ctatttctgt cctgaaagca gagagggccc ttttcttggg acctctccgc   2280
catctctgcc tccactccca gctgctgtca gctctggcct ggcccctgca ggaagcaatc   2340
actggtctcc ctgttcccca tctggcccca aggtctgttc ttgcccttcg accagagagg   2400
tttgaaagca caactcgggc cctgcgtgcc ctgctcccca gggctccaca cctctgagca   2460
cccgcgcagt aacggaggct cccagccccg cctcgcccca gggtcccctc caacactctc   2520
tggccttggg cctttgctat acccggggcc tggaagggcc ccctcatccc caagtgtca    2580 ggcaaaggtc tcagagcact gtccctgccc ggcgtgcttg gtcctgactg ctaggcccca   2640
aatcattcct tttcccatta cctcttggtt tctctgtagc tggggtcact accccaaatt   2700
cttgaattga ctgacgtgtc caactatttc atgttttccc cctctacact gggagcccta   2760
caagggcagg gccccctggg caagaatagt gccagccagg agcccctgga gaagatagct   2820
acacatgtgc cccaggcccc agatggcact cagccctgcc tgtcaatgct ggacataggg   2880
cagtttttat cctggctttc tacacaagga ggaaagacta accatgccag cgggcagcgg   2940
ccggatcacg tatgtcagta gaactctgac ccctgagaag cctggaagcc aaaccacacc   3000
tctgtagcaa tcacgccaca gactcaggcc acggctaacg gctgccagtt cacctatttt   3060
tgcccccaac tcaagaccaa ctggaggaag gcaaatatgt ccctgacgaa gggtggccgc   3120
ctccagcctc cccagcccag agcctcagcc tccccagccc actgcctcca gcaacacaca   3180
tctgaagcct tctctgttgg ttggttttat tggtattttg gaagattgtt tgttttttgt   3240
tatgagatgg agcctcgctc tgtccccag gctggagtgc agtggcgcga tctcggctca    3300
ctgcaagctc cgcctcctgg gttcaagcca ttctcctgtc tcagcctccc gagtagctgg   3360
gactacaggc acccgccacc gtgccaggct gatttttttg tattttagt agagacgggg     3420 tttcaccatg ttagccatga tggtcttgat ctcctgacct catgatctgg ccatctcggc   3480
ctcccaaagt gctgggatta caggcgtgag ccactgcacc tggcctttgg aaggtctttt   3540
atacctttat tgagataaaa ttcttatgac ataaaactta gcataaactg tagacttagt   3600
tggtgtgact ttagagtagt ctcagaattg tgcaaccatc accactgcct acttttagaa   3660
cattttcaac atcccaaaga cagaaccccg taggcacctg ttagcagcca ctccccaccc   3720
agtccacgaa gccccaggca gccactcacc aatctacttt ccattaattt gcccattcta   3780
aacacttgaa aaaatggta tcacaatggt cttttgggtt tggcttcttt ccctcagcat     3840 catacccctca aagttcatcc atgttgtagc tcgtatcggt acttcattca tttttatggc   3900
tgaataatat tccactgtat ggatagaccg atattttgtt tatttattta ttcattgatg   3960
aacatttgaa ttgttcccac ttttttagcta ttaaaactag tgctggctgc gtgcagttgc   4020
tcatgcctgt aatcctagca ctttgggagg atgaggcagg cggatcactt gaggccaaga   4080
gtttgagacc agcctggcca acatggtgaa accccatct ctaataaaaa tacaacaatt     4140
```

```
agccagacac ggtcatgcgt gcctgtaatc tcagctactc aggaggctga ggcaggggaa      4200
tctcttgaat ccggggggca gaggttgcag tgagccaaga tcgcgccact gcactccagc      4260
ctgggcaaca gaccaagact ctgtctcaaa aaacaaaaca aaacaaaaca aaacaaacca      4320
gtactgctat gaacatgcat gtgcatattg ttatacagac atatgctttc atttctcttg      4380
gatacacaca cacacacaca cacacacaca cacacacacg tatatctagg                 4440
actggaattg ctgattttta tggaaactct atatttagca ttttgagaaa cggccagtct      4500
gttttccgaa gtggctgcac tattttgcat tcccaccagc aatgaaggag ggttccaatt      4560
tctccatacc tctgccaaca cttgttattg tctgtctctt ttatttatag ccatcttgat      4620
gggtgcatcg tggtatctcg ctgtgttttg atttgcattt ccctgatgac taatgatggg      4680
gacatctttt catgagctta tcggtcatat gtacatcttc tttggagcaa gctctattct      4740
aatcctttgc ccatcattaa aggtaggtgg tttgtcttct tgttgataag ttagagttct      4800
ttacatgttt agatactagt cccttatcaa atagatgatt cacaaatgtt tgctgtcatt      4860
tcttgggttg tcttccact tccttgatgg tgtcttttca cgcacaaatg tttttagctt       4920
tggccaagtc caatttatct atttttctct ttgttgcctg tgcttttggt agtgtatatt      4980
aaaaaccatt gtttaacaca aggtcaccaa gatttattcc tatgttcttt cctaaggatt      5040 ttatttttc ttttctttt tttctttt tttgagacaa agtctctctc tgtcgccaaa          5100
gctggagtgc aacggcacaa tctcagctca ctgcaacccc tgcctcctgg gttcaagcga      5160
ttcttctgcc tcagcctccc gagtagctgg gattacaggc gcccaccacc atgcccagct      5220 aattttgtg tttttagcag agacggggtt tcaccatgtt ggccaggctg gactcaaact       5280
cctgatctca ggtgatccac tcgcctcggc ctcccaaact gctgggatta caggtgtgag      5340
ccactgcgcc tggccttcct aaggatatca taattttagt gcttacattt aggtctacga      5400
tccattttga gttaatttt gtgcacagca tgaggtaggg gtccaacttc attcttttgc       5460
acatggatat ctagttgtcc cagcaccatt ttctgaaaag actattcctt ccccattga       5520 attgtcttgg taccttgtc aaaaatcaac tgatggccgg tctgaaggta gtgagttatc       5580
tcaattgatt gttcacagtc agttacagat ggaacacctc gttctactct ttcccgcctt      5640
ctcactgctg cacttgaaca gtctttaaaa aaatcaattg accataaatg caaggatttg      5700
ttcttggagt ctcaacttta ctgcattgat ctgtaggtct atccttatgc cagtaccaca      5760
ttgtcttgat tactgtagct ttgcagtaag tttgaatcag gaaatgtgag ccctccggtt      5820
ttgctcttct cttttctagat tgttttggct attctgaaac ccttgtattt ccttatgaat      5880
ttgaggatca gcttgtaaaa agacagatgg gattttgata gagattgtga agctatagat      5940
gaattcggga gtttggccat cttaacatta tgtctcctga tccatgactg caggatatct      6000
ttccatttaa ttcgatactc tttgattcct tcaaaaata ttttgtattt ttcagtacac       6060 aagtttatg catcttttgt tgcatttatt tctaggtatg ttcttttgc caatattata        6120 aatgagattg tcttcttcac ttcattttg gatggttcat tgctagtgta tagaaataaa       6180
atcgatgttt gtatattgat cttgtatcct gccacattgc tatgcatgtt tattagttttt     6240 aagggtttta gtggattttc tatatataat gtcatataat cagcaaatag aaagtttaat      6300
gtcttagtcc ttttgagctg ccacaacaga ctaccataaa ctgagtggct tataaacaac      6360
acaaatgtat ttcccacagt tctggagact gggatgtcca agatcaagac acccgtaggt     6420
ttggtgtctg gtcggggcct acttctgggt tcatagatga ctgtcttctc gctgtgtccc      6480
ccccatagtg aaaggaaggg gcccagggtc tttctaaggc ttcttttata aggacactaa      6540
```

```
tccaatatag gaaggctctg ccctcataac ctaatctccc aaaggcctca cttccaaatt    6600
ccatcacctg gggagtaaga atttcaacac tgggggdaca cagatattca gacatagcat    6660
ttttcttctt cctttctaat atgggtgccc ttgacatctt tttcttacct aattgccctg    6720
ccagagcctt ccagacagtg ttgaatggaa gtggggagca ttcaccccac cttactcctg    6780
atcataggdg aagaactatc cggctttcac cactgagcac cacgttagct ggggtatttt    6840
tgtcagcgct ctttatcagg tggaggcagg tcccttctat ttctagtgag ttcagtgctt    6900
tttttttttt ttaatcaggg aagagtgtga gcttgtgttt gggtgccttc cctgcgtctg    6960
ttgagatgat cttacggttt ctgtctctta ttctattgat atggcgtatt tattaccttg    7020 gttgctttt ggatgttgat aacatccaaa ctcttctgcc accccttta atagaaagct     7080 gtacaactcc ccaacctgcc tgggcgtgtc tgcccaagat gagtgctagt ggccgactcc    7140
ctgctagagt gagcactgca taaacagcct ctgcttgtcc tcatttgagt gatcttcatg    7200
tattccacga gaaatcaagg cacaggggtc tcatggtctc atgaatggct ccaccaactg    7260
aaggtgtgct ccatcggggc tgtgagtcac ctcacgccag gcagaaaggt ctctctgtca    7320
aacatggctt caaggaacca gggacctggt tcctcccaca ggccaggccc tgcccctaag    7380
tgcaatggga atatatgcac atgtcacctg tcccaaaatg ctgggagatg cacttctgc     7440 agatggggaa actgagggac cagcccgaag tcacggggag gggaagactc ctacacacag    7500
ggaggagaag aacccagccg ggctgcaaac gcctgccctt cctcaacgtg cctccggctg    7560
tgcccacatc gctccagcag ctctgccttc ctcaggcata agccttctca gggcagggga    7620
ggcccaggga gcggcgctcc catcccaggc cgggctgctg agcaagcccc tccccttct    7680 cccctcatcc tctgacagag tccacctgaa tatttgtcct ggagccagga tggaagctcc    7740
accaggccca gctaacaaca ggaacccttt cagacgcact tctgggtgcg tactgtgcca    7800
gtatcacaca gacacaagcc atgtccttgt cagccatggg atccccaagg tccccatgag    7860
gtcacaccag tgggccactg ggaagggcac ttcagatgtg gagctcccat gggccaggcc    7920
ctgcgaagtg gtcctcctac cccctcatag ccagtcttcc ctgtgagcct gcaagtgact    7980
gtgaatgtga gttccactct ggagctaaga cgggctgctg cccccgcaat cagatgtcag    8040
gcccatgaag ccctccatca tcccactgca gtcagaataa aatgcagcct ccctctggcc    8100
tccaggtccc aaggccagcc cccctgcctc ccaggctcac acctgcccct aacctgtgtc    8160
cagccccttt cccctggctc tgtctcctgc ttcccttgtg ttcctccaac ctcacctgtc    8220
tgtctggagt gctcctcccc ggctctgcct agctggctcc ttctcaggca tcagggcctg    8280
gatccactgt ggctcttcca agcctctgca cttggagtgc ctcagcccg tggttgagga     8340 gtgccccaac cctgtgaccc tctagcaagc atcctaggaa ttccgtccct ccccagcact    8400
gatatgacca tcgtgctgtg acacgtgtca tctccgccag agttgcagat cctccagggg    8460
aggggtctgc tgcctggctc ccacagccag ggcctggaac agtgcctgac acacagcagg    8520
cacccactaa atatttgatg catggctgaa gaggacaggc aggctggctg ctggctgggc    8580
atggcctgct tctgaggctg gtggtcaagg acacagtgtg catggatctg cccctcctc     8640 ccacttcctg agagtggagc cagtgtctcc ctccacctac caccccctgc tgaggacaca    8700
gctcacacct ttaacgggaa atgtcccat cactggggac agcagggagc tgatgggaga     8760
gcaggtgtcc aggacatcca gagaaatgtt tcctcacact ggaacccttt tctattccct    8820
tctaaacaaa aagaatcctc gaagactctc aagtgaccat atagtgtctt ttcttataat    8880
gtcacttcga caggcacaaa atgtaaaacc aggcataaac tactagtgct tgcagttctt    8940
```

```
acgcaggcat gaagccaaaa ccagtttaca aattaaccac caagaaaacc ggtagagcac    9000
agatgatgac gatagagctg ttttgtccaa tgtgagcgct actggccacc cagggccatg    9060
tgaatttaaa ttacgatgaa acacaatgaa aaatttggtt ccttgtggcc acatttccag    9120
tacccagtag tcatctgtgc caggggggtta tccaggtaca gaacattccc atcgttgcag    9180
aaggttctat cagctagcac tgggttggac gacacttgcc aagacgagct ggctagagga    9240
tggttctccg gacctggtcc cacgtggttc ccaggtaagc ccccgcccag gatgcagccc    9300
cgttgtccat cagttttctt ggagagggca tgggaaacct tcgtcagtgt gtcatctcct    9360
gcaaaggcct tcgctccttc ctctggggag aaagcaccct tcactctctg aatcattagc    9420
ccaaagcagt aagtgcagca ggcctggccc cacaccttcc ggaagagcca cggtgtgagg    9480
ctggcatccc tggggcacga cacaaccagg atgtagacga aatagatgca atatctggag    9540
gttctcctat aggtgtctct ggcctcctgg acacttcaca ctgttctggg agctgccctc    9600
tcaggcccca gtgacctttt cagatgcaga ctcccacagc atgggtcagc aattctcccc    9660
ttccgtgaga cagggattgg ttacctgtac taggaccttg aggccaacac tgactagggg    9720
gcctcatgcc tgcccaggtt ccagccccgg agagcaatgt gagcaaagct tgctgtcttt    9780
gcaaagccaa ccactgtggc atcaactcct tcaggaagcc ctcccggatt gtccaaggtg    9840
ctcacctcct ttggggagcc ctcccagatt gtccaaggtg cttgagggag ggaggaatgg    9900
gttgttctcc cggcaccggg gctgcactcc tgggcagacg ctgcatgcct gtcctcaggc    9960
gcggccctgc tgccaccccc ttgggggctc ggagcgcgac agcagcttgg ggacgcctcc    10020
cgcgcccagc acggtgcacc tgggccctga ggtcctggcc gaaacgcgcc aagttggggg    10080
taggtgcagc gaccccatac ccctcggctg cgcgccctgg cggcaggagg cggggccggg    10140
ggcggggcgt gagctggccg ggggcggggc ctatggaggg gcgggaccgc ggcgccctat    10200
aagtactgcg gagcgcaggc gcgcgcccgg ccagagagcg agcgcgcaac ggcggcgacg    10260
gcggcgaccc caccgcacat cctgccaggc ctccggcgcc cagggcgcac ggcgcgcccc    10320
cgtgccggcg gcccctgcgc ccatttcttg gcgcccccgc ccggtcggcc cgccaggccc    10380
ctttgccggc caccagccag gcccgcgcc ggccgcccg ccgcccagga ccggcccgcg     10440
ccccgcaggc cgcccgccgc ccgcgccgcc atgggagtgg agggctgcac caagtgcatc    10500
aagtacctgc tcttcgtctt caatttcgtc ttctgggtaa gggctgcgcc gggggccggg    10560
gcgggagggg gcaggcacac actccacgtt gggcaggtcc cgcggcagcg tgctaggccc    10620
cgcgggcgca gcgcgggccg cgaagttgtg gggccacctg tgggctccag gagcggggtg    10680
gggggtcgcc cggggccacc gcgcccccg acattgggc tgaggctgc gagccgagtt        10740 tcggggcctc tgtgctcggg ggcccacctc tgcggccggg ccggggcttc tggggccgc     10800 cgggcagttc ccgctgtggt ggtgatgggt gcgtggtcg cgggtcggga cccgagtacc      10860
cggccgcccc tcagctaagg aggggcctgc gcgggtccct ggccgcggat tccggactgc    10920
tgcttcgcgg ggacgagggg ggggctcgcg ggcgggactc ctggcgcccc gccccatga     10980 gctcatcaag agccgccgcc cctggatggt ggggcggggg cgcacacttt gccggaggtt    11040 ggggcgatc cgcctcactc tttcccagc ccagctcact ctccaatctg cggtcaccac     11100
ccgagacctt cctgggggtc gcgcctaaaa ggagcgcaga ctcccgccgg gatggcccag    11160
aagctggggt gcgcgcaccc tggccgtccc tgcctgggag ccgatctccc tctcctcacc    11220
cagacacgtt ccagcggagg cctcctccca gaagggctct ggaggcctcg caggagtggg    11280
gatcccgcgg ttctgagttg gcacaaggaa gagagtggca ccaggggcct ggagtggatg    11340
```

```
gcagggtccg ggagtggggc cgctgctttg caagaggggc ccccacgctg ggcatctttg    11400
ggtgccagcg tgggtggagg agggtctttt gctgagaatg gctttctcct daccgcagtc    11460
tttgctgctg ggaagtgact gatgggcttt cgccttttgt ttccatttcc tgtcggtgtt    11520
agaattgggg aggggtgga aatcccttct tggcctggaa ggactggagt gggtgtccat    11580
ggccgcggcc tccccgtggc cacgcccctg gcatagact gcaagcccct ccccgtgccc    11640
cccaggctgt caccccttc tcgtggaaga ctcggctgat gtcccagtgg accgagtgtt    11700
tctcaagttg aggcagggag ggcaaacttt ttaaatggcc cctggagcca gtgtgtggga    11760
ccagagacat ctgtttccca tctggacggc tgaggatccc agtgcggatg attatttgga    11820
gggggaagga cggaggctga actgaactct cagctgggag atgagtgggg cagtcacatc    11880
ccaccttccc caagccgggc tgttctgcac agcctgcttg gacgctggt gggagtcact    11940 gtggctttcg gcactgccct ggcagtgggg gcagctaggc catttgggag gggctcgctt    12000
tccccaggcc gggccctggg acctcagccg ttgcttagtg gtggcctgct tcagcccagg    12060
catgtgggag aggcaccaga cacaggatgt ccctctgcca gcccctgaag ccccgtcccc    12120
tgacgaggcg agtgtggacc tggggtggg ggctgaggga gactgtggac ctgggggtgg    12180
gggctgaagg aaggtgtgga cctgggggca ggggccgagg gaaggtgtag gcctggggt    12240 agtaggggct gagggagagt gtggacctgg gagtaggggc tgaggagggg tgtaggcctg    12300
gggtgggggg ctgagggaga gtgtggacct gggggtaggg gctgagggag agtgtggacc    12360
tgggggtggg ggttgaggga gggtgtggac ctgggggcag gggctgaggg agagtgtgga    12420 cctagggca gaggctgaag gggagtcacg ggaggggact tctccggagg tggattttg    12480 ctctctggac ggtgtgtcag cactgggtga gccctcctg cctgcccagg ctgagaggtc    12540
tccctggcag cccctggga gtgtcgccag ggcgggcctg gaagtttccc aggcagctgg    12600
ggtggagacc tgacacatcc caagggtgct tgttattaag gctcaaggaa atgtctctga    12660
ggcctcaccg ctcctctccc cagggcctgc tccctgcaaa gcattgagaa ctgagtccgt    12720
ccacagtcac tgtggaccca cccatccact ggggctcagt ggtagccagc aatgccaggc    12780
tgggtgaggt ggggttggtg ggcaccaccc tggtggaccc ccctccaccc tggtgtcgca    12840
gggtgtgtgg ctgagagcac agtgccatgg gcttgggcct ccttggtgga gtccccaaca    12900
cactgctctg gtcctgggcc tcggccttcc ccgtctgcag tgggggccca cagtgagcct    12960
acctcctggt ggtgttggtg gatttgctga catgcctgag tgttgacagg gggcttggtg    13020
caggaagggc tcagggcgtg ggtgttggcc aggggtccaa agggacctct gcctcagaga    13080
gcccagccca gacaggcagg atgtgcagtg ggaaggggc tgcgggaacc ctgcagggtc    13140
cagaaggaca cagtgcagtc ctgtgggctc tggggaggct ggtggggagg aggttgacaa    13200
tggatatctg ggtggggcac ttgttagaag ttccattta gagaggaaag aggccttgcc    13260
tgtgggagaa ggcagctggg gtagcctgac ctctttccca ggaaggagcc cacacacaca    13320
cgcacaggca ctcacacaca cgaatgtgca cacacacaca ctcccaccta cacacacact    13380
cacactcttg ctgtctccct tcccaagcca aggtgcgagg gggaaggtct gggcagcatg    13440
cacctgcgcc ctgaccgctt tggggccag tgagaactgg gctccctggg tgcgcggcgg    13500
gcccaagcag ggaggacatt gcagatgccc tggccaagca gcgtggaaat cctgtccctt    13560
gggtgggtct cggagcctcc atcagaggcg gctggcacct gagacccacc tgctgccagg    13620
agcagggcag gagagtttgt gtcccgggac agggaactgg cctgtgggag ccttgccttc    13680
ctcatctgtg taatggatat aagagtcttc tcctcggggg ctggccaggg agtccagaag    13740
```

```
aggtgtcacc agtccccgca gggagaagag cggtgtcccc cgcctgggac tggctgctcc   13800
cccaagctaa tgcagctggt agccacctcc cagtggcagg gcagccaaac ccggccggga   13860
aagagactga ttagaagcct cgctcacggg tatttctcgc ttccagacag cacatgactg   13920
tcatttggca cgtctttcgc cgtccttccg ggagaggggc tgcaaccctg gcaggcgctg   13980
tgggggaggg ggctaggaca tcctgtgcct ggtttcacca agtgggtgtg tggacttttcc  14040 ctggctcccc caggctgtct ggctgcacag ctttgggaa acggccactg ggtcaagcgg    14100
gccgagaaga ggaagtctgt ggtttgtctc tgctacagac tggccccagt gaggctgtcc   14160
agcagtgcag ggcacagagc aaaagcaggg aggtatgggc ctacttcccc ggtcgcccct   14220
gtggctggct gtggctctgc cgggtgctga caagtcactc gccctccctg cggtcaccag   14280
ggtgcatgcc cgaaagccct ccattctttc ctgggtttga gggtccttct cctgcaccca   14340
ccccagcgcc cagttcagct caactttcag aaatctggtt cacccccaat ccctttctca   14400
taactgcttc caagcccaga caaggagaca daccccaaaa gatccctacc cctatttccg   14460
cacctgaaat cgcaccacgg gaagagcttt gctcatagag tcaataaggc ttagagtcca   14520
ggcgcctgtg cgagggagca ggtcatcacc cttgtaccca ccgtggtttt agacaggacc   14580
ctgaggttgg ggtggggctg gggctggaga ggagccaggt gccctgcccc ttgcttgggc   14640
cccgtgtccc tgtgatccag gctgggcgtg ctatgggtgc tgggtgatat ccagccctg    14700 caggtgtccg ccttgttccc agcacccctc tgggcaagaa gaaccaggct ctcccagaaa   14760
tgggcttcag tgatctccac ttccaagtcg tccccacctg ccttgtagga cacagtggta   14820
cctggtatgc tgggcagcct tccaggaacc tctggactta ctcagtgtcc cccagcccta   14880
cacaccattc tttgtgtttc tgggcccaaa ctaagccccc caacctgggc tgcagagcaa   14940
gtgctgaatc atgagagacc cttgagggtc ctccaggtag gcccccagtg ctggaggagt   15000
cccctcaggc aggggccac gcccaagggt gtggaaggtc agctggcagc cggatctcac   15060
ttttggggct gtaggcttcc tgcactggcc gccaatgcca tggccgtggg atggccagga   15120
taaggcatct gccccccacc cccacccccc gcacaaggtc tttgagggct gcgggctcaa   15180
ggagttggcg gtagggctgg gggaccaggg gcacagagct tgtaagcgcc tctctccagg   15240
atgtgggtgg cccagcaggg gagctttgag agtccaggtg tgagattcca aatgctaggg   15300
gcctgagagg agggagccac cagcttggcc agagcctggt ggatcacgcc cccaccacgc   15360
cttgcccttc tctctggtca tgtgctctcc caccacgttt ggaaagttac tgcttccctc   15420
ttcctcagcc cctcgggctc ccagttatgg aagtggcgtg attcagagaa ggtaaaggat   15480
gggagggaga gggctgggtg atgggggacc ccgcagggcg ccctgtgctg ttacatggag   15540
ctccaggatc agggcaggtg ggcagcctgg ggtcctcact tctctcccca gccaggccag   15600
gtccctcaca gccctgccag gagcatgata tccgctgcgg tgcagaacta atctcaaagc   15660
tcaaacccag gtaacagtgt aggtaaaaca gatgacaggg catgagactc accccaggac   15720
aggcgaagga cccaggccga tgggggccca gaacagtcct gatcctggag ctccttcccg   15780
agtgggaccc caggggtttc cgagggggctt agagtagggc ttagaggctt agagtagggc   15840
tagggacttc ctggcttccc tgcctcggga acagctggtc ctggaagggg cttggtcctc   15900
ggggcactgg tgcccaccac ccctgatgcc tgggagacac cagcatcctc tgagcatgtg   15960
tgcgtcctcc tggtcccgag ggaagtgact cctcacatcc cccagctggc ggggccagag   16020
ggccagcatc ctcgcctgac acctatttt agatgctgag acaggcggct tcctcggggc    16080
caggggccct gtgagtggag cttccgcttc ctggcctagg agagaattcc tgctcctctt   16140
```

```
ccctccatgc tgccttttcg cccctggagg ccacaacggg gtcagagggg cagctgctca   16200
ccacctagga gggcctgaga gggccctacg tcacccaggg aggagtctgg ccccgtcccc   16260
aacctccaca cccaggcctg gcactgcccc ttcttggtgg gcagagagtg aggggttggc   16320
ctgcagggac ccaggctgga ggggccgttc acctccggcc cccagcgtcc cttcctggaa   16380
gcaccttggt gagcccctcc cctccttcac ccagtatctc caggggtact tcctcctttc   16440
cttcctgcct cagggcctca ctgtcctcct ggggagggtg tctcaggccc cagcacctcc   16500
cagtggctga gccgaatggg cacttcccgg tgtgtttccc atatgtgcag tccctaggtg   16560
tcggtgagca ggcacagagc ccgcagcgtg gccctgcctg gtgaccccc tccccaagag   16620
catcaaggga gggcctggac tagagacaca cagatgccca gcctgtacgt aaaggcgggt   16680
gagctgatgt accatcgtcc tcgtccccca ctggggtgcc tgggcaggac ttggggtgac   16740
cacttggccc gtctgggtgg gggtaaggta tgggtggggc gaccagatcc ctgccctttc   16800
ctgcagctgt ggggtgtgt gtgctggcct ggagagctcc cacccgaagt tctggctcct   16860
ggctgtccgg ggcctgcggg ggcagcgagc agctggcatg ggtaggggag ctgacctagg   16920
cctgcccggg cagcgcctgc tgccttttgc tccctttcag ctgcttcttg gaaacagcgg   16980
acaggctggg caggaaccca gtgtgcttgg cagccccct tttaaagtcg attctgttat   17040
ttattaattc ccaggaagga gaaagaaaga aacaatcctt catagagtac aaacactgct   17100
tttagtagcc ttgcaaggag ccctccagga accccacagg ttacctgggc tccatcctga   17160
gagccaccct ccatccccaa tccccagcag agcatcttgt ggggtggggc ggcttgtggg   17220
gcggggcgcc ttgggaggcg gggtgtctcg ggaagcgggg cgtctcggga ggtggggtgg   17280
cttgtgggggt gggcatttc ctggggtggg gcgtctcgtg gggtgggaca gcttgggggg   17340
tggggcatct cggaggcgg ggcgtcttgt ggggtagggc ggcttgtggg gtggggcatc   17400
ttgtggggta gggcggcttg tggggtgggg catcttgtgg ggtgggacgg cttgtggggt   17460
ggggcatctc gggaggtggg gcatctctgg ggcccggcca cttgggaggc ggggcatcct   17520
gggggcgggg catctcagag ggcgcctccg gaggctggag tatcttggga ggtgggagca   17580
ggtggcagag aggcttccca caggtgagct ttgagcaggg aggtgcctgt atggatggct   17640
ctgtggggag aggggtgaca ggagttccag attccggcac ttatgaaacc tcacagtgat   17700
ggagagccga gtgctgctgt gcaggctaag ttgtgtgcat gtcagcttct gcactttat   17760
ttccttgttt gtagacaagg cagagagaag ctgagatggg cctgaggtcg ccttggtgaa   17820
aggcactcag cagccagggc cttgggctgc cctccctcat caccgtgaaa gcgggactct   17880
cttttaactg acatcgggct ccatagttac tccagtccta actttgatgg atcctaaaag   17940
tgcacttcta aggacgcggc ttcggtgttt cccatgccgc tgcttgcccc tgggaagcgt   18000
tggctctgcc tcggaagaag ttagcgccaa gatggcagcc tggggtcttt ggggcccaga   18060
agaaacactg gccccgggga gttcagtcat cagggactta ggatgtgggg gcttttcaaa   18120
cagctttatt tagacgtgat tgacacacag taaatacaga tgtttaaggg tacaacttgg   18180
taagttttga caaatttata cccccgtgaa accatcacca actccccagg tgcccctggg   18240
gcccttggga tctctgcttc ctgccccctcc tccccgtccc agggcaacca cgggccgtcg   18300
ctgtgggtgc acacagcatg catttcttca acaagcggac tcagaaggca cttgcacatc   18360
gttgctgttc tgcctctttg cttcagcatg attacccaga ggcgcacccg tgccgtggcc   18420
tgcccgtcgt ctatgcaccc gtgctgtggc gtgcccgtcg tctgtgtggc atgcctgtct   18480
gtgcacccgt gctgtggcgt gcccgtcgtc tgtgtggcat gcctgtctgt gcacccgtgc   18540
```

```
tgtggcgtgc cgtcgtctg tgcacccgtg ctgtggtgtg cccgtcgtct gtgcacccgt   18600
gccgtggcgt gcccgtcgtc tgtgcacccg tgctgtggtg tgcccttcgt ctgttccttt   18660
tattgccggg cagggttgca cccacatgtg caagccagcg acggacccca ggttcacccg   18720
ttcaccggtc agtgggcata tgggttgttt cagtttgggg catttacaag aaacgtgcta   18780
gaacatttgt gtacaagtct tgtgtgaacc taagttcatt tctcttgggt aaatacctgt   18840
gcgtggagca gctgggtcat gtggtgaatg tgggtttcac tgcttaagca gcagttttac   18900
ataactgcca aactgttatt caaggtggct ggaccgtttt acagcccccg ttgtatgcgt   18960
cccagttgcc tcccccagca gcatgtggtg tggttggtct ttttcgtggc agccagtcca   19020
ctgggtgcgc tcggcatgtg gctgcagctt gacctgggtt tcctggtccc tgcaaggtg    19080 gagcatctct tcatgtgctt ttttgctgtg tgtggatctt gcggggaagg gtctgttcct   19140
gttttttgcc catctttcaa agattgggtt gccagttttc ttgctgttga gtttggaaag   19200
ctctgcatac gttcagggca caggtccttt accaggctct gccccaggtc tttcggagag   19260
caggtgtctt tcgcattcct gactctgggg aacctctagc cctgccacat ggggtttgtt   19320
atggggcagg ggcacctgtg cctttcccac cacggggctt ggggatttgg tgctgccatt   19380
gccctccctc gtaggtggcc ctagggggt ccctccgcct ccgtttcctc atccagaaac    19440
cggcagtgac catcaccacc attgttgtca cctagctcca gctcaaggtc cctgctgaag   19500
gtcggagagc ttggcatggc cccgtttgtc catgctaggg ctgggaagac caaggctcag   19560
gtgaggcctc tgcccagtgc ctggcactcc ttcttgcccc attttccac ccagggtggc    19620 tcccgactac ttctggtagc ctcggggaca gttgaggtgg acaggctggc gtcaccccca   19680
tttccggctg tccctcccac cccctcctgg cccagctgtt ctgccctatt aaaagtcaca   19740
tgggccctcg ggtccttcct ggtgttggcc caggctcttt caggccctgc aggccaggac   19800
cagccttccc tgcaaccctc ggcagaggcc tgggccggg gcttgtctag gggcagcctc    19860
cccatacggc cctggagtct gaacagaagc cccttcccag agcacagcaa gaagctgcaa   19920
cgtggcctga gtcccacca ttagcaggtt tggggtttag gctgagcttt gccatcacta    19980
cctttctgtt aggacggtat gcccattaga tgggatcatc ccctcagcgc ccaggctaga   20040
ggaggggtgg tccctgccca gccagggagg gctgggggtg gatgggcctc tacagagcag   20100
cttccgagcc aggcacggtt ccatgatcag ctctgtttta tagaggggga cactgaggaa   20160
ccgggagcct ggggaccttc cagtggcccc acagctcctg tggctgagtc agggtttgtc   20220
accaggcctc tgtggggatg aggctccccc atccacctgc cccactctgt cctggaacag   20280
ctctcaaaac ggtctctgga ccacagtttc aaaagaaaat aagcaatgtt ttcaaaggcc   20340
ctggaggaag ccagagttac cacggcaact ctcggcctcg ccacctcctc ccgccaggct   20400
gcatctggag ccagctcagg agggcagcag ggtgaggaca gccaggctct ctggggccac   20460
cccccagccc ccaccttcc tgcctctcct gcactgtcca cggccctccc tgtgctccca    20520
cgggtataat gggcacagaa gaaccaggag ctgtctgccc ctgcaggatt ctggaagcca   20580
gggccccctg gcctccctgg ggccttgtca tgtgaggggc acacgtgggg tcccagctgc   20640
cacatggctt ccagcgctgc ccgcaggtgt atgttgggcc cttggtgact ctaatgcacc   20700
ttccactcgg cacagaagag cttcagtctg gggcctgggg ggggaagta ggctgccatc    20760 ctcgctaaac caaagtgtga aaattgagtt gaaactccca taggagggca ggaggcacag   20820
ctcctcagaa gaaggtctga gaaaccacag cccaggttgt tgtttcgggt gtgtggaaa    20880 ggtgctctgg cagtcctgct acagggggac catcaacagc ccctttgggg tgagagcccc   20940
```

```
gtggctgctg gcaccagcag cccctatgag gcttatttta ttttgagac agggtcttgc    21000 tctgtcaccg aggctggagt gcagtggcac aatcataact cactgtagcc tcaacctcct   21060
gagctcaagc gatcctcctg cctcagcctc caaaggtgct gggattacag gcgcttgcta   21120
ccacgcccag cccctctgg ccttattgtt tgccaggccc agctcaggtc ccggaggagg    21180
ggagacagga gtgtgaggga aaggggaag aggtatagag cccccagctc ctccacccac    21240
ccgaaccctc accgaggccc tagaccctag accggcctga ccgggggtc ctcaggccgg    21300 ggacttgggt gcaggccatg gtgctggggc ctgaagctca cgctctgctg agcacagccc   21360
cctgcccaac cccaccctgg ggccctgctt ccctggccag ggccattgga acaggagtgg   21420
ggctgtccag gtggtgttct tgggtccagc cctcagtttc tcttctgcag ttgaccggca   21480
gccctgcatc tgtggtgggg tcggcgcctg gtgctggtga ggcaaggcct cagctgctgg   21540
gacaggacct gcctggcacc cagctggtgg cagagccaag cattccgact cagctctggg   21600
agcagctgcc ttctgggctg gcattctccg ccagggggt tgtgccctcg tggcccccc    21660 cgggtgcctc ctcacctggc tgatttcatc tcctgtcccc ctgcctcctc ctccaggaag   21720
cccccagggc ctggccctcc ttgagagtgg catggaggag gaagaagact cgcccaggcc   21780
catgggagtc ggatggtggc cgcacttgtg gggccctgac cccataggct tcttcagcac   21840
gccctggcct gggtgatccc tgcctgaggg ctgtgcacgg ctcatctgcc agaccagatt   21900 ttagggatt cttgtactgt cctcctggag cagcaggggg taaagcctga cccacccaga   21960
ctgtccagca acaagggcct cctgctgtgg gccaggacc ctggaactga ccaattgtgt    22020
cctagggacg cagagtcccc aggctgctag agggctgtgg ggccctgttt catgcctgaa   22080
gcaggaagaa accccaggag aggtctgaag gggacccagc ccccacccctg tctagcaggg   22140 aggagcctct gcaagaggcc gagggtgct gaagtggagg aggatagagg cagcaggact    22200
cagggtcact ggtcatttat ggggatcaca cggctgcagt gtgccctgca tggtgctagg   22260
caccagggac agcagaggac aagcctgtgt cctctcccac caccagaggg ctgggcactg   22320
cccctaggga gagagggggc cttggtgtgt gcagagggg gcctggggca cgtgcctggc    22380
ctggtcagat gatcagagtg ggctgggctg ggcctggtct ggggcccagt ctcaagggca   22440
gaccccacct ggctagagtt gattgtgtgc acaccggatg accggcgtt gaaggcctct    22500 cctctctgtg agcctcatcc ccacctgcca gactcccagc acagcctgct tcctgcccca   22560
gctgctgagc gacagcgctg ggccggcttc tgcgcgcccc ttcccccagc ccatcttgga   22620
aaccacagca gcgtccttcc tcccaagtcc cttcccaggg ctgacatccc acagcaggga   22680
tgtatcccac aaacccgca ggccctggtg cctacagctt ggcctggtaa catcaaatcc    22740
taccctctcc tcctggcagc aaagatgggg tgccccacc ccagagttct cagcaccccc    22800
agacagaagc agtcccccag cgacctcaga actcttgggg cgctgccaca cccttgcagg   22860 aggggcagt gttcctggga tgctcaggtc ctggtatcac ctctggccag atacggaagg    22920
tgaaactaca gggcatccaa ttcaccttga acttcagata aacaccagat tatttttttg   22980
tatgtcccgt gcaatatttg ggacacactt accctaaaga agtattctgt tttcatctga   23040
gaggcagatt taaccggcgt cccgtgtctt cctggcagtc ctgccctgga gtcacactcc   23100
acaggtgcag gcagggcca ggctccaagt agatggcggc caaagcaccc gccccatgct    23160
cctgactccc ggggctcttc agggcattgc gaaaccagc agcagagctg acacctggtc    23220
cctgctcggg agccagcaag gcaggaggct gcttaggcct tgcgtgtggg gtgggcgcac   23280
tccctgctgc agtgctcttc gtacatgtga cactgttccc gctctttccc agctggctgg   23340
```

```
aggcgtgatc ctgggtgtgg ccctgtggct ccgccatgac ccgcagacca ccaacctcct   23400
gtatctggag ctgggagaca agcccgcgcc caacaccttc tatgtaggtg agtgcacatg   23460
tggccgcaga cgcattcagg gagggcttct aggaggaggc aggtcctagc cttttggatg   23520
gggacatgga gggtgaaaga cagtcgggca tggcgtgtcc gggcagggag gcggccctgg   23580
aaagggctct gggcacaagg gttgagatgg aggtgggcct gtggcctgct ggcccttctg   23640
gtctgagcca gggcagggggtggcagctag gcctgggcag ggactgtgtg gagaccttgc   23700
ttattttaag tgtggggtta tttcggggga ggctccctga aagggtggg gctggatgcc   23760 tgggccacac agagcagccg aggcagctgg cgctgtggag cccgggaggg agggagggat   23820
ggagctcaag ggatggaacc cagtgagggg tggagacggg gcaggggagg ggtggagagg   23880
ggtggagacg ccccagaggc ggtgtgactc agctgcccct gcaggcagct gcaccttgct   23940
gccttattag gctgcgtgtg ggggactggg ctgccctccc tgcccccagg agcaggagca   24000
ggagtgatgg aggaggagga ggggaggggc aaggccagga ggaggaggag ggccatctca   24060
ctgtgcagag agcagcaccc ttcctcctgg tgccctggc agggctggtg ctggtggggc   24120
tctgggagca tttgttgaga tgcttctggc cttgaaagga ggccctggg atggctctgt   24180 tgccctcaca ggctgagggg tgggtgaggt gggcagcctg tgtgtcccca gtcctcaggg   24240
cttccctcag ccggcaggtg cccccaggcc tggagctgca gggccaggcc cctgccagt   24300 tacggaggct gcttggcttg gttgctgaac cagggcccca ggaggccgaa atagccccac   24360
acctgcgccg tcccacctct ttgtccagtc accccagggc caggtgaggg ccctggccac   24420
acagcgtgcc cgttccttct tccccatgcc ccgctcatgg gtcagagggc cggtgctggg   24480
gtccagatgg tgtcaacagg gatggtccct gtcctcccca gagacagaag cctgtggccc   24540
acggagggtt tctgggccca gccgatccta gggagggtcc catggccctg cccataggtt   24600
cctggcctct ctcggggccg tggtgccctc acaggtggtg tcaggaagga cgggaaaggc   24660
tgcttgtccc aggggctcat gtggagacca ccccctgcac gcagctgggg cgctcctgcc   24720
tgtgtcctca gaagcactcg gcttagcttt gcccatgtgc ctgggctgtg ggtggcagag   24780
cccggccagc atcctccgat ctccaagggt gcatctctac tggaggcccc tcctgggcct   24840
cttgctcccc gcttcccaga tcattaggat atttggggtc cagaagggcc tcccagccat   24900
cctgggcctt gtcctccggg gccaccagtc cagccagtga caaccacagc atccccggcc   24960
tggaacgagg ctgcccccag cacgttcctc gtactcctgt ccaggacag gaggggctgc   25020 ccctgccacc gagtccccctt ctccaggacc tggggcctgt gggtgtgagg caggtgttct   25080
tggaaggggt cactctccag gcacccggcg gccaaggctt gtggctggag cagctcccgc   25140 tgtgggtcg gcgtcgggcc ccgtgtggcc ggagaggagc tgaagggtca cttagcttcg   25200
ggctggggcg aggacagggg acaccccaga gaggtatgcc aggcctcctt cctgcgcccc   25260
actctcggca gaagcagagg tcacaggctg tgctgaggcc ccatggtgct gcccccatga   25320
tgccagggtg aggctggcgt tggaagcagg tgtctgacct gcatggtgtc accgtggcca   25380
catcagagct ccagccccag agccgcccac cctcggtcct tggctgtggt ttccctgggc   25440
tggaggagcc tgccgttgtg ttggccacac gaccacagga cctgccaccc ccgacgtggg   25500
ctctgcctgg gcccccactg gacagggacc ccttggagct cctctggcca ccaagtcctc   25560
gcccattcca gaatcggcct tctggagcct cttgctgtcc ctgatgcggg ctgggccttg   25620
ccaagggctt ttttttcctgc gccgggaaca gggtggattt gctgggctca ctcccctcag   25680
agacgctgcg ggtgcggtgg gttaggccca agggcgttaa gagaggaggc tggggtgggg   25740
```

```
ctggggcctg gcaggggtc  tggcagccct gggcctccca cctcctgtca ggaccaaaaa   25800
aggcaacgcg cctctcctga cctgtacccc ggagtgaacc caaccttgca acccaggagt   25860
gtcagggcct gaggggaggg agacctggct cctgggtgcc gtgcccgtaa ggaggtggcc   25920
acctgcaggg cattcctggc agaggcttca tctggccagg taggaggctg ggtggccgag   25980
ccccaaatct gggtgtgttc tctgcctggc ggtgggtcct gccccaggca ccttctcctc   26040
tgggctggct gggcagggac aatgggcctg gctgcgagga ggggcctgg  gctgccttct   26100 gcattgcctc ggtgacggga gatgcccct  gcctgctgag ggataggga  gtgggcaggc   26160 agtgagagac actgacagct gtcccgcggg tacagggccc tgtctgggtg gccaggccca   26220
tgtctcgggc ccacagtgcg ccccccaccc ttggacggcg ccttctccct ccccaggtgc   26280
atgctgccca gccagggagc gtgggggagt tcgggagggc tggcctacac gccctggtcc   26340
agctgtccca ggtggggtgc tgggcttcag ccctcagccc agggcctagg aatccaactt   26400
gatcctcccc acacagcagc caggttcaaa tgcaggtccc gtaacggaag tgctgctgtg   26460
cagcccagat tgggggcag  gagccagcag ggccccccca ccctcttctc gcaccacact   26520
ggggaggcag cattggttcc agttccggtt cctgggctgc cctctcaacc ccggcctaca   26580
gtggggccca ccctgtgcct tctgatgcca ctcccacccc acgccaagtc ccagaggctt   26640
tgggagcggg tgaaggcggt gggtggcggg tgcaggtgc  aggcggtggg tggtgggtgt   26700
ggcaggtggc gggccccacc gcaggtgtca tccctgcgaa gcacctgtcg ccagcactca   26760
gagcgctcat gaggtgccca gtccccatgt ggcctcctta gtctccgtcc tgtgtcatgg   26820
aagaggtaac tgaggcacag aaaactcacc aggccaggct gggatgtgag gtcccttgct   26880
gctcatccct ggcagtcagc aaccctacat cttcccagct gggcggcccg tggtgggttc   26940
ggcacccagg accctccggg gtcttgggct gtggcgagtg tgtaggcacc cacctggtgt   27000
ctctctcccc gcaaggcatc tacatcctca tcgctgtggg cgctgtcatg atgttcgttg   27060
gcttcctggg ctgctacggg gccatccagg aatcccagtg cctgctgggg acggtaaggc   27120
agggaggcgg gcctgtgcct gggccgggga ggggctgggg gctgcgtctg gccctgagga   27180
gggggcagag ctggtgctca gggcggagcc tagaattctg ggggaggtgg ctcctgtgcc   27240
ctgcttttcc cgtttggttt ttaaattaaa tcccaccgtg cttggtctcc atcgtggcca   27300
gttcctacgt gaccgctttt ctttgtcaaa aaatagccac aaatataaca gggagcaagc   27360
ctcagctctg aggccagcct cggcgtcccg ggcacaccgc ccctgtggg  aagcccaggc   27420 ctggctgtgc catccagggc ctggccagtc caggaagagg gagcctatgc ccgtgtctcc   27480
agtgggggaa actgaggcag atcccatggc tcccccttcc gtggggagca ggaacaaggg   27540
ggtggggaag atcagtcagg ggtcatgctg ctgcacacgc ctccctgggg gctgcagaca   27600
tcctggactc accagcctgt gaccccaaac cacacgcccc gccccatcca ccccgtcctg   27660
tggagcctgg tgccgcgtgg ggacatcctg ggctttgacg gctcctccct gcgctgagtt   27720
ttagcctctg tgccccaggg ctccacacaa gccgctcact cctggtcagg tcgtgggctg   27780
gtggctccca ctagcccctc acagacacgc ctgctgggca cctgggtgtg tgtccttggg   27840
ccccgcctac agcctgccct ctttcctccc tctggccact gcccggctcc agttcttcac   27900
ctgcctggtc atcctgtttg cctgtgaggt ggccgcggc  atctgggct  ttgtcaacaa   27960 ggaccaggtg agcctgggtg tgcagggaca gggtggggtg ggtgacgggg gcaccctcct   28020
ctcctgtcgc gggtgggggt tgggctgact catggcttgt gggagctctt tgggctcttc   28080
ctgggtccca cttgccagga ggatctccag gggctttatg gaggaggcag cattgggct    28140
```

```
gagcaccagg ccagcctccc gtgtcccagc actcccgggg cagctgagag tgcagagtcc   28200
ttgtcctctg gggtctagcc tcgaagccac cctgcccagg gagagcctgg gaaaagtgcg   28260
tccgcctggg gcggggcggg gtgggggcaa ggagggggag gttcccctg tgcatgtgac    28320 cgcacccctc ccccagatcg ccaaggatgt gaagcagttc tatgaccagg ccctacagca   28380
ggccgtggtg gatgatgacg ccaacaacgc caaggctgtg gtgaagacct ccacgagac    28440 ggtgcggccc cggggggcga gggcggggag cagggccccg ggaacccggc ggggtgtgtc   28500
tcgtcctgga tgaatcctgc ctacgcccag acctcaggag caggaggtgc ccttgggacc   28560
tccaggaccc ctggtctcaa ctggtcctcg ggtgggaacc tagtgggcca gggtggccca   28620
gggtgcggaa agctctgagc agcgcagctg aggaggaaga aggctggccc ctggatgcat   28680
tctgcagtgg ggagcgctgc gtacccctgg ccacctcccc atgggttccc tagagccacc   28740 gtcccctgg gcacatccag ggctgacctt gcacccctgc tctctgcagc ttgactgctg    28800
tggctccagc acactgactg cttgaccac ctcagtgctc aagaacaatt tgtgtccctc    28860
gggcagcaac atcatcagca acctcttcaa ggtgcgcgag gccggtgggg ccgcgcctga   28920
ccccccgcat gtcccgcccc tgggtggggt cctaggggtg gcaggtcac acggcagccc    28980 cacagggagc gaccacactg ggtggcatgg cccctgtcag ggctgctctg ctgggagggt   29040
tgggtgggaa ccgcatctgg cccacgagga aggcaggcgc cctgtgctgc gcattccggg   29100
tgaagaaggt ggaggctctg gggggtggga actcacctgc accccagct ccacgtgtgc    29160 actcgtgggt gtggacgccc ctgacagcct gtagctggca gggcctgcag gccatatagt   29220
gccctgtgga agtttcctgc tgaggcctca gtggaagtcg tcatcagtga tgctttaggg   29280
gtctagtgac accaatgacc gtgatctcag tggaaaaggg cacagtgtgt cccaggcatt   29340
tcgcgtttat gttaaaacgg gtggaagata gcaagccggc agaggccggg ccgctgcacc   29400
cgcctgttcc gaggtgggta gggggtgggg ggctgttccc aggattcccc tctacgcttt   29460
ctgtggtgac cacggattac tgcgtgacaa cgggaagccg ggagccgagg cccggtccct   29520
gaccacgcgt gcctggccac ccctgcagga ggactgccac cagaagatcg atgacctctt   29580
ctccgggaag ctgtacctca tcggcattgc tgccatcgtg gtcgctgtga tcatggtgag   29640
cgggcggggg cggagggcct gctctctggg ctgccccttc cgcggggcct tgtgctgact   29700
gcgcccccca ccaccctcct gcagatcttc gagatgatcc tgagcatggt gctgtgctgt   29760
ggcatccgga acagctccgt gtactgaggc cccgcagctc tggccacagg gacctctgca   29820
gtgcccccta agtgacccgg acacttccga gggggccatc accgcctgtg tatataacgt   29880
ttccggtatt actctgctac acgtagcctt tttacttttg gggttttgtt tttgttctga   29940
actttcctgt tacctttcca gggctgacgt cacatgtagg tggcgtgtat gagtggagac   30000
gggcctgggt cttggggact ggagggcagg ggtccttctg ccctggggtc ccagggtgct   30060
ctgcctgctc agccaggcct cctgggag ccactcgccc agagactcag cttggccaac    30120 ttgggggct gtgtccaccc agcccgcccg tcctgtgggc tgcacagctc accttgttcc    30180
ctcctgcccc ggttcgagag ccgagtctgt ggcactctc tgccttcatg cacctgtcct    30240
ttctaacacg tcgccttcaa ctgtaatcac aacatcctga ctccgtcatt taataaagaa   30300
ggaacatcag gcatgctacc aggcctgtgc agtccctcag tgccagtggt gtctgagacc   30360
taggggttgg ccggagggca ggggaatctg acatcggtgg ggcttggctc tgtggactct   30420
gtggggtcca gggtgagggt gggtgggtcg ggatccctgg tgttcaccaa aggagtcact   30480
ctgtaaaatt tggggagtta tttattctga gccaaatatg agcaccggtg gcctgtgaca   30540
```

```
cagccccagg tcctgagaac ttgtgcccaa ggcggtctgg ctacttaatt gtatacattt   30600
tagggacata ggacattgat cattacatct aagatgtacg ttggtttagt cggaaaggtg   30660
ggacgatttg aagggaggg actttcaggt cataggcgga ttaaaagatg ttctgattaa    30720
taattggttg attttatcta aagacctgaa atcaatagaa tggactatct gggttaagag   30780
gagttgtgga gaccaagatt attatgcaga tgaagccgcc agattgtaaa tgtttcttat   30840
cagacttaaa aaggtaccag aatcttagtt aattctctcc tggatcagga aatagacctg   30900
gaaagggagg gggattctct atagaatgta gattttccca agagacagct ttgcagggcc   30960
atttcaaaat acatcagaga aatatatttt ggggtaaaat acttcggttt ctttcagggc   31020
ctgctgtcac gttggtatct tattactaca gagtctgttt tgtgagtctt aaggtctttt   31080 tattttaga cagagttttg ctcttgtcac ccaggttgga gtgcaatggc gtgatctcag    31140
ctcactgcag cctcccctcc acctcccagg ttcaagcgat tctcctgcct cagcctcctg   31200
agtagctggg acaacaggca tgcaccaccc cacccagcta attttgtatt tttagtagag   31260
acggtgtttc gccacggtgg ccaggctagt ctcgaactcc tgacctcacg tgacacacca   31320
ggttttggga ttacaggtgt gagccaccac accggactaa ggtctctgtt ttaatgtgaa   31380
tgctggtcag ctgtgcctat gaggcatgtt cggccaccca cagtcatcat ggcctcaacg   31440
agcttttcag gttacttta gaatgcattt ggccaagagg tgcccattca gttggttggg    31500
gttgcttaga attttacttt gggtttaaac cagggagcaa ctccaggtag caagggccct   31560
ttttgggagc gttctctcta ttctcttttg ggagaggccc tgtgttgcct gcagccactt   31620
ccaccctgcc ccttgggcac acaaggggca cacagtgtaa gcaggtgggc aggagggggtc  31680 gggcagccag ggaatgcagt gagatgggct tggggtaggg gctgggtgcg ctgcaggact   31740
cctcttcctc ctgagggatg gtaaaggatg gacacactgc cccctcccga gcatttgagg   31800
gtctctgccc tgcccatctg ttacctgtaa atgttccttt gaggagctga tggctcaggc   31860
ctgagccaca tctcagaggg tctggagggg aagaaagacc tcatcctact agggagcccc   31920
cccagcccac cagcgagcgg tggttggggg cagacaggct gtggggctaa ggagcccctg   31980 cactccccg tccttttccc tttgtctgag cacctccagc cagtgggctt ggtctagact    32040
ctcctatctt tccccacatc gtggggtggg gcttgctctg ggttaggcta ctttttccta   32100
gttgtgggga gggggtgct ggcacatttc actgttccct ggaggaaatg agtgcctggg    32160
aattcatatc tagggctccc agcagcctct ttgcaggcca atttggaaac tgtccccagc   32220
cctgcatttt aggggttac agagtctctc agcaggccct cctcccctgc tgctcccaac    32280
ttgcaagcct gcactggttg ggagaacata atggtccaag gagccccctc tctactttcc   32340
gctgtgttcc ctgtggggag ggaagagcag tttaagaaat aaggaatccc aaaggcgcac   32400
agcagaccgg gggccgagga gtgggtcctg cttcccctcc ttttttctag gctgagccac   32460
agcaggtcct tgaatcctat ttcccagcgg atgccaggac agcaggccct ggggagttc    32520 tctctcgagc ctttcagagg gaccagaggt ctagcagcca aggagaactc agaatccttg   32580
agtgtgtggg gcaggaactc tcccagctga aaggggcac aagtgccaa ccatctaggg     32640 cccagtggcc aaggaagacg cggcttgtcg cagggagaat ctgggccctg gtcctccctt   32700
tcagggcggg cagctgacct gcccctgct gcggacaggc gaggccaggc tgctggctcg    32760
caagcatggc ggagcccaaa ccttccctgc tgccgcccgc ccagccacgg ctgacttgga   32820
agcttgagga gcgttcagca gcctccatcc tgcccgggag gaccggggac ctggaagggc   32880
ctggccctcg cttccctgca gcgccctagg gggacgtctc agtgcctccc ggagcccgga   32940
```

```
ccaatgcacc agagctgagg gcccaagggt gtgagggtgg ccgggcagtg gccccgagga   33000
cggcgcccca caagtttgcg gccagggccc agcaaacccc tagggqtggg aaagcgtcgg   33060 cccagctagc gggtccagca gggctgcccc cttcaccgtg gcccagcggt cacgacccca   33120
cgtcctcatc gcgggctggg actgcctctg cgtctggcct gagcgggacc gtgggatcct   33180
ggggagcccc gcctcggtgc actgacagag cccagaagga gtgacggtta ccgcttccgg   33240
tcaggaccgg aagtgccggg aacggcattc gtcctccgtg cgagatgacg cacttcctgc   33300
ctgaggcggc cgctgttctc gcggcttccg gcaggtggcg ctgagaccac gggaagccag   33360
cctggctgtc ggttagccct cgagcattct gggaattgca ggcctggccc ctcctcttcc   33420
tgttcttggt caattccggt cttgtttccc aacaaatgc cgtcgtttcc ggggctgctt    33480
ccgagccgga cccaagggcc ggggcgtgga ggagtagagg ggcgagcgca tgcgcacagg   33540
actacacgtc ccgacaggcg tcgggagcgg cggcccagtt ccttgtggga gctgtagttc   33600
tgcaggcgcg gaagccgtgg tgctcggccg gcagagcact cggtttccca gagggctgag   33660
cgcgccgcac ggaggtgcgg cgccgaccaa gatggagact gccgagcagc cttgagccgg   33720
taggtttgtg gtgagggagg acgggccgcg cgggccggcc gagcctccgg gaggtcaccg   33780
agcgcagctt taatacctga gctcgaaggc cccgctgtgc tcgccgaccc ccgtacctcg   33840
cggccgggcc cttgggaccc acagcatcct tgtgaggccc ggaggcctgt ccagcccgac   33900
tggacagtgc cgaggggcac cgagagccag cttggcaccg agagttcgtt tgttctctgg   33960
cggggaggtc ttgctggcac atatagtgga gaaaggccgg gctctgcgtt catgtggaga   34020
aagagacggc ttccttcagc ctacggacat gaaggagtca actctacctt ccactcgttg   34080 ccggcttttcg ccgagaaccc cgagaaacgg actaccggag tccctatctt gcagcccgat  34140
ccccgctacc cgtcggagtg ccccgctgac caggctgctt ctggccgcgg cggcgttccg   34200
ctgcagagga cgggagtgcg aatctgggaa gcagggttct ggttgaactc cagcttcgtc   34260
tgcaacatac tgtgtgactt gggcaaaatta tttccccgc cccgttcctg ccagctttaa    34320
aacggtcatc agtgggggt gctgcgtatc cccttttcact ggggtggctt cttcactgag   34380
gagagtcgcg cctcagagga actgaggtcc tgcctgtgtt cgacctggtg gggggcacta   34440 agagccctg atagtacccc tgaccccatc cttattgggt gcacaagaca caggtcactc    34500
tgggcgggca aggagttttg gtagcaggag aggagtcggt ggatggatgg ctgaggacag   34560
tgcagaaggg tgtggctggg ccgtcttttt ttgcctggaa attcaagttc tgaggcaccc   34620
agtcactcca gcactaaatg ggtgcaggag gcagcacttg tctgcccagc tggaaaggca   34680
gggtatgtgc tgagtgttac aggtggaagg ccactggagg tcgctccagg agccgcgggg   34740
atttacctct gcctaacagg gctgctcaag gtgatggtcg acaccccact ttcctgagag   34800 cttgacccctc agatgccagg gccttggctg cagattcctt gggagctccc ggggatcttc   34860
cagcaaatag gagcaaatct tttcccgtg gatcaggaag gtgcacgctc tttgtggaat   34920
acgactgctc accccgcaca gcaagcagct tataagtggc cctcctgcct gatttcagcc   34980
ctgggttcaa gccctgggtg gctgcttact accaaaatcg ctcagtagct ccaagcctgc   35040
ctgcagaggg ttggcaccat taaatgaggt aacgagtcaa aagtccctac cctgggtcct   35100
agcctgtcag gggctccgaa aacccaggct caggtcggtc ctgcccggca cctgtttcac   35160
acatgtacac tccggtctga ggttggtcct ctcccccacc ccacccacct gcagttgagc   35220
agctgaacag aggccatgcc ggggcactcc gaggcctgag acgaccacgc ctgtgccgct   35280
gaggaccttc atcagggctc cgtccacttg gcccgcttgg ctgtccaatc acactccagt   35340
```

```
gtcaaccact ggcacccagc agccaagaga ggtgagagga gggcttggag ggggaggcgg    35400
gactccaccc tgtgtgggac agttctgtca gttgaccctc cacttgtcca ggggcagtgg    35460
atctgcaggg ggaactcatt ctcaatactg ttcctcctga gaaacaaatt ttctgggctg    35520
ttttggttta ggtgtggcgt ggccctgggg acgcatggct gaggcaggaa caggtgagcc    35580
gtcccccagc gtggagggcg aacacggac ggagtatgac acgctgcctt ccgacacagt    35640
ctccctcagt gactcggact ctgacctcag cttgcccggt ggtgctgaag tggaagcact    35700
gtccccgatg gggctgcctg ggaggagga ttcaggtcct gatgagccgc cctcaccccc    35760
gtcaggcctc ctcccagcca cggtgcagcc attccatctg agaggcatga gctccacctt    35820
ctcccagcgc agccgtgaca tctttgactg cctggagggg gcggccagac gggctccatc    35880
ctctgtggcc cacaccagca tgagtgacaa cggaggcttc aagcggcccc tagcgccctc    35940
aggccggtct ccagtggaag gcctgggcag ggcccatcgg agccctgcct caccaagggt    36000
gcctccggtc cccgactacg tggcacaccc cgagcgctgg accaagtaca gcctggaaga    36060
tgtgaccgag gtcagcgagc agagcaatca ggccaccgcc ctggccttcc tgggctccca    36120
gagcctggct gccccactg actgcgtgtc ctccttcaac caggatccct ccagctgtgg    36180
ggaggggagg gtcatcttca ccaaaccagt ccgagggtc gaagccagac acgagaggaa    36240
gagggtcctg gggaaggtgg gagagccagg caggggcggc cttgggaatc ctgccacaga    36300
caggggcgag ggccctgtgg agctggccca tctggccggg cccgggagcc cagaggctga    36360
ggagtggggc agccaccatg gaggcctgca ggaggtggag gcactgtcag ggtctgtcca    36420
cagtgggtct gtgccaggtc tcccgccggt ggaaactgtt ggcttccatg gcagcaggaa    36480
gcggagtcga gaccacttcc ggaacaagag cagcagcccc gaggacccag gtgctgaggt    36540
ctgagaggga gatggcccag cctgaccca ctggccactg ccatcctgct gccttcccag    36600
tggggctggt caggggcag cctggccact gcctagctgg aatgggagga agcctgcagg    36660
tggcaccggt ggccctggct gcagttctgg gcagcatcct cccaagcaga gaccttgctg    36720
aagctcctgg ggtgtgggt gtgggctgga agcactggct ccctggtagg gacaataaag    36780
gttttgggtc tttctgagac tttgtgtcta tctgggccct gcttacccaa agggctcagt    36840
tggcagcaag agctccccac acctgaccct cggtgccgga ccactcgagg gtggctgaca    36900
cctgcatccc tcaccagcac atcacccagg tgacagtgag aattggaaac cccaggcctc    36960
ctctagggct tgtggctcag tggcaggtgt ccagtgagtg ccctcaatgg gcctgagtgg    37020
gtacagaatc tgccctcccc caaccaaagc ccacatgatg ccatcagccc caggcctagt    37080
gcagaccaca gcttgggaag cgaaagggag atg                                 37113
```

<210> SEQ ID NO 12
<211> LENGTH: 15540
<212> TYPE: DNA
<213> ORGANISM: Homo sapiens

<400> SEQUENCE: 12

```
agccaagcat tccgactcag ctctgggagc agctgccttc tgggctggca ttctccgcca       60
ggggggttgt gccctcgtgg ccccccccgg gtgcctcctc acctggctga tttcatctcc      120 tgtcccctg cctcctcctc caggaagccc cagggcctg gccctccttg agagtggcat       180
ggaggaggaa gaagactcgc ccaggcccat gggagtcgga tggtggccgc acttgtgggg      240
ccctgacccc ataggcttct tcagcacgcc ctggcctggg tgatccctgc ctgagggctg      300
tgcacggctc atctgccaga ccagatttta ggggattctt gtactgtcct cctggagcag      360
```

-continued

```
caggggggtaa agcctgaccc acccagactg tccagcaaca agggcctcct gctgtgggcc      420
agggaccctg gaactgacca attgtgtcct agggacgcag agtccccagg ctgctagagg      480
gctgtggggc cctgtttcat gcctgaagca ggaagaaacc ccaggagagg tctgaagggg      540
acccagcccc caccctgtct agcagggagg agcctctgca agaggccgag gggtgctgaa      600
gtggaggagg atagaggcag caggactcag ggtcactggt catttatggg gatcacacgg      660
ctgcagtgtg ccctgcatgg tgctaggcac caggacagc agaggacaag cctgtgtcct       720
ctcccaccac cagagggctg ggcactgccc ctagggagag aggggggcctt ggtgtgtgca     780 gagggggggcc tggggcacgt gcctggcctg gtcagatgat cagagtgggc tgggctgggc    840
ctggtctggg gcccagtctc aagggcagac cccacctggc tagagttgat tgtgtgcaca     900
ccggatgacc cggcgttgaa ggcctctcct ctctgtgagc ctcatcccca cctgccagac     960
tcccagcaca gcctgcttcc tgccccagct gctgagcgac agcgctgggc cggcttctgc    1020
gcgccccttc ccccagccca tcttggaaac cacagcagcg tccttcctcc caagtccctt    1080
cccagggctg acatcccaca gcagggatgt atcccacaaa ccccgcaggc cctggtgcct    1140
acagcttggc ctggtaacat caaatcctac cctctcctcc tggcagcaaa gatggggtgc    1200 cccccacccca gagttctcag cacccccaga cagaagcagt ccccccagcga cctcagaact   1260 cttgggcgc tgccacaccc ttgcaggagg gggcagtgtt cctgggatgc tcaggtcctg    1320
gtatcacctc tggccagata cggaaggtga aactacaggg catccaattc accttgaact    1380
tcagataaac accagattat tttttttgtat gtcccgtgca atatttggga cacacttacc   1440
ctaaagaagt attctgtttt catctgagag gcagatttaa ccggcgtccc gtgtcttcct    1500
ggcagtcctg ccctggagtc acactccaca ggtgcagggc agggccaggc tccaagtaga    1560
tggcggccaa agcacccgcc ccatgctcct gactcccggg gctcttcagg gcattgcgaa    1620
aaccagcagc agagctgaca cctggtccct gctcggagc cagcaaggca ggaggctgct    1680
taggccttgc gtgtggggtg ggcgcactcc ctgctgcagt gctcttcgta catgtgacac    1740
tgttcccgct cttccccagc tggctggagg cgtgatcctg ggtgtggccc tgtgctccg    1800 ccatgacccg cagaccacca acctcctgta tctggagctg ggagacaagc ccgcgcccaa    1860
caccttctat gtaggtgagt gcacatgtgg ccgcagacgc attcagggag gcttctagg    1920 aggaggcagg tcctagcctt ttggatgggg acatggaggg tgaaagacag tcgggcatgg    1980
cgtgtccggg cagggaggcg gccctggaaa gggctctggg cacaagggtt gagatggagg    2040
tgggcctgtg gcctgctggc ccttctggtc tgagccaggg caggggtgg cagctaggcc    2100 tgggcaggga ctgtgtggag accttgctta ttttaagtgt ggggttattt cggggaggc    2160 tccctgagaa gggtggggct ggatgcctgg gccacacaga gcagccgagg cagctggcgc    2220
tgtggagccc gggagggagg gagggatgga gctcaaggga tggaacccag tgaggggtgg   2280
agacggggca gggagggggt ggagaggggt ggagacgccc cagaggcggt gtgactcagc    2340 tgccctgca ggcagctgca ccttgctgcc ttattaggct gcgtgtgggg gactgggctg    2400
ccctccctgc ccccaggagc aggagcagga gtgatggagg aggaggaggg gaggggcaag    2460
gccaggagga ggaggagggc catctcactg tgcagagagc agcacccttc ctcctggtgc    2520
ccctggcagg gctggtgctg gtggggctct gggagcattt gttgagatgc ttctggcctt    2580
gaaaggaggc ccctgggatg gctctgtttgc cctcacaggc tgaggggtgg gtgaggtggg    2640
cagcctgtgt gtcccagtc ctcagggctt ccctcagccg gcaggtgccc ccaggcctgg    2700
agctgcaggg ccaggccccc tgccagttac ggaggctgct tggcttggtt gctgaaccag    2760
```

```
ggccccagga ggccgaaata gccccacacc tgcgccgtcc cacctctttg tccagtcacc   2820
ccagggccag gtgagggccc tggccacaca gcgtgcccgt tccttcttcc ccatgccccg   2880
ctcatgggtc agagggccgg tgctggggtc cagatggtgt caacagggat ggtccctgtc   2940
ctccccagag acagaagcct gtggcccacg agggtttct gggcccagcc gatcctaggg   3000
agggtcccat ggccctgccc ataggttcct ggcctctctc ggggccgtgg tgccctcaca   3060
ggtggtgtca ggaaggacgg gaaaggctgc ttgtcccagg ggctcatgtg gagaccaccc   3120
cctgcacgca gctggggcgc tcctgcctgt gtcctcagaa gcactcggct tagctttgcc   3180
catgtgcctg ggctgtgggt ggcagagccc ggccagcatc ctccgatctc caagggtgca   3240
tctctactgg aggcccctcc tgggcctctt gctccccgct tcccagatca ttaggatatt   3300
tggggtccag aagggcctcc cagccatcct gggccttgtc ctccgggcc accagtccag    3360 ccagtgacaa ccacagcatc cccggcctgg aacgaggctg ccccccagcac gttcctcgta   3420 ctcctgtcca gggacaggag gggctgcccc tgccaccgag tccccttctc caggacctgg   3480
ggcctgtggg tgtgaggcag gtgttcttgg aaggggtcac tctccaggca cccggcggcc   3540
aaggcttgtg gctggagcag ctcccgctgt ggggtcggcg tcgggccccg tgtggccgga   3600
gaggagctga agggtcactt agcttcgggc tggggcgagg acaggggaca ccccagagag   3660
gtatgccagg cctccttcct gcgcccact ctcggcagaa gcagaggtca caggctgtgc    3720
tgaggcccca tggtgctgcc cccatgatgc caggtgagg ctggcgttgg aagcaggtgt    3780
ctgacctgca tggtgtcacc gtggccacat cagagctcca gccccagagc cgcccaccct   3840
cggtccttgg ctgtggtttc cctgggctgg aggagcctgc cgttgtgttg ccacacgac    3900 cacaggacct gccaccccg acgtgggctc tgcctgggcc cccactggac agggacccct   3960
tggagctcct ctggccacca agtcctcgcc cattccagaa tcggccttct ggagcctctt   4020
gctgtccctg atgcgggctg ggccttgcca agggctttt ttcctgcgcc gggaacaggg    4080
tggatttgct gggctcactc ccctcagaga cgctgcgggt gcggtgggtt aggcccaagg   4140
gcgttaagag aggaggctgg ggtggggctg gggcctggca gggggtctgg cagccctggg   4200
cctcccacct cctgtcagga ccaaaaaagg caacgcgcct ctcctgacct gtaccccgga   4260
gtgaacccaa ccttgcaacc caggagtgtc agggcctgag ggggagggaga cctggctcct   4320 gggtgccgtg cccgtaagga ggtggccacc tgcagggcat tcctggcaga ggcttcatct   4380
ggccaggtag gaggctgggt ggccgagccc caaatctggg tgtgttctct gcctggcggt   4440
gggtcctgcc ccaggcacct tctcctctgg gctggctggg cagggacaat gggcctggct   4500
gcgaggaggg ggcctgggct gccttctgca ttgcctcggt gacggagat ggcccctgcc    4560 tgctgaggga tagggagtg gcaggcagt gagagacact gacagctgtc ccgcgggtac     4620
agggccctgt ctgggtggcc aggcccatgt ctcgggccca cagtgcgccc ccacccttg    4680 gacggcgcct tctccctccc caggtgcatg ctgcccagcc agggagcgtg ggggagttcg   4740
ggagggctgg cctacacgcc ctggtccagc tgtcccaggt ggggtgctgg gcttcagccc   4800
tcagcccagg gcctaggaat ccaacttgat cctccccaca cagcagccag gttcaaatgc   4860
aggtcccgta acggaagtgc tgctgtgcag cccagattgg ggggcaggag ccagcagggc   4920
ccccccaccc tcttctcgca ccacactggg gaggcagcat tggttccagt tccggttcct   4980
gggctgccct ctcaaccccg gcctacagtg gggcccaccc tgtgccttct gatgccactc   5040
ccaccccacg ccaagtccca gaggctttgg gagcgggtga aggcggtggg tggcgggtgg   5100
caggtgcagg cggtgggtgg tgggtgtggc aggtggcggg ccccaccgca ggtgtcatcc   5160
```

```
ctgcgaagca cctgtcgcca gcactcagag cgctcatgag gtgcccagtc cccatgtggc    5220
ctccttagtc tccgtcctgt gtcatggaag aggtaactga ggcacagaaa actcaccagg    5280
ccaggctggg atgtgaggtc ccttgctgct catccctggc agtcagcaac cctacatctt    5340
cccagctggg cggcccgtgg tgggttcggc acccaggacc ctccggggtc ttgggctgtg    5400
gcgagtgtgt aggcacccac ctggtgtctc tctccccgca aggcatctac atcctcatcg    5460
ctgtgggcgc tgtcatgatg ttcgttggct tcctgggctg ctacggggcc atccaggaat    5520
cccagtgcct gctggggacg gtaaggcagg gaggcgggcc tgtgcctggg ccggggaggg    5580
gctgggggct gcgtctggcc ctgaggaggg ggcagagctg gtgctcaggg cggagcctag    5640
aattctgggg gaggtggctc ctgtgccctg cttttcccgt ttggttttta aattaaatcc    5700
caccgtgctt ggtctccatc gtggccagtt cctacgtgac cgcttttctt tgtcaaaaaa    5760
tagccacaaa tataacaggg agcaagcctc agctctgagg ccagcctcgg cgtcccgggc    5820
acaccgcccc ctgtgggaag cccaggcctg gctgtgccat ccagggcctg gccagtccag    5880
gaagagggag cctatgcccg tgtctccagt gggggaaact gaggcagatc ccatggctcc    5940
cccttccgtg gggagcagga acaagggggt ggggaagatc agtcagggt catgctgctg    6000 cacacgcctc cctgggggct gcagacatcc tggactcacc agcctgtgac cccaaaccac    6060
acgccccgcc ccatccaccc cgtcctgtgg agcctggtgc cgcgtgggga catcctgggc    6120
tttgacggct cctccctgcg ctgagtttta gcctctgtgc cccagggctc cacacaagcc    6180
gctcactcct ggtcaggtcg tgggctggtg gctcccacta gccctcaca gacacgcctg    6240 ctgggcacct gggtgtgtgt ccttgggccc cgcctacagc ctgccctctt tcctccctct    6300
ggccactgcc cggctccagt tcttcacctg cctggtcatc ctgtttgcct gtgaggtggc    6360
cgccggcatc tggggctttg tcaacaagga ccaggtgagc ctgggtgtgc agggacaggg    6420
tggggtgggt gacgggggca ccctcctctc ctgtcgcggg tggggttgg gctgactcat    6480 ggcttgtggg agctctttgg gctcttcctg gtcccactt gccaggagga tctccagggg    6540
ctttatggag gaggcagcat tggggctgag caccaggcca gcctcccgtg tcccagcact    6600
cccggggcag ctgagagtgc agagtccttg tcctctgggg tctagcctcg aagccaccct    6660
gcccagggag agcctgggaa aagtgcgtcc gcctggggcg gggcggggtg ggggcaagga    6720
ggggagggtt cccctgtgc atgtgaccgc accctcccc cagatcgcca aggatgtgaa    6780
gcagttctat gaccaggccc tacagcaggc cgtggtggat gatgacgcca caacgccaa    6840 ggctgtggtg aagaccttcc acgagacggt gcggccccgg ggggcgaggg cggggagcag    6900
ggccccggga accggcgggg tgtgtctcg tcctggatga atcctgccta cgcccagacc    6960
tcaggagcag gaggtgccct tgggacctcc aggacccctg gtctcaactg gtcctcgggt    7020
gggaacctag tgggccaggg tggcccaggg tgcggaaagc tctgagcagc gcagctgagg    7080
aggaagaagg ctggcccctg gatgcattct gcagtgggga gcgctgcgta ccctggcca    7140 cctccccatg ggttccctag agccaccgtc ccctgggca catccagggc tgaccttgca    7200
cccctgctct ctgcagcttg actgctgtgg ctccagcaca ctgactgctt tgaccacctc    7260
agtgctcaag aacaatttgt gtccctcggg cagcaacatc atcagcaacc tcttcaaggt    7320
gcgcgaggcc ggtggggccg cgcctgaccc cccgcatgtc ccgccctgg gtggggtcct    7380 aggggtgggc aggtcacacg gcagcccac agggagcgac cacactgggt ggcatggccc    7440
ctgtcagggc tgctctgctg ggagggttgg ggtgggaccg catctggccc acgaggaagg    7500
caggcgccct gtgctgcgca ttccgggtga agaaggtgga ggctctgggg ggtgggaact    7560
```

```
cacctgcacc cccagctcca cgtgtgcact cgtgggtgtg gacgccctg acagcctgta    7620 gctggcaggg cctgcaggcc atatagtgcc ctgtggaagt ttcctgctga ggcctcagtg    7680
gaagtcgtca tcagtgatgc tttaggggtc tagtgacacc aatgaccgtg atctcagtgg    7740
aaaagggcac agtgtgtccc aggcatttcg cgtttatgtt aaaacgggtg aagatagca     7800 agccggcaga ggccgggccg ctgcacccgc ctgttccgag gtgggtaggg ggtgggggggc   7860 tgttcccagg attcccctct acgctttctg tggtgaccac ggattactgc gtgacaacgg    7920
gaagccggga gccgaggccc ggtccctgac cacgcgtgcc tggccacccc tgcaggagga    7980
ctgccaccag aagatcgatg acctcttctc cgggaagctg tacctcatcg gcattgctgc    8040
catcgtggtc gctgtgatca tggtgagcgg gcgggggcgg agggcctgct ctctgggctg    8100 cccccttccgc ggggccttgt gctgactgcg ccccccacca ccctcctgca gatcttcgag   8160
atgatcctga gcatggtgct gtgctgtggc atccggaaca gctccgtgta ctgaggcccc   8220
gcagctctgg ccacagggac ctctgcagtg cccccctaagt gacccggaca cttccgaggg   8280
ggccatcacc gcctgtgtat ataacgtttc cggtattact ctgctacacg tagcctttt    8340 acttttgggg ttttgttttt gttctgaact ttcctgttac cttttcaggg ctgacgtcac    8400
atgtaggtgg cgtgtatgag tggagacggg cctgggtctt ggggactgga gggcaggggt    8460
ccttctgccc tggggtccca gggtgctctg cctgctcagc caggcctctc ctgggagcca    8520
ctcgcccaga gactcagctt ggccaacttg ggggctgtg tccacccagc ccgcccgtcc     8580
tgtgggctgc acagctcacc ttgttccctc ctgccccggt tcgagagccg agtctgtggg    8640
cactctctgc cttcatgcac ctgtcctttc taacacgtcg ccttcaactg taatcacaac    8700
atcctgactc cgtcatttaa taaagaagga acatcaggca tgctaccagg cctgtgcagt    8760
ccctcagtgc cagtggtgtc tgagacctag ggggttggccg gagggcaggg gaatctgaca   8820
tcggtggggc ttggctctgt ggactctgtg gggtccaggg tgagggtggg tgggtcggga    8880
tccctggtgt tcaccaaagg agtcactctg taaaatttgg ggagttattt attctgagcc    8940
aaatatgagc accggtggcc tgtgacacag ccccaggtcc tgagaacttg tgcccaaggc    9000
ggtctggcta cttaattgta tacatttag ggacatagga cattgatcat tacatctaag    9060
atgtacgttg gttagtcgg aaaggtggga cgatttgaag gggagggact ttcaggtcat    9120
aggcggatta aaagatgttc tgattaataa ttggttgatt ttatctaaag acctgaaatc   9180
aatagaatgg actatctggg ttaagaggag ttgtggagac caagattatt atgcagatga    9240
agccgccaga ttgtaaatgt ttcttatcag acttaaaaag gtaccagaat cttagttaat    9300
tctctcctgg atcaggaaat agacctggaa agggaggggg attctctata gaatgtagat    9360
tttcccaaga gacagctttg cagggccatt tcaaaataca tcagagaaat atattttggg    9420
gtaaaatact tcggtttctt tcagggcctg ctgtcacgtt ggtatcttat tactacagag    9480
tctgttttgt gagtcttaag gtctttttat ttttagacag agttttgctc ttgtcaccca    9540
ggttggagtg caatggcgtg atctcagctc actgcagcct ccctccacc tcccaggttc     9600 aagcgattct cctgcctcag cctcctgagt agctgggaca acaggcatgc accacccac     9660 ccagctaatt ttgtattttt agtagagacg gtgtttcgcc acggtggcca ggctagtctc    9720
gaactcctga cctcacgtga cacaccaggt tttgggatta caggtgtgag ccaccacacc    9780
ggactaaggt ctctgttta atgtgaatgc tggtcagctg tgcctatgag gcatgttcgg     9840
ccacccacag tcatcatggc ctcaacgagc ttttcaggtt tacttagaa tgcatttggc     9900 caagaggtgc ccattcagtt ggttgggggtt gcttagaatt ttactttggg tttaaaccag   9960
```

```
ggagcaactc caggtagcaa gggccctttt tgggagcgtt ctctctattc tcttttggga   10020
gaggccctgt gttgcctgca gccacttcca ccctgcccct tgggcacaca aggggcacac   10080
agtgtaagca ggtgggcagg aggggtcggg cagccaggga atgcagtgag atgggcttgg   10140
ggtaggggct gggtgcgctg caggactcct cttcctcctg agggatggta aaggatggac   10200
acactgcccc ctcccgagca tttgagggtc tctgccctgc ccatctgtta cctgtaaatg   10260
ttcctttgag gagctgatgg ctcaggcctg agccacatct cagagggtct ggaggggaag   10320
aaagacctca tcctactagg gagcccccce agcccaccag cgagcggtgg ttggggcag   10380 acaggctgtg gggctaagga gcccctgcac tccccgtcc ttttcccttt gtctgagcac   10440
ctccagccag tgggcttggt ctagactctc ctatctttcc ccacatcgtg gggtggggct   10500
tgctctgggt taggctactt ttccctagtt gtggggaggg gggtgctggc acatttcact   10560
gttccctgga ggaaatgagt gcctgggaat tcatatctag gctcccagc agcctctttg   10620 caggccaatt tggaaactgt ccccagccct gcattttagg gggttacaga gtctctcagc   10680
aggccctcct cccctgctgc tcccaacttg caagcctgca ctggttggga aacataatg   10740 gtccaaggag ccccctctct actttccgct gtgttccctg tggggaggga agagcagttt   10800
aagaaataag gaatcccaaa ggcgcacagc agaccggggg ccgaggagtg ggtcctgctt   10860
cccctccttt tttctaggct gagccacagc aggtccttga atcctatttc ccagcggatg   10920
ccaggacagc aggccctggg ggagttctct ctcgagcctt tcagagggac cagaggtcta   10980
gcagccaagg agaactcaga atccttgagt gtgtggggca ggaactctcc cagctgagaa   11040
ggggcacaag gtgccaacca tctagggccc agtggccaag gaagacgcgg cttgtcgcag   11100
ggagaatctg ggccctggtc ctcccttttca gggcgggcag ctgacctgcc ccctgctgcg   11160
gacaggcgag gccaggctgc tggctcgcaa gcatggcgga gcccaaacct tccctgctgc   11220
cgcccgccca gccacggctg acttggaagc ttgaggagcg ttcagcagcc tccatcctgc   11280
ccgggaggac cggggacctg gaagggcctg gccctcgctt ccctgcagcg ccctagggg   11340 acgtctcagt gcctcccgga gcccggacca atgcaccaga gctgagggcc caagggtgtg   11400
agggtggccg ggcagtggcc ccgaggacgg cgccccacaa gtttgcggcc agggcccagc   11460 aaaccctag gggtgggaaa gcgtcggccc agctagcggg tccagcaggg ctgcccctt   11520 caccgtggcc cagcggtcac gacccacgt cctcatcgcg ggctgggact gcctctgcgt   11580
ctggcctgag cgggaccgtg ggatcctggg gagccccgcc tcggtgcact gacagagccc   11640
agaaggagtg acggttaccg cttccggtca ggaccggaag tgccgggaac ggcattcgtc   11700
ctccgtgcga gatgacgcac ttcctgcctg aggcggccgc tgttctcgcg gcttccggca   11760
ggtggcgctg agaccacggg aagccagcct ggctgtcggt tagccctcga gcattctggg   11820
aattgcaggc ctggccctc ctcttcctgt tcttggtcaa ttccggtctt gtttccccaa   11880
caaatgccgt cgtttccggg gctgcttccg agccggaccc aagggccggg gcgtggagga   11940
gtagaggggc gagcgcatgc gcacaggact acacgtcccg acaggcgtcg ggagcggcgg   12000
cccagttcct tgtgggagct gtagttctgc aggcgcggaa gccgtggtgc tcggccggca   12060
gagcactcgg tttcccagag ggctgagcgc gccgcacgga ggtgcggcgc cgaccaagat   12120
ggagactgcc gagcagcctt gagccggtag gtttgtggtg agggaggacg ggccgcgcgg   12180
gccggccgag cctccgggag gtcaccgagc gcagctttaa tacctgagct cgaaggcccc   12240
gctgtgctcg ccgaccccg tacctcgcgg ccgggccctt ggacccaca gcatccttgt   12300 gaggcccgga ggcctgtcca gcccgactgg acagtgccga ggggcaccga gagccagctt   12360
```

```
ggcaccgaga gttcgtttgt tctctggcgg ggaggtcttg ctggcacata tagtggagaa    12420
aggccgggct ctgcgttcat gtggagaaag agacggcttc cttcagccta cggacatgaa    12480
ggagtcaact ctaccttcca ctcgttgccg gctttcgccg agaaccccga gaaacggact    12540
accggagtcc ctatcttgca gcccgatccc cgctacccgt cggagtgccc cgctgaccag    12600
gctgcttctg gccgcggcgg cgttccgctg cagaggacgg gagtgcgaat ctgggaagca    12660
gggttctggt tgaactccag cttcgtctgc aacatactgt gtgacttggg caaattattt    12720
cccccgcccc gttcctgcca gctttaaaac ggtcatcagt gggggggtgct gcgtatcccc    12780 tttcactggg gtggcttctt cactgaggag agtcgcgcct cagaggaact gaggtcctgc    12840
ctgtgttcga cctggtgggg ggcactaaga gcccctgata gtaccctga ccccatcctt    12900 attgggtgca caagacacag gtcactctgg gcgggcaagg agttttggta gcaggagagg    12960
agtcggtgga tggatggctg aggacagtgc agaagggtgt ggctgggccg tcttttttg    13020 cctggaaatt caagttctga ggcacccagt cactccagca ctaaatgggt gcaggaggca    13080
gcacttgtct gcccagctgg aaaggcaggg tatgtgctga gtgttacagg tggaaggcca    13140
ctggaggtcg ctccaggagc cgcggggatt tacctctgcc taacagggct gctcaaggtg    13200
atggtcgaca ccccactttc ctgagagctt gaccctcaga tgccagggcc ttggctgcag    13260
attccttggg agctcccggg gatcttccag caaataggag caaatctttt ccccgtggat    13320
caggaaggtg cacgctcttt gtggaatacg actgctcacc ccgcacagca agcagcttat    13380
aagtggccct cctgcctgat ttcagccctg ggttcaagcc ctgggtggct gcttactacc    13440
aaaatcgctc agtagctcca agcctgcctg cagagggttg gcaccattaa atgaggtaac    13500
gagtcaaaag tccctaccct gggtcctagc ctgtcagggg ctccgaaaac ccaggctcag    13560
gtcggtcctg cccggcacct gtttcacaca tgtacactcc ggtctgaggt tggtcctctc    13620
ccccacccca cccacctgca gttgagcagc tgaacagagg ccatgccggg gcactccgag    13680
gcctgagacg accacgcctg tgccgctgag gaccttcatc agggctccgt ccacttggcc    13740
cgcttggctg tccaatcaca ctccagtgtc aaccactggc acccagcagc caagagaggt    13800
gagaggaggg cttggagggg gaggcgggac tccaccctgt gtgggacagt tctgtcagtt    13860
gaccctccac ttgtccaggg gcagtggatc tgcaggggga actcattctc aatactgttc    13920
ctcctgagaa acaaattttc tgggctgttt tggtttaggt gtggcgtggc cctggggacg    13980
catggctgag gcaggaacag gtgagccgtc ccccagcgtg gagggcgaac acggacgga    14040 gtatgacacg ctgccttccg acacagtctc cctcagtgac tcggactctg acctcagctt    14100
gcccggtggt gctgaagtgg aagcactgtc cccgatgggg ctgcctgggg aggaggattc    14160
aggtcctgat gagccgccct cacccccgtc aggcctcctc ccagccacgg tgcagccatt    14220
ccatctgaga ggcatgagct ccaccttctc ccagcgcagc cgtgacatct ttgactgcct    14280 ggaggggggcg gccagacggg ctccatcctc tgtggcccac accagcatga gtgacaacgg    14340
aggcttcaag cggcccctag cgccctcagg ccggtctcca gtggaaggcc tgggcagggc    14400
ccatcggagc cctgcctcac caagggtgcc tccggtcccc gactacgtgg cacaccccga    14460
gcgctggacc aagtacagcc tggaagatgt gaccgaggtc agcgagcaga gcaatcaggc    14520
caccgccctg gccttcctgg gctcccagag cctggctgcc cccactgact gcgtgtcctc    14580
cttcaaccag gatccctcca gctgtgggga ggggagggtc atcttcacca aaccagtccg    14640 agggggtcgaa gccagacacg agaggaagag ggtcctgggg aaggtgggag agccaggcag    14700
gggcggcctt gggaatcctg ccacagacag gggcgagggc cctgtggagc tggcccatct    14760
```

| | |
|---|---:|
| ggccgggccc gggagcccag aggctgagga gtggggcagc caccatggag gcctgcagga | 14820 |
| ggtggaggca ctgtcagggt ctgtccacag tgggtctgtg ccaggtctcc cgccggtgga | 14880 |
| aactgttggc ttccatggca gcaggaagcg gagtcgagac cacttccgga acaagagcag | 14940 |
| cagccccgag gacccaggtg ctgaggtctg agagggagat ggcccagcct gaccccactg | 15000 |
| gccactgcca tcctgctgcc ttcccagtgg ggctggtcag ggggcagcct ggccactgcc | 15060 |
| tagctggaat gggaggaagc ctgcaggtgg caccggtggc cctggctgca gttctgggca | 15120 |
| gcatcctccc aagcagagac cttgctgaag ctcctgggt gtggggtgtg ggctggaagc | 15180 |
| actggctccc tggtagggac aataaaggtt ttgggtcttt ctgagacttt gtgtctatct | 15240 |
| gggccctgct tacccaaagg gctcagttgg cagcaagagc tccccacacc tgaccctcgg | 15300 |
| tgccggacca ctcgagggtg gctgacacct gcatccctca ccagcacatc acccaggtga | 15360 |
| cagtgagaat tggaaacccc aggcctcctc tagggcttgt ggctcagtgg caggtgtcca | 15420 |
| gtgagtgccc tcaatgggcc tgagtgggta cagaatctgc cctcccccaa ccaaagccca | 15480 |
| catgatgcca tcagccccag gcctagtgca gaccacagct tgggaagcga agggagatg | 15540 |

<210> SEQ ID NO 13
<211> LENGTH: 25760
<212> TYPE: DNA
<213> ORGANISM: Homo sapiens

<400> SEQUENCE: 13

| | |
|---|---:|
| gatcacgata gccaagaaat agactcacac atgaggacag ctagtttgac aaaggtgcaa | 60 |
| agtcagttta atagagaaat tgtatctttt caaccaatga tgctggaaca attggatatc | 120 |
| cacctgcaaa aagacaaaat aactttgacc aattcctcaa gctgtattca aattcattaa | 180 |
| tgtaaaatga attagtaacc taatataaat gtaaaactgt gaaactgtta gatgaaaaca | 240 |
| tggtggaaaa tctttgtgac cttagattag tcacagaaag gatatgacgg caaaggcaca | 300 |
| attcataaaa gaaaggtggc taaatggaat gtcatcaaaa tttaaaaatt ccactctttt | 360 |
| gaaaggcagt cataagagaa taagaaaagc aagccatcag ctgataggaa atattcacaa | 420 |
| atcatattac gatgaaggac ttatatccag aatattcatt gcatattctc tgtgtatttt | 480 |
| caaaaatgaa tagtaagaaa acaaccctat aaaaatgagc aaaaaagata tacagatatc | 540 |
| tcctacacac ttgaccaaag aagatatatg gataataaat aaggtcatga aaacatgctc | 600 |
| aacatcatta atcattagga aaatgaaaat taaaaatcgt aatgagatat cgctacacac | 660 |
| ctattagaat ggttaaattt tcttgcttta aaactgatca taccaacttt tggcaaaggt | 720 |
| aggagaaact gtaattctca tgcactgtga gtgggaagat taatggtaca accccttttaa | 780 |
| aaaatgattt ggtagattct taaaaggtga acacacacc ggccggccat atgatccatc | 840 |
| cattccactc ctaggtattt attcaagaaa aatgaaagca tttgtctcca caaagacttg | 900 |
| ttcatgaatg tttatagcat tggatcatag atagcccaaa ccagaaacaa tccaagtgac | 960 |
| gcctaacaag tgaaggtata agcaaatata cccattcatg ttatttatca ataaaaataa | 1020 |
| atgaacgatt gatacctgca acaatatcaa tgaatctcaa ataagtata tggcatgaga | 1080 |
| taagccagac aaaagaatac atcctgtatg tgtccattga cataacaccg tagaatgcaa | 1140 |
| agaatacctg atagaaggcg gatcagtggt tacctaaggc tggggaggag gggtgggagg | 1200 |
| aagggattac acagttgtaa tttaattacg aatttaaaac ttacaagaaa ttgttgacgg | 1260 |
| tgatgatggt ctcactgttg tacacatatg tcaaattca taaaactctg cattttggcc | 1320 |
| cagtgtggta gctcacgcct gtaatcccag cactttggga ggctgaggca ggtggatcac | 1380 |

```
ctgaggtcag gggttccaga cctgcctggc aacgtggtg  aaacctcatc tctattaaaa   1440
atacaaaaaa cttagccggg cgtggtggca cgcacctata gtcccagcta ctcaggaggc   1500
tgaggcagga taattgcttg aaccctagat gcagaggttg cattgagccg agattgcacc   1560
actgcactct agcctgggca acagagagag acctatctaa aaaaaaaaaa aaaaaaaaaa   1620
aaaaaaaaaa acaaaaaaaa acctctatat tttaaatatg tgtagtttat tgtatgtcag   1680 ttagcccca  ataaacctat aacttcccag gggaaatggc tgagattgat gccaccttca   1740
aagagttaaa gaaggcctag gtagtaaccc ccaccatctc tctcgtgatt tccctctct    1800 ggcctctctg cagactggct gaatcagaat agatgattgc agacctcaaa ctcaaccaag   1860
tagcaacacc aaatgggctg ccaggccaga tgtggtatct tcgtttaatc ttagattaaa   1920
ttagattcat ttaatctaag attaaattaa cactgcccct ggtacccggt atcagtagct   1980
acggattctg tgaatgaatt ctcttccatc tcatcaggag agagtgtgag aagcaatttg   2040
cattcgcaca ggagggacaa cagtacacag tcacagtttt gccccaggga tatgttaatt   2100
cttctgctct ttgtcacagt atagtccaaa gggaaaaggc cctctggaca ttccacagat   2160
tatcacgtta gttcactata ctgatggcag tctgttaact ggatctgacg agcaagcagg   2220
ggaaagtact ctggacgccc caagtaaggc acacgagcca ggctgggaga taaattccac   2280
gaagctttag aggcctgcta catcatgatc ttattaccat gaagttattg ccataaaatc   2340
tggcaaatcc catggtacaa gaggtatttg caatggagaa agacaccaca cacacagagc   2400
ccctggagaa cttcaaagaa gagtcatggc ccagactcct tgggctctgg aagaaggccg   2460
tgcagagaac gataccattc agaaagaggt tcctgctctc ctgtgggaac tctagagaa    2520 agagtttctg gtcatggacg ttaagtgacc atgtggtcag agatgcccat cttgagctag   2580
gatctgttaa acccaccaaa tcagaaggtc aggcaagccc agcagcatcc agtatacatg   2640
ggaaaagaca cctcctggga ctgcgaacaa gcagagggca aaagaaagcg acataatccg   2700
gggatcggaa cccccacgtc atctaccagt gttgcactga cacctcttct tcagtccaca   2760
cctgtggcct cctgcagagg tccctctgac cagccgatgg agaaggaagg ggcctgagct   2820
tcactcattg gcaggttagc tagaaacgtt agtgagcccc caaaggactg ctcctgcact   2880
gcagcccact caggtggtgg tgatggtggc gatggggtaa ccctcccagg gggccgagct   2940
ttgagtgcag gacctggtcg tgcacttgta gggagagaag cgaaccaaat cagtggttct   3000
atttctagca gttttaggct ctacagggcc attcccagag cgggacgctt ccaccggaag   3060
acgctattaa gacagcttcc acctggtcac ttcgggctcc tggtatcaac aatctggcag   3120
agagaatgaa gttcccatac tggcaggggt aactggctgg gagcatcatg agaaggtatg   3180
aatacagtca tcaatggggg cgggcaggtg acccaccagg ggcatctctt ggtgctgcca   3240
tgcacagatc ttcccgcaag tagcaagcgc cacagtgtga gcatgataag gccatggtga   3300
ccacaggctg ctcaaggtcc cggctatctg acacggatgg aggaggaagg ggcggtggct   3360
atcagtcagg gccccaggca atgaaaatgg caatggcaat ggcaggagta ggcactggcg   3420
ttcatcccac tcagcctgtt agtgtcaatt tccctggttt tgggaccaa  tttgatcctg   3480 gagaagctct cctcagggga gcaaacctcc tacacaggtg gctgtgcgg  ggggtggggg   3540 tggagtaagg cgtgttgggt catgggtgct actggtgtcc tccccaactc cttttatctg   3600
gaccgtgtgc ctatccccca gctgttaagt gttgacaact aatggctcaa tgaagagctg   3660
tttagctaaa gggaagcccc acatcccgga cgtgtgtgcc ctgggggaca cacagcaaat   3720
gactgacaag gaggaacaga aggcagcctc ttgcttccag tcctgggaga ccatgctgaa   3780
```

```
gccctgcctc ctggcttatc tgtatctcct gcacaagaat tccagcccag gctctgtttc   3840
tagggagtgt gccctgagat gccagcgctt gagcttcgag agcacgaggg ggtaggttct   3900
ggtggacagg gaccccggtg tgacgacaac tgcaaggttc accttggacc ctggcactat   3960
cctcccacca ggctggaaaa ggagaccagg acatggcccc agcacagccc ccaggtgggc   4020
aaaccggcag gctgggctgg ctaagctctt ggtgttcttt gtgtggggt aggtggggct   4080
ggtgagggcg ggactggctg caggtccttc agcgggtccc tgctggacct ccgtggcggg   4140
gacagggatg aaattaaaac agacccgact ccattcaatc tcagcgatcc atgactcagt   4200
gatgcccgga gctgcctccc tttctcctcc ctgggctccc accccgccgc gccccacccc   4260
attatgatcc cccccaaaat gcagagagcc cactagaggg aggaggctga gggctccagg   4320
ctgccctggt cagacaacac atcatgttcc ttcacctgca gatagaccct gagcccatca   4380
gtgaaacaag gggcccccag gagaatcaga atcctgaccc catcccaccc tccacaccag   4440
ctcaacggac tcccaggctg ccagaaaggc ctcatacgtc aaagtcagcc tcccagtcgg   4500
cctccgtttc caggtgtggg ctggagtgc cgtggcccag gtggtatcag aagctcgcag   4560
ggataggcct aagaggtgac cccaggggag gccaggcca aggagctgca gagagggctg   4620
gggaagctcc agatccccca cctccttcaa aacacacctg aaacaccagc cagcaccagc   4680
accaccaaga tgagaaaggg ccctggaccg tctccaccag tgtcatgcag cagctgggct   4740
ggtcccctcc cttgggtccc catctgcccc acttgtacag gagctaacga cgcctgctgc   4800
ccacccagga ggacctagca ggagcccagt gtgaaggtgt ttgcaaaact ctggggaaag   4860
tgaaggtcag aggtgactcc cagcttccac ttaggacata gagagctgga aagagcccgg   4920
ctcccatcct taaactgcag cagcaacaaa aggcaccaag caacctgaaa agtcaggact   4980
tttctcaaaa ctctctgaga gctgaggtca cagggcaacc aactaaccca aaacaaaggg   5040
aaggcaggcg cctgcaggag gagacgggat gcaggctgtc accgagacag acgaggccag   5100
acaccaggaa gaagaacaca gccaaaatgt ttaatgagtt ggcaagggtc ggtgtggggt   5160
aatgggagag cacagaagcc ccaggggctg cggagtgaag ggaaatccac atccactgga   5220
aggtccccgt ggatttcacg ggatgctctc tttgtggtgt aggcccagca gaggggaaca   5280
gcagccactg tcccaaaggt acaaaaccta cataggttat tctcctcaat ggaacaaaac   5340
ccttagattg ctggaggaaa ggcaaaaaag gcaaaaaaca ctgtcacact tagggcacga   5400
gtagaaacca tcgaaactgg gggaatccta aaagccctgt gccctgggga gggataagct   5460
acatggtggg cccagagcta cagctgagcg tagggcagga gtcccaagaa tgcttcaccc   5520
acaagaccca aaggacatag ggttaatcag aaaaaaccga acagcccccc acctccagca   5580
cctgctgaca agcaccatgt aacaagtgac cctggagtgg gagaggccgc agagtgtggc   5640
ctgggagagt ctgcggagtg tggaaaccct ctccaaggta agcttatagc cgaaggctgg   5700
ttggacactg ggaaaagcct ctctatggta aacacaaagt agtgctggag ggatttgatg   5760
actgtggtgc tccagagata accatgacaa caccaaactg aaaccagct caactctgga   5820
cgagattagc cccaagcccc gcagtaaagg aacagcaaaa agaagggtat gcccatttcc   5880
aaaagcacaa aacgaatttc ttcagtctct actgtcctct gcacgatgtc tggatttcaa   5940
aaaattgatg aggcctatta aaaaataaa taaataggcc agggtctgtg gctcacgcct   6000
gtaatcccag cactttggga ggccgaggca ggtggatcac gagttcaaga gatcgagacc   6060
atcctggcca atatggtgaa accccatctc tactaaaaat acaaaaatta gccgggtgtg   6120
gtggcacacg cctgtagtcc cagctacttg ggaggctgag gcaggagaat cgcttgaacc   6180
```

```
cgggagacag aggttgcagt gagccgagat cgcgccactg cgctccagcc tgggcaacaa   6240
gtgagactcc gtctcgaaaa ataaataaat aaataaataa taaataatag atgaatagat   6300
aacgtgctat caagacaaag caagcaaaat aatcagactg aaaggctggt ctcagtggct   6360
cacacctgga atcccagcac tttgggagac tgaggtggga ggatcgcttg agcccaagag   6420
tttgagacca gcctgggcaa cacagagaga cctacctcta caaaaaataa aaataaaaaa   6480
atcaactgtg catggtggtg cccacctgtg gttccagcta ctcgggaggc tgaagcagga   6540
gaatcacttg agcccaggag gtcaagcctg cagtgagtta agattgtact tctctactcc   6600
ggcccggggc agcagagtga ggccttgtct caaaataata atgataaaaa aagaaacaga   6660
ctcagatatg acacagccgt cggaactgtc agacaggaca ttttaaatac aataaatatg   6720
ctaaagactc taaggaccct aatggagaag ggggaaaata tgcaagctca gataggtcac   6780
ttcagcaaag agatggaaac tagaagaaga aatcaaatgg aaaagctaaa ataaaaaaca   6840
gtaacagcca tgagaagaag cctctggtgg gctcatgaat gtactagaca cagcaggaca   6900
gggtccgtga acttgaacac agttcagtaa aaaatcccta aaatgcagag gaaaaaatat   6960
tgaaaagggg gaaaaagatg cccaaatctt tccaagaagt gtgggacata ttaagtgatc   7020
taacatatgt gtgaatggaa atctcagaaa gaaaagatag aaaacacagt gaaaagacaa   7080
gagttgaaga ataatgggt aagaatttta taaaatcatt gacaaacaat aagccacatg   7140
gccaagttca gagaatacca agcaagataa gtaccacatt tttttttttt ttttgagaca   7200
tagtttcgct cttgtcgccc aggctggagt gcaatggtgt gatctcggct cactgcaacc   7260
tctgcctcct gggtccaagt gattctcctg cctcagcctc ccaagtagct gggattacag   7320
gtgcctgcta ccaggcccgg agtagagaca gagtttcacc atgttggcca ggctggtctg   7380 gaaccctga cctcaggtga tccacccacc tcagcctccc aaaggctggg attacaggtg   7440
tgagccactg tgcccggccg gtaagtacca ttttttaaaa actgaaggca tatcacattt   7500
aaactgctga aaacccaaga caaaagcgaa atcttgaaa gcaaccagag aatacaggta   7560
cattccatag agacacaaga aaaacagaaa tatggtagca gacttctaaa cttctcgtca   7620
gaaacaaagt cagccaggga tgaaagaaaa acaacaacaa aaaactgtt gattcagaat   7680 tctatatccg gtacaaatat cttcagaaa aaaggagaa ataaagtctt tctcagacaa   7740
acaaaaactg tagaatttgt tactgaaaga ccttcactat aagaaatgtt aaaggaagtt   7800
cttcaggcaa aaacatgata ccagacagag acttggatct acacaaagaa gcaaagtgca   7860
ctagaaatgg aataaatgaa agtacaaata gaatttcttt ctttctcatt tttaattgct   7920 ctaaagata actgactaaa gaaaaaattg tggtcacgta ttatatgtct atagtataat   7980
gtaaaataga atgtatgaca ataatagcac aaacagtggg aggaaggaat tgagaatatg   8040
cagttgtaaa tttattatat aacacacaga gcaaggtaat atcatttggt agacaatgat   8100
tatttaaaga tgtatattat aaaacctaag acaactatta atttaaaaaa taagatataa   8160
atgataagcc aatagtggaa actaaatgga atcataaaaa gtactcagtt aatccaaaag   8220
aaggcagaaa agggagtggg gggacaacag acggaataaa tagaaaagag ttagcaagat   8280
ggtaaattaa atccaagcat atggccagaa gcagtggctc gggcatgtaa tcccaacatt   8340
ttaggaggct aaggtgggag gattccttaa gcccaggagt tcagaggcta taatgagcta   8400
tgatcatacc accgcactcc agcctgggca acagaatgag atcccatctc taaaaaaaga   8460 aaacactcc aaatacataa ataaataatt atattaatct caacacacca atgaaaagag   8520
atgatcaatt tgaataaaca aaagacccaa ctatatgcta tctatatgaa acccacttta   8580
```

```
aatataaaga cataaataag gttaaagtaa aaggatggaa aatatgtgac acagaagcat    8640
gcgtcaaaat aaagatgcag cagctacatt catctcagac aaagtaggct tcagaacaag    8700
gactattaca agggataagt gagacctcac ataacaataa aggagttgca ttttctgaga    8760
aaacaatcct cagtgtgtag gcacctacca acaaaggctg aaaacacaga aagcaaaaaa    8820
tgataaaata aaatgtaaca ctcattcatg atttttaaaa aactgtcaac aaacaaggaa    8880
tgtaagagaa ctgaacctaa taaaaggcga agctgaaata caaaaaaaaa aaaaaaaaaa    8940
gctaacatac taaatggtga aaggctgagt accectaaga ttgtaaagaa ggtatgatat    9000
cccctctcac acttctttt tttttttttt gagagtctcg ctctgtcgcc caggctggag     9060
tgcagtggcg cgatctcggc tcactgcaag ctccgcctcc tgggttcacg ccattctcct    9120
gcctcagcct cccaagtagc tgggactaca ggcgcccacc accacgcctg gctaattttt    9180
tttgtatttt tttagtagag acggggtttc accatgttag ccaggatggt cttgatctcc    9240
tgacctcatg atctgcccgc ctcggccttc caaagtgccg ggattacagg cgtgagccac    9300
tgcacccggg cccctctcac acttctattc catattttac aggaaggcct agccaagata    9360
ttaaggcaag aaaagaaag aaatggtata caaatttgaa aggcagaaat aaaactaagt     9420
caattcacaa tgacatgaat gttgcataga aaattcccca aacaactaga gaaaactcct    9480
caaatgaaca ggagagttga gcaagatctc agtataaagt caatatacaa aagtgagttg    9540
tattaatatt tctgtttgct agcaacaaac aattagaatt ttacattttc aaaatagatc    9600
cacttataat aatgctcccc atatgaaaaa cttgggcaca gatgtaacaa aaaaagtatt    9660
ctgatctaaa cgaacagaaa aatatactat gttcatggat tagatgagtc aatattatta    9720
agatgtcagt tctccccacg ttgatctaga tattcataca tcccaataat tttcccagca    9780
gaatgttttg tagatgttga caagttgatt caaaaattca tatggaaatt aaaatgctct    9840
aggatagtca aaataattta ggaaaattat tttctggtca ctatctgatt tcactgatat    9900
gttactatat atttactatt tactacctga tttgactata aagctatagc aatcaagaca    9960
ctgaggtatt ggtgaaggcg tagactcagc tcagtgggat tgaatagaga gcccagaagt   10020
ggatccatat aaatatagtc aagtcaattt tggcaaagat gcaaagggaa atcagtagag   10080
aaagggcagc cttatcaaca aacggaactg gatctattgg atgtccatat gcaaaaaatg   10140
aacctggaca cacatatatc acaccttaca caaaaattaa ctctaaatga atcatagacc   10200
ttaacgtaaa atatacaact ataaaacttc tagaagaaaa cagagaaaat ctttgtgcct   10260
ataggaaagc cagggtcttc agcctcggta ctgttgccat ttggggatgt agctcctgtg   10320 tggggggctgg tctgtgcacc agggaggttt agcagcggtg tgctccagtt gtgacaacta   10380
acaatgtccc cagacactgc ccaatgtcct ctggggggcaa aacaggcctg aattgagaag   10440
agaaagttct cagctgtgac gtggaagcat aacccataac aggaaaaaaa aaagttaata   10500
cacgggactt tgttaaatgt aaaacttttc ttctgtaaat ggccatgtta agatattgaa   10560
aagacaaacc acaggctggg aaaaaatatt tgcaattaca ttatcagatg cagaatttgt   10620
attcagaata cacaaagaac tcgaaactca acaatcagaa aacaaacagc ccaattaaaa   10680
aaatcggcaa agggcttgac agacatgtca ccaaagaagg gaggcagatg gcaagaagc    10740 cccaaaagat gtgccacagg gttcgtttca gggaaatgca aaccgcaaga gacctgtgtg   10800
ctcctgcgtg ctcccgtgtg ctcctgctta ctcctgtgtg ctcccgtgtg ctcctgtgta   10860
ctcctgctgc gaagggtaaa atgaagcaaa acagcgaaaa ctcacagcac acaacctagt   10920
gccagcgagg atggggagca agtgggcctc acgccctgct gcagagtgca ctatggcaca   10980
```

```
gcccctgtgt gtgcctgggg ggcctgtggg tgacagggggg acaaagaaga ggttggcaga    11040
gatggcagag cagcctcctg gtgctggact tcctcaccca gccaggatgg cctgggcctg    11100
caccagtgct gcctgagaca gcgagtctca acctgctcca ggggcgtgtg cgtttctgcg    11160
tgtgtgtgtg tgtgtgtgtc catgcatgtg tctctatgaa tatatgtgct gtatttgcat    11220
gtgtgtgtgt gtctatgtgt gcatatgtct gtgtctgtgt gtctttctgt gtgtgcggtc    11280
tgtgtctgtg ggtctacacg tgtatatgtg catgtgtctg tgtgtgtcgc agtgtgttac    11340
tgtgtctgcg cgtgtgtgca tgcatatgtg caggagggag ggagggctca ggccttagca    11400
gagtccctgg ggctctggga gtggagggca gtgaggctga ggctggtgca aaggtggttt    11460
caggcgctca ggtgaagtgg agcagaaaca gaagttggaa tccagcccca gcgggcgggc    11520
ggcagcagca gtgccggccc tgcccagaac aggttcgacc tgagccggca ctgcccggct    11580 gccctgggc tagggaggct gagacagaga agggaagcca gagggtgggg gtggggccc    11640 ggcactggca gagctgcctg ccctcaacga ccgcccctgc cggagacccc cgccccaccc    11700
gctgtggttc tgctggccca ggtttcgctg ggcccactcc cagggtttgg catcactgga    11760
gcccagggtc cccccgcac cctccccaca gccttggccc tgctgctgcc tgcctcctcc    11820
agggtacccc gaggcccacg tcaggagacc cgcctcaggc agcagtggcc cggtggctgc    11880
ttctgcctag cccgcagcac gtgccaccct gggcgcactg ccttcccgaa ggctctcctc    11940
cctccccggg gcgctccctc ccactctgga atgcctccct gcctgcacag caggagtgtt    12000
tggctgaggt ctgcagcccc gacacaggtc acctcccacg cctatggggg cttcagaaag    12060
tcccggaatc ggccgggcgc cctggctcat gcctgtaatc ccagcacttt gggaggccga    12120
ggcgggcgga tgatgaggtg aggagatcga gaccatcctg gctaacacag tgaaaccccg    12180
tctctactaa aaatacaaaa aattagccgg gcgcggtggc gggcgcctgt agtcccagct    12240
actcgggagg ctgaggcagg agaatggcgt gaacccggga ggcggagctt gcagtgagcc    12300
gagatcgcgc cactgcactc cagcctggga gacagagtga gactccgtct caaaaaaaaa    12360 aaaaaaaaa aaagaaagt cccagaatcc cagacatcta acaggatggg gtcccagaga    12420
ccctccaccc acccatctcc ctgacttcca cacaggcagg gatgaaggac tgagggagag    12480
tgggagaggg taactgtggc ggtcacgaag ggtcctcagg tccccgtcct tatcccaagc    12540
cccatccagg ccagaaccgc ggagtgggtg tgcagagcac tcaggcagcc tgtgaatccc    12600
cacagccact tccctaccct gagacctcag agaatgacct ggcctctgtc tttctgtttc    12660
attttattta ttttatctc cagcttgttt gtgaagttca ggggtaccag tgcaggatgt    12720
gcaggatcct tgtcacaagc atccttctca cgaccctgcc tcactccaaa aggggtatca    12780
ggtaggtgag cagaaacgcc ccttcctgaa tgcctgtcct tgtcccacca caaggatgag    12840
gatgcctgct cagagggcac agggagaagc caatggcata gggtgcacag cagcgagggc    12900
caagggacaa ggagtggggg gcccccacct gcccagcgtg acctgctgac cacagctcct    12960
cagcggcggg acaaagcctg cccatggggc cctcagtggc caccctggat gcaaacacgg    13020
ttaatggtca ggcccagcct gtcccctcct gcgcacaaac tcaggcaga gcagagagct    13080 tacatccacc aagacccaga caaagaaag ccccaagaac accccttaaag gcagccaaac    13140 cctggagctg cctcggccc atcgatggga gcacaagagg tgaatcctgc tacgggcacc    13200
gtggccgtct acgcgaccgc agcaaagagg aacatggacg actcacagac gcagagacgg    13260
ggggtccatg ctgtgtggtg atgttcacct gcagctcagg gacaaaccct acctacggtg    13320
acagatgtca ggaggggtga agggtgaggg agggagggcc tgttagctgg agcgggtctc    13380
```

```
agggatgcct gctgctgctg ctggaaacat tctgcacagg ggttcgggtg gaggttctgg    13440
gagtgtcacc cgtgcacact tgtcagcatg ctctccaggt cctgcatttg aggtgcctgt    13500
accccagtgg aaagatgacg gacagagctg ctcaaccact gccctggacc gcattctgca    13560
gggtgcctta gaaggcccag gaggaaaggg gactccaggc tgggcaccgg tggtccacag    13620
gcttccagag cagcccagct tggccgttgt gtcccagtca ctgggagcta acgaggacgc    13680
accctcatgg gggtatgtgc ccacccagtc ccctccgtag agagcctggg agcctctgtg    13740
atagggcgtc ctggcccagg gctcccaagg ccaagtatga agtctcattc ccccagacaa    13800
ccttcacctc caggctgcat aacctctact gacccctctc aatcccacct cttcttttg     13860 tccatgaagg cagtcgggaa atgcagcctg tgcttcggag aggcgggcag ggctggggtc    13920 accccgccc caggcagtgg dataggagat gcgccagggt caggtccctt gctgcaagcc     13980
tgcaacccgt gcctgtatgt gccagccggg cctgccaatc catccttcac cctgcaggac    14040
cctcccgtct acaggtccca gctctgtgtg ggcctggcca gccctggggc catggctgag    14100
acctgagtcc tcaaaggact gccccttctg agagcagaat cctgctgccc ccagaagacc    14160
aggtgttcaa cctgagccct gatcctaaaa cccatggtcc tctctctcct ccagaatccc    14220
tctgccagcc tccaagagcc gcctgctgct ctcctggtgc ttctcacacc cctggggggat   14280 ggcagggggg cggggagccc agcagaaatt ggagcagaga ggacatggag ggctgagggg    14340
tgagggggca gaccgaatgt atcctctctg cccatgcgtc ttcccccagg atgctacctg    14400
aggtctcggg agaggggcat ctgggaaggc ttcctggagg aagatgagtg cctctctctc    14460
atgagggagg ggctccaggg aggtcagtgt gaacttgtgt tggcacaaag gcagccctgg    14520 ccgaggggge gaaggcagtg tgaagtggga ctcacttccc ccaaagatgc agagggatgt    14580
cgggagacct ggcaggcggc cctgggcagt tcagttgacc ccaccttacc ctaccaggct    14640
gcaggaagcc cctgccccca cctggagccg ctacgggttt tcctagctca gccctaaagg    14700
ctcagcccga ctagatacag gccaactaga gaggtcatgt cagggctgag ggggtggctg    14760
ccaggggtgg ctgctgtggg gaagagcatc ccagcccgca ggccctgcta ccccaggcag    14820
agctgcccgt tgtgtcccgc acgaagagct ttccctgcct gggaatcccg ctctgccccc    14880
caccagccag tggctttgga agttcgtcca gcaaccctgg agtctcagtt tccatgcctg    14940
taatatgggc acagcactca ctccaggatg aacagaagcc gggccaggaa agcagtccct    15000
ggcctggcac cacagcaggg gctgtgaggg ggatggttcc acagttgctg gaggtcgaca    15060
gggaccgaag cacacatgag tgccagatgg gccccacgat gggattccgg cgagggtggt    15120
gcagggagcc acctatacag aggacaattg actgcagaag tgccaggctc atgccctcca    15180
cggatggaga ggccgtcacc tccgggggat gccccagggc cgcatacccg tgcagtggcg    15240
ctggagtggc agtgggcgcc tgccccacac taatgcacac acacatcagt gcacacccac    15300
agccacgcca gagaaagcca caggccctga ggggctgccc catgccagcc tgccagctgc    15360
cacacccctc ccacaaagcc tggctctggc ccgggacaca gggagcccag acccatccag    15420 cttttcccctc aatgccccgg gtcctcccac aaattcatcc tgcctcaagc ctcagtctcc    15480
acttccgaca aatgggtctc aagctctctg ctctgtccac cctgcatggc ggtgtgggca    15540
gcacagagcc agcctggtgg gggctgggga ctctggaagg ggtgctcagg gaggggccgg    15600
gctctggggc ccagaaggcc ttggaaggta gtccaggcgg gtcccggaac aagtgttgca    15660
tgagcaccaa atggctcaga gctcccgaaa cctggcgtgc ctgtgagagc cgttgagacc    15720
ccttttcaag gccctgcctg acagcccaca aaagacattc aaatgagaga caaatatttg    15780
```

```
gggccccaag gttgagccca gcccagcctc tcaggcccag cccaagctgc tcccaggctc   15840
tcatttgggt attaattgca tttcgtttag agatttgcat gcttatcacg cgggtggtgg   15900
ccagccgtgg gggcctggcc agcctggaca gaatcccaag gctcgtaggc aaatgccagg   15960 aggaggggt gggcagagga cccaggagcc tcccgaatgg tatcaggaga gcaagcctgg    16020
gctaggctgc gggccatcag cgtgggccct gggccacgac ctggcatcca tgtggacctg   16080
agcacgacaa caggacaagc agagaaaaaa gtggatccca aaaacagggc tcccaggcca   16140
acttctccct aacaccagct cccagcaccc caccggggac tgcagcccct ccatggtcaa   16200
tcagggtagc cctgggtcc ctgtcacatg acgtatgccc accctccgac agccctgcag    16260
cctgtgggac ggcccgtgtg ctcgccgagg cgcttggaac cttggaggc aggctctcag    16320 aagattggct cagggaccct ctggtccacc ctctcggcat cccagggtgt cctggtccca   16380
ggagatgcct catcccaggc cacacggggc cctaggcctt ccgtcctca gccctgtcta    16440 ctctaccctc tacaagagag gtccagaagg ggcagtgctt gacccaagaa gaagaggctg   16500
taactatgga gaggttggga ggggaagtg gccctaaggg ctggagtttt agaaagccct    16560
cttgttcctg cccattatgg gttggatttt atgccctcca gactcacatg tggctgtttt   16620
tggagccagg gcctttaaag aggtaattaa gttaaagtga ggtcattggg gggaccctaa   16680
tcccatgtga ccgatatcct tagtaagagg aggtgaagac acagacacgc acagagggat   16740
ggccacgtga agacacaggg agaaggcagc gtctacaagc caaggagaga ggccttcgga   16800 ggtgggggc ctgcggaatg tgagagact aatttctgct gtgtaggccc cctagtgtgc     16860
ggggcttttt cacgcagcac aggccaaccc attgcagcct ctcctgctgt taggacccca   16920
agtccatcct cagggacatt aattaacata ggaacttttt atcctgatgg tgtcacctcc   16980
taggcagaac agggacccgg aggcaggcct agctgcgaac ccccagccct ccctgtcctt   17040
ctcgcaggac agcgggtctg gggctgaagg ctgtgacgct gccctgcct ggatcacaac    17100 aggcaggacg gctgagcagg cacacatctg tctctccctc tgctgatctg tggccttgga   17160
caggggctac tctgggggag ctgacaggtg acccccccag gaggccctc cctgcctctg    17220 ggctgggaat ccacctctgt ggagcctg gaatggcct gtttcaaata cgtaagtggg     17280
agcaaggtct catcctcagc gggggacatc gctgggggca aggccagtgg gtgggtggga   17340
aggtttctgt ggcactgggg cctcctgttg attgattcac ccaattaatc acagccagca   17400
gctggggagg gggtaggaag gcggtgaagg gaaaaggagc ccacagccgg gaggccctgg   17460
gaggttggca gaggcctgca cctgcctgca gccagccctc cggcccagcc ctcttccctc   17520
ctttcggagg ggccagagca tggggtgcta agggctcagt cttaacccc tcccagctc     17580 tcagggagcc cctcccatgc tccccaggcc tctgcccac ttgcacctcc ccgggcccca    17640
gggcacagga cgctttcccc acccttggg aggctgaggg tgtcaggagg cctgggctga    17700
gtgctggctt ccgtctcact ggcttgcaga caagaccctc catttcggtg gaaaaacagc   17760
aagaacagca ccccctcca ggcagaccca agggaggcat cggtgtgagg gcttcaagct    17820
ctgtactgtg ggtttaagcc ttgcacctct ggatacctgt gggcctcggg cagatcactg   17880
agcctccctg catctggaag tcggggtgag acccctcaga gggggctggg aggaggaagg   17940
gcccctcttg atgggcagcc cccacccctcc acctactgcc ctgccctccc agccttcagg  18000
gtcctcccca gcttctgtgg gctcccaggt ggacctgggc caccctgag accccgaaga    18060 gctcaaggcc agctaatagc ccacaggctc aggacagcac tggacaggcc tctgggccca   18120 cctggccca ctcccgattt ttatgggaac aaagactgaa ggtgtggccc caaggaacc     18180
```

| | |
|---|---|
| acccctcccc cagtgccccg ctgctgggaa aagggtcagc agagtttggg tctcccccca | 18240 |
| caagccctct gggctgtgcg tgctacagct gaggacatgg cgttgagggg caggccgcct | 18300 |
| ccaacccgt ccaccttgcc ctgtctagct ctgtccaagg ctctctccgg ctggctaatc | 18360 |
| acctctgggc acagctgtgc tgctgaggtc tctgggatga ctgaaggtct ttgaaggcca | 18420 |
| ctttgggaga agcgaaggtg catggacacc agggaccctg ctcacagcga gtgtccctgc | 18480 |
| cccatccctt tctgcattga gtgggacaag cttgcttcca tttggggat cgccatctga | 18540 |
| ctattccact tgtcttaggg tggggcagag attaggtgat gtggagggc ttctctacat | 18600 |
| ggccccctg ccccagctct gaggggtagc accagagtgg gtttcaccag cgtagggcac | 18660 |
| gtaggccccg ccatgaacag ggccccaacc ttggtttaat gctttgctac tgccatctta | 18720 |
| aagttctttt tttattttt attttgcttt attttttatt agagatgggg tctcccagtg | 18780 |
| ttgcccaggc tggtcttgaa ctcctggctc aagcaatcct ccggcctcag cctcccaaag | 18840 |
| cactgggatg acacgtgtga gccaccttgc ctggcctttg gaatctgact acttttatct | 18900 |
| tctaacttgt tttgcaggtg caggccaacg gcatacagca gcactcacat aagcaaagga | 18960 |
| gagcgtgcac aaggcgccaa atgtatatcc accctcactc gtcccccac ttgagtagcg | 19020 |
| catccacgat gcccacagac accaggccac acagaaaagg tgccagggac ccacagcagt | 19080 |
| gcaaggcagc gtgtcacacc tacgcatgag caagccgggc gctgatggcc accgagcagc | 19140 |
| cacgttttcc attcaaatcc gcacttgcta aggatgcagc aggaagccag tggtgttcta | 19200 |
| acaaacgtgc aggacccggg aacctgtcat gtcctttctt acttgtgcga cttctctgtg | 19260 |
| ttagccgagg tctcttgctg atggatctac ccacagtgcc ttttgtcttt gaacttgtcc | 19320 |
| cttccctcct tcctcgccca tcagcgagca ggaggtggag ggtgctggtg aacaagcct | 19380 |
| gcgtcaagga gtgaaatcag ctgatttcat ttttgtgcag tttccactgt tctagtagca | 19440 |
| aatgaaatag agacgcctgt gccaggacaa aacacacact gtgtcattcc agtgattccg | 19500 |
| catagaagtt aaatgctctt atgcttgcat tttaaactgg catcacataa tataaagatg | 19560 |
| gataactaca ttcacgctag tcacttaaat tcctaatctt tcttactcag aatggcatta | 19620 |
| aatagtgagt ataaaataag aagtataaaa tagtaagtca agaggttgac tatagaagaa | 19680 |
| agaaaaatgc tttatatttt agcaccttga acatgacatc acgatcacct tctccctgga | 19740 |
| atcagtttct aacttccagg tggggactag gcctggacca tgagctccta gcagagccct | 19800 |
| gctgccccca cagcagagcc caggacaggc tggcacctgg gccaggtgag gctctgtcca | 19860 |
| ggctcactga tctcaaatgc tgaactgcta aggatgtcat gtccccaaag gagccgccag | 19920 |
| gctcagcctc acttcctgga aggcgtgaac attgcaagaa tgtggaagtg aaagagtcca | 19980 |
| gggcttaaat ctcaattctc atcattttca agctgagtcc aagggagaga agacagtcat | 20040 |
| ggattcttag tttctgtttc tggttgagcc agcagggtcc cttcctcatc cctcttttct | 20100 |
| gcttatcact agagacagaa actaaaacca tgacttagg ctgctgagag cctaaaacaa | 20160 |
| aacgacagca agagaaggtg ggttggacca gcttgcctgt gacttcaggc acttcatctt | 20220 |
| tactgggcac tgggtgaatg acagtgtggg gaggggtctt cataacacgg caatcagcag | 20280 |
| cccactgtgc ccaggagact cgcctgtggt cctggttatc aaccacagcc ctttccagtc | 20340 |
| tcaaaaatgt ccccgctggg acagcaagtt acatcgtcgc tacaagtcct gtctcctggg | 20400 |
| agatgcagtc cagcagcact acatcctctg agcagcaggt gccaagtggg atgaactgga | 20460 |
| taaggactgc attcggggaa acgcccgtgt gaaggaaat acacaggaag gaggtggcaa | 20520 |
| cgggtgggaa gccactagac cacgacgcga ttctgcccca gtgaaggcga ggggatagcc | 20580 |

```
tgggcctaga tcgctgtgag gtctatggaa gtttccacaa gcttgctggg tagttctcga   20640
ggcaaactcg gaaagggagt cccttgtctc cctggaacgg atctttcttg gcatctctgt   20700
cacactcatt aggtgggcct ggtgtcaacc ccatttgcag gccacccaa acttgatcaa    20760 aggtccgctt ctggcacccc ataccctgtc ctacaggaaa tacagggaca ggctcccaat   20820
aacaacaccc agcacggtgc catcaacacc accacgcaca cggggctca acggaacaga    20880 catctccgct tcttcaatga agacactgga gggaaattgc ttacaaggcg cttaagagac   20940
ctattaagca aacttgatgt gtggacctgc ggcggatccc gattctataa ggccaactgc   21000
acaaaaccac gagacccct gaggactgcg ccattggctg ggtccccgat gatatgaaag    21060
aacggtggtt catttgagcg ggtgatgttt ttgcggtttc ctttagaggc acacgtgaaa   21120
catgacgggt gaaaggattc aaagtctggg atttgcttca aagcaacgca gggatggcgt   21180
gggggatgga tggggcagga agggccttga aactggtgct ggaggcttcc cagggctgcc   21240
ctggagccca gtgcgtcctc caccggccag actgtacaac ggttggatcc tgtgtccact   21300
gctaggaccc aggctccacg agcacgggct tgtgtggcac acggatgcac cctaagtcct   21360
ggcacagaga ctgctcaaca aaggcctcgg tgcttttgtg tatgtttgaa attttccata   21420
ataaaatgaa aaatgggaaa atgggaaaac aaaaatggca gcactactta ccctctgcag   21480
agttttgtcc gcttcacgcc agtgggtggc agtcgtttcc tctgccctgg ccttccatcg   21540
tttcccccct accctcttca cccacccaac agcccctgt ggtcctggca gctgtgggcc    21600
tttccttgag gtcaaggtgt ggagtcctgg ggagggctca gggaggccac cgacccgggt   21660
gtggattctg ggagaagcct gtgggatgtc cctccctggg tgaccacggc aatgtgcccc   21720
ctcctgtccc ttggccaagg ccagttccct gagccctgca gccccaagcc acagctggtc   21780 cactgaccc agttgagcct ggtcctcatc agaccagctg accccttga ccccgctac      21840 agactcggct ttgaccttgg ctgctgagga gcccccacct ggactgaggc tgcagctggc   21900
gagagaggag ccctgagctc ctctgataag aagggacctg gccagcctga cgtttgagac   21960
ccaggcatcc cggtagcctg ggtgtcctgt tgccgtggtt attcaggagc cacccactct   22020
gggacaacac cagctgctcc cacctcgcag ggctcccacg gctctgtccc aaccactcct   22080
ttctgaagga aggggtgcct ctgcgcccta aagaaaccgg gggagcccca caaccccctcc  22140 cccaccagga cactaaaagg cagctttcgg tacagtgaga catcaaagcc tcctaggccc   22200
tgagtcaaag gtatagccgt gtaatatccc agtgccagct ctccggctgc ggggagcctg   22260
gcgcaaagct tccaagcctt ccttgttcct ttcaagagcc gctcttagaa ttcaggtgag   22320
cggagacctg cagggcctcc ccagtgcggg caaaacccaa agctagcgag agggcagcct   22380
ccaggcacct ctcactaact cctcccagag gccgttgagg tgggtctggt caaacccatt   22440
tgcaagttaa cccacttgcc ctgggctgcc cagctgccac gttagtggag atctgagcgt   22500
ggtggcctgc gcaggagccc atgccctcag ccccacagcc ggtgctctct ggtcagacca   22560
cctcagccta gccccacacc cagcacttac cccagccctc gggatgggtc agcagcctcc   22620
agcctgcagc ttccaagcca gcgagtagcc ctgtctggac aacccaccag cccaccacct   22680
cctggaggat gccccagcc tcacaaggtg tcccaatggc tccgctatca acggcctggc    22740
tgcactccag atctcaccca gacccaccct acggaggagg cagcagggtt tgaggagtag   22800
tgaccacgga agtctggccg tcacctggga agtgtaggtg ataggagcca ctggtaaaca   22860
gaactgattt atttataaag ttcacgctcc cttgaagagg tgtgccccac acaggcttct   22920
ccctagcaga gcagcagtgc ccacaaaccc acccaggt gggctgtcac gggggcctca     22980
```

```
cgccagggac cccgcccctc agggactgct cgtgtccaga tcttggccag catggaaaac   23040
tccagatagt gggggcaggg gtccaggtca tctttattac gccccaggtc aagggttctt   23100
tgtacaaaaa taggtctccg tttgccagca gtgtccctcc agcagctcaa gttaatgtgt   23160
agaaaatgga ttctctgtgc ccttagaaaa tcctctcccc tccggaaaaa tctccaagtg   23220
ttggtgcccc ccgccccact gcagtcgaga agctgtgggg aggggcggcg tcggaggaag   23280
ccgccagccc ttatggggcc agctccaagc ccgtttccac cgcggcattg gtcaggctgg   23340
gccggacgaa cgaggcggcg tcggcggtgc gggggtggt gggtgggtcc ccggctcgct   23400
gggggcggag cgcgggccgg tccacctggc gggctccccg gcgatgagcg cgccggccgc   23460
tcgctcggct tccggggctg aggctgcggg gggaaggtgg ggaaccaaac gcgcgtcaac   23520
gcgggcgcgg gccgggggca gaccccgccc gggccggccc tgcccgcacc tcccccaagc   23580
gaactcggca gtttcgtttg ctcggttggt tttggagtct tgagtccgtg ggtgccgcga   23640
ctcggtctga gacacggcgg gggcggggcg ggcgctcgga ccgcggtga gtcagggctc   23700 cgcgcccgcc gactcatttc tgccgccccg gcccgggagc gcgatttgca atgcaaagtc   23760
accccgcctc cagcacccca atctgcccca ggatccgcca gcactagaga cctcaacggc   23820
ccgacggccg ctcccctccc ctcgtctacc cctccctcgt cggcggctga gccgcgaggg   23880
gaagttttgc aatcccggac aaacaaacgc cggtcttgca cgggcttgaa aaactttggg   23940
ggaaatgaag agtgagcgaa atcgaagcca tcgctcgggc ctggcgctcg gctccgcggg   24000
ctcctggggg cgcgacccgc cgggcctgcc caccccgtcc ctccacccg gccccggcc    24060 ctccctcctc cctgcctccc ggctgttacc tcataggtcg agggcgctca gtagcccct   24120 aaccagctgg agaagtcgag tagctcgcgc tccgcaggac tcagcgcgcc ttcgcagccg   24180
ctgtcgtccg acgagtaggc ggaacgcggg gagccgggct ccgagctgcc cccgcggccc   24240
ggggacgaag aagcgcggga gggcgaggcg cgaccgggg tggtccctgg cggcccgcgg   24300
ggcgcagacg gccgcacggc ctgcggcctc agccctcccg ccagcgcgtt gcgcacggcg   24360
tcgtgctcgg ccagcaggcg ctgcagcgcg cggatgtact ccacggctga gcgcagcgtc   24420
tccaccttgc tcagcttctt gctggcgccg ccgtgcggca cgtgctgccg cagcgcctgg   24480
aagcccaagt tcaccagctt cacgcggttg cgctcgcgct cattgcgccg cgctacggcc   24540
gctgcgccgc ctccggtctc tgcggtgcc ggtcgccgcc gccggctgca gcgcaacagt   24600
tccggggacg cgggtctccg ccgggcagcg cagccgacag ggacgggggg cgcagggggc   24660
gcggacctgg gcagtgtgcc gccgtccatc gcgcctgcat ccacccgccc gctccaggtc   24720
ccggcgcgcc gcaggaaggt gcaggcagag gaaccggagg cgacggggaa aactgtggcg   24780
ccccaagggg gcttctggca cggcgccgcc aggcaactcc ccagggcacg cgtcctaggt   24840
cgtctggagc ccggggatag gaggcctagt ggtggcaggc cgtacgcgcc agggagcgtg   24900
ggacgctcgt gtccgcgcg tgcggccgga ctctcccagg tctccgcagg cgcggcgcag   24960
gcggctggtt tttaaatgta tagataaccc tcctccgcgc cgccgccgtc gcctttctca   25020
cgccctcctt ccttcgcctc gccctcccgc cacgcttcgc cctccccctc gcgcgatcac   25080
attctgtaag gccccaaagcg tgcgcatgtc cccctagccc atcccccgga cgcagtccac   25140 agatcccag tgcgcccaac tggcgaaatc tgcgagttcc cggtgcgccc cctgctcccg   25200
gcaggtgctt agtgcgcccc caaagcaagg tacgcaggtc ctgggttgag ccttcccgta   25260
cccccaccct aaccccgcgc gcagcccgc cagtcccaag agccgccaga ccttcgcacg    25320
cgcagcgcgc gctgtgggag ggaaggcgcg gccctggcga caacacggct gttcgggagg   25380
```

```
cgcgcaagat ccccgggggc agcacgcgcc gcgcagccca cacccacgcc ccaccctcct    25440
ggggccgagg aggcggggc cagggtctca gccaatcgtg ggccaccgt ttggccaatc    25500 gcgcagggcg cggctccacg cccggcccca ttgaggaagc gcgtacgcgt ggcgcgtggc    25560
tcacggggag catcgctaac aaagctgggt tcctgctggg ccccgccctg ctcctcgccc    25620
ccgcgactgg gctgggcgcg ctgtccccta gcgcagctat gtcccgagcg cgccccacc    25680 tgtgcgttaa tctactggga atgggggtgg actgcgcctt acctggggcg gggtggggct    25740
taaggagtgg tcgagactga                                               25760
```

```
<210> SEQ ID NO 14
<211> LENGTH: 38360
<212> TYPE: DNA
<213> ORGANISM: Homo sapiens

<400> SEQUENCE: 14
tgtgcaaggg accttcagag gaggaaaggg aggaaacagg tcaacctctc acggcaggca      60
aggcaagaca ccccctggtt tgagggggtc ttctgcaaat ttcagggagt tgaacctcat     120
acaaacctcc ggtagtaaga aaatattca gagttctcct ttcccttctt ctcgggggaa     180
gaaagaggct aagctccact ccgcttgtcc cttccctagg ggaaggggaa ggagaaggga     240
gaatagcagc ataagcgact ggcagaggca gggaaagacc ggcagaaagg aaagagaaac     300
tgggagagga agtcagagag agagagagac aaagagggag tcaaagagag agaaagagag     360
agacagagag tcagagagag agaaagagag agacagagac aaagagggag ttagagagag     420 aaaagagag acagagagta agagagagag agtcagagag agagaaagag aagtagtaaa     480
gagaaaacag tgtaccctat tcctttaaaa gccagggtaa atttaaaacc tataattgat     540
cattgaagat cttctctgtg accctagaac actccaatac tgcctgtaaa gaagcaagac     600
gagtcacacc agtgactgca agaccctaga gctattaacc agttagtcca aactacccac     660
cctgttgtta cagtaataga tgtaaaagat gccttctggg cttgtccatt tgcagaggac     720
agccaggacc tatatgcctt tgagtgagaa gaccctcact ccggtggaaa atggtaatac     780
caatagacgg tcttacccca agggtttacg gagtctccaa atttatttgg tcaaatattc     840
aaataagtca tttaattagc aaaggtaaac agaaaattga gcttgaatgg attgaaggca     900
tcacattctt gcctctgctg gagactaaat aagagcttag aaaattttgg gattagttgt     960
atggataccg tcgtctatgg gtagactcat gccctaaaaa caaaactctt acacaaaaag    1020
ctcacacgag acagaccaaa ccccctcatg tggcaattac cagaaatcca acaggtggga    1080
aggttaaaac atctattagt aactgcccct gtcctagctt tactctcctt aagcagccat    1140
tccaccttgt tggtggtgta acaacggcg tagcccaaaa acactgaggc cactgacaac    1200
ccatagcctt cctaatcaaa aatccttaac ccagtaaccc gcggatggtc caaatgcatt    1260
caatctgtag cagcaacttc tttgctgaca gaagaaagta gaaaaataac tttgagaaga    1320
aacctcattg tgagcacacc tcaccaggtc agaactatcc taagtcaaaa aaaaaaaaaa    1380 aaaagaaaa gcaaaaaggt agcttactaa ctcaaaaaat ttaaaatatg aagcgattct    1440
gtcagaaaaa gatgatttaa cattaaccac tgatcattcc cttaacccag caggtttgct    1500 aacagggat ctaactctta atgaattacc atacaaaggt ccaaccagac ctagaaggaa    1560
ctcccttcaa gacaggacaa tagatggttc ctcccaggtg aatgagggaa aaagccacaa    1620
tgggtattca ttaagtaatg gggaaatagg agtagagtta ggaaaattgc ctaggagttg    1680
gggagttgtt tgcactgagc caagccttaa gatactgaca gaatcaggaa ggagtcattg    1740
```

```
tgaaaagtga agtagagttt acctcctcaa aagactttcc tcccccatct aatcaggaat    1800
aaatagtaac ttctcttagt agcaaaatgt attcaaagac cagcgctaac attcttaaat    1860
atctgctaga cgtaataaag aaatcaatgt actttatgtc cttagctccc acaatttagt    1920
ctaaatgttt gctctggcat gcttatactg gtccaggcaa gcattaggtc ctatcctgtt    1980
cctcttcctt gtttgtgtct cacatgtccg tgtgaaaaga ccaccaaaca ggctttgtgt    2040
gagcaacaag gctgtgtatt tcacctgggt gcaggcgggc tgagtccgaa aagagagtca    2100
gcaaagggtg gtggattatc attagttcct acaggttttg gggtaggcgg ttgggttagg    2160
agcaatgttt tgccagcagg gggtggatct cgcagagtac attctcaagg gtggggagaa    2220
ttacaacgaa ccttcttaag ggttggggag attacagagt acattgatca gttagggtgg    2280
ggcagaaaca gatcacaatg gtggaatgtc atcagttaag gctattttca cttcttttgt    2340
ggatctttgg ttgcttcggg ccatctggat gtatacgtgc aggtcacagg ggatatgatg    2400
gtttagcttg ggcccagagg cctgacagtt tgaaggtgtt tttaccttcc tcagcattcc    2460
acgagttact tcttcctttg ttctcctctg cctttgcctc ttttaaaaag ttctaagttg    2520
ctagccagtc gggacaaatg cagaatgtca ggcctctgag cccaagctaa gccatcgcat    2580
cccctgtgac ttgcacgtat atacgcccag atggcctgaa gtaactgaag aatcacaaaa    2640
gaagtgaata tgccctgccc caccttacct gatgacattc caccacaaaa gaagtgtaaa    2700
tggccggtcc ttgccttaag tgatgacatt accttgtgaa atcccttctc ctggctcatc    2760
ctggctcaaa aatctccccc actgagcacc ttgcgacccc ccactctgct cgccagagaa    2820
caactccact ttgactgtaa ttttccttta tctacccaaa tcctataaaa cggccccacc    2880
cttatctccc ttcgctgact gtcttttcgg actcagcccg cctgcaccca ggtgaaataa    2940
acagccgcgt tgctcacaca aagcctgttt ggtggtctct tcacacggac gcgcgtgaaa    3000
cagaatgtga ggtcccgttc cagccaatgg aaaccagaca cagcagtagg gtggacgcgt    3060
caggttataa atgaccctgt ctcctttgct cagtgtactc tcgtggcaaa actgctgccg    3120
agtgtaccct ttctacagaa agtataaaaa tgaccttgcg taggaaatta aatttatgtt    3180
caagtgccat ttcttatgg caccggggag caagcatttc aaacatcatt tgtaccaatt    3240
ctaagttaaa tttggactaa acaaggtctt attaatagca aaggataatt gaatcccaa     3300 acttacaagg ttttcaacaa aagtaaagtt tgctaaaagt taacagtata acatgtatta    3360
tcctaacttc taatgttgtg accttaggct gtctagtcca cagacataaa ggaagttcgc    3420
tttggaaaag aatggttatc atctttgaga gaaaaaaaat tgtttcgaag gtttaagcaa    3480
gttttgaaat attcattgta aaggaaacat attggctaaa gttaaagggg tatcttccag    3540 ttttctgtg aactggacat taaaataaaa gcccagtggg tttttcttaa agcgctaacc     3600
tgctctttaa caaaaattac gaaaggttaa aaattataaa agtttaaaaa aagagtctgg    3660
aaatctcacc ttgtggtcag accttaaaat tggatacata tgtctacaag gttttattaa    3720
aatgaagttt aacacgaata acacactaat gtaaaggtga aatttagctg atctggtata    3780
aaatcacaca ggaagcactg tcaaatataa aatggtgttt ggctttcttt ggtctaaaaa    3840
ctaataaaaa taggtactaa aggaaatttc tcagcaagaa ggcactaagg actataaaat    3900
ccactgctga tgtccccacc tttaaaacaa aagatcaatt tttagaaatg atatacttgg    3960
tttatcctcc acccttaaaa caaaaggtct tctagcacag gccctgccct gagagtttcc    4020
agtacatcag caccagcctg gggatcccgt tctcatcaaa gggtggaaag aagggaaact    4080
ggagccagcc tgggaaggac cctgccttgt gctgctgact accgagattg ctattcgtac    4140
```

```
aacggaaagg gggtggacac gtcccaccag agtcaagcaa gcaccattat caacagaatc    4200
atgggccatt gtttctggat caagccctac caaattaaag ctaaggaaag ctgagtctat    4260
ctctttcctt tccttcccta acccagtgcc tatatccatg actattccta ccactagcaa    4320
ctctaacccc actttagaga gtttctgtgg tttgggagca gaggtcactg gaagggatcc    4380
tataggcttc aaggtgcgct tgttctccc tcctccacct cctacgactg cccctttccc    4440
aaacctacaa catcaaacta tgcctcgcct catgccaaat gacacaagca agttcttaga    4500
agtagaaata ggagacccaa ggcaaaccct agccattgaa agagggtata aagacataaa    4560
tgccggttaa aacggattaa atatcccgtt cgcactttaa gcaaaagtga ccattaagct    4620
tgtgggcgcg gtaggccaga ggctcaggat gcctcctttc cactgggacg gtcctcaaat    4680
caagcggaca tggagtgcgt ggtagctctt ttcgaagatt ccaccacctg gaataacgaa    4740
ttgtgccaag ctcttttctct gctatttcct gaagttcagt gccctgtggg tcagcccccg    4800
agggccatcc agccttcatc ttccaaaacc aattttacct cgtgtctcca acaacgaggg    4860
gaaaaaactt ggcattcctt ggagacttaa aaggttgcag taaagtcagg cacctccaaa    4920
agctgaccca tcggtctgcc cttattcatc cctgagcgga tgtatggtgg tattatggag    4980
gacctttact ggacactctg ccaaataatg agagcagtac tgatgctgta gttcagttgg    5040
ctatcccttt tactctggca tttcatcaac cagaaaaaga aaaaaaaatg tagcctcaat    5100
tcttacctct ttaacaacgc taataagtat actctttctt cgtaggtgtt atgtcgtacc    5160
atacatccag gagttcatca aaacaactaa gccaagacat gctaagaaag tttgaagagg    5220
aaaactatac agtaaaagag gagggaattg taggaagtaa aaagtttctg cttcaaagtt    5280
ccccttcttg ttaaagaata aatcataagt cttagaaata atagattctt ttaaagacta    5340
attttcttca agcctccttg ctttgtgcta atagctcttt gttaagccct atcctatgta    5400
actgttggac atgctcacag acacattcca gctcacagcc tatgcccctt ccttaattgg    5460
aaatgttatt gcttcctgaa acctttgta agcaacttct tgttcttcc ttgcacttac    5520 ctatttagga aagtttcaaa tcgggtatca gtttaagata gtgaggtccc actccagcca    5580
atggatgcag gacacagcag taaggacaac ccaaatgcgt aagggataaa tacatctgct    5640
tttcctttgt tcaggtgtgc tctcaccatt gttccatctg cagttgagca ccctttctgc    5700
agaaagtaaa gatggccttg ctgagagatc ttttgtctct gtgctgactc ttcttcgcag    5760
caccgattat ctattcctaa caattttggt atttctaaca ggcccacaca cactgtgtgg    5820
gccaagctgc ttcactcagt ccactgatca aatgctcatc tcatcctcac agacacaccc    5880
aggatactgc ttgaccaaat atctggacaa cccatggccc agtcaagtcg acagaccaaa    5940
tgaactgtca cagacagctt ctgtccttgg aacggggtgg gattccacgg actctctccc    6000
ttcacagtgg agatgctcag tcagcaagct gccagaagtt cagagctggg gaagatataa    6060
agaggactgg gcatggaagc tgcaggaact agtcaggaac tgggagtacc taggagtcag    6120
ctcctgagtg tgcaggatca tggtgaaata gaaagttaga gaaggaagag tgtgtcaata    6180
tcagagcatt gtcttatagc acaggactta accctctcct aaggttccag ggagacagtg    6240
ccaaatcatc acttgagtgg tgcttagaag cttcagggca aaagagccaa ccctaagtac    6300
atttgtctac tggggctgcc atcacaaagc accgcagaca gggtggctta taacagac    6360 tcattgtctc acaatcctgg cggctggagt ccaagatcaa ggttttgcaa ggctagctcc    6420
tcctgaggcc tctcttggct tgtagatgac cggggccttc tctctgtgtc ctcacagggt    6480
cttccctcag tgcgtgtccg tgtcctcacc tcctcttgta agactccagt cctatgagat    6540
```

```
taggacccac tgtcatgaac tcatttactg ttgattacct ttgttttatg ttttttgttt    6600
ttttgagaca gggtcagtct ctgtcaccca ggctggagtg cagtggtgca atcatggctc    6660
actgcagcct caaactcctg ggctcaagga atcctcccac ctcaatctcc caagtagctg    6720
ggactacaga tgcataccac tgtgcctggg tgtattagtc tgttattgca cagctataaa    6780
gaaatacctg agagtgggta acttataaag aaaggaggtt taattggctc acggttcata    6840
gctgcttctg gggaggcctc aggaaagttt cagtcatggt ggaaggtgaa ggggaagcag    6900
acacgtctta cacggccaga cagttcctcc tacactggct gacactctct cctgccacct    6960
tgtgaagaag gtgcctgctt ccttttctgc catgactgta agtttcctga ggcctcccca    7020
gccatgtggg actgtgagtc aattaaacct cctttgttta taaattgccc agtctccggt    7080
agtatcttta taacagtgtg aggatgagct aatacacaca ggaagcagca atgccatcaa    7140
agagccaggg gccttgactg gcagaactag tgagaccatc accaaaacat ggcattcctt    7200
gggcaaggca ggtgcgcagc cagcaaggta ttgcttaatc tacatgatca aaagacatca    7260
ggatggttgt tcaggaggct gagaacagcc atcctattat ggctgagttg tgtcccctca    7320
aaatttatat actgaagtct taaccccccca ggacctcagt gtgtaagtat ttggagaaag    7380
ggcctttaaa gatgtagtta aattaaaatg aagacattag ggtgggccct aatccaatct    7440
gactggtgtc cttgtaagaa gaggagatga ggacacatgc agaggcatga ccacatgagg    7500
acacagggag aaggtggcca tctgcaaatc aaggagtgag gcctcgggag gaaccagcac    7560
taccaacacc ttgatctcgg acttccagtc tccagaacca tgagatgatg aaagtctgtg    7620
tttaagctgc ccagtctgtg atattgtttt gcaaccctaa tagatgaata catccccaa    7680 tgaaaaagca tgatctcttg cccagttct gcacctgaga cagttttcaa acccaaaccc    7740
cactgattga aggagggatt aggtcccagg aggacggacc ctgcagtacc atagcaggct    7800
cccccagtcc ttccccaccc caccactaaa ggtgtatttc agtaactgtg cactaggaaa    7860
agggcaatgc ccagggctgg gggactccgg gaccaagttg acactgagag ctggagtcaa    7920
ggtaccatca tgggcccact agagtagggc gtatggaggc cagcaaagtg caatcctggt    7980
ccacctctag ctcacactga gtcatccctt tgcattccca gaatgctgca tattccccca    8040 gacccctaaaa gtacactcag acaatcttgg tagttggcag aatcctcacg taggctcatt    8100
gtcctgtagg gtaaaaacta tcatagtgtt accaagtaga aacttctgaa actgcccacc    8160
accttagcca aggcaataca ccaaaaagaa aatctcattg gtggggaatg gcagagatgt    8220
gggccccttt ggaagacttg aaggttgcag gtgaggcgat tcccatcatc tcccccattt    8280
tccagagaat gctaacagac tactgtcaac ttgtgatggg aaattttatg cgtccacttc    8340
actgggccat ggtgcccaga tgtttggtta acattattc tgggtgtgtc tgcaaggtgt    8400
ttctggatat gcttagcatt tgaatctgtg gactgagaaa agcaggtcac tctctctggt    8460
aaaggtgggc ctcatccaat cagttgaagg tctgactaaa acaaaaagat taagcaagag    8520
aaaattcgct ctccctgcct gtcttagtct gtttatgttg ctataaagga atattggagc    8580
ctgggtaatt gataaagaaa agaggtttat ttggctcatg gttctgcagg ctgtacaaga    8640
aacatgacat ctgcatctgc tgctggtgag ggcctcaggc tgcttccact cctgacagaa    8700
gatgaagggg agccagtgtg tgcagaggtc acatggtgag agaaacaagt gaacatggga    8760
ctgccaggtt gttttcaaca accagctgtc aggggaactc agagtgagaa ctcactcact    8820
accatgagga tggcaccaag ccatccatga gggatctgcc ctcacaaccc aaacaccccc    8880
attagacacc acctccagca ctgaggacca aatttcaaca tgattgatag cccagctcaa    8940
```

```
agagccgctt gtctttgagc tgggatatca gtgttctgcc ttcacactca gattggaact    9000
tacaccatca gctctcctgg gtctccagct tgcagatggc agatggggat actttccaac    9060
ctccataatc acaggagcca attcccccta aaaagcccct gtgtatatgt acagctaatc    9120
ccaagctcca ctgagcagta gcccagtgga ttgttgctgt gccagctgtg ctatatttgc    9180
tggagcagag ggctgtggaa tggggtacat gttaagcacc cattagtggg tggatttgtt    9240
ctatgccatc cctatttaaa aagagccctg gacaccttt  ggggacatc atcattctgc     9300 ccaccacccc gggacaggag gcacatgaat gaactcacag gtgtggccat gagaggtgaa    9360
gagcttggta tcacgtgttc attcccaaca gagagcatcc accagggagc cactaagcaa    9420
ccagttagac agaatggccg cagtccttga cttcagccag cctctgtccc cgaccacctg    9480
agtgctggcc ccctgggtgc atgcatggag cagctttggt ggtagaaagg gatgctgacc    9540
atgaaatcaa cagcacagct ccacccacca aggctggtct agccactgct gccacaaatg    9600
cccaacctgt ctgcaacatg ggctgctgag aagcccccac taggcactat ccatagagaa    9660
agttgacaag gcaacagaag catccatccc attggggggca gcaattcaac tccactagaa    9720
ttgacacata acccaggctg atccccaggc cttattaagt gttgatccac caaacagggc    9780
atgcgtagca gtgccttgga ccaagggacc cactttacaa cacagggagg aggtgcagcc    9840
atggcacatg gcacatggca catggccatg gcatctgctg gtcctatcac agcccacacc    9900
actcagacgc agccagcacc acagagcagg ggagcagcct tttcagagct ccatgaaggc    9960
cccagcgtgg gggtgatact gttcaaggat ggggtgtcac attgtggaac tcagtagtca   10020
ctccaactca acagccacca tggggtgcta tgtccccaac aggcctcgga accaaggggc   10080
agaagcagca gcggcccctg taccaccact gccagtgacc tgctgtgggt tttgtgcatg   10140
ctgttccctc cactctaggc tgccagtccg gggtcgtggt ttccacaggg gacaacgcca   10200
ccagtggaca gataggagac ccactgaaat ttaggctaca gccgatgcct tgtcactttg   10260
gattatttgt ccctggagac caacagtcat gacaacgagc ccccaaactg ggagggaggt   10320
gggccgtggc catcaggagg cagtagaact gctactccat gaggggacag gaaagaatac   10380
atttggtgcc tggtgatcca agtggtggga cttgggggac ttggtgttcc ctcaactgct   10440
ttattcatga gtggacaagt acaacagcca tggcctgagc agggatggtg accagggccc   10500
cagacccctc actgaggagg gtcccagttg gcccactggg taggccacag agactagaag   10560
aggtgcccac tgacagggaa ggaaccaaac atgagtcagg gaagaacaag ggtcatgaca   10620
gccatggcca agacgctatg gggcacaggc tgtagttggc tgtttctcta aacttgtaaa   10680
cccaggtatt agtcagcgtt ctccagaaa  tcagaacccc aggatatata catacagaca   10740
tatgagagga tttatgaggg gaatcggctc acatgattat gcaggctgag aagtctcatg   10800
acaggctgtc tgcaagctgg aaacctagag aagctggtgc ggggctcatt ccaagtccaa   10860
aggcctcaga accaggggag cggattgtgt aactctgagt ccgaggccaa aggcctgaaa   10920
actggtggtg gtggagtggc tactggtgtg agtcccagag cacaatggct ggagaacccg   10980
gagttccgat gtcacagtc  aggagaagat gggttgccta gccctggaga aggagaat    11040 tcgtcattcc ctgccttttt tctctctcta ggccctcaac ctattggatg gtgccaacca   11100
catcaagtga gggtagatct tccttattca gtccatggat tcaaataaca atctctttca   11160
aatctaccct cacagatacc cagaaataat gctttgcaag atgtgatggt taattttggg   11220
tgtcaacttt actagattaa gtgataccca ggtatctgga aaagcattat ttctgggtgt   11280
gtctgtaata taggttggat gtcaccctct accccctacc caaatctcat gttgaattgt   11340
```

```
aatccttcat gctggaggtg gggcctggtg ggaggtgatt ggatcacgag gtggatcctt   11400
catagcttga tgatgtcctc atggcagtca taagatcagg ctgtttgaaa gtgtgtggca   11460
cctcccccac ctctctcttg ctcctgcttt tgccatgtga tgtgcctatt ccccctttgc   11520
cttccaccat gattggaagt ttcctgaggc gtccccagaa gcagatgctt ctatgcttcc   11580
tgtacagcct gcagaactgt gagccaatta aacctctttt cttataaatt atccagtctc   11640
ttttatctca ggtctttctt ttcttttctt ttcttttctt ttctttcttt tctttctctt   11700
ctctttctct ttctttcttt ttcttcttt ctgtctttct ttctttcaga cagatttccc    11760
tcagtctcct acagtgcagt ggcgcaatct cagctcactg caacctccac atcccaggtt   11820
caagccattt ttgtgcctca gcctctcgag tagctgggat tacagtcatg caccactgtg   11880
cccagctaat tttgtgtttt tggtagacac agggtttctc catgctggcc aggcttgtct   11940
caaactcctg acctcaggtg atccacctgc cttggcccct caaagtgctg ggattatagc   12000
caccatgcct ggccccaggt attttttac aggagtgcaa gaatggccta atacagaaac    12060
ttggtaccag ggagaaagat atttctataa agatatctga aaatgtggaa gcaactttgc   12120
aactgggtta caggcagaag ttggaagatc ttgaaaggct cacaagaaga gaggaagatg   12180
aaggaaagtt tggaacctct tagagactgg ttaaatggct gtgaccaaaa tgctaatagt   12240
gatatgacga gtgaaggaca ggctgatgaa gtctcagatg gaaatgagaa acttatttgg   12300
aactacagca aaagtcacat gtgttatgcc ttagcaaaca cttgactgca tcctgttcat   12360
gccttaggga tctgtggaag tttgagcttg agagtgatga ctcaaggtat ctggcagaag   12420
atatttctag gcagcaaagc attcaagatg tggcctggct gcttctaaca acctacacac   12480
agatgcggga gcaaagaaat gacctaaagt tggaatttac atttaaaagg aaagcagagt   12540
gtaaacattt aaaaaaattt gcagcctggt caagtggtag agaaagaaac agcttttca    12600 ggaaataaat tcaagcacac tctggagcta ccgcttacta gagaaatttg cacaactgaa   12660
acagagccaa gtgctaatat ccaaagacaa tggggaaaag gcctcaaagg catttcagaa   12720
acttccaaag aagcccctcc catcacaagc tcagaggcct aggaggaaag aatggtttca   12780
tggaccaaac ccagggccca gtgccctgca cagccttggg acactgttcc ccacatctcg   12840
gccactctgg gttcagcctc agctaaaacg ggtccaggta caacttgggc tgccattaca   12900
gctccagaga gtgcaagcca taagccttgg cagcttccgt gtagtgttaa acctgcagcc   12960
acacagaatg taaaagtgaa ggaggcttag gagcctccac ctagatttca gaggatgtat   13020
ggaaaagcct gggtgcccag gaggaagcct gccacagggg cagttacctc acagagaacc   13080
tctactaagg cagtgcaggg ggggaatgtg gggctgagg ccccacacag agtctccagt    13140
ggggcacttc ctagtggacc catgggaagg aagggggcca ctgtcctcca ggccccagga   13200
tggtagatcc actggaagct tgcactctgc acatagaaaa gcagcaggca ctcaacaacc   13260
tgtgacagca gccacaagag ctgcaccctg cagagataca ggggcagagt ggcccaaggc   13320
ctggggtggc acacccctcg caccagcatg ccctggaaat gggacatgga gtcaaaggag   13380
actaccctag agctttaaga tttaatgact gccctgctgg gttttggact tgtatgcagc   13440
ctgtagtccc tttctttttgg ccaatttctc ccttttggaa catgaatgtt tacccaatgc   13500
ccatatcccc aatgtatctc agaagtaaat aacttttta atttacagg cttgtagatg     13560 gaagggactt gccttgactc agttgagaca ttgaactttt gagttaatgc tgaaatgagt   13620
gaagactttg gaggactatt aggaaggtat gattgtattc ggcaacagga gaaggatatg   13680
agatttggag gcccaggggc taaatgatat agtttggatg tcctttccaa acttcatgtt   13740
```

```
gaacagtaat ctccaatgtt ggaagtggag ccttggtggg aggtgattgg atcacagggg    13800
cagatcccac atggcttggt gatgtccttg atctggacac aagatctggc tgtttaaaag    13860
tgtgtggcac ctccccccac ctctctcttg ctcatgcttt tgccatgtga catgcctgct    13920 cccccttttgc cttttgccat gattggaagc ttcctgaggc ctccccagaa gcagatgctg    13980
ctgtgcttcc tatacagcct gcagaaacat gagccaatta catctgtttt cttataaatt    14040
acccagttgc aggtctttcc taatagcagt gcaatgacag cctaatacag tctgtgaagg    14100
tgttctcaga agacatcggc acttgaatca gtggactgag tgtcttagtc catttgtgct    14160
gctataagaa aatgcctgaa actgggtact ttatagagaa gataaactta ttttctcaca    14220
gttctgaggg ccgggaagtt caagatcaag gtgccagcaa gtatattgtc tggtgaggga    14280
ccctatctct gcgtccaaga tggtgtgttg tggcagcctt ctccagaggg aacgaatgct    14340
ggggtcctcg catggaggat agtggaagag caatacaggg tgaactgtcc ttgaagcctt    14400
tttgacaggg tagtaattca gttatgagga cagagcctgc ataacttaat cacttcccaa    14460
aagccctact tcttaatacc accacaatgg gattacattt caacatgaat ttctaggggg    14520
tatgttcaaa tcatagcatt ctactcctag tcccccaaaa tgtatgacct tatcacatta    14580
aaaatacata cattccatcc cagtaactcc aaaagtctta actcattcca gcatcaactt    14640
taaaatcaaa gtccaaagtc ttatttaaac atcgtctaca tcagatatga ttgacactct    14700
aggtaacatt catcttgagg caaattgctc tccagctgta aacctatgaa atcaaacaag    14760
ttacatgctt ccaaaatatc atggtaggac agacagggga tagatatttc cattgcaaaa    14820
gggaacacta ggaaagaaaa aagcgataat agatcccaag taaatccaaa atccaacaag    14880
gcaagcaaaa tcagatcttg aaacttgaca atgatctcct ttgactccct gtcatgcctt    14940
ccagataccc tagggtggga gttgggcccc caagtctcca ggtggtcctg cccccatggc    15000
tttgccggct gtggctccca agcatgacag tcccctgctt ttggctgtcc caggctggag    15060
ttgcacagca gtgtttctac tggcttgtgg ttgaggggc cctgacccca tggctctatt    15120
aggccatgcc tccatagcac gtgctctgtg tgtgcctgca gaagatgctg ccaaggcgta    15180
ttgcctgtgc ctctggaggg gcagcctgag ccacacctgg gcccatgtga gccatagctg    15240
aggcagctga ggagtgctac actggaatgc agggagcaga gacttgaggc agtactgggc    15300
atgaaggccc aaggtcccat aggtactcag ggaccctcca gagccctggg ttcctcccttt   15360 gactccattc tgccctcaaa gcaaatgcag ggagcagaga cttgaggcag tactgggcat    15420
gaaggcctaa ggtcctgtag gtacccaggg accgtccaga gccctgggtt cctcccttga    15480
ctcccttctg ccctcaaagc cctagaactc taagcctgtg atggccatgg cagcctggaa    15540
gagctttgag atgccgtcag ggcctttctt ccattgtctt aacggacagc acctgacttc    15600
cctctatcgc caggaatctt atcaaatggt ccctgggcca cacccttttgt tttctctcct   15660 acacgcgtgg ccaagctgag actcttccaa acctttaagt tctgcttctc ttttgattat    15720
agattctgtc tttaactcat ttctctcttt cttgcatttt accatacaca gttgagagaa    15780
gccatgcagc tcccttagcg ttttgcttag agatttcttc ctctgaatat tctagttcat    15840
cactgttaaa ttctgcctcc cacaaagccc tcaggcacag acacaattca gcctagttcc    15900
ttaccacttt gtaacaggaa cggtctttcc tccagattcc aataagatat tccttgctgt    15960
gatctaacac ttcatctttaa ctattcatat ttctaccagc attgggatca tgattactta    16020
aacatttctc ttttttttt agatggagcc ttgctctgtc gcccaggctg gagtgcagtg    16080
gtgggatctc ggctcactgc aagctccacc tcccggggttc acgccattct cctgcctcag    16140
```

```
cctcccgagt agctgggact accggcgccc gccaccacgc ccagctaatt ttttgtattt   16200
ttagtagaga cggggtttca ccgtgttagc caggataatc tctatctcct gaccttgtga   16260
tccgcccacg tcggcctccc aaagtgctgg gattacaggc gtgagccacc gcgcccggcc   16320
cacttaaaca ttcctaagaa gactgaggct ctgtctacag atctcctctt cttctaaacc   16380
tgcaccagaa ttgcctttaa tactctgttc atagccattt aggcttttc tgccatgcac    16440
tctgaaacac ttccagactc taccagcagt ttgaaatctg cttccacatt ttcaggtatt   16500
tataacatca acacccccact tatgtttagc aaattatgtc tccgtcccctt tgtgcggcca  16560
taataaaata cctgtaactt ggtcatttct acaacagatt tattatgtca cagtacggga   16620
ggctggaaaa agtgcaagat caggacactg gctgttttgg tgtctggtga gggtcccagt   16680
ctcttcttca agatgaagac ttgttgctgc ctctcctgaa ggggacaaat gctgtgtcac   16740
cacactgtgg atagtggaag agcaatacaa ggtgaactgt ctctgaagcc ttttttataa   16800
gagcgttggt ccattcatga ggactgagcc ctcatgactt aatcacttct caaaaaacgc   16860
taccgcttaa taccaccaca gcggggatta agtttaaata taatgtttgg aggccaggtg   16920
cagtggctca tgcctgtaat cccagcactt gggaggggtg aggcgggcag atcgcttgag   16980
gtcatcagtt caagaccagc ctggccaaca tggagaaact ctatctctac aaaatacaaa   17040
aattaactgg gcgtggtggt gcgtgcacac ctatggtccc agctactcgg gaggttgagg   17100
catggcttaa agccaggagg ttgcagtgag ctgagatcgc gccactgcac tccagcctgg   17160
gcaacagact gagactctgt ctcaaaaaaa aaaaaaaaa acttggagaa ggcaaattca    17220
aagcacgaca gtagagaagg tccatcctcg cccaacgtga gtgggcactg tccaatcagc   17280
agtgggccca gataaggaaa aaaggtagaa gaaaggcgaa ctctccctct ctgcctctcc   17340
ccactctccc ttctgcagct gggacaccca tcttctcttg cctttggata tcagaactcc   17400
agattcttca gccttcgcac tctgagactt gtaccagtgg cctccgggtc tcaggccttc   17460
agctgcagac tgagagttac ccaactggct ttcctgattg acgcttagac tgtaccacat   17520
aaatggcttc cctggtcccc agcttgcaga tggcctattg tgggaattttt cagcctctgt   17580
aatcattgta atcatatgag cccattccca taataaatcc cttctcatgt atctatgtat   17640
ctatacctgt atcaatccta tttctttctt tttttttttt ttgagacaga gtcttgctct   17700
gtcacccagg ctggagtgca gtggcgtgtt ctcagctcaa tgcaacctcc gcctcccagg   17760
ttcaggcgat tctcctgcct cagcctcccg agtagctggg actacaggca cccgccacca   17820
cgcccagcta ttttttgtat ttttagtaga cgggggtttt catcatgttg ccaggatag    17880
tctccatctc ttggcctcgt gattcacccg cctcggcctc ccagagtgct gggattacag   17940
gcgtaagcca gcacacctgg cctcgatgct atttctatcc tatcggttct gtttacctga   18000
agaaccctaa cataggtttt ggtatcagga tgattctaga gaaacagaat cataagaatg   18060
agttttctga atgtgtattg tgttttcgg aattggtttt ctaatatgac ttgacttaaa    18120
agtgagaaga actctacttc caacagtaca caggacactg atggtccatg gtgtgaatag   18180
tttatgaaaa tatgcaaatt tctgcattgt atactcctag taaaccactt acaagaggca   18240
aggagcttag tgactctgta tatgatattt tcgaacattt gtggaaaacc agggaatata   18300
gtgacgtggg ctggttacca gttggttgct ggacaaagtg atgaaatcac aggatgtgct   18360
cagtgattca aattcccagt tccagctctg tataaataac ctgtgagtgg ctgagtgaac   18420
cctgaaggag aacctccttt cctgtagccc tggggccaag actgctgaaa agcaaccaca   18480
agtcctcgtc ctgaaactgg atgaattaca acgcaagttg aactctcagc cttgcggggt   18540
```

| | |
|---|---|
| gtccactgtt ccagtgaggg cattggctgg gaaacagagg atcctgtaag ttgggatgaa | 18600 |
| gacatatgga aggaccctga tgaagctggg gacggtcagc ctctaagtta ggatgagtca | 18660 |
| ttttgtcagc agaagcagcc tccctgcacc cagtggcagt gctacaccca ccccagtgc | 18720 |
| tacacccctc ccccagtggt actggccttt ccaccttctc tgaggcatta atctgtgttg | 18780 |
| cctgaggaaa gggtaaggac ttcccctaag gcagttgctg attctcctcg ggtccctccc | 18840 |
| ccaacccttc cctttgcttt aagacctata acaagactca cagcccagca ggcccctgaa | 18900 |
| ggtgaggccc acagtgtgac acaggaggag gcgagccaca ccccagaaga gccactcgac | 18960 |
| ctctctgatt tatacagaca gacacctggg agcatgagtg ggaacggacg ttgggtgtag | 19020 |
| ggcactgggg gaggaacatg gaggtggagg gaccaggtgt gcaggcatgt ccaccaagta | 19080 |
| gagcctgaat tccaggctgc aactcaggga cttggaaaag ctctaactgg ctggtcggtt | 19140 |
| gaaacatgga tcaaaggatg cctgcagtga gcgagctgga gatgcctaaa ctcccttggc | 19200 |
| ttaacataga ggaagggggtt caaaggctca ttcccaaagg agatcagaat gtgacaatga | 19260 |
| aaacctcctc acctaccctg ggagggccca aaacgcagac cttttcacaac agggatcccc | 19320 |
| aaccccccgg gccatggact ggtactggtc catggcctgt taggaactgg gccacacagc | 19380 |
| aggaggtgag cggtgggtga gtgagtgaaa tccgtattta tagccactcc ccatcacttg | 19440 |
| catgaccacc tgagcttggc ctcctgtcag atcagcagca gcatcagatt tctcatagagg | 19500 |
| tgcaaaccct actgtgaact gcacatacga aggatctagg ctgcaacgct ccttatgaga | 19560 |
| atctaatgcc tgatgatgtg tggctgtctc ccatcctccc cagatgggac tgtctagttg | 19620 |
| caggaaatcg agcgcaggcc tcccactgat tctacatgat ggcgagttgt ataattattt | 19680 |
| ccttacatat tacaatgtaa taataataca gataaagtga acaataaatg taatgtgttt | 19740 |
| gaatcatccc aaaaccatcc tccaactccg ggtctgtgga aaaatattct gccatgaaac | 19800 |
| tagtccctca tgccaaaaag gttgaggact gctgtctcac aacactgaaa tatagacttg | 19860 |
| tgagggagcc cagtctcctt gaagagctct gagattgttc ttctctgtag gccagactca | 19920 |
| ctgtgggaac tgcagtcaat caactgagaa acttacatgt gatgggaata attggatcct | 19980 |
| gggggtagcag tggccaagtg ggggcattca agcaccaaag gcaaagttgg catggttacc | 20040 |
| atgatagaca gcagaggcaa agtagcagtc agacctgagt tacaggtcca acccatgtag | 20100 |
| acctatggca ctggctggtt accatgttttt tcctagcagt gaaacagatg ggaagcctgc | 20160 |
| tcaattccta ctggatacaa gcagaaaact tacagatcaa gtggacaaaa ctctaagtcc | 20220 |
| aatcataaaa acagagaatc atggcctcag tctttcacag acttgagcca gtctatgaac | 20280 |
| ccagaaagag tgaaagaaag gctgggtacc cttgaggaag gacccagga tggccaaaaa | 20340 |
| tgtatatata ctgttaattc tttccctggt cttctccaaa ggggtctatg gccttctatc | 20400 |
| tgtgtaactg tgtattggaa aaaagaaaat aatgtggcat ttcaggacga ttggacactg | 20460 |
| gctctgtcct gacattgatt ttaggagatg ctggaacgac actgtggccc tccagttagg | 20520 |
| gaggggctta gggagccagg tgatcaatgg agttttagct caggtctgac tctgtgggtc | 20580 |
| cagcgggtac ccagcccatc ctgtggtcat cttcccagct ccagatgtgt aagtggaaca | 20640 |
| gacacactca gcagccagca gagtccccac atgcgtcccg tgacctggtg tgtgaaggct | 20700 |
| actgtggtgg gaaaggccaa gtggaagcca ttagagaggt ctctacctag aaccgtcagt | 20760 |
| caaaagccat cccacatccc tggagggact gcagacatca gtgccaccac caaggacttg | 20820 |
| agaggtgcag gggcggcgat ccccaccaca gcccattctc cccacctatt cggcccacag | 20880 |
| gggagacagg tgggtcctgg agaatgacag gggactgtcc taagtttgac tccagctgca | 20940 |

```
gctgctgggc cagacgaggt tccatcgctt gagcaaatta gcacatctcc tgctccctgg   21000
tgcgaagctc ttgatccagc aaatgcgttc tcctccaccc ccgtccacag ggcccagcag   21060
aagccaggcc agccgatgcac cctcgccgcc ccacctgagg ggcctctcgc ctctccagcc   21120
cgtgtcagag gtaattctca ggagtctcga tcacctctcc cttccccagg atgtcacact   21180
ggcccattac actggtgaca tcatgttgat gggacgtaag gcacaagaag tagcctccat   21240
cctagacttg ttggtgtcgg agggtgggga ataaacccaa ctggaattca gagccttcta   21300
cctcagggaa atttccagtg gtgtgaggcc tgttctaagg tgaaggacag gttgttgcag   21360
ctgaaccctc ctacaaccaa aagagaagaa cggcactaag tgggcctgtc tgatgtgggg   21420
ttgacacgtt cttctctctt gaggtgtcca actctgtcca tttactgagt gatttgaaaa   21480
gctgctagtt agttttaagc atggcccaga gcaagagaag tctctgcagt aggtccaggc   21540
tctgtgcatg ccgctctgcc acgtgggcca catgacccgg cagatccact ggtgcctggg   21600
gtgtcagtgg cagacagaga ccctgtgtgg agtctttgcc aggcccctgt aggtgaatca   21660
cggctcaggc ctttaggatt ttggaggaag gtcctgtcat cattcacaga taacccactc   21720
tccttcagag aaacagctct tgccctgctt ctgggccttt gtagaaatta aacacttggc   21780
agtgtgaatc tataatccca gcactttggg aggctgaggt gggcaggtca cctgaggtca   21840
ggagttcaag accagcctgg ccaacatggc gaaaccctgt ctctactaaa aatacaaaat   21900
tagccaggtg tggtggcgag tgcctgtaat accagctact gggaggtgg aggcacgaga   21960 atcagttgaa cccgggaggc ggaggttgca gtgagccaaa atggtgccgc tgcactccag   22020
cctgggtgac agagggagac tctgtctcat aaaaaaagaa aagaaaagaa agaaaaaaag   22080
aaaaggaaac taaactagac aagggccacc aagttaccac gtgacttgaa tggctcatca   22140
tgatctgggg actttctgac ccacgtagcc ataaagtcgt gtgcacagca gtgctgcatc   22200
agccagtgga agcaggggat aggtgatcag gcccaagcag gtcctgaagg cacaaggaag   22260
ttacgtgaag tagtggccca aagcctgtgg ccccactgct gctcccctgc cttctccctc   22320
cctgtctgca cctgtggctg catggggagt tcctctgatt agttgacgga ggaagagaag   22380
actcaggccg gacttacaaa tggttctgct cagtatgcag acactaccgg aaagtggaca   22440
gctgcagccc tgtagcccct gggggatatc cctcagacag tggtgaagag gaatcttccc   22500
cgtgggtaga acttccggca tgcacctgtg tgtgctccgc ttagaaggag cagatgtgtg   22560
atgatatttc attcatggct gttgccagta atttaagtgg atggaggtgc ttgaaaggaa   22620
catgattgga aaattggtga tgaagaaatg tgtggaagag atgtatagat agcccttct   22680 gaacatgcta atgacatcca gatatttgtg tcccatgtga atgctcacca aagggtgacc   22740
tcagcagagg acttcagtaa tcaggtggac agcatgagct actctatgga caccagtgag   22800
ccttttccca gccaccccctc tcatcaccca gtgagctcct gagcgaagtg gctgtggtgg   22860
cagggatgga ggttgtgcgt gggctcagca acatggactt ccactgacca aggccaagct   22920
gagtaccacc agcactgtat gcccagtgtg ccagcagcag agaccaacac tcagcctgat   22980
aagctccatt cctgagtgat cagcccagtg cctgggggca ggtgggtgac actggacagc   23040
tcccatcatg gaaggggcgc tgaggctcca ttccccagcg tgttgagccc ggtgcctggg   23100
ggcgggtggg tgacactgga cggttcccat catgggaggg gcgctggttt gttctcactg   23160
ggataggcgc ctgccatgga tatggatttg tcttccctgc acacagtgct tctgtcgtca   23220
ctaccatctg tgggctcaga actcctcatc taatgccgtg ctgtccacac agcattgctt   23280
tgacgaagga actcactttg cagccaaaga agcgtggcag tgggctcatg ctcgtggtat   23340
```

```
tcacgggtct taccgtgttc tccatcatcc tgaagcagct ggcgtgatag aacggtggaa    23400
tgggcttttg cagacacagc tccagcacaa gctgggtggc agtcccttgc agggctgggg    23460
caaggtgctg ctccaggagg ctgtccgtgc tctgaatcag tgtccaatat gtggagctgt    23520
ctctcccaca gtcaggattc acccgtccgg gaaccaaggg gcagaagtgg gagtggcacc    23580
acccaccatc agccccagtg acccactagc agtgttttg tttcctgttc ccatgacttt    23640
acgctctgct ggcctagggg ccttggttcc aaggtgagga atgctgccac caggagacac    23700
aacaatgact ccattgaact ggaagttaag gtggcacctg ggcagttggg gctcctcaag    23760
cctcagaatc aacaggccga taagagagtt tggatgctgg ctggggattg atccagagga    23820
cccaggggac atcgaactgc actccacacc agaggtgcgg aagagcacgg ggaatgcagg    23880
aggcccctta gggcttcttt aagtgtaacc acaccctgtg gttaagatcc ctggggccag    23940
gctcggtggc tcacgcctgt aatcccagca ctttgggagg ccgaggcggg cggatcacga    24000
ggtcaggaga ttcagaccat cctggctaac acggtgaaac cccatctcta ctaaaaatac    24060
caaaaaatta gccgggcatg gtggcaggca cctgtagtcc cagctacttg tgaggctgaa    24120
gcaggagaat ggcgtgaacc cgggaggcgg agcttgcagt gagccgagat cgcgccactg    24180
caccccagcc tgggcgacag agcaagactc cgtctcaaaa ataaaaaata ataataaaaa    24240
aataatccct gggaaagcac agcaatgcaa gtttccttag gaaactacag caaggccgag    24300
acccttaagc actgaggcct tgggtcacct ggccaggtac agaaccacta ccggctgagg    24360
tgcttgctga gggcaaaggg actacagaat gggcagtggt tataaacacc aggtactcct    24420
gtagcttggc cagtagcaga aatgaggatt gcaactttca cgagtgtttc ctctccattt    24480
tgttaagaaa gcatttgtgc atatgtgtac ataagttaag caaatatctg ttttcttcc    24540 tctcttactc ctttatcatg taacataaga tctattgatt ttgtctcagt atcaaggtat    24600
cgtgaatttt acatgacagt attgaggtcg tgcgatatcg ggagagtcga catcactcga    24660
ggacttcacc tcctcttcca gggaaggagt cagtgcgtgt ctggttgtat gcgggacagt    24720
catcacatgt tagttggaac catgacccttg ctgctgtcta tttggagatg aagtacggtt    24780
taaggaggtg tgtatggggtt ccaagctgac aaggagtgaa cttgtgacgg ttcgtttcag    24840
ctgtcaactt gactggatga agggatatcc agagagcatg aaagcattat ctctgggtgt    24900
gcctgtgagg gcatttccgg agagactggc gattgaatcc gtgggctgaa taaggaagat    24960
ctgtcttcac ccaaagtggg agggcaccat ccaatccact gagggcccag gcagaacggg    25020
aagatgaatt cgtgctctct tgctctctct tcccccacca gagctgggac acccacctcc    25080
tactgccctt agacatcaga actcctggtt ctctgggctt tggaccctgg aacttatacc    25140
agtggcccct ctgactgcga gttacactgt cggcctccct ggttctcaga tcttcaggct    25200
tgaactgagc cacactacca gcctccctgg gtctccagct tgcacagaca gggcaaatca    25260
tgggacttct cagtctccat actcatgtga gccgattccc atcataaacc cccttttcttc    25320 catccatcca tccatccatc catccatcca tccatccatc catccagcta tctatctagc    25380
taccgagcta gctacctgta tctttactta tctctatcta tgtctaccta tatctatatc    25440
tctgtctaca tctctatatc tatctgatct atctctatct ctatggtaat ctcaatctgt    25500
ctgtctgtct gtccgtctct ctgtctatct gtctccctcc ctgtctgtct atctgcctgt    25560
ctgcctgcct gtctatctgt ctgtctgcct gtctgcctgt ctgtctgcct gtctgcctgt    25620
ctatctgact gtctgcctgc ctatctgtct gtctgtctgt ctttatctct atggatctgt    25680
acttatttat ctatctcatt ccgtgtatct gtctctatat ctatacatct acatcatgga    25740
```

```
ggactatggt agatgctcac tgctgtgcac tgcaccgtcc ctcccagcgg gaccacagca  25800
ctggtccagc cagctgccca cagctctcag cttgctcctc ccgaggaaat gccctcagcc  25860
aaaggcagct gcctcaccca tggcttctcc ctgcccctgga agccacctct acccaatgaa  25920
tggtcgatgg aggaagcaac aggtcaggtc cttcacctga attcatggcc tctctaaagg  25980
gccccttcag ctccaaaagc acccgaggca tcatcagaaa ccttctttgc gagtggagca  26040
cagctcagct gcccccacct gctccttccc tctctcacag cctttgtccc caagagcact  26100
tgccacttta cccttgacct acatgtctct atctggcagt gtctcttggg gaaccgaacc  26160
tcagacagtt tgcaagcaac aaattccaaa ggtcgtgcct gggcctggag ctctgctgac  26220
atggaagcca tgcccacctg ggacctgagg gtgtttcttg tctcacaggc ctgatattga  26280
gtggtgtgca tctgcatacc caggtggttg ttaaaacaca gaacggcttc catgctggtt  26340
gaacgacccc taccttgagc ctccaggtgt cccccagagg ccaccccggt tccttccccc  26400
agggtccaag cagggcacga cagacagctt ctggaacatc actcaatgcc gtggccagcc  26460
ccattctgat gggtctgcac caatcggggc tgcttgttaa gcatgactaa agtctcctgc  26520
agtcgtctgc taggactgcc acagcaaagc gccacagtct ggcagccttc acagagacat  26580
ttatctcccc agccctgggg gcctcaagtc caagctcaag ttgttgttgg ggctggttcc  26640
ttcgggggct acgaggtggc ctctgcccag tccctccagc ctctgcccag tccctccagc  26700
ctctggggct cccaggcagc ctcgtgtttc ttggctcgtg gagcatcact ctaatctctg  26760
ccttcacctt cacatggcgt ccttcctgtg tgtgcgtctg catccaactt cccctgttcc  26820
taaggtcacc ggtcagatct gagcaggata ctaatggcca tatcttagtt acatctgcag  26880
tgaccctatt tccaaataag gtcacatatg aggcactgaa ggtcgggact gcaacatgct  26940
tgttctccta tcatggaatc agaccagcag gtgggtcaca ttccgccaga gggagagtgg  27000
gcagacgccc aaagggctgg atgtatacag ctccaggaag aaccgcagtt gcagctgctt  27060
ggacaggtgt gggcactcac agcctcccat gacagccctg gctgggggct ccatccacag  27120
cccctggtgg ggtggggcaa ggcccttcct tctgacccac aggaccttgg acccctgggg  27180
cactgcagag ggactcaggg tcagaccagc agcctttgac atggccaaga gtgaaagtga  27240
tggggaccca cgagccatca gagctctgtc tccagagcct gcacaggag tgttgggaca  27300 aggagcaaag gaatcgggag cacatcaagg caggcaccag atttggaaga acgcccgg  27360 ggaggtgctc ccaggcgagt ggggcagagg gcagtctcct cctgggcttc cctgggtccc  27420
agcccggccc ggctgggcgt cccactgtct ttggtgtggt gtgctccctg cctgtggccc  27480
tgtgatggga gtcctgcttc tctaaacagt gagaccctca cagaaccgt cagcatgtcc  27540 aaagcacctg gaggagaaaa gatttgtctc ctcattcgtc actaggttca tggttgaggc  27600
tctcacagca aaagacagat taacaagaga aaagcagaca catttattca atataagttt  27660
catctcgtat aggagccttc ggaaatgagg acccagcact tcgggaggcc gaggtggaca  27720
gaccatttga agtcaggagt tccgagacca gcctggccaa catggtgaaa ccccatctct  27780
actaaaaata caaaattagc cgggcatggt ggcatgtgcc tgcagtccca gctaccgggg  27840
tggctgaggc aggagacttg cttgaacccg ggaggtggag gttgcagtga gccgagatca  27900
cgccattaca cttcagccag ggtgacagag tgaaactccg tctcaaaaaa aaaaaaaaa  27960 agaaaaagaa aaggaaaaag aaatgaggac ccaagggaag agggaaaccc gtgtattttt  28020
atgtggagtt tgatggagag tcatgcagag tgtgattgga ttagacaaag tgggtgtact  28080
cgtccgttct tgcactgtat aaagaatact tgagactgcg taattcataa agaaaggagg  28140
```

```
tttacttggc ttacagttcc ccaggctgta cagaaagcat ggtgctgca tccacatggc    28200 ttctgggggc gggctcagga aacttacaat catggcggaa ggcaaaggag gagctggcac    28260
ttcacgtggc cggagcagga ggaagcccag agggagagag gggaggtgcc atatgccttt    28320
aaacaagcag gtctcatgag aactcactat cacgagaaca gcactggggg gaaatccacc    28380
cccatgagcc aatcacctcc agcaggcccc acctccagca ttggggatta caattcaaca    28440
tgagatttag gcaggtacac agatccaaac cgtatcaggg tgtggcctaa tggtgataca    28500
ctggggagac ttggcctgtg gtcttagtcc atcgtgtgct gttagaacag aaaaccacag    28560
actggctaac ttattggccc ctggtcctag aggctgggag gtccgagatc gacaggccac    28620
ctctggcaag ggtctttgtg ctgccttatc ccatgacaga agggcaaaga gagggagaga    28680
gagacagcca gagagaaggg gaccaaactc atccttctgt cagagcccgc tcccacgaca    28740
atgatgttag tccatcatga ttacagagat gggggacaca ttcagaccac agcagccccc    28800
tcaacccgca cacactgcac attgagggga gggccgggga actggaagga aacatcagag    28860
tctggagaag accaccagga tcaccagggc tatgctctca cccggcaccc agcaccgagg    28920
ggctcatggg aaacaagacg ggtctctcgg tgcacgagtg ctgggcacac atagtccacc    28980
gtgcatcctg ggctgatgat ctggaccctg gtcctgtgca gccctggggt ggggctccag    29040
gctgagatca gccacgtctg ggggaggaga cagtgttccc agtctcacct tgccccacgg    29100
actctgacag gggttgaaga agcaaggagg ctccaaggac tggggagggg gagtctggcc    29160
gacgatctag gagcatcaag gcgcctgctc cctctcggcg tggcccggtc ctgtaggtgg    29220
tcagttatgc aatgccactg ccttcctacc tcacaaggag ggtgggtgga ctcagaagcc    29280
aggcccaggc ttccttcttg gctcaggcaa ggaacatagg gggctttgag ctttgcttat    29340
tcatttaaca actgaacccc tagtctgtgc caggccccca tttaaatggt ccctgggata    29400
cagcagggtc cagaatgggc ccagaccctg cccccatagc tgaccttctg gagagcctga    29460
ggagtgaggg gtgccctcca ggcacggcag acggggcagg ctctgcattc gggggctcca    29520
gctgctttcc caccacccac ccactccacc cgagcccttc tgggtcagct gggctcctgg    29580
ctctgcccgc ctggggtgca agacgccaag ttccttcctg gacagtgaga gaaccatgcc    29640
aaaaagaaat gaaaggaagg cagacggcga gatgagggag agggtgggca cccagccagg    29700
gaccgcagag acgaggagga ggcacagaga cccactgtcc ccagccactg ccagtgaggc    29760
tggcccaggg ccaggggctg ggcgtccctg gcatgcatgt ggctcccagt gccccacgt    29820 ccaacaggag tggggcggcc ccctcttctg ccacatcccc atcccacctc ccattccatt    29880
cactggtctc attttttaagt ttttctctcc cagttattca ggattgattt ggagagcaga    29940
gcgatggctg caggtggctc ttcatttttcc ttcacctaag aagcaaacca tcatccaccc    30000
caagcttgtc tctccagcct gcccctaca tgaggacaac ctccctcctc ttccacggtg    30060
gcgctgttcc cactggaggc ccaggcttgg ccatccgttc attcttggag tcctcaagag    30120
attgtcagct ctgcagtggg gagcagccgc tgtcaaagac cctggaactt cctccctgct    30180
gcgtccacca acccccactg cccgctgggc actcccaacc tgaaacaagc ttgctcgctg    30240
caaaagcctc acctctgacc caacttccca ctcccaggat acccaacctg gccttccctc    30300
tggatacccc tgtgggctcc cctctgctga tgggttcccc tctccagctg tggcttccct    30360
ctgctgatgg ggtcccctct ccagctgggg ctccctccac tgatgggtt ccctctacag    30420 ctgtggctct ctccactgat ggggtcccct ctccagctgg ggctccctcc actgatgtgg    30480
tcccctcttc agcttgggct ccctccactg atggggtccc ctcttcagct ggggctcctc    30540
```

```
tccactgaca gggtctcctt tccatctggg gctcccttgg ctgatgaagt cccttctcca   30600
ggtgaggctg ctctctgctg acagggtccc ctctccagct aggtctcctc tctgttgata   30660
gggtcccctc tccgggtggg ctcccctctg ctgacgggt cctctgatgg ggtccctact    30720
ccaggggggc tcccctccat agatgagctc cccttcctgg gttgggtgac ccctccgccc   30780
tatctgtgtc tgcaggttgg ggctaggcag tgctggccag catctgacaa cctccccttt   30840
ctgttcttgg gcactgctca cttattcagg tctcagccag gcagcccctc caatggtaat   30900
cttcagagtc cccttcagca acacagcttc ccctctgtgg cccagctcat gctgaagtaa   30960
acaaggcaat gtcattaacg gctggtatca gcttgtacgg ggaaccagtg gccccagaag   31020
cctctgggga ggcccaggct gtgaggatca ggggtccgga agagcctcta gagcgggaga   31080
aagaggcctc aggggtccct cctcacaggg gatggtgaca acacggtagg gaatggaggg   31140
gtcagggctg ggtccaggac acggtgaccc tggccagaaa aggccgggcc tggctggcac   31200
ccgcacgaag ggaacggagc cagtgtggaa aagcaggccc gcgtcctctt ctgcactccc   31260
agccccttta aactacacac agcttgtagg aaggggatca gaggccctg gcgtcccat    31320
ggctatgctg cacctgggga catgaagcct agggtagctc agccagctct ggtcacggct   31380
gacagacagc ctcaccccaa cagcctcacc catccctcct cagggaacag ggtcctaaca   31440
agctgctttc cccatcccag tgttgaacaa aaactcatgg gtttagacaa gagtgaaggt   31500
gactcctcca ccacccatcc cacctccagc aggcagccac ccccaaaatt attgatttat   31560
taataaatca atgacaggtg ccagccagcc ccacctgtcc ccaacctgca aatgcagaca   31620
ggggtcactt ggtccaggga gaggagaccc tcagtggagg ggagacaccc tggagagggg   31680
acccccatcag caaaggggag ccccagctgg agacagtaaa taggcagact attcactgtc   31740
ttcccccctca agccaggccc acagagtcac agagtatagc caccagcctc ctgggcccac   31800
ccggaggcc ccaaccacac tcccctgct cagctcagcc cggatttctg gattctgctg    31860
cctgccaggg atcctgagga ggagatggta tcagagcctc accagcccctt ctcatacccca  31920
ggagtcctca tgatgataac agtgtgtgcg ccaggctgtg caggtgctgg ccggatcct   31980
ctgaggggac gagatctcca tgggagggca ccactctgat gtccatcctg ggcttccgtg   32040
gccctgcctg gccactgccc gctgctcttg gtcaagatca tggaccctca gaggccaacc   32100
aggcctcagc ctgtgcctac agcatcctct ctactgccgg gcttctgaat tgctccttcc   32160
tcctgtctcc cacccagagc aagaacgaag gggaggcccc cagagccctg cagcgccggg   32220
agagactccc atccccaccc cgcatgccat caacacaaac tgccggagag tttaggggat   32280
cccacgactt ggggtctcca aagagacccc cgggacatct catcgagacc ccctggca    32340
ctgcatgctc aggcttccca cccctggccc accccatggg gtgtgccag tccgcatct    32400
caccccatat ccatgcatgc atgcatgaac ctgaaagcac cccacaccct ctggtgctca   32460
gtcctcccct cctccctggg gtcccctccc ctccctgccc ccaagccttt gcatcccct    32520
gcaaacctca caaggggaaa ctatttctgt cctgaaagca gagagggccc tttcttggg   32580
acctctccgc catctctgcc tccactccca gctgctgtca gctctggcct ggcccctgca   32640
ggaagcaatc actggtctcc ctgtttccca tctggcccca aggtctgttc ttgcccttcg   32700
accagagagg tttgaaagca caactcgggc cctgcgtgcc ctgctcccca gggctccaca   32760
cctctgagca cccgcgcagt aacggaggct cccagcccg cctcgccca gggtcccctc    32820
caacactctc tggccttggg cctttgctat acccgggggcc tggaagggcc ccctcatccc   32880
ccaagtgtca ggcaaaggtc tcagagcact gtccctgccc ggcgtgcttg gtcctgactg   32940
```

```
ctaggcccca aatcattcct tttcccatta cctcttggtt tctctgtagc tggggtcact    33000
accccaaatt cttgaattga ctgacgtgtc caactatttc atgttttccc cctctacact    33060 gggagccta caagggcagg gccccctggg caagaatagt gccagccagg agccctgga     33120 gaagatagct acacatgtgc cccaggcccc agatggcact cagccctgcc tgtcaatgct    33180
ggacataggg cagttttat cctggctttc tacacaagga ggaaagacta accatgccag     33240
cgggcagcgg ccggatcacg tatgtcagta gaactctgac ccctgagaag cctggaagcc    33300
aaaccacacc tctgtagcaa tcacgccaca gactcaggcc acggctaacg gctgccagtt    33360
cacctatttt tgccccccaac tcaagaccaa ctggaggaag gcaaatatgt ccctgacgaa   33420
gggtggccgc ctccagcctc cccagcccag agcctcagcc tccccagccc actgcctcca    33480
gcaacacaca tctgaagcct tctctgttgg ttggttttat tggtattttg gaagattgtt    33540 tgtttttgt tatgagatgg agcctcgctc tgtcccccag gctggagtgc agtggcgcga    33600
tctcggctca ctgcaagctc cgcctcctgg gttcaagcca ttctcctgtc tcagcctccc    33660
gagtagctgg gactacaggc acccgccacc gtgccaggct gattttttg tattttagt     33720 agagacgggg tttcaccatg ttagccatga tggtcttgat ctcctgacct catgatctgg    33780
ccatctcggc ctcccaaagt gctgggatta caggcgtgag ccactgcacc tggcctttgg    33840
aaggtctttt atacctttat tgagataaaa ttcttatgac ataaaactta gcataaactg    33900
tagacttagt tggtgtgact ttagagtagt ctcagaattg tgcaaccatc accactgcct    33960
acttttagaa cattttcaac atcccaaaga cagaaccccg taggcacctg ttagcagcca    34020
ctccccaccc agtccacgaa gccccaggca gccactcacc aatctacttt ccattaattt    34080
gcccattcta aacacttgaa aaaaatggta tcacaatggt cttttgggtt tggcttcttt    34140
ccctcagcat catacccctca aagttcatcc atgttgtagc tcgtatcggt acttcattca    34200 ttttatggc tgaataatat tccactgtat ggatagaccg atatttgtt tatttattta     34260 ttcattgatg aacatttgaa ttgttcccac ttttagcta ttaaaactag tgctggctgc     34320
gtgcagttgc tcatgcctgt aatcctagca ctttgggagg atgaggcagg cggatcactt    34380
gaggccaaga gtttgagacc agcctggcca acatggtgaa accccatct ctaataaaaa     34440 tacaacaatt agccagacac ggtcatgcgt gcctgtaatc tcagctactc aggaggctga    34500
ggcaggggaa tctcttgaat ccggggggca gaggttgcag tgagccaaga tcgcgccact    34560
gcactccagc ctgggcaaca gaccaagact ctgtctcaaa aaacaaaaca aaacaaaaca   34620
aaacaaacca gtactgctat gaacatgcat gtgcatattg ttatacagac atatgctttc    34680
atttctcttg gatacacaca cacacacaca cacacacaca cacacacaca cacacacacg    34740
tatatctagg actggaattg ctgattttta tggaaactct atatttagca ttttgagaaa    34800
cggccagtct gttttccgaa gtggctgcac tattttgcat tcccaccagc aatgaaggag    34860
ggttccaatt tctccatacc tctgccaaca cttgttattg tctgtctctt ttatttatag    34920
ccatcttgat gggtgcatcg tggtatctcg ctgtgttttg atttgcattt ccctgatgac    34980
taatgatggg gacatctttt catgagctta tcggtcatat gtacatcttc tttggagcaa    35040
gctctattct aatcctttgc ccatcattaa aggtaggtgg tttgtcttct tgttgataag    35100
ttagagttct ttacatgttt agatactagt cccttatcaa atagatgatt cacaaatgtt    35160
tgctgtcatt tcttgggttg tcttttccact tccttgatgg tgtcttttca cgcacaaatg    35220
tttttagctt tggccaagtc caatttatct atttttttctt ttgttgcctg tgcttttggt    35280
agtgtatatt aaaaaccatt gtttaacaca aggtcaccaa gatttattcc tatgttcttt    35340
```

```
cctaaggatt ttattttttc ttttcttttt ttttcttttt tttgagacaa agtctctctc   35400
tgtcgccaaa gctggagtgc aacggcacaa tctcagctca ctgcaacccc tgcctcctgg   35460
gttcaagcga ttcttctgcc tcagcctccc gagtagctgg gattacaggc gcccaccacc   35520
atgcccagct aattttttgtg ttttttagcag agacggggtt tcaccatgtt ggccaggctg   35580
gactcaaact cctgatctca ggtgatccac tcgcctcggc ctcccaaact gctgggatta   35640
caggtgtgag ccactgcgcc tggccttcct aaggatatca taattttagt gcttacattt   35700
aggtctacga tccattttga gttaattttt gtgcacagca tgaggtaggg gtccaacttc   35760
attcttttgc acatggatat ctagttgtcc cagcaccatt ttctgaaaag actattcctt   35820
cccccattga attgtcttgg tacccttgtc aaaaatcaac tgatggccgg tctgaaggta   35880
gtgagttatc tcaattgatt gttcacagtc agttacagat ggaacacctc gttctactct   35940
ttcccgcctt ctcactgctg cacttgaaca gtctttaaaa aaatcaattg accataaatg   36000
caaggatttg ttcttggagt ctcaacttta ctgcattgat ctgtaggtct atccttatgc   36060
cagtaccaca ttgtcttgat tactgtagct ttgcagtaag tttgaatcag gaaatgtgag   36120
ccctccggtt ttgctcttct cttctctagat tgttttggct attctgaaac ccttgtattt   36180
ccttatgaat ttgaggatca gcttgtaaaa agacagatgg gatttttgata gagattgtga   36240 agctatagat gaattcggga gtttggccat cttaacatta tgtctcctga tccatgactg   36300
caggatatct ttccatttaa ttcgatactc tttgattcct ttcaaaaata ttttgtattt   36360
ttcagtacac aagttttatg catcttttgt tgcattatt tctaggtatg ttcttttgc   36420 caatattata aatgagattg tcttcttcac ttcattttttg gatggttcat tgctagtgta   36480
tagaaataaa atcgatgttt gtatattgat cttgtatcct gccacattgc tatgcatgtt   36540 tattagttttt aagggtttta gtggattttc tatatataat gtcatataat cagcaaatag   36600
aaagtttaat gtcttagtcc ttttgagctg ccacaacaga ctaccataaa ctgagtggct   36660
tataaacaac acaaatgtat ttcccacagt tctggagact gggatgtcca agatcaagac   36720
acccgtaggt ttggtgtctg gtcggggcct acttctgggt tcatagatga ctgtcttctc   36780
gctgtgtccc ccccatagtg aaaggaaggg gcccagggtc tttctaaggc ttcttttata   36840
aggacactaa tccaatatag gaaggctctg ccctcataac ctaatctccc aaaggcctca   36900
cttccaaatt ccatcacctg gggagtaaga atttcaacac tgggggggaca cagatattca   36960 gacatagcat ttttcttctt cctttctaat atgggtgccc ttgacatctt tttcttacct   37020
aattgccctg ccagagcctt ccagacagtg ttgaatggaa gtggggagca ttcacccac   37080 cttactcctg atcataggg aagaactatc cggctttcac cactgagcac cacgttagct   37140
ggggtatttt tgtcagcgct ctttatcagg tggaggcagg tccccttctat ttctagtgag   37200 ttcagtgctt ttttttttt ttaatcaggg aagagtgtga gcttgtgttt gggtgccttc   37260
cctgcgtctg ttgagatgat cttacggttt ctgtctctta ttctattgat atggcgtatt   37320
tattaccttg gttgcttttt ggatgttgat aacatccaaa ctcttctgcc accccttta   37380 atagaaagct gtacaactcc ccaacctgcc tgggcgtgtc tgcccaagat gagtgctagt   37440
ggccgactcc ctgctagagt gagcactgca taaacagcct ctgcttgtcc tcatttgagt   37500
gatcttcatg tattccacga gaaatcaagg cacagggtc tcatggtctc atgaatggct   37560
ccaccaactg aaggtgtgct ccatcggggc tgtgagtcac ctcacgccag gcagaaaggt   37620
ctctctgtca aacatggctt caaggaacca gggacctggt tcctcccaca ggccaggccc   37680
tgcccctaag tgcaatggga atatatgcac atgtcacctg tcccaaaatg ctgggagatg   37740
```

```
gcacttctgc agatggggaa actgagggac cagcccgaag tcacggggag gggaagactc  37800
ctacacacag ggaggagaag aacccagccg ggctgcaaac gcctgccctt cctcaacgtg  37860
cctccggctg tgcccacatc gctccagcag ctctgccttc ctcaggcata agccttctca  37920
gggcagggga ggcccaggga gcggcgctcc catcccaggc cgggctgctg agcaagcccc  37980 tccccttttct cccctcatcc tctgacagag tccacctgaa tatttgtcct ggagccagga  38040
tggaagctcc accaggccca gctaacaaca ggaacccttt cagacgcact tctgggtgcg  38100
tactgtgcca gtatcacaca gacacaagcc atgtccttgt cagccatggg atccccaagg  38160
tccccatgag gtcacaccag tgggccactg ggaagggcac ttcagatgtg gagctcccat  38220
gggccaggcc ctgcgaagtg gtcctcctac cccctcatag ccagtcttcc ctgtgagcct  38280
gcaagtgact gtgaatgtga gttccactct ggagctaaga cgggctgctg cccccgcaat  38340
cagatgtcag gcccatgaag                                              38360
```

ISOLATED GENOMIC POLYNUCLEOTIDE FRAGMENTS FROM THE P15 REGION OF CHROMOSOME 11 ENCODING HUMAN SMS3

PRIORITY CLAIM

This application is a divisional of application Ser. No. 09/999,121 filed Oct. 31, 2001, the contents of which are incorporated herein by reference. This application also claims priority under 35 U.S.C. 119(e) from provisional application Ser. No. 60/244,705, filed Oct. 31, 2000, the contents of which are incorporated herein by reference.

FIELD OF THE INVENTION

The invention is directed to isolated genomic polynucleotide fragments located in the p15 region of chromosome 11.

BACKGROUND OF THE INVENTION

Chromosome 11 contains genes encoding, for example, KCNQ1, a voltage-gated potassium channel; IPL, a homolog of a mouse apoptosis-inducing entity; human achaete-scute homolog 2 (HASH2), human SMS3, human tumor suppressing subtransferable candidate 6 (TSSC6), human ribosomal protein L26 (RIBO26), cluster of differentiation antigen 81 (CD81) and tumor suppressing subtransferable candidate 4 (TSSC4). Human achaete-scute homolog 2 (HASH2), human SMS3, human tumor suppressing subtransferable candidate 6 (TSSC6), human ribosomal protein L26 (RIBO26), cluster of differentiation antigen 81 (CD81) and tumor suppressing subtransferable candidate 4 (TSSC4) are discussed in further detail below. Genes for the latter six proteins are located in the p15 region of chromosome 11, a region known to be associated with the Beckwith-Wiedemann Syndrome (Itoh et al. Am. J. Genet. 92, 111-6, 2000) and some childhood tumors.

Beckwith-Wiedemann Syndrome is characterized by pre and postnatal overgrowth up to 160% of normal birthweight, macroglossia, hypoglycemia, hemi-hypertrophy and childhood tumors, such as Wilm's tumor (Reik et al., 1998, Trends Genet. 13:330-334). This syndrome appears to be associated with deregulation of imprinting. Imprinted genes are genes that are predominantly expressed from one of the parental chromosomes. There appears to be two imprinted subdomains, since the imprinted gene domain of 11p15 contains at least two imprinted subdomains (Lee et al., 1999, Hum. Mol. Genet. 8:683-690). Mosaicism may also play some role in the Beckwith-Wiedemann Syndrome phenotype and may explain the variable phenotypes in Beckwith-Wiedemann Syndrome patients (Itoh et al., 2000, Am. J. Med. Genet. 92:111-116).

Human Achaete-Scute Homolog 2 (HASH2)

HASH2 is a basic helix-loop-helix protein that serves as a critical transcription factor for the development of the trophectoderm. Mice deficient in the HASH2 homolog, MASH2, die 10 days postcoitum due to placental failure (Guillemot et al., Nature 371, 333-6, 1994).

Human Tumor Suppressing Subtransferable Candidates 4 and 6 (TSSC4 and TSSC6)

Both TSSC 4 and TSSC6 are believed to function as tumor-suppressing proteins in that the genes are among the genes of a subchromosomal fragment that suppresses in vitro growth of the rhabdomyosarcoma cell line RD (Koi et al., Science 260, 361-4, 1993).

Human Ribosomal Protein L26 (RIBO26)

RIBO26 is one of the approximately 80 proteins that compose the human ribosome (Kenmochi, N. et al., Genome Res. 8, 509-23, 1998). It has been found in mice to be induced by LPS and IFN gamma but is down regulated by TNF-alpha (Segade et al., 1996, Life Sci. 58:277-285).

Human Cluster of Differentiation Antigen 81 (CD81)

CD81 (also called TAPA1) binds the E2 envelope protein of the human hepatitis C virus and is believed to play a role in hepatitis C infection (Pileri et al., Science 282, 938-41, 1998). CD81 also appears to play a role in T cell activation (Witherden et al., 2000, J. Immunol. 165:1902-1909).

OBJECTS OF THE INVENTION

Although cDNAs encoding the above-disclosed proteins have been isolated, their precise locations and exon/intron/regulatory element organizations on chromosome 11 have not been determined. Furthermore, genomic DNA encoding these polypeptides have not been isolated. Noncoding sequences play a significant role in regulating the expression of polypeptides as well as the processing of RNA encoding these polypeptides.

There is clearly a need for obtaining genomic polynucleotide sequences encoding these polypeptides. Therefore, it is an object of the invention to isolate such genomic polynucleotide sequences.

There is also a need to develop means for identifying mutations, duplications, translocations, polysomies and mosaicism associated with Beckwith-Wiedemann syndrome.

SUMMARY OF THE INVENTION

The invention is directed to an isolated genomic polynucleotide, said polynucleotide obtainable from human chromosome 11 having a nucleotide sequence at least 95% identical to a sequence selected from the group consisting of:
(a) a polynucleotide encoding a polypeptide selected from the group consisting of human achaete-scute homolog 2 (HASH2) depicted in SEQ ID NO:1, human SMS3 depicted in SEQ ID NO:2, human tumor suppressing subtransferable candidate 6 (TSSC6) depicted in SEQ ID NO:3, ribosomal protein L26 (RIBO26) depicted in SEQ ID NO:4, cluster of differentiation antigen 81 (CD81) depicted in SEQ ID NO:5, and tumor suppressing subtransferable candidate 4 (TSSC4) depicted in SEQ ID NO:6;
(b) a polynucleotide selected from the group consisting of SEQ ID NO:7 which encodes human HASH2 depicted in SEQ ID NO:1, SEQ ID NO:8 which encodes human SMS3 depicted in SEQ ID NO:2, SEQ ID NO:9 which encodes human TSSC6 1 depicted in SEQ ID NO:3, SEQ ID NO:10 which encodes ribosomal protein L26 (RIBO26) depicted in SEQ ID NO:4, SEQ ID NO:11 which encodes human CD81 depicted in SEQ ID NO:5 and SEQ ID NO:12 which encodes human TSSC4 depicted in SEQ ID NO:6;
(c) a polynucleotide which is a variant of SEQ ID NOS:7, 8, 9, 10, 11 or 12,
(d) a polynucleotide which is an allelic variant of SEQ ID NOS:7, 8, 9, 10, 11 or 12:
(e) a polynucleotide which encodes a variant of SEQ ID NOS:1, 2, 3, 4, 5, or 6;
(f) a polynucleotide which hybridizes to any one of the polynucleotides specified in (a)-(e);
(g) a polynucleotide that is a reverse complement to the polynucleotides specified in (a) to (f) and (h) containing at least 10 transcription factor binding sites selected from the group consisting of AP1FJ_Q2, AP1_C, AP1_Q2, AP1_Q4, AP4_Q5, AP4_Q6, ARNT_01, BRN_01, CDPCR3HD_01, CEBPB_01, CETS1P54_01, CMYB_01, CP2_01, CREB_02, CREB_Q4, CREL_01, DELTAEF1_01, E47_01, FREAC7_01, GATA1_02, GATA1_03, GATA1_04, GATA1_06, GATA2_02, GATA2_03, GATA3_02, GATA3_03, GATA_C, GC_01, GFI1_01, HFH2_01, HFH3_01, HFH8_01, IK1_01, IK2_01, LMO2COM_01, LMO2COM_02, LYF1_01, MAX_01, MYCMAX_02, MYOD_01, MYOD_Q6, MZF1_01, NF1_Q6, NFAT_Q6, NKX25_01, NKX25_02, NMYC_01, OCT1_02, PADS_C, RORA1_01, S8_01, SOX5_01, SP1_Q6, STSSC6_01, SRV_02, STAT_01, TATA_01, TCF11_01, USF_01, USF_C, USF_Q6 and VMYB_02, as well as nucleic acid constructs, expression vectors and host cells containing these polynucleotide sequences.

The polynucleotides of the present invention may be used for the manufacture of a gene therapy for the prevention, treatment or amelioration of a medical condition by adding an amount of a composition comprising said polynucleotide effective to prevent, treat or ameliorate said medical condition.

The invention is further directed to obtaining these polypeptides by
(a) culturing host cells comprising these sequences under conditions that provide for the expression of said polypeptide and
(b) recovering said expressed polypeptide.

The polypeptides obtained may be used to produce antibodies by
(a) optionally conjugating said polypeptide to a carrier protein;
(b) immunizing a host animal with said polypeptide or peptide-carrier protein conjugate of step (b) with an adjuvant and
(c) obtaining antibody from said immunized host animal.

The invention is further directed to polynucleotides that hybridize to noncoding regions of said polynucleotide sequences as well as antisense oligonucleotides to these polynucleotides as well as antisense mimetics. The antisense oligonucleotides or mimetics may be used for the manufacture of a medicament for prevention, treatment or amelioration of a medical condition. The invention is further directed to kits comprising these polynucleotides and kits comprising these antisense oligonucleotides or mimetics.

In a specific embodiment, the noncoding regions are transcription regulatory regions. The transcription regulatory regions may be used to produce a heterologous peptide by expressing in a host cell, said transcription regulatory region operably linked to a polynucleotide encoding the heterologous polypeptide and recovering the expressed heterologous polypeptide.

The polynucleotides of the present invention may be used to diagnose a pathological condition in a subject comprising
(a) determining the presence or absence of a mutation in the polynucleotides of the present invention and
(b) diagnosing a pathological condition or a susceptibility to a pathological condition based on the presence or absence of said mutation.

The invention is also directed to an isolated polynucleotide from the p15 region of human chromosome 11 selected from the group consisting of SEQ ID NOS: 13 and 14. SEQ ID NO:13 consists of nucleotide sequence immediately preceding the HASH2 gene; SEQ ID NO:14 consists of the gap between the RIBO26 and CD81 gene. Both of these polynucleotides are located in the imprinted subdomains of 11p15. Oligonucleotides derived from these sequences may be used to identify mutations, duplications, translocations, polysomies and mosaicism associated with Beckwith-Wiedemann syndrome. Furthermore, oligonucleotides derived from SEQ ID NO:13 may also be used as a marker for the HASH2 gene and SEQ ID NO:14 may be used as a marker for the RIBO26 and/or CD81 gene.

DETAILED DESCRIPTION OF THE INVENTION

The invention is directed to isolated genomic polynucleotide fragments that encode HASH2, human SMS3, human TSSC6, human RIBO26, human CD81 and human TSSC4, which in a specific embodiment are the HASH2, SMS3, TSSC6, RIBO26, CD81 and TSSC4 genes, as well as vectors and hosts containing these fragments and polynucleotide fragments hybridizing to noncoding regions, as well as antisense oligonucleotides to these fragments.

As defined herein, a "gene" is the segment of DNA involved in producing a polypeptide chain; it includes regions preceding and following the coding region, as well as intervening sequences (introns) between individual coding segments (exons).

As defined herein "isolated" refers to material removed from its original environment and is thus altered "by the hand of man" from its natural state. An isolated polynucleotide can be part of a vector, a composition of matter or can be contained within a cell as long as the cell is not the original environment of the polynucleotide.

The polynucleotides of the present invention may be in the form of RNA or in the form of DNA, which DNA includes genomic DNA and synthetic DNA. The DNA may be double-stranded or single-stranded and if single stranded may be the coding strand or non-coding strand.

The HASH2 gene is 17290 base pairs in length and contains a single exon (see Table 1 below). The HASH2 gene is situated in genomic clone AC002536 at nucleotides 17081-34370. The SMS3 gene is 25970 base pairs in length and contains 3 exons (Table 2). The SMS3 gene is situated in genomic clone AC002536 at nucleotides 34371-60340. The TSSC6 gene is 30196 base pairs in length and contains 9 exons (Table 3). The TSSC6 gene is situated in genomic clone AC002536 at nucleotides 51731-81926. The RIBO26 gene is 21630 base pairs in length and contains a single exon (see Table 4 below for location of the exon). As will be discussed in further detail below, the RIBO26 gene is situated in genomic clone AC002536 at nucleotides 77701-99330. The CD81 gene is 21573 base pairs in length and contains 8 exons (Table 5). The CD81 gene begins at nucleotide 120961 in genomic clone AC002536 and extends to nucleotide 3640 in the downstream genomic clone AC003693. Clones AC002536 (140977 base pairs) and AC003693 (155074 base pairs) have a 2084 base pair overlap. The TSSC4 gene is 15540 base pairs in length and contains a single exon (Table 6). The TSSC4 gene is situated in genomic clone AC003693 at nucleotides 3641-19,180.

The polynucleotides of the invention have at least a 95% identity and may have a 96%, 97%, 98% or 99% identity to the polynucleotides depicted in SEQ ID NOS: 7, 8, 9, 10, 11 or 12, as well as the polynucleotides in reverse sense orientation, or the polynucleotide sequences encoding the HASH2, SMS3, TSSC6, RIBO26, CD81 or TSSC4 polypeptides depicted in SEQ ID NOS:1, 2, 3, 4, 5 or 6 respectively.

A polynucleotide having 95% "identity" to a reference nucleotide sequence of the present invention, is identical to the reference sequence except that the polynucleotide sequence may include, on average, up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identify, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total numbers of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time, the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for purposes of the present invention.

A polypeptide that has an amino acid sequence at least, for example, 95% "identical" to a query amino acid sequence is identical to the query sequence except that the subject polypeptide sequence may include, on average, up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted (indels), deleted, or substituted with another amino acid. These alterations of the reference sequence may occur at the amino or carboxy terminal positions of the reference amino acid sequence or anywhere between those terminal positions, interspersed either individually among residues in the referenced sequence or in one or more contiguous groups within the reference sequence.

A preferred method for determining the best overall match between a query sequence (a sequence of the present invention) and a subject sequence, also referred to as a global sequence alignment, can be determined using the FASTDB computer program based on the algorithm of Brutlag et al. (Com. App. Biosci. (1990) 6:237-245). In a sequence alignment, the query and subject sequence are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

The invention also encompasses polynucleotides that hybridize to the polynucleotides depicted in SEQ ID NOS: 7, 8, 9, 10, 11 or 12. A polynucleotide "hybridizes" to another polynucleotide, when a single-stranded form of the polynucleotide can anneal to the other polynucleotide under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a temperature of 42° C., can be used, e.g., 5×SSC, 0.1% SDS, 0.25% milk, and no formamide; or 40% formamide, 5×SSC, 0.5% SDS). Moderate stringency hybridization conditions correspond to a higher temperature of 55° C., e.g., 40% formamide, with 5× or 6×SCC. High stringency hybridization conditions correspond to the highest temperature of 65° C., e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA.

Polynucleotide and Polypeptide Variants

The invention is directed to both polynucleotide and polypeptide variants. A "variant" refers to a polynucleotide or polypeptide differing from the polynucleotide or polypeptide of the present invention, but retaining essential properties thereof. Generally, variants are overall closely similar and in many regions, identical to the polynucleotide or polypeptide of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred.

The invention also encompasses allelic variants of said polynucleotides. An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The amino acid sequences of the variant polypeptides may differ from the amino acid sequences depicted in SEQ ID NOS:1, 2, 3, 4, 5 or 6 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, as well as these in reverse.

Noncoding Regions

The invention is further directed to polynucleotide fragments containing or hybridizing to noncoding regions of the HASH2, SMS3, TSSC6, RIBO26, CD81 and TSSC4 genes. These include but are not limited to an intron, a 5'-non-coding region, a 3'-non-coding region and splice junctions (see Tables 1-6), as well as transcription factor binding sites (see Table 7). The polynucleotide fragments may be a short polynucleotide fragment which is between about 8 nucleotides to about 40 nucleotides in length. Such shorter fragments may be useful for diagnostic purposes. Such short polynucleotide fragments are also preferred with respect to polynucleotides containing or hybridizing to polynucleotides containing splice junctions. Alternatively larger fragments, e.g., of about 50, 150, 500, 600 or about 2000 nucleotides in length may be used.

TABLE 1

Exon/Intron Regions of the human achaete-scute homolog 2 (HASH2) gene, 17290 bp, reference cDNA accession number U77629; reverse strand coding.

| Exon | Location (nucleotide no./amino acid no.) |
|------|------------------------------------------|
| 1    | 7031-7609                                |
|      | 193-1                                    |
|      | stop codon 7028-7030                     |

TABLE 2

Exon/Intron Regions of the human SMS3 gene, 25970 bp, reference cDNA accession number AB029488; reverse strand coding.

| Exon | Location (nucleotide no./amino acid no.) |
|------|------------------------------------------|
| 3    | 18962-19210                              |
|      | 132-50                                   |
| 2    | 20023-20118                              |
|      | 49-18                                    |
| 1    | 21261-21311                              |
|      | 1-17                                     |
|      | stop codon 18959-18961                   |

TABLE 3

Exon/Intron Regions of the human tumor suppressing subtransferable candidate 6 (TSSC6) gene, 30196 bp, reference cDNA accession number NM_005705; plus strand coding.

| Exon | Location (nucleotide no./amino acid no.) |
|------|------------------------------------------|
| 1    | 5011-5100                                |
|      | 1-30                                     |
| 2    | 6249-6347                                |
|      | 31-63                                    |
| 3    | 10879-10953                              |
|      | 64-88                                    |
| 4    | 15797-15898                              |
|      | 89-122                                   |
| 5    | 16628-16714                              |
|      | 123-151                                  |
| 6    | 18372-18455                              |
|      | 152-179                                  |
| 7    | 18719-18811                              |
|      | 180-210                                  |

TABLE 3-continued

Exon/Intron Regions of the human tumor suppressing subtransferable candidate 6 (TSSC6) gene, 30196 bp, reference cDNA accession number NM_005705; plus strand coding.

| Exon | Location (nucleotide no./amino acid no.) |
|---|---|
| 8 | 19488-19664 |
|   | 211-270 |
| 9 | 20005-20064 |
|   | 271-290 |
|   | stop codon 20065-20067 |

TABLE 4

Exon/Intron Regions of the human ribosomal protein L26 gene, 21630 bp, reference cDNA accession number AF083248; reverse strand coding.

| Exon | Location (nucleotide no./amino acid no.) |
|---|---|
| 1 | 11490-11924 |
|   | 145-1 |
|   | stop codon 11487-11489 |

TABLE 5

Exon/Intron Region of the human CD81 gene, 37113 bp, reference accession number NM_004356; plus strand coding.

| Exon | Location (nucleotide no./amino acid no.) |
|---|---|
| 1 | 10471-10536 |
|   | 1-22 |
| 2 | 23333-23446 |
|   | 23-60 |
| 3 | 27015-27113 |
|   | 61-93 |
| 4 | 27893-27964 |
|   | 94-117 |
| 5 | 28334-28441 |
|   | 118-153 |
| 6 | 28790-28891 |
|   | 154-187 |
| 7 | 29549-29635 |
|   | 188-216 |
| 8 | 29725-29784 |
|   | 217-236 |
|   | stop codon 29785-29787 |

TABLE 6

Exon/Intro Region of the human tumor suppressing subtransferable candidate 4 (TSSC4) gene, 15540 bp, reference cDNA accession number NM_005706; plus strand coding.

| Exon | Location (nucleotide no./amino acid no.) |
|---|---|
| 1 | 13982-14968 |
|   | 1-329 |
|   | stop codon 14969-14971 |

TABLE 7

TRANSCRIPTION FACTOR BINDING SITES

| BINDING SITES | HASH2 | SMS3 | TSSC6 | RIBO26 | CD81 | TSSC4 |
|---|---|---|---|---|---|---|
| AP1FJ_Q2 |  | 14 | 8 | 10 | 16 |  |
| AP1C | 4 | 6 | 8 | 10 | 8 |  |
| AP1_Q2 | 4 | 7 | 5 | 10 | 6 |  |
| AP1_Q4 |  |  | 4 | 5 | 5 |  |
| AP4_Q5 | 30 | 44 | 55 | 12 | 71 |  |
| AP4_Q6 | 14 | 22 | 26 | 4 | 34 |  |
| ARNT_01 | 7 | 4 |  |  | 6 |  |
| BRN2_01 | 5 |  |  | 4 |  |  |
| CDPCR3HD_01 |  |  |  | 5 | 8 |  |
| CEBPB_01 |  | 9 | 5 | 13 | 4 |  |
| CETS1P54_01 |  |  |  |  | 5 |  |
| CMYB_01 | 4 |  |  |  |  |  |
| CP2_01 |  | 4 | 5 |  |  |  |
| CREB_02 |  |  |  |  | 4 |  |
| CREB_Q4 |  |  |  |  | 4 |  |
| CREL_01 | 5 | 11 | 11 |  | 7 |  |
| DELTAEF1_01 | 42 | 49 | 67 | 57 | 84 |  |
| E47_01 |  |  | 6 |  | 17 |  |
| FREAC7_01 |  | 4 | 6 |  |  |  |
| GATA1_02 | 6 | 7 | 6 | 9 | 11 |  |
| GATA1_03 | 8 | 7 | 4 | 15 | 5 |  |
| GATA1_04 | 9 | 16 | 10 | 11 | 10 |  |
| GATA1_05 |  | 5 | 7 | 5 |  |  |
| GATA1_06 | 4 | 7 |  |  |  |  |
| GATA2_02 | 7 | 12 | 6 | 8 | 4 |  |
| GATA2_03 |  | 6 |  |  |  |  |
| GATA3_02 | 4 | 6 |  |  |  |  |
| GATA3_03 |  | 4 |  |  |  |  |
| GATA_C | 6 | 13 | 5 | 7 | 7 |  |
| GC_01 |  |  |  |  | 7 |  |
| GFI1_01 |  | 6 |  |  |  |  |
| HFH2_01 |  |  | 4 | 4 |  |  |
| HFH3_01 | 5 |  | 9 | 7 | 4 |  |
| HFH8_01 |  |  | 4 |  | 5 |  |
| IK1_01 |  |  | 4 |  |  |  |
| IK2_01 | 22 | 24 | 34 | 33 | 56 |  |
| LMO2COM_01 | 21 | 33 | 41 | 18 | 57 | 7 |
| LMO2COM_02 | 13 | 15 | 10 | 11 | 14 |  |
| LYF1_01 | 5 | 7 |  | 4 | 6 |  |
| MAX_01 | 4 |  |  |  |  |  |
| MYCMAX_02 | 4 |  |  |  |  |  |
| MYOD_01 |  |  |  |  | 4 |  |
| MYOD_Q6 | 13 | 13 | 22 | 5 | 34 | 11 |
| MZF1_01 | 73 | 106 | 136 | 63 | 211 | 21 |
| NF1_Q6 |  | 5 | 6 |  | 6 |  |
| NFAT_Q6 | 23 | 33 | 20 | 39 | 16 |  |
| NKX25_01 | 6 | 4 | 4 | 7 | 4 |  |
| NKX25_02 |  |  |  | 4 |  |  |
| NMYC_01 | 14 | 15 | 4 | 10 |  |  |
| OCT1_02 |  |  |  | 6 |  |  |
| PADS_C |  |  | 6 |  | 4 |  |
| RORA1_01 |  | 4 |  |  |  |  |
| S8_01 | 5 | 25 | 15 | 23 | 7 |  |
| SOX5_01 | 5 | 9 | 5 | 8 | 11 |  |
| SP1_Q6 | 6 |  |  |  | 11 |  |
| SRY_02 |  | 4 |  | 6 | 9 |  |
| STAT_01 | 5 |  |  |  | 5 |  |
| TATA_01 |  |  | 6 |  |  |  |
| TCF11_01 | 24 | 27 | 27 | 43 | 43 | 9 |
| USF_01 | 14 | 16 | 4 | 10 | 12 | 4 |
| USF_C | 14 | 16 | 4 | 10 | 12 | 6 |
| USF_Q6 |  | 10 |  |  | 6 |  |
| VMYB_02 | 9 | 5 |  | 4 | 11 |  |

Abbreviations:
HASH2, human achaete-scute homolog 2;
TSSC6, tumor suppressing subtransferable candidate 6;
RIBO26, ribosomal protein L26;
CD81, cluster of differentiation antigen 81; and
TSSC4, tumor suppressing subtransferable candidate 4.

In a specific embodiment, such noncoding sequences are expression control sequences. These include but are not limited to DNA regulatory sequences, such as promoters, enhancers, repressors, terminators, and the like, that provide for the regulation of expression of a coding sequence in a host cell. In eukaryotic cells, polyadenylation signals are also control sequences.

In a more specific embodiment of the invention, the expression control sequences may be operatively linked to a polynucleotide encoding a heterologous polypeptide. Such expression control sequences may be about 50-200 nucleotides in length and specifically about 50, 100, 200, 500, 600, 1000 or 2000 nucleotides in length. A transcriptional control sequence is "operatively linked" to a polynucleotide encoding a heterologous polypeptide sequence when the expression control sequence controls and regulates the transcription and translation of that polynucleotide sequence. The term "operatively linked" includes having an appropriate start signal (e.g., ATG) in front of the polynucleotide sequence to be expressed and maintaining the correct reading frame to permit expression of the DNA sequence under the control of the expression control sequence and production of the desired product encoded by the polynucleotide sequence. If a gene that one desires to insert into a recombinant DNA molecule does not contain an appropriate start signal, such a start signal can be inserted upstream (5') of and in reading frame with the gene.

The invention is further directed to antisense oligonucleotides and mimetics to these polynucleotide sequences. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides of the present invention, is used to design an antisense RNA oligonucleotide of from about 10 to 40 base pairs in length. A DNA oligonucleotide is designed to be complementary to a region of the gene involved in transcription or RNA processing (triple helix (see Lee et al., Nucl. Acids Res., 6:3073 (1979); Cooney et al, Science, 241:456 (1988); and Dervan et al., Science, 251: 1360 (1991)), thereby preventing transcription and the production of said polypeptides.

Expression of Polypeptides
Isolated Polynucleotide Sequences

The human chromosome 11 genomic clone of accession number AC002536 has been discovered to contain the HASH2 gene, the SMS3 gene, the TSSC6 gene, the RIBO26, part of the CD81 gene by Genscan analysis (Burge et al., 1997, J. Mol. Biol. 268:78-94), BLAST2 and TBLASTN analysis (Altschul et al., 1997, Nucl. Acids Res. 25:3389-3402), in which the sequence of AC002536 was compared to the HASH2 cDNA sequence, accession number U77629, the human SMS3 cDNA sequence accession number AB029488, TSSC6 cDNA sequence accession number NM_005705, and the RIBO26 cDNA sequence, accession number AF083248. The remainder of the CD81 gene and the TSSC4 gene were found by similar means in the downstream clone AC003693. The accession numbers for the CD81 and TSSC4 cDNAs are, respectively, NM_004356 and NM_005706.

The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: *A Guide to Methods and Application*, Academic Press, New York. Other nucleic acid amplification procedures such as ligase chain reaction (LCR), ligated activated transcription (LAT) and nucleic acid sequence-based amplification (NASBA) or long range PCR may be used. In a specific embodiment, 5'- or 3'-non-coding portions of each gene may be identified by methods including but are not limited to, filter probing, clone enrichment using specific probes and protocols similar or identical to 5'- and 3'-"RACE" protocols which are well known in the art. For instance, a method similar to 5'-RACE is available for generating the missing 5'-end of a desired full-length transcript. (Fromont-Racine et al., 1993, Nucl. Acids Res. 21:1683-1684).

Once the DNA fragments are generated, identification of the specific DNA fragment containing the desired HASH2 gene, the SMS3 gene, the TSSC6 gene, the RIBO26 gene, the CD81 gene, the TSSC4 gene, SEQ ID NO:13 or SEQ ID NO:14 may be accomplished in a number of ways. For example, if an amount of a portion of the HASH2 gene, the SMS3 gene, the TSSC6 gene, the RIBO26 gene, the CD81 gene or the TSSC4 gene or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). The present invention provides such nucleic acid probes, which can be conveniently prepared from the specific sequences disclosed herein, e.g., a hybridizable probe having a nucleotide sequence corresponding to at least a 10, and preferably a 15, nucleotide fragment of the sequences depicted in SEQ ID NOS:7, 8, 9, 10, 11, 12, 13 or 14. Preferably, a fragment is selected that is highly unique to the polypeptides of the invention. Those DNA fragments with substantial homology to the probe will hybridize. As noted above, the greater the degree of homology, the more stringent hybridization conditions can be used. In one embodiment, low stringency hybridization conditions are used to identify a homologous HASH2, SMS3, TSSC6, or RIBO26 polynucleotide. However, in a preferred aspect, and as demonstrated experimentally herein, a nucleic acid encoding a polypeptide of the invention will hybridize to a nucleic acid derived from the polynucleotide sequence depicted in SEQ ID NOS:7, 8, 9, 10, 11 or 12 or a hybridizable fragment thereof, under moderately stringent conditions; more preferably, it will hybridize under high stringency conditions.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties as known for the HASH2, SMS3, the TSSC6, RIBO26, CD81 or TSSC4 polypeptide.

A gene encoding HASH2, SMS3, TSSC6, RIBO26, CD81 or TSSC4 polypeptide can also be identified by mRNA selection, i.e., by nucleic acid hybridization followed by in vitro translation. In this procedure, fragments are used to isolate complementary mRNAs by hybridization. Immunoprecipitation analysis or functional assays of the in vitro translation products of the products of the isolated mRNAs identifies the mRNA and, therefore, the complementary DNA fragments, that contain the desired sequences.

Nucleic Acid Constructs

The present invention also relates to nucleic acid constructs comprising a polynucleotide sequence containing the exon/intron segments of the HASH2 gene (nucleotides 7028-7609 of SEQ ID NO:7), SMS3 gene (nucleotides 18959-21311 of SEQ ID NO:8), TSSC6 gene (nucleotides 5011-20067 of SEQ ID NO:9), RIBO26 gene (nucleotides 11487-11924 of SEQ ID NO:10), CD81 gene (nucleotides 10471-29787 of SEQ ID NO:11) or TSSC4 gene (nucleotides 13982-14971 of SEQ ID NO:12) operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

The invention is further directed to a nucleic acid construct comprising expression control sequences derived from SEQ ID NOS: 7, 8, 9, 10, 11 or 12 and a heterologous polynucleotide sequence.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

The isolated polynucleotide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The control sequence may be an appropriate promoter sequence, a nucleic acid sequence which is recognized by a host cell for expression of the nucleic acid sequence. The promoter sequence contains transcriptional control sequences which regulate the expression of the polynucleotide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the prokaryotic beta-lactamase gene (Villa-Komaroff et al., 1978, *Proc. Natl. Acad. Sci. USA* 75: 3727-3731), as well as the tac promoter (DeBoer et al., 1983, *Proc. Natl. Acad. of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (WO 96/00787), NA2-tpi (a hybrid of the promoters from the genes encoding *Aspergillus niger* neutral alpha-amylase and *Aspergillus oryzae* triose phosphate isomerase), and mutant, truncated, and hybrid promoters thereof.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, Yeast 8: 423-488.

Eukaryotic promoters may be obtained from the genomes of viruses such as polyoma virus, fowlpox virus, adenovirus, bovine papilloma virus, avian sarcoma virus, cytomegalovirus, a retrovirus, hepatitis-B virus and SV40. Alternatively, heterologous mammalian promoters, such as the actin promoter or immunoglobulin promoter may be used.

The constructs of the invention may also include enhancers. Enhancers are cis-acting elements of DNA, usually from about 10 to about 300 bp that act on a promoter to increase its transcription. Enhancers from globin, elastase, albumin, alpha-fetoprotein, and insulin enhancers may be used. However, an enhancer from a virus may be used; examples include SV40 on the late side of the replication origin, the cytomegalovirus early promoter enhancer, the polyoma enhancer on the late side of the replication origin and adenovirus enhancers.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

The control sequence may also be a signal peptide coding region, which codes for an amino acid sequence linked to the amino terminus of the polypeptide which can direct the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. However, any signal peptide coding region which directs the expressed polypeptide into the secretory pathway of a host cell of choice may be used in the present invention.

The control sequence may also be a propeptide coding region, which codes for an amino acid sequence positioned at the amino terminus of a polypeptide. The resultant polypeptide is known as a proenzyme or pro-polypeptide (or a zymogen in some cases). A pro-polypeptide is generally inactive and can be converted to a mature active polypeptide by catalytic or autocatalytic cleavage of the propeptide from the pro-polypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, the *Rhizomucor miehei* aspartic proteinase gene, or the *Myceliophthora thermophila* laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the polynucleotide of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. An example of suitable selectable markers for mammalian cells are those that enable the identification of cells competent to take of the nucleic acids of the present invention, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980).

The vectors of the present invention preferably contain an element(s) that permits stable integration of the vector into the host cell genome or autonomous replication of the vector in the cell independent of the genome of the cell.

For integration into the host cell genome, the vector may rely on the polynucleotide sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional polynucleotide sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMBβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a polynucleotide sequence of the present invention may be inserted into the host cell to increase production of the gene product. An increase in the copy number of the polynucleotide sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, or a *Streptomyces* cell, e.g., *Streptomyces lividans* or *Streptomyces murinus*, or gram negative bacteria such as *E. coli* and *Pseudomonas* sp.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian cell (e.g., human cell), an insect cell, a plant cell or a fungal cell. Mammalian host cells that could be used include but are not limited to human Hela, embryonic kidney cells (293), lung cells, H9 and Jurkat cells, mouse NIH3T3 and C127 cells, Cos 1, Cos 7 and CV1, quail QC1-3 cells, mouse L cells and Chinese Hamster ovary (CHO) cells. These cells may be transfected with a vector containing a transcriptional regulatory sequence, a protein coding sequence and transcriptional termination sequences by lipid-mediated, calcium phosphate mediated or DEAE-dextran mediated transfection (reviewed in Sambrook and Russell, Molecular Cloning, A Laboratory Manual, Cold Spring Harbor Laboratory Press, Cold Spring Harbor, N.Y., 2001). Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells. The polynucleotide may be directly introduced into the eukaryotic cell via electroporation, bolistics, or polybrene (reviewed in Sambrook and Russell, supra).

The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). The fungal host cell may also be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980). The fungal host cell may also be a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology*, Methods in Enzymology, Volume 194, pp 182-187, Academic Press, Inc., New York; Ito et al., 1983, *Journal of Bacteriology* 153: 163; and Hinnen et al., 1978, *Proc. Natl. Acad. Sci. USA* 75: 1920.

Methods of Production

The present invention also relates to methods for producing a polypeptide of the present invention comprising (a) cultivating a host cell under conditions conducive for production of the polypeptide; and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, the presence of the HASH2 and RIBO26 protein may be detected using standard transcription assays. The presence of TSSC4 and TSSC6 may be detected by assaying for tumor suppressor activity in rhabdomyosarcoma cells (Koi et al., 1993, Science 260:361-364). The presence of CD81 may be detected by assaying for binding to E2 hepatitis C protein (Allander et al., 2000, J. Gen. Virol. 81:2451-2459).

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Antibodies

According to the invention, the HASH2, SMS3, TSSC6, RIBO26, CD81 or TSSC4 polypeptides produced according to the method of the present invention may be used as an immunogen to generate any of these antibodies. Such antibodies include but are not limited to polyclonal, monoclonal, chimeric, single chain, Fab fragments, and an Fab expression library.

Various procedures known in the art may be used for the production of antibodies. For the production of antibody, various host animals can be immunized by injection with the polypeptide thereof, including but not limited to rabbits, mice, rats, sheep, goats, etc. In one embodiment, the polypeptide or fragment thereof can optionally be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the HASH2, SMS3, TSSC6, RIBO26, CD81 or TSSC4 polypeptide, any technique that provides for the production of antibody molecules by continuous cell lines in culture may be used. These include but are not limited to the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al., 1984, J. Bacteriol. 159-870; Neuberger et al., 1984, Nature 312:604-608; Takeda et al., 1985, Nature 314:452-454) by splicing the genes from a mouse antibody molecule specific for the HASH2, SMS3, TSSC6, RIBO26, CD81 or TSSC4 polypeptide together with genes from a human antibody molecule of appropriate biological activity can be used; such antibodies are within the scope of this invention.

According to the invention, techniques described for the production of single chain antibodies (U.S. Pat. No. 4,946,778) can be adapted to produce polypeptide-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for the HASH2, SMS3, TSSC6, RIBO26, CD81 or TSSC4 polypeptides.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$, fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a particular polypeptide, one may assay generated hybridomas for a product which binds to a particular polypeptide fragment containing such epitope. For selection of an antibody specific to a particular polypeptide from a particular species of animal, one can select on the basis of positive binding with the polypeptide expressed by or isolated from cells of that species of animal.

Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Uses of Polynucleotides

Diagnostics

Polynucleotides containing noncoding regions of SEQ ID NOS:7, 8, 9, 10, 11, 12, 13 or 14 may be used as probes for detecting mutations from samples from a patient. Genomic DNA may be isolated from the patient. A mutation(s) may be detected by Southern blot analysis, specifically by hybridizing restriction digested genomic DNA to various probes and subjecting to agarose electrophoresis. Alternatively, these polynucleotides may be used as PCR primers and be used to amplify the genomic DNA isolated from the patients. Additionally, primers may be obtained by routine or long range PCR that yield products containing contiguous intron/exon sequence and products containing more than one exon with intervening intron. The sequence of the amplified genomic DNA from the patient may be determined using methods known in the art. Such probes may be between 10-100 nucleotides in length and may preferably be between 20-50 nucleotides in length. Specifically, probes derived from SEQ ID NOS: 13 or 14 may be used to identify mutations duplications, translocations, polysomies and mosaicism associated with Beckwith-Wiedemann syndrome.

Thus the invention is thus directed to kits comprising these polynucleotide probes. In a specific embodiment, these probes are labeled with a detectable substance.

Antisense Oligonucleotides and Mimetics

The antisense oligonucleotides or mimetics of the present invention may be used to decrease levels of a polypeptide. For example, HASH2 is required for development of the trophoblast. Therefore, the HASH2 antisense oligonucleotides of the present invention could be used as an antifertility agent. RIBO26 is expressed in abundance in small cell tumors of the lung. RIBO26 antisense sequences could be used to inhibit small cell tumor growth. CD81 plays a role in T cell activation, and its antisense sequences may help control autoimmune disorders in which T cell activation is uncontrolled. CD81 also binds the human hepatitis C virus; thus CD81 antisense sequences may, by reducing CD81 expression, reduce the infectivity of the human hepatitis C virus. The TSSC4 and 6 proteins act as tumor suppressors. Therefore, antisense sequences may act as antiapoptosis agents.

The HASH2, SMS3, TSSC6, RIBO26, CD81 and TSSC4 genes are all situated in a region of chromosome 11 known to be associated with the Beckwith-Wiedemann Syndrome. Thus, antisense sequences of any of these six genes may provide means of managing patients with the Beckwith-Wiedemann Syndrome. Furthermore, antisense oligonucleotides of SEQ ID NOS:13 or 14 may be used for the same purpose.

The antisense oligonucleotides of the present invention may be formulated into pharmaceutical compositions. These compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention, the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ as found to be effective in vitro and in vivo animal models.

In general, dosage is from 0.01 ug to 10 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 10 g per kg of body weight, once or more daily, to once every 20 years.

Gene Therapy

As noted above, HASH2 is necessary for development of the trophoblast, RIBO26 is a component of the ribosome, TSSC6 and TSSC4 are involved in repressing tumor growth, and CD81 is involved in T cell activation. Therefore, the HASH2 gene may be used to treat some forms of infertility. The CD81 gene may be used in patients whose ability to activate T cells is impaired. CD81 also binds the human hepatitis C virus, thus gene therapy designed to yield a secretable form of CD81 may, by binding the virus in an excretable form, reduce the spread of hepatitis C. Given the tumor suppressing actions of TSSC6 and TSSC4, their genes may be used to prevent tumor growth. RIBO26 may be used to treat disorders in which ribosome assembly is defective. The SMS3 gene is situated within the Beckwith-Wiedemann Syndrome locus and may thus be useful for treatment of patients in which the SMS3 gene is nonfunctional.

As described herein, the polynucleotide of the present invention may be introduced into a patient's cells for therapeutic uses. As will be discussed in further detail below, cells can be transfected using any appropriate means, including viral vectors, as shown by the example, chemical transfectants, or physico-mechanical methods such as electroporation and direct diffusion of DNA. See, for example, Wolff, Jon A, et al., "Direct gene transfer into mouse muscle in vivo," *Science*, 247, 1465-1468, 1990; and Wolff, Jon A, "Human dystrophin expression in mdx mice after intramuscular injection of DNA constructs," *Nature*, 352, 815-818, 1991. As used herein, vectors are agents that transport the gene into the cell without degradation and include a promoter yielding expression of the gene in the cells into which it is delivered. As will be discussed in further detail below, promoters can be general promoters, yielding expression in a variety of mammalian cells, or cell specific, or even nuclear versus cytoplasmic specific. These are known to those skilled in the art and can be constructed using standard molecular biology protocols. Vectors have been divided into two classes:

a) Biological agents derived from viral, bacterial or other sources.

b) Chemical physical methods that increase the potential for gene uptake, directly introduce the gene into the nucleus or target the gene to a cell receptor.

Biological Vectors

Viral vectors have higher transaction (ability to introduce genes) abilities than do most chemical or physical methods to introduce genes into cells. Vectors that may be used in the present invention include viruses, such as adenoviruses, adeno associated virus (AAV), vaccinia, herpesviruses, baculoviruses and retroviruses, bacteriophages, cosmids, plasmids, fungal vectors and other recombination vehicles typically used in the art which have been described for expression in a variety of eukaryotic and prokaryotic hosts, and may be used for gene therapy as well as for simple protein expression. Polynucleotides are inserted into vector genomes using methods well known in the art.

Retroviral vectors are the vectors most commonly used in clinical trials, since they carry a larger genetic payload than other viral vectors. However, they are not useful in non-proliferating cells. Adenovirus vectors are relatively stable and easy to work with, have high titers, and can be delivered in aerosol formulation. Pox viral vectors are large and have several sites for inserting genes, they are thermostable and can be stored at room temperature.

Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, and the like. Alternatively, the promoter may be an endogenous adenovirus promoter, for example the E1 a promoter or the Ad2 major late promoter (MLP). Similarly, those of ordinary skill in the art can construct adenoviral vectors utilizing endogenous or heterologous polyA addition signals. Plasmids are not integrated into the genome and the vast majority of them are present only from a few weeks to several months, so they are typically very safe. However, they have lower expression levels than retroviruses and since cells have the ability to identify and eventually shut down foreign gene expression, the continuous release of DNA from the polymer to the target cells substantially increases the duration of functional expression while maintaining the benefit of the safety associated with non-viral transfections.

Chemical/Physical Vectors

Other methods to directly introduce genes into cells or exploit receptors on the surface of cells include the use of liposomes and lipids, ligands for specific cell surface receptors, cell receptors, and calcium phosphate and other chemical mediators, microinjections directly to single cells, electroporation and homologous recombination. Liposomes are commercially available from Gibco BRL, for example, as LIPOFECTIN™ and LIPOFECTACE™, which are formed of cationic lipids such as N-[1-(2,3 dioleyloxy)-propyl]-n,n,n-trimethylammonium chloride (DOTMA) and dimethyl dioctadecylammonium bromide (DDAB). Numerous methods are also published for making liposomes, known to those skilled in the art.

For example, Nucleic acid-Lipid Complexes—Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA which, generally, has a negative charge. Cationic lipids have also been shown to mediate intracellular delivery of plasmid DNA (Felgner and Ringold, Nature 337:387 (1989)). Intravenous injection of cationic lipid-plasmid complexes into mice has been shown to result in expression of the DNA in lung (Brigham et al., Am. J. Med. Sci. 298:278 (1989)). See also, Osaka et al., J. Pharm. Sci. 85(6):612-618 (1996); San et al., Human Gene Therapy 4:781-788 (1993); Senior et al., Biochemica et Biophysica Acta 1070:173-179 (1991); Kabanov and Kabanov, Bioconjugate Chem. 6:7-20 (1995); Remy et al., Bioconjugate Chem. 5:647-654 (1994); Behr, J-P., Bioconjugate Chem 5:382-389 (1994); Behr et al., Proc. Natl. Acad. Sci., USA 86:6982-6986 (1989); and Wyman et al., Biochem. 36:3008-3017 (1997).

Cationic lipids are known to those of ordinary skill in the art. Representative cationic lipids include those disclosed, for example, in U.S. Pat. No. 5,283,185; and e.g., U.S. Pat. No. 5,767,099. In a preferred embodiment, the cationic lipid is $N^4$-spermine cholesteryl carbamate (GL-67) disclosed in U.S. Pat. No. 5,767,099. Additional preferred lipids include $N^4$-spermidine cholestryl carbamate (GL-53) and 1-($N^4$-spermidine)-2,3-dilaurylglycerol carbamate (GL-89).

The vectors of the invention may be targeted to specific cells by linking a targeting molecule to the vector. A targeting molecule is any agent that is specific for a cell or tissue type of interest, including for example, a ligand, antibody, sugar, receptor, or other binding molecule.

Invention vectors may be delivered to the target cells in a suitable composition, either alone, or complexed, as provided above, comprising the vector and a suitably acceptable carrier. The vector may be delivered to target cells by methods known in the art, for example, intravenous, intramuscular, intranasal, subcutaneous, intubation, lavage, and the like. The vectors may be delivered via in vivo or ex vivo applications. In vivo applications involve the direct administration of an adenoviral vector of the invention formulated into a composition to the cells of an individual. Ex vivo applications involve the transfer of the adenoviral vector directly to harvested autologous cells which are maintained in vitro, followed by readministration of the transduced cells to a recipient.

In a specific embodiment, the vector is transfected into antigen-presenting cells. Suitable sources of antigen-presenting cells (APCs) include, but are not limited to, whole cells such as dendritic cells or macrophages; purified MHC class I molecule complexed to beta2-microglobulin and foster antigen-presenting cells. In a specific embodiment, the vectors of the present invention may be introduced into T cells or B cells using methods known in the art (see, for example, Tsokos and Nepom, 2000, J. Clin. Invest. 106:181-183).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosure of which are incorporated by reference in their entireties.

What is claimed is:

1. An isolated polynucleotide selected from the group consisting of: (a) an isolated polynucleotide consisting of a nucleic acid sequence which is at least 99% identical to the polynucleotide of SEQ ID NO: 8; (b) a polynucleotide fragment of (a) comprising at least nucleotides 18959-21311 of SEQ ID NO:8 or (c): a reverse strand of the polynucleotides of (a) or (b).

2. A nucleic acid construct comprising the polynucleotide of claim 1.

3. An expression vector comprising the polynucleotide of claim 1.

4. A recombinant host cell comprising the polynucleotide of claim 1.

5. An isolated polynucleotide at least 100 nucleotides in length identical to a region of SEQ ID NO: 8, said region selected from the group consisting of a 5'-noncoding region, an intron, a 3'-non-coding region and a contiguous coding and non-coding region of SEQ ID NO:8 or reverse strand of said polynucleotide.

6. The isolated polynucleotide of claim 5, wherein the 5'-noncoding region consists of nucleotides 21312-25970 of SEQ ID NO:8, the intron is selected from the group consisting of nucleotides 20119-21260 and 19211-20022 of SEQ ID NO:8 and a 3'-noncoding region consists of nucleotides 1-18958 of SEQ ID NO:8.

7. A composition comprising the polynucleotide of claim 1 and a carrier or diluent.

8. A composition comprising the polynucleotide of claim 5 and a carrier or diluent.

9. A kit comprising the polynucleotide of claim 1.

10. A kit comprising the polynucleotide of claim 5.

11. A method for detecting the presence or absence of a nucleic acid sequence of SEQ ID NO: 8 or its complementary sequence in a sample, said method comprising contacting the sample with the polynucleotide of claim 5.

12. A method of detecting the presence or absence of a variant of a nucleic acid sequence of SEQ ID NO: 8 or its complementary sequence in a sample using the polynucleotide of claim 1.

13. A method for obtaining the polynucleotide of claim 1 comprising
   (a) isolating genomic polynucleotide from a subject;
   (b) providing primers, probes and optionally polymerase, wherein said primers or probes are at least 100 nucleotides in length identical to a region of SEQ ID NO: 8, said region selected from the group consisting of a 5' noncoding region, an intron, a 3'-non-coding region and a contiguous coding and non-coding region of SEQ ID NO:8 or reverse strand of said regions and
   (c) incubating (a) and (b) under conditions promoting the isolation of said polynucleotide.

14. A method for obtaining the polynucleotide of claim 5 comprising
   (a) isolating genomic polynucleotide from a subject;
   (b) providing primers, probes and optionally polymerase, wherein said primers or probes are at least 100 nucleotides in length identical to a region of SEQ ID NO: 8, said region selected from the group consisting of 5" noncoding region, an intron, a 3'-non-coding region and a contiguous coding and non-coding region of SEQ ID NO:8 or reverse strand of said regions and
   (c) incubating (a) and (b) under conditions promoting the isolation of said polynucleotide.

15. The polynucleotide according to claim 1, wherein said polynucleotide is DNA or RNA.

16. An isolated polynucleotide consisting of a 5'-noncoding region, an intron, a 3'-non-coding region or a contiguous coding and non-coding nucleic acid region of SEQ ID NO:8 or reverse strand of said polynucleotide, wherein the 5'-noncoding region consists of nucleotides 21312-25970 of SEQ ID NO:8, the intron is selected from the group consisting of nucleotides 20119-21260 and 19211-20022 of SEQ ID NO:8 and a 3'-noncoding region consists of nucleotides 1-18958 of SEQ ID NO:8.

17. An isolated polynucleotide fragment of the isolated polynucleotide of claim 16, wherein said fragment is at least 500 nucleotides in length.

18. The method according to claim 13, wherein said polynucleotide is DNA or RNA.

19. The method according to claim 14, wherein said polynucleotide is DNA or RNA.

20. The polynucleotide according to claim 5, wherein said polynucleotide is DNA or RNA.

21. The polynucleotide according to claim 16, wherein said polynucleotide is DNA or RNA.

22. The kit comprising the polynucleotide of claim 16.

* * * * *